US012780897B2

(12) United States Patent
Bleakley et al.

(10) Patent No.: US 12,780,897 B2
(45) Date of Patent: Nov. 3, 2026

(54) TCRS SPECIFIC FOR MINOR HISTOCOMPATIBILITY (H) ANTIGEN HA-1 AND USES THEREOF

(71) Applicant: Fred Hutchinson Cancer Center, Seattle, WA (US)

(72) Inventors: Marie Bleakley, Seattle, WA (US); Robson Dossa, Seattle, WA (US); Daniel Sommermeyer, Munich (DE)

(73) Assignee: Fred Hutchinson Cancer Center, Seattle, WA (US)

( * ) Notice: Subject to any disclaimer, the term of this patent is extended or adjusted under 35 U.S.C. 154(b) by 661 days.

(21) Appl. No.: 18/456,389

(22) Filed: Aug. 25, 2023

(65) Prior Publication Data

US 2024/0279307 A1 Aug. 22, 2024

Related U.S. Application Data

(60) Continuation of application No. 16/700,998, filed on Dec. 2, 2019, now abandoned, which is a division of application No. 16/362,551, filed on Mar. 22, 2019, now Pat. No. 10,538,574, which is a continuation of application No. PCT/US2017/053112, filed on Sep. 22, 2017.

(60) Provisional application No. 62/399,291, filed on Sep. 23, 2016.

(51) Int. Cl.

| | |
|---|---|
| ***A61P 35/02*** | (2006.01) |
| ***A61K 35/17*** | (2015.01) |
| ***A61K 40/11*** | (2025.01) |
| ***A61K 40/22*** | (2025.01) |
| ***A61K 40/32*** | (2025.01) |
| ***A61K 40/41*** | (2025.01) |
| ***A61K 40/42*** | (2025.01) |
| ***C07K 14/705*** | (2006.01) |
| ***C07K 14/71*** | (2006.01) |
| ***C12N 5/0783*** | (2010.01) |
| ***C12N 9/22*** | (2006.01) |

(52) U.S. Cl.

CPC .......... *C07K 14/7051* (2013.01); *A61K 35/17* (2013.01); *A61K 40/11* (2025.01); *A61K 40/22* (2025.01); *A61K 40/32* (2025.01); *A61K 40/418* (2025.01); *A61K 40/42* (2025.01); *A61P 35/02* (2018.01); *C07K 14/70503* (2013.01); *C07K 14/70517* (2013.01); *C07K 14/70596* (2013.01); *C07K 14/71* (2013.01); *C12N 5/0636* (2013.01); *C12N 9/22* (2013.01); *A61K 2239/31* (2023.05); *A61K 2239/38* (2023.05); *C07K 2319/40* (2013.01); *C07K 2319/41* (2013.01); *C12N 2510/00* (2013.01)

(58) Field of Classification Search

None

See application file for complete search history.

(56) References Cited

U.S. PATENT DOCUMENTS

| | | | |
|---|---|---|---|
| 5,420,032 | A | 5/1995 | Marshall et al. |
| 6,410,319 | B1 | 6/2002 | Raubitschek et al. |
| 6,833,252 | B1 | 12/2004 | Dujon et al. |
| 7,446,191 | B2 | 11/2008 | Jensen |
| 7,514,537 | B2 | 4/2009 | Jensen |
| 8,697,359 | B1 | 4/2014 | Zhang |
| 8,822,647 | B2 | 9/2014 | Jensen |
| 9,574,000 | B2 | 2/2017 | Langermann et al. |
| 10,189,880 | B2 | 1/2019 | Heemskerk et al. |
| 2004/0002092 | A1 | 1/2004 | Arnould et al. |
| 2004/0087025 | A1 | 5/2004 | June et al. |
| 2006/0078552 | A1 | 4/2006 | Arnould et al. |
| 2006/0153826 | A1 | 7/2006 | Arnould et al. |
| 2006/0206949 | A1 | 9/2006 | Arnould et al. |
| 2007/0117128 | A1 | 5/2007 | Smith et al. |
| 2011/0189141 | A1 | 8/2011 | Kieback et al. |
| 2011/0243972 | A1 | 10/2011 | Jaffee |
| 2011/0301073 | A1 | 12/2011 | Gregory et al. |
| 2014/0068797 | A1 | 3/2014 | Doudna et al. |

(Continued)

FOREIGN PATENT DOCUMENTS

| | | | |
|---|---|---|---|
| EP | 2836511 | B1 | 11/2017 |
| WO | 2007017201 | A1 | 2/2007 |

(Continued)

OTHER PUBLICATIONS

Robbins et al. (J Clin Oncol. Mar. 1, 2011;29(7):917-24). (Year: 2011).*
Kim Margolin (Curr Oncol Rep. Dec. 2011;13(6):427-9). (Year: 2011).*
Pont et al. (PLoS ONE 11(5): e0155165 (2016), pp. 1-20 and Supplemental Methods S1 pp. 1-4). (Year: 2016).*
Wilke et al. (The Hematology Journal (2003) 4, 315-320). (Year: 2003).*
Parikh et al. (Semin Hematol. Oct. 2012 ; 49(4): 304-311). (Year: 2012).*
Komrokji et al., Haematologica. Jul. 2014;99(7):1176-83. (Year: 2014).*
Glenthoj et al., Int J Mol Sci. Jun. 15, 2016;17(6):944. (Year: 2016).*
Locke et al. (Blood. Jan. 4, 2018;131(1):5-7). (Year: 2018).*
NCT01352286, May 28, 2013, pp. 1-14. (Year: 2013).*

(Continued)

*Primary Examiner* — Zachary S Skelding

(74) *Attorney, Agent, or Firm* — Seed Intellectual Property Law Group LLP

(57) ABSTRACT

The present disclosure provides compositions and methods for targeting a minor histocompatibility (H) antigen (HA-$1^{H}$) to, for example, prevent or manage relapse of a hematological malignancy after allogeneic hematopoietic stem cell transplantation (HCT). Also provided are transgene constructs encoding engineered binding proteins, such as a T cell receptor or a chimeric antigen receptor, optionally encoding additional components such as a co-receptor and/or safety switch. Such transgene constructs can be transduced into an immune cell, such as a T cell, and used as an immunotherapy in a subject having a hematological malignancy or at risk for recurrence of the hematological malignancy (e.g., leukemia, lymphoma, myeloma).

22 Claims, 43 Drawing Sheets

Specification includes a Sequence Listing.

(56) References Cited

U.S. PATENT DOCUMENTS

| | | | |
|---|---|---|---|
| 2014/0186843 | A1 | 7/2014 | Zhang et al. |
| 2016/0045594 | A1 | 2/2016 | Geraghty et al. |
| 2016/0046724 | A1 | 2/2016 | Brogdon et al. |
| 2016/0263155 | A1 | 9/2016 | Heemskerk et al. |

FOREIGN PATENT DOCUMENTS

| | | | |
|---|---|---|---|
| WO | 2010065818 | A1 | 6/2010 |
| WO | 2013025779 | A1 | 2/2013 |
| WO | 2013074916 | A1 | 5/2013 |
| WO | 2013153391 | A1 | 10/2013 |
| WO | 2014031687 | A1 | 2/2014 |
| WO | 2014059173 | A2 | 4/2014 |
| WO | 2015066262 | A1 | 5/2015 |
| WO | 2015071474 | A2 | 5/2015 |
| WO | 2015132598 | A1 | 9/2015 |
| WO | 2016040724 | A1 | 3/2016 |
| WO | 2016054638 | A1 | 4/2016 |

OTHER PUBLICATIONS

Stone et al., "A novel T cell receptor single-chain signaling complex mediates antigen-specific T cell activity and tumor control," Cancer Immunol Immunother. 63(11): 1163-1176, 2014. (23 pages).
Stone et al., "Role of T cell receptor affinity in the efficacy and specificity of adoptive T cell therapies," Frontiers in Immunology T Cell Biology 4(244), 2013. (15 pages).
Straathof et al., "An inducible caspase 9 safety switch for T-cell therapy," Blood 105(11):4247-4254, 2005. (20 pages).
Stromnes et al., "Re-adapting T cells for cancer therapy: from mouse models to clinical trials," Immunol Rev. 257(1):145-164, 2014. (34 pages).
Supplementary European Search Report and Search Opinion, dated Feb. 7, 2020, of European Application No. EP17854051.4, 10 pages.
Sussman et al., "Isolation and Characterization of New Homing Endonuclease Specificities at Individual Target Site Positions," J Mol. Biol. 342:31-41, 2004.
Terentis et al., "The Selenazal Drug Ebselen Potently Inhibits Indoleamine 2,3-Dioxygenase by Targeting Enzyme Cysteine Residues," Biochemistry 49(3):591-600, 2010.
Tey et al., "Inducible caspase 9 suicide gene to improve the safety of allodepleted T cells after haploidentical stem cell transplantation," Biol Blood Marrow Transplant. 13(8):913-924, 2007. (22 pages).
Thakral et al., "Differential Expression of the Human CD8B Splice Variants and Regulation of the M-2 Isoform by Ubiquitination," The Journal ofimmunology 180:7431-7442, 2008.
Thakral et al., "The Human CD8B M-4 Isoform Dominant in Effector Memory T Cells Has Distinct Cytoplasmic Motifs That Confer Unique Properties," PLoS ONE 8(3):e59374, 2013. (12 pages).
The Union for International Cancer Control's (UICC), "4th International Conference on Immunotherapy in Pediatric Oncology (CIPO2015)," event information, last updated Mar. 10, 2015, event Sep. 25, 2015- Sep. 26, 2015, URL=https://www.uicc.org/4thinternational-conference-immunotherapy-pediatric-oncology-cipo2015, download date May 13, 2019. (3 pages).
Till et al., "Adoptive immunotherapy for indolent non-Hodgkin lymphoma and mantle cell lymphoma using genetically modified autologous CD20-specific T cells," Blood 112( 6):2261-2271, 2008. (12 pages).
Torikai et al., "A foundation for universal T-cell based immunotherapy: T cells engineered to express a CD 19-specific chimeric-antigen-receptor and eliminate expression of endogenous TCR," Blood 119(24):5697-5705, 2012. (10 pages).
Torikai et al., "Aberrant expression of BCL2AI-restricted minor histocompatibility antigens in melanoma cells: application for allogeneic transplantation," Int J Hematol 87:467-473, 2008.
Torikai et al., "Genetic editing of HLA expression in hematopoietic stem cells to broaden their human application," Scientific Reports 6:21757, 2016. (11 pages).
Torikai et al., "The HLA-A*0201-restricted minor histocompatibility antigen HA-1H peptide can also be presented by ar1other HLA-A2 subtype, A *0206," Bone Marrow Transplantation 40: 165-174, 2007.
Torikai et al., "Toward eliminating HLA class I expression to generate universal cells from allogeneic donors," Blood 122(8):1341-1349, 2013. (10 pages).
Van Bergen et al., "Selective graft-versus-leukemia depends on magnitude and diversity of the alloreactive T cell response," J Clin Invest. 127(2):517-529, 2017.
Van der Harst et al., "Recognition of Minor Histocompatibility Antigens on Lymphocytic and Myeloid Leukemic Cells by Cytotoxic T-Cell Clones," Blood 83(4): 1060-1066, 1994. (8 pages).
Van der Torren et al., "Possible Role of Minor H Antigens in the Persistence of Donor Chimerism after Stem Cell Trar1splar1tation; Relevance for Sustained Leukemia Remission," PLoS ONE 10(3):e0119595, 2015. (18 pages).
Van der Zouwen et al., "Collateral Damage ofNonhematopoietic Tissue by Hematopoiesis-Specific T Cells Results in Graft-versus-Host Disease During an Ongoing Profound Graft-versus-Leukemia Reaction," Biol Blood Marrow Transplant 20:760-769, 2014.
Van Lochem et al., "Functional expression of minor histocompatibility antigens on human peripheral blood dendritic cells and epidermal Langerhans cells," Transplant Immunology 4: 151-157, 1996.
Van Loenen et al., "A Good Manufacturing Practice procedure to engineer donor virus-specific T cells into potent anti-leukemic effector cells," haematologica 99(4):759-768, 2014.
Van Loenen et al., "Extracellular Domains of CD8a and CD8B Subunits are Sufficient for HLA Class I Restricted Helper Functions of TCR-Engineered CD4+ T Cells," PLoS ONE 8(5):e65212, 2013. (7 pages).
Van Loenen et al., "Optimization of the HA-1-specific T-cell receptor for gene therapy of hematologic malignancies," Haematologica 96(3):477-481, 2011.
Voogt et al., "Cellularly Defined Minor Histocompatibility Antigens are Differentially Expressed on Human Hematopoietic Progenitor Cells," J Exp. Med. 168:2337-2347, 1988.
Wang et al., "A transgene-encoded cell surface polypeptide for selection, in vivo tracking, and ablation of engineered cells," Blood. 118(5):1255-1263, 2011. (18 pages).
Wang et al., "Engraftment of human central memory-derived effector CD8+ T cells in immunodeficient mice," Blood 117(6):1888-1898, 2011. (12 pages).
Wang et al., "Optimizing Adoptive Polyclonal T Cell Immunotherapy of Lymphomas, Using a Chimeric T Cell Receptor Possessing CD28 and CD137 Costimulatory Domains," Human Gene Therapy 18:712-725, 2007. (17 pages).
Warren et al., "Therapy of relapsed leukemia after allogeneic hematopoietic cell transplantation with T cells specific for minor histocompatibility antigens," Blood 115(19):3869-3878, 2010. (22 pages).
Weinberg et al., "Chapter 13: Dialogue Replaces Monologue: Heterotypic Interactions and the Biology of Angiogenesia," The Biology of Cancer, pp. 536-539, 2007. (5 pages).
Wilke et al., "Quantification of the HA-1 gene product at the RNA level; relevance for immunotherapy of hematological malignancies," The Hematology Journal 4:315-320, 2003. (7 pages).
Willemsen et al., "Redirecting human CD4+ T lymphocytes to the MHC class I-restricted melanoma antigen MAGE-AI by TCR aB gene transfer requires CD8a," Gene Therapy 12:140-146, 2005.
Wolfe et al., "Analysis of Zinc Fingers Optimized via Phage Display: Evaluating the Utility of a Recognition Code," J Mol. Biol. 285:1917-1934, 1999.
Woodsworth et al., "Sequence analysis of T-cell repertoires in health and disease," Genome Medicine 5:98, Oct. 30, 2013. (13 pages).
Xie et al., "sgRNAcas9: A Software Package for Designing CRISPR sgRNA and Evaluating Potential Off-Target Cleavage Sites," PLoS ONE 9(6):e100448, 2014. (9 pages).

(56) References Cited

OTHER PUBLICATIONS

Xu et al., "Multiple pro-tumorigenic functions of the human minor Histocompatibility Antigen-I (HA-1) in melanoma progression," Journal of Dermatological Science 88:216-224, 2017.
Zhou et al., "Improving the Safety of T Cell Therapies using an Inducible Caspase-9 Gene," Exp Hematol. 44(11):1013-1019, 2016. (14 pages).
Zhou et al., "Inducible caspase-9 suicide gene controls adverse effects from alloreplete T cells after haploidentical stem cell transplantation," Blood. 125(26):4103-4113, 2015. (20 pages).
Zhou et al., "Long-term outcome after haploidentical stem cell transplant and infusion of T cells expressing the inducible caspase 9 safety transgene," Blood. 123(25):3895-3905, 2014. (21 pages).
Zhou et al., "Serial Activation of the Inducible Caspase 9 Safety Switch After Human Stem Cell Transplantation," Molecular Therapy 24(4):823-831, 2016.
Jinek et al., "A Programmable Dual-RNA-Guided DNA Endonuclease in Adaptive Bacterial Immunity," Science 337:816-821, 2012.
Karpanen et al., "T-cell receptor gene therapy—ready to go viral?," Molecular Oncology 9:2019-2042, 2015.
Kennedy et al., "Multiple roles for CD4+ T cells in anti-tumor immune responses," Immunological Reviews 222:129-144, 2008.
Kennedy et al., "T Helper Lymphocytes Rescue CTL from Activation-Induced Cell Death," J Immunol. 177(5):2862-2872, 2006. (25 pages).
Kessels et al., "Generation of T Cell Help through a MHC Class I-Restricted TCR," J Immunol 177:976-982, 2006. (8 pages).
Kieback et al., "A safeguard eliminates T cell receptor gene-modified autoreactive T cells after adoptive transfer," PNAS 105(2):623-628, 2008.
Kim et al., "High Cleavage Efficiency of a 2A Peptide Derived from Porcine Teschovirus-1 in Human Cell Lines, Zebrafish and Mice," PLoS ONE 6(4):e18556, 2011. (8 pages).
Kircher et al., "Hematopoietic Lineage-Restricted Minor Histocompatibility Antigen HA-1 in Graft-Versus-Leukemia Activity After Donor Lymphocyte Infusion," J Immunother 27(2):156-160, 2004.
Kircher et al., "Induction of HA-I-specific cytotoxic T-cell clones parallels the therapeutic effect of donor lymphocyte infusion," British Journal of Haematology 117:935-939, 2002.
Klein et al., "The Hematopoietic System-specific Minor Histocompatibility Antigen HA-1 Shows Aberrant Expression in Epithelial Car1cer Cells," J Exp. Med. 196(3):359-368, 2002.
Kloosterboer et al., "Direct cloning ofleukemia-reactive T cells from patients treated with donor lymphocyte infusion shows a relative dominar1ce of hematopoiesis-restricted minor histocompatibility antigen HA-1 and HA-2 specific T cells," Leukemia 18:798-808, 2004.
Kuball et al., "Facilitating matched pairing and expression of TCR chains introduced into human T cells," Blood. 109 (6):2331-2338, 2007. (17 pages).
Leen et al., "Improving T Cell Therapy for Cancer," Annu. Rev. Immunol. 25:243-265, 2007. (26 pages).
Lefranc et al., "IMGT unique numbering for immunoglobulin and T cell receptor variable domains and Ig superfamily V-like domains," Developmental and Comparative Immunology 27:55-77, 2003.
Li et al., "Memory T cells from minor histocompatibility antigen-vaccinated and virus-immune donors improve GVL and immune reconstitution," Blood 118(22):5965-5976, 2011. (22 pages).
Liu et al., "Selective inhibition of IDO 1 effectively regulates mediators of antitumor immunity," Blood 115(17):3520-3530, 2010. (12 pages).
Liu et al., "Systematic comparison of 2A peptides for cloning multi-genes in a polycistronic vector," Scientific Reports 7:2193, 2017. (9 pages).
Manning et al., "Alanine Scanning Mutagenesis of an αβ T Cell Receptor: Mapping the Energy of Antigen Recognition," Immunity 8:413-425, Apr. 1998. (13 pages).
Marijt et al., "Hematopoiesis-restricted minor histocompatibility antigens HA-1- or HA-2-specific T cells can induce complete remissions ofrelapsed leukemia," PNAS 100(5):2742-2747, 2003.
Marijt et al., "Minor Histocompatibility Antigens HA-1-, -2-, and -4-, ar1d HY-Specific Cytotoxic T-Cell Clones Inhibit Human Hematopoietic Progenitor Cell Growth by a Mechanism That is Dependent on Direct Cell-Cell Contact," Blood 82(12):3778-3785, 1993. (9 pages).
Matte-Martone et al., "CD8+ but not CD4+ T cells require cognate interactions with target tissues to mediate GVHD across only minor H antigens, whereas both CD4+ and CD8+ T cells require direct leukemic contact to mediate GVL," Blood. 111(7):3884-3892, 2008. (18 pages).
Mautino et al., "Abstract 491: NLG919, a novel indoleamine-2,3-dioxygenase (IDO)-pathway inhibitor drug candidate for cancer therapy," AACR 104thAnnualMeeting, Washington, D.C., Apr. 6-10, 2013. (4 pages) (Abstract Only).
Mavilio et al., "Peripheral Blood Lymphocytes as Target Cells of Retroviral Vector-Mediated Gene Transfer," Blood 83(7): 1988-1997, 1994. (11 pages).
Medina et al., "Genetic Engineering of CD4+ T lymphocytes to Target MHC-class-1 Restricted Tumor Antigens, A Novel Approach to Prevent Leukemia Relapse After Allogeneic Hematopoietic Stem Cell Transplantation (HCT)," 4th International Conference on Immunotherapy in Pediatric Oncology (CIPO2015), 2015. (27 pages).
Meij et al., "Generation and administration of HA-I-specific T-cell lines for the treatment of patients with relapsed leukemia after allogeneic stem cell transplantation: a pilot study," haematologica 97(8):1205-1208, 2012.
Morgan et al., "Cancer Regression in Patients After Transfer of Genetically Engineered Lymphocytes," Science. 314(5796): 126-129, 2006. (10 pages).
Morris et al., "A critical role of T cell antigen receptor-transduced MHC class I-restricted helper T cells in tumor protection," PNAS 102(22):7934-7939, 2005.
Mutis et al., "Generation of minor histocompatibility antigen HA-1-specific cytotoxic T cells restricted by nonselfHLA molecules: a potential strategy to treat relapsed leukemia after HLA-mismatched stem cell transplantation," Blood 100:547-552, 2002. (7 pages).
Mutis et al., "Tetrameric HLA class I-minor histocompatibility antigen peptide complexes demonstrate minor histocompatibility antigen-specific cytotoxic T lymphocytes in patients with graft-versus-host disease," Nature Medicine 5(7):839-842, 1999.
Nakanishi et al., "CTL mobilization to virus-infected tissue requires CD4+ T cell help," Nature. 462(7272):510-513, 2009. (12 pages).
Nicholls et al., "Secondary anchor polymorphism in the HA-1 minor histocompatibility antigen critically affects MHC stability and TCR recognition," PNAS 106(10):3889-3894, 2009.
Ochi et al., "Application of Adoptive T-Cell Therapy Using Tumor Antigen-Specific T-Cell Receptor Gene Transfer for the Treatment of Human Leukemia," Journal of Biomedicine and Biotechnology 2010, 2010. (10 pages).
Paques et al., "Meganucleases and DNA Double-Strand Break-Induced Recombination: Perspectives for Gene Therapy," Current Gene Therapy 7(1):49-66, 2007.
Perler et al., "Protein splicing elements: inteins and exteins—a definition of terms and recommended nomenclature," Nucleic Acids Research 22(7):1125-1127, 1994.
Philip et al., "A Highly Compact Epitope-Based Marker Suicide Gene for Safer and Easier Adoptive T-Cell Gene Therapy," Molecular Therapy 20(1):S35-S36, 2012.
Philip et al., "A highly compact epitope-based marker/ suicide gene for easier and safer T-cell therapy," www.bloodjournal.org, 2014. (21 pages).
Philip et al., "A highly compact epitope-based marker/suicide gene for easier and safer T-cell therapy," Blood 124(8):1277-1287, 2014. (12 pages).
Pont et al., "Microarray Gene Expression Analysis to Evaluate Cell Type Specific Expression of Targets Relevant for Immunotherapy of Hematological Malignancies," PLoS ONE 11(5), e0155165, 2016. (20 pages).
Porteus et al., "Gene targeting using zinc finger nucleases," Nature Biotechnology 23(8): 967-973, 2005.

(56) References Cited

OTHER PUBLICATIONS

Portolano et al., "Lack of Promiscuity in Autoantigen-Specific H and L Chain Combinations as Revealed by Human H and L Chain "Roulette"," The Journal of Immunology 150(3):880-887, Feb. 1, 1993. (8 pages).
Ray et al., "MHC-I-restricted melanoma antigen specific TCR-engineered human CD4+ T cells exhibit multifunctional effector and helper responses, in vitro," Clinical Immunology 136:338-347, 2010.
Robins et al., "Comprehensive assessment of T-cell receptor β-chain diversity in αβ T cells," Blood 114(19):4099-4107, Nov. 5, 2009 [Published online Aug. 25, 2009]. (10 pages).
Sadelain et al., "The basic principles of chimeric antigen receptor (CAR) design," Cancer Discov. 3(4): 388-398, 2013. (21 pages).
Sandberg et al., "Assessment of tumor characteristic gene expression in cell lines using a tissue similarity index (TSI)," PNAS 102(6):2052-2057, Feb. 8, 2005. (8 pages).
Schmitt et al., "T Cell Receptor Gene Therapy for Cancer," Human Gene Therapy 20: 1240-1248, 2009.
Scholten et al., "Codon modification of T cell receptors allows enhanced functional expression in transgenic human T cells," Clinical Immunology 119: 135-145, 2006.
SeattleChildrens, "CIPO 2015: Adoptive T Cell Immunotherapy Targeting the Minor Histocompatibility Antigen HA-1," YouTube Video, Oct. 20, 2015, URL=https://www.youtube.com/watch?v=na6v_LcW40Q, download date May 13, 2019, 2 pages. ( Screenshot).
Sommermeyer et al., "Chimeric antigen receptor-modified T cells derived from defined CD8+ and CD4+ subsets confer superior antitumor reactivity in vivo," Leukemia. 30(2): 492-500, 2016. (20 pages).
Spierings et al., "Multicenter Analyses Demonstrate Significant Clinical Effects of Minor Histocompatibility Antigens on GvHD and GvL after HLA-Matched Related and Unrelated Hematopoietic Stem Cell Transplantation," Biol Blood Marrow Transplant 19: 1244-1253, 2013.
Spierings et al., "Steric Hindrance and Fast Dissociation Explain the Lack ofImmunogenicity of the Minor Histocompatibility HA-1 Arg Null Allele," The Journal of Immunology 182: 4809-4816, 2009.
Argast et al., "I-Ppol and I-Crel Homing Site Sequence Degeneracy Determined by Random Mutagenesis and Sequential in Vitro Enrichment," J Mol. Biol. 280:345-353, 1998.
Ashworth et al., "Computational redesign of endonuclease DNA binding and cleavage specificity," Nature. 441(7093):656-659, 2006. (11 pages).
Belfort et al., "Homing endonucleases: keeping the house in order," Nucleic Acids Research 25(17):3379-3388, 1997.
Bleakley et al., "Augmentation of anti-tumor immunity by adoptive T-cell transfer after allogeneic hematopoietic stem cell transplantation," Expert Rev Hematol. 5(4):409-425, 2012. (27 pages).
Bleakley et al., "Engineering Human Peripheral Blood Stem Cell Grafts That are Depleted of Nai:ve T Cells and Retain Functional Pathogen-Specific Memory T cells," Biol Blood Marrow Transplant. 20(5):705-716, 2014. (24 pages).
Bleakley et al., "Exploiting T Cells Specific for Human Minor Histocompatibility Antigens For Therapy of Leukemia," Immunol Cell Biol. 89(3):396-407, 2011. (26 pages).
Bleakley et al., "Leukemia-associated minor histocompatibility antigen discovery using T-cell clones isolated by in vitro stimulation of naive CD8+ T cells," Blood 115(23):4923-4933, 2010. (12 pages).
Bleakley et al., "Molecules and Mechanisms of the Graft-Versus-Leukaemia Effect," Nature Reviews Cancer 4:371-380, 2004.
Bleakley et al., "Outcomes of acute leukemia patients transplanted with naive T cell-depleted stem cell grafts," The Journal of Clinical Investigation 125(7): 2677-2689, 2015.
Bonini et al., "Safety of retroviral gene marking with a truncated NGF receptor," Nature Medicine 9(4):367-369, 2003.
Bonnet et al., "CD8+ minor histocompatibility antigen-specific cytotoxic T lymphocyte clones eliminate human acute myeloid leukemia stem cells," Proc. Natl. Acad. Sci. USA 96:8639-8644, 1999.
Boria et al., "Primer sets for cloning the human repertoire of T cell Receptor Variable regions," BMC Immunology 9:50, 2008. (9 pages).
Bowerman et al., "Engineering the Binding Properties of the T Cell Receptor: Peptide:MHC Ternary Complex that Governs T Cell Activity," Mal Immunol. 46(15):3000-3008, 2009. (23 pages).
Brentjens et al., "Genetically Targeted T Cells Eradicate Systemic Acute Lymphoblastic Leukemia Xenografts," Clin Cancer Res 13(18):5426-5435, 2007. (11 pages).
Chevalier et al., "Design, Activity, and Structure of a Highly Specific Artificial Endonuclease," Molecular Cell 10:895-905, 2002.
Cole et al., "The molecular determinants of CD8 co-receptor function," Immunology 137: 139-148, 2012.
Dangaj et al., "Novel recombinant human B7-H4 antibodies overcome tumoral immune escape to potentiate T cell anti-tumor responses," Cancer Res. 73(15):4820-4829, 2013. (19 pages).
De Bueger et al., "Tissue distribution of human minor histocompatibility antigens. Ubiquitous versus restricted tissue distribution indicates heterogeneity among human cytotoxic T lymphocyte defined non-MHC antigens," The Journal of Immunology 149(5): 1788-1794, 1992. (8 pages).
De Kreuk et al., "The Human Minor Histocompatibility Antigenl is a RhoGAP," PLoS ONE 8(9):e73962, 2013. (15 pages).
Den Haan et al., "The Minor Histocompatibility Antigen HA-1: A Diallelic Gene with a Single Amino Acid Polymorphism," Science 279(5353):1054-1057, 1998. (5 pages).
Desjarlais et al., "Use of a zinc-finger consensus sequence framework and specificity rules to design specific DNA binding proteins," Proc. Natl. Acad. Sci. USA 90:2256-2260, 1993.
Di Stasi et al., "Inducible Apoptosis as a Safety Switch for Adoptive Cell Therapy," N Engl J Med. 365(18): 1673-1683, 2011. (16 pages).
Dickinson et al., "In situ dissection of the graft-versus-host activities of cytotoxic T cells specific for minor histocompatibility antigens," Nature Medicine 8( 4):410-414, 2002.
Dossa et al., "Development ofT-cell immunotherapy for hematopoietic stem cell transplantation recipients at risk ofleukemia relapse," Blood 131(1): 108-120, 2018. (14 pages).
Dossett et al., "Adoptive Immunotherapy of Disseminated Leukemia With TCR-transduced, CD8+ T Cells Expressing a Known Endogenous TCR," Molecular Therapy 17(4):742-749, 2009.
Dujon et al., "Mobile intrans: definition of terms and recommended nomenclature," Gene 82: 115-118, 1989.
Epinat et al., "A novel engineered meganuclease induces homologous recombination in yeast and mammalian cells," Nucleic Acids Research 31(11):2952-2962, 2003.
Faber et al., "Recognition of Clonogenic Leukemic Cells, Remission Bone Marrow and HLAidentical Donor Bone Marrow by CD8+ or CD4+ Minor Histocompatibility Antigen-specific Cytotoxic T Lymphocytes," J Clin. Invest. 96:877-883, 1995.
Falkenburg et al., "Growth Inhibition of Clonogenic Leukemic Precursor Cells by Minor Histocompatibility Antigen-specific Cytotoxic T Lymphocytes," J Exp. Med. 174:27-33, 1991.
Fehse et al., "CD34 Splice Variant: An Attractive Marker for Selection of Gene-Modified Cells," Molecular Therapy 1(5):448-456, 2000.
Floros et al., "Anticancer Cytokines: Biology and Clinical Effects ofIFN-a2, IL-2, IL-15, IL-21, and IL-12," Semin Oneal. 42(4):539-548, 2015. (17 pages).
Franssen et al., "A phase 1/11 minor histocompatibility antigen-loaded dendritic cell vaccination trial to safely improve the efficacy of donor lymphocyte infusions in myeloma," Bone Marrow Transplantation 52:1378-1383, 2017.
Fujii et al., "Expression of Minor Histocompatibility Antigen, HA-1, in Solid Tumor Cells," Transplantation 73(7): 1137-1141, 2002.
Garcia et al., "How the T Cell Receptor Sees Antigen—A Structural View," Cell 122:333-336, Aug. 12, 2005. (4 pages).

(56) References Cited

OTHER PUBLICATIONS

Ghorashian et al., "CD8 T Cell Tolerance to a Tumor-Associated Self-Antigen is Reversed by CD4 T Cells Engineered to Express the Same T Cell Receptor," J Immunol 194: 1080-1089, 2015. (11 pages).
Gimble et al., "Substrate Recognition and Induced DNA Distortion by the PI-Seel Endonuclease, an Enzyme Generated by Protein Splicing," J Mol. Biol. 263:163-180, 1996.
Giuntoli Il et al., "Direct Costimulation of Tumor-reactive CTL by Helper T Cells Potentiate Their Proliferation, Survival, and Effector Function," Clinical Cancer Research 8:922-931, 2002. (11 pages).
Govers et al., "T cell receptor gene therapy: strategies for optimizing transgenic TCR pairing," Trends in Molecular Medicine 16(2):77-87, 2010.
Griffioen et al., "Autosomal Minor Histocompatibility Antigens: How Genetic Variants Create Diversity in Immune Targets," Frontiers in Immunology 7(100), 2016. (9 pages).
Griffioen et al., "Genetic engineering of virus-specific T cells with T-cell receptors recognizing minor histocompatibility antigens for clinical application," Haematologica 93(10): 15 3 5-1543, 2008.
Hambach et al., "Human cytotoxic T lymphocytes specific for a single minor histocompatibility antigen HA-1 are effective against human lymphoblastic leukaemia in NOD/scid mice," Leukemia 20:371-374, 2006.
Hambach et al., "Targeting a single mismatched minor histocompatibility antigen with tumorrestricted expression eradicates human solid tumors," Blood 112(5):1844-1852, 2008. (10 pages).
Harris et al., "Adoptive T Cell Therapies: A Comparison of T Cell Receptors and Chimeric Antigen Receptors," Trends Pharmacol Sci. 37(3):220-230, 2016. (21 pages).
Heemskerk et al., "Reprogramming of Virus-specific T Cells into Leukemia-reactive T Cells Using T Cell Receptor Gene Transfer," J Exp. Med. 199(7):885-894, 2004.
Hinrichs et al., "Adoptively transferred effector cells derived from naive rather than central memory CD8+ T cells mediate superior antitumor immunity," PNAS 106(41): 17469-17474, 2009.
Hobo et al., "Association of disparities in known minor histocompatibility antigens with relapse-free survival and graft- versus-host-disease after allogeneic stem cell transplantation," Biol Blood Marrow Transplant. 19(2):274-282, 2013. (21 pages).
Inaguma et al., "Construction and molecular characterization of a T-cell receptor-like antibody and CAR-T cells specific for minor histocompatibility antigen HA-1H," Gene Therapy 21:575-584, 2014.
International Search Report and Written Opinion dated Jan. 3, 2018, in corresponding PCT Application No. PCT/US2017/053112, 16 pages.
Janeway, Jr. et al., "Chapter 3: Antigen Recognition by B-cell and T-cell Receptors," Immunobiology, 5th Edition, pp. 106-108, 260-263, 2001. (9 pages).
Jasin, "Genetic manipulation of genomes with rare-cutting endonucleases," TIG 12(6):224-228, 1996.

* cited by examiner

TCRS SPECIFIC FOR MINOR HISTOCOMPATIBILITY (H) ANTIGEN HA-1 AND USES THEREOF

STATEMENT OF GOVERNMENT INTEREST

This invention was made with government support under CA154532 awarded by the National Institutes of Health. The government has certain rights in the invention.

REFERENCE TO AN ELECTRONIC SEQUENCE LISTING

The contents of the electronic sequence listing (455C2_SegListing.xml; Size: 222,124 bytes; and Date of Creation: Aug. 23, 2023) is herein incorporated by reference in its entirety.

BACKGROUND

Patients with hematologic malignancies can be treated with allogeneic hematopoietic stem cell transplantation (HCT). In the United States, for example, allogeneic HCT transplants have risen steadily over the past 35 years, with approximately 8,000 transplants per year since 2013 (see CIBMTR 2016 Summary). However, relapse of the hematologic malignancy can occur thereafter. Currently, a significant number of patients who receive HCT for the treatment of acute leukemia relapse (approximately 2,000 patients relapse post-HCT each year in the U.S. alone, or about 25 to 50%; see Sucheston-Campbell et al., *Curr. Hematol. Malig. Rep.* 10:45-58, 2015). Relapse rates are especially high in patients who are not able to achieve deep complete remissions and/or are unable to tolerate intensive conditioning regimens prior to HCT. The prognosis for patients with post-HCT relapse is abysmal: two year survival rates for patients relapsing at <100, 100-200 and >200 days after HCT are 3%, 9% and 19%, respectively. Patients who receive a second HCT may have better outcomes, but to be eligible for a second HCT, the patient must first achieve remission, which typically only occurs in about 30% of patients.

Acute leukemia relapses can, in some cases, be treated with donor lymphocyte infusions from the original stem cell donor. This graft-versus-leukemia (GVL) effect of donor lymphocyte infusion, however, is often accompanied by graft-versus-host disease (GVHD), causing serious mortality and morbidity and is not always effective. If GVL could be selectively increased without enhancing immune responses against normal tissues (graft-versus-host disease, GVHD), post-HCT relapses might be prevented.

Certain minor H antigens are expressed on leukemic stem cells and blasts (see, e.g., Bleakley and Riddell, *Nat. Rev. Cancer* 4:371-380, 2004; Bleakley et al., *Blood* 115:4923-4933, 2010; Bleakley and Riddell, *Immunol. Cell. Biol.* 89:396-407, 2011; van der Harst et al., *Blood* 83:1060-1066, 1994; Bonnet et al., *Proc. Natl. Acad. Sci. USA* 96:8639-8644, 1999; Hambach et al., *Leukemia* 20:371-374, 2006), and have been targeted using cancer-specific T cells. In a small clinical trial of minor H antigen-targeted T cell immunotherapy in patients with post-HCT relapse, clinical responses were observed in some patients (Warren et al., *Blood* 115:3869-3878, 2010). Technical advances in genetic modification of T cells and growing knowledge of T cell biology means that therapeutic doses of antigen-specific T cells can now be prepared efficiently, given to patients, and persist and exert potent anti-tumor effects in vivo (Heemskerk et al., *J. Exp. Med.* 199:885-894, 2004; Morgan et al., *Science* 314:126-129, 2006; Griffioen et al., *Haematologica* 93:1535-131543, 2008; Ochi et al., *J. Biomed. Biotechnol.* 2010:5212248, 2010; Schmitt et al., *Hum. Gene Ther.* 20:1240-1248, 2009; Stromnes et al., *Immunol Rev.* 257:145-164, 2014). However, there is a need for cell-based therapies that target leukemia-associated antigens. Presently disclosed embodiments address these needs and provide other related advantages.

Figure 21:
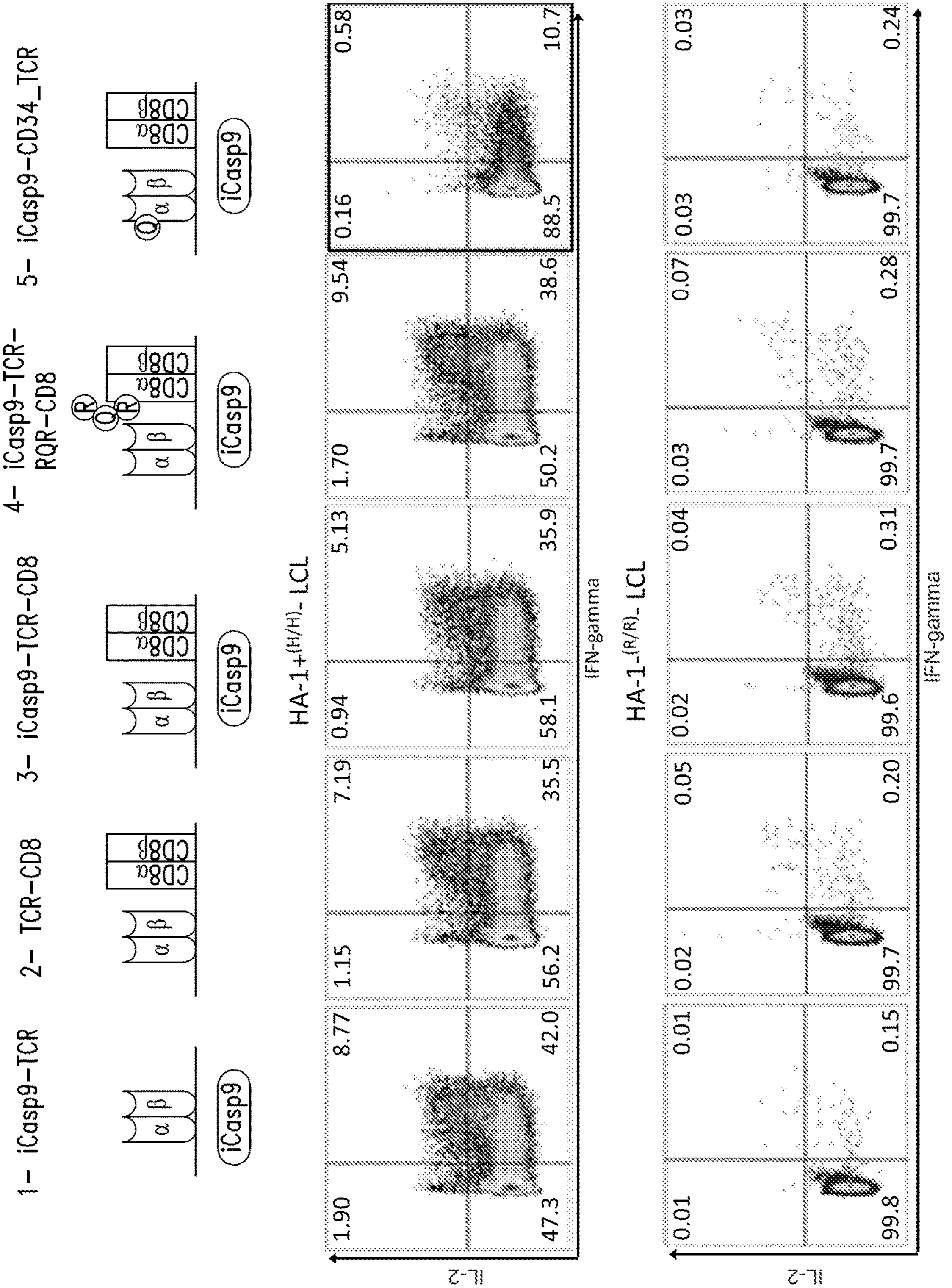

FIG. 21 shows cytokine elaboration by T cells transduced with the indicated transgene constructs following stimulation with HA-$1^{H+}$(top) or HA-$1^{H-}$ (bottom) cell lines.

Figure 22:
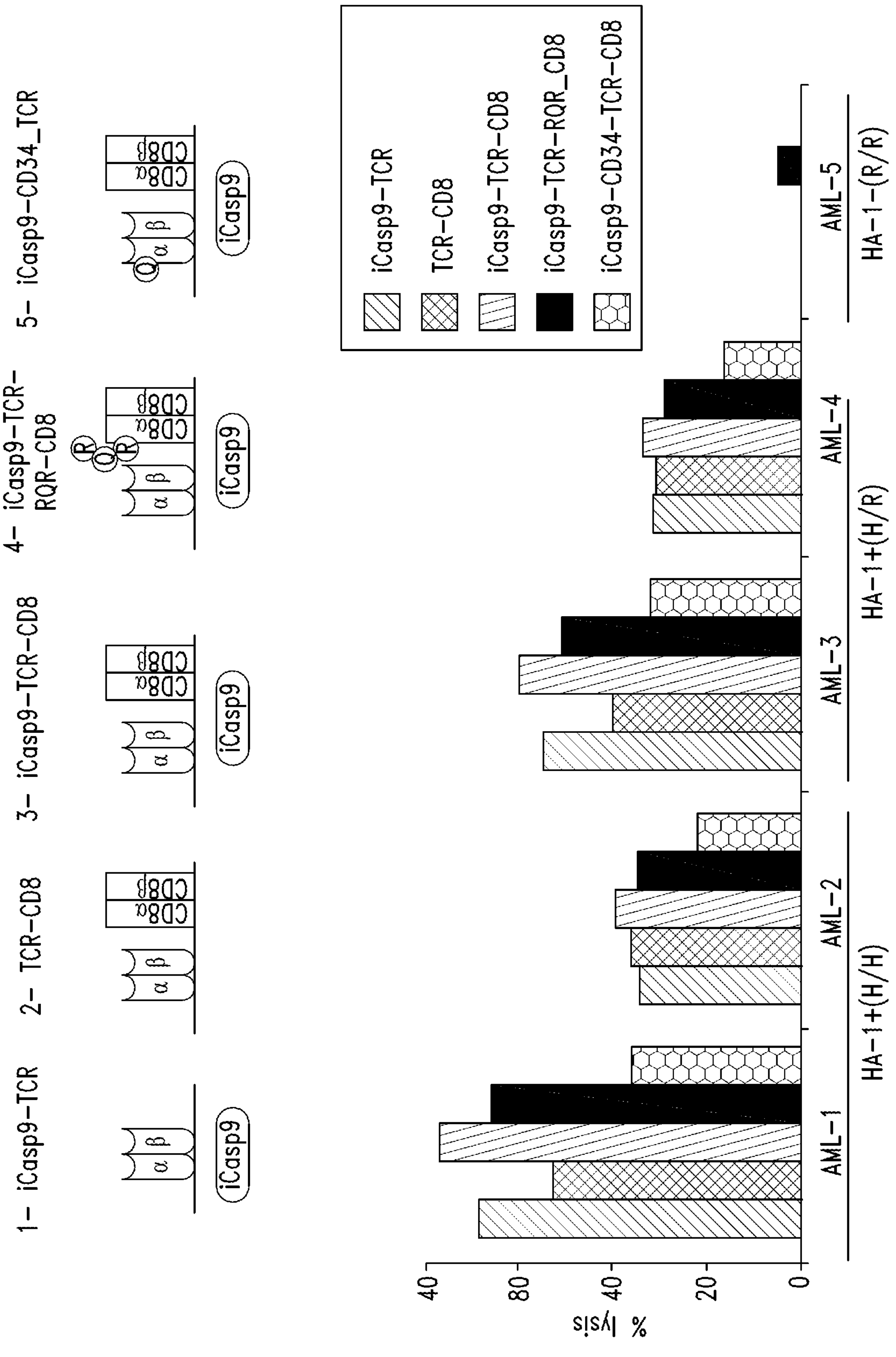

FIG. 22 shows cytolytic activity (bottom) of T cells transduced with the transgene constructs (top) against indicated target cell lines.

Figure 23:
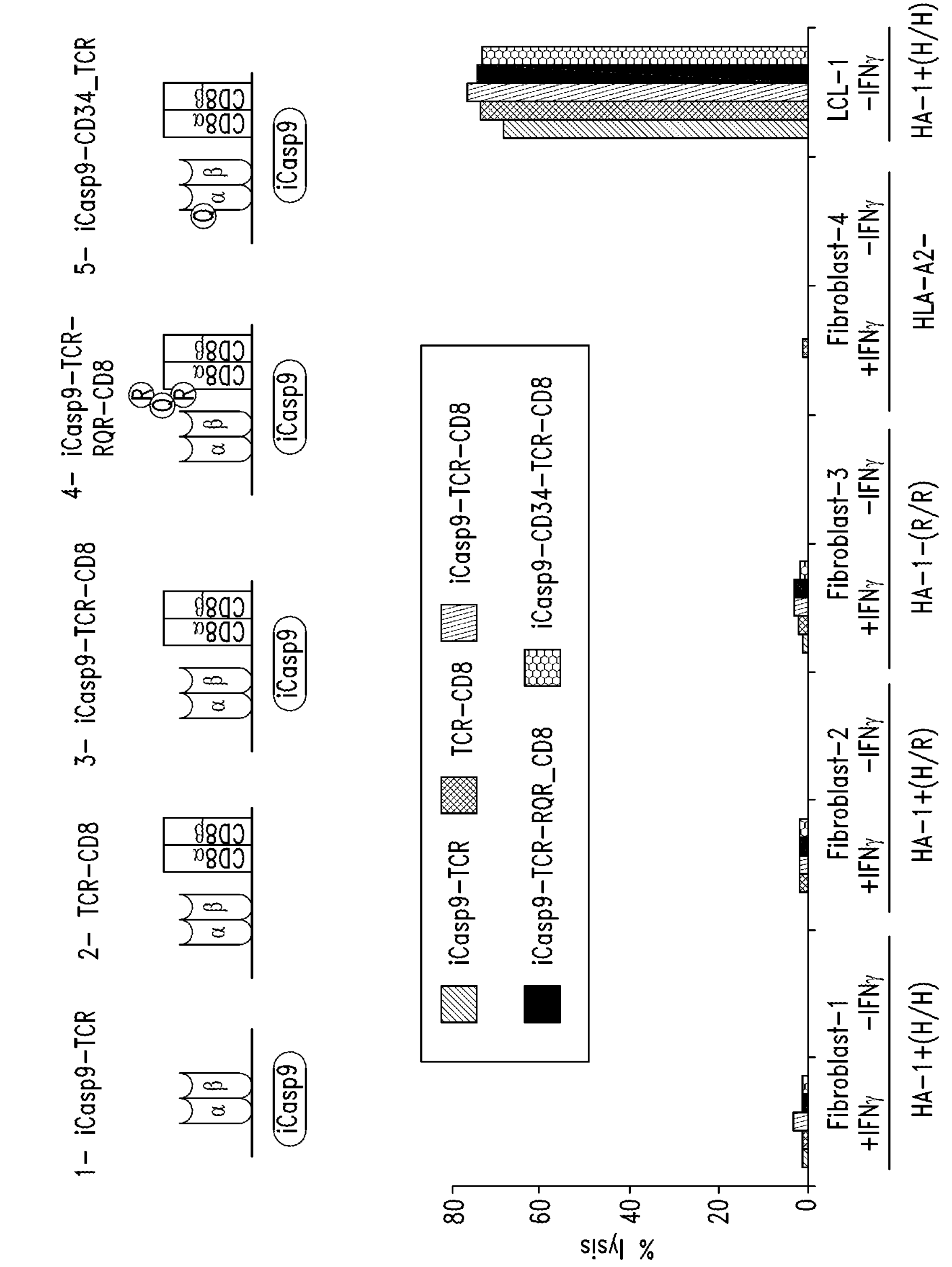

FIG. 23 shows the absence of cytolytic activity of T cells transduced with the indicated transgene constructs against indicated non-hematopoietic cells in the presence or absence of interferon-gamma. HA-$1^{H+}$ hematopoietic control cells were killed by the T cells.

Figure 24:
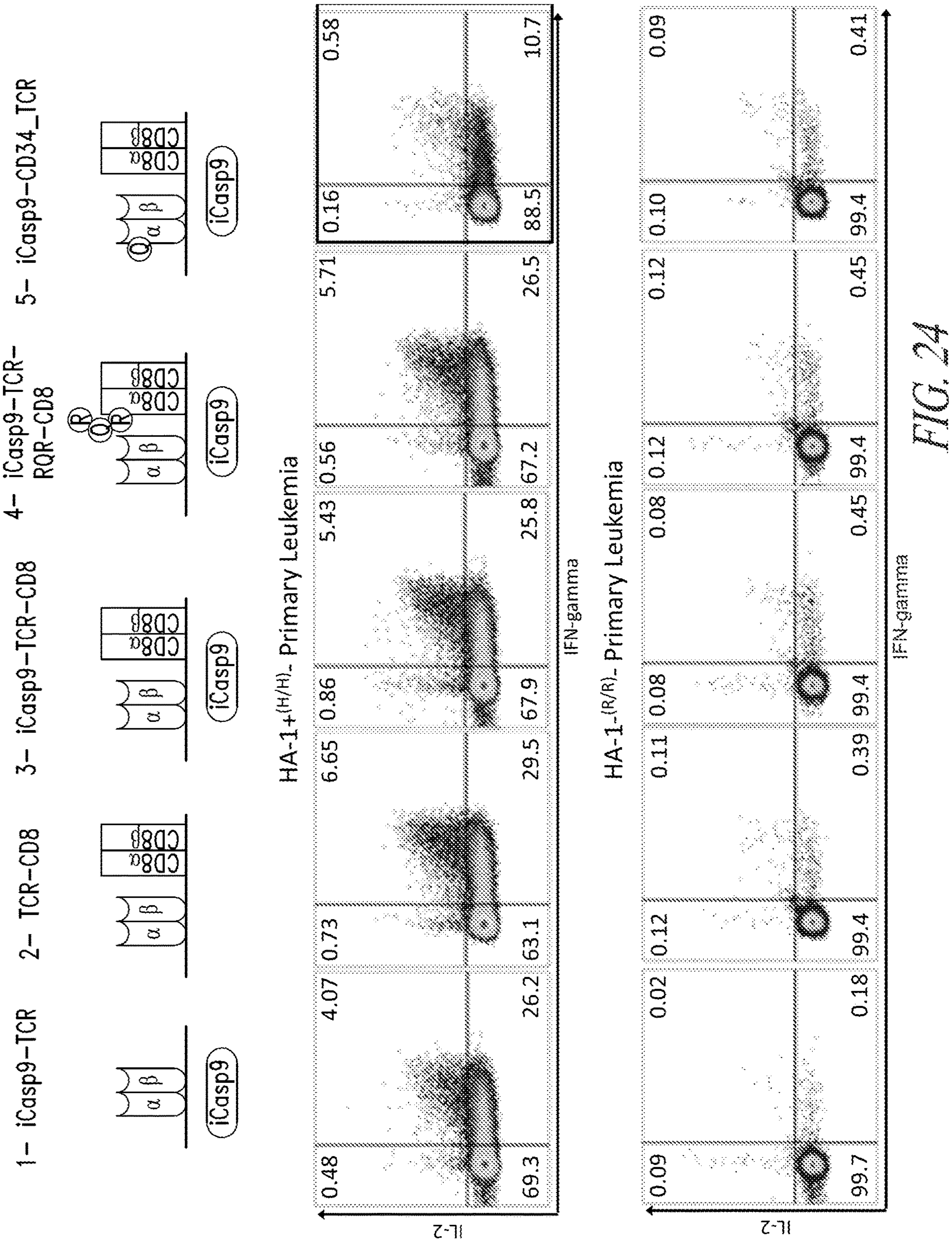

FIG. 24 shows cytokine elaboration by cells transduced with the indicated transgene constructs when exposed to primary leukemia cells.

Figure 25:
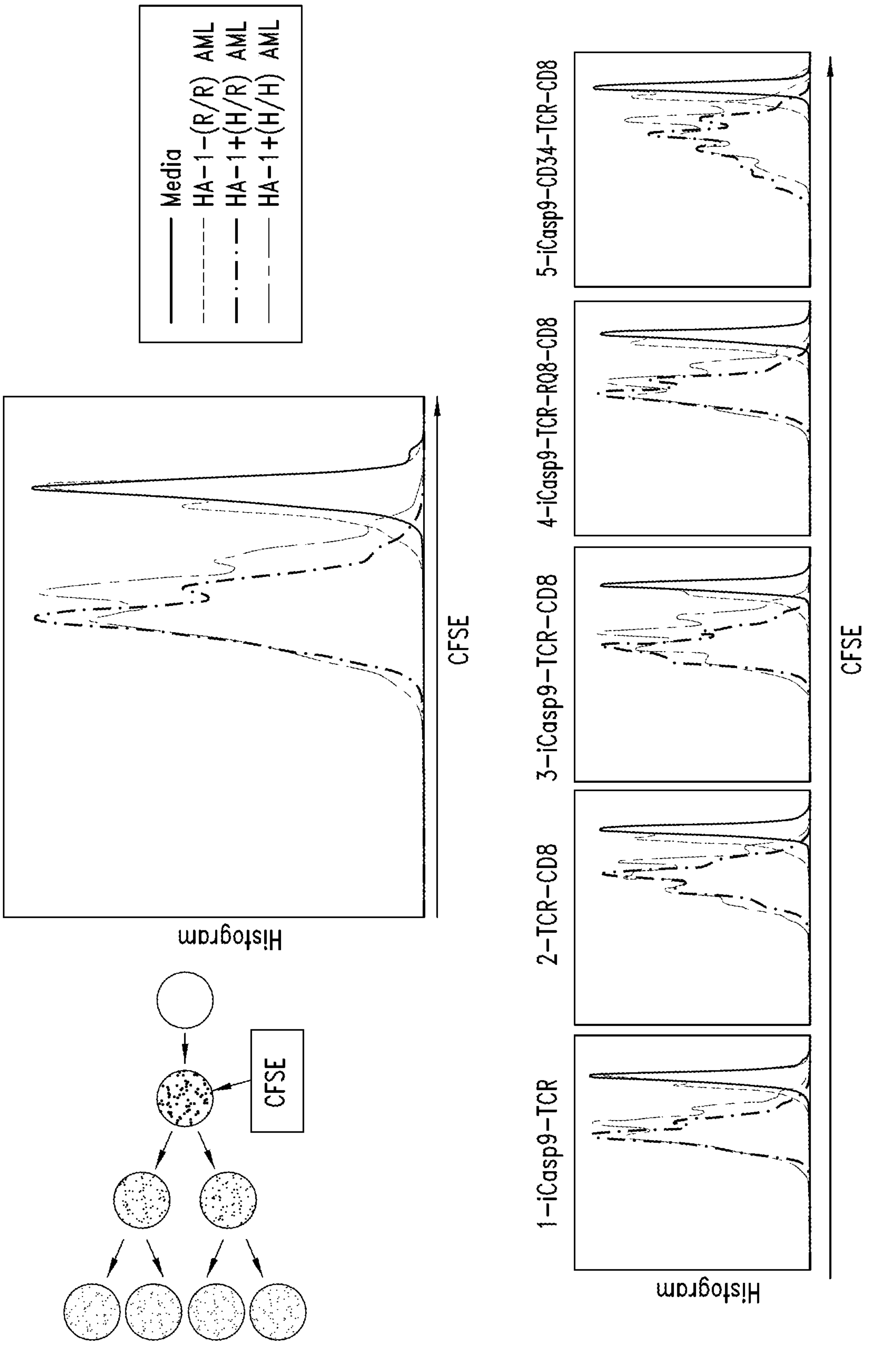

FIG. 25 provides flow cytometry histograms showing proliferation of transduced T cells when stimulated with HA-$1^{H+}$ primary leukemia cells. Top: scheme for measuring proliferation by staining F1 cells with CFSE (left), and representative proliferation data from a T cell transduced with a transgene constructs of the present disclosure. Bottom: proliferation of T cells transduced with the indicated transgene constructs.

Figure 26:
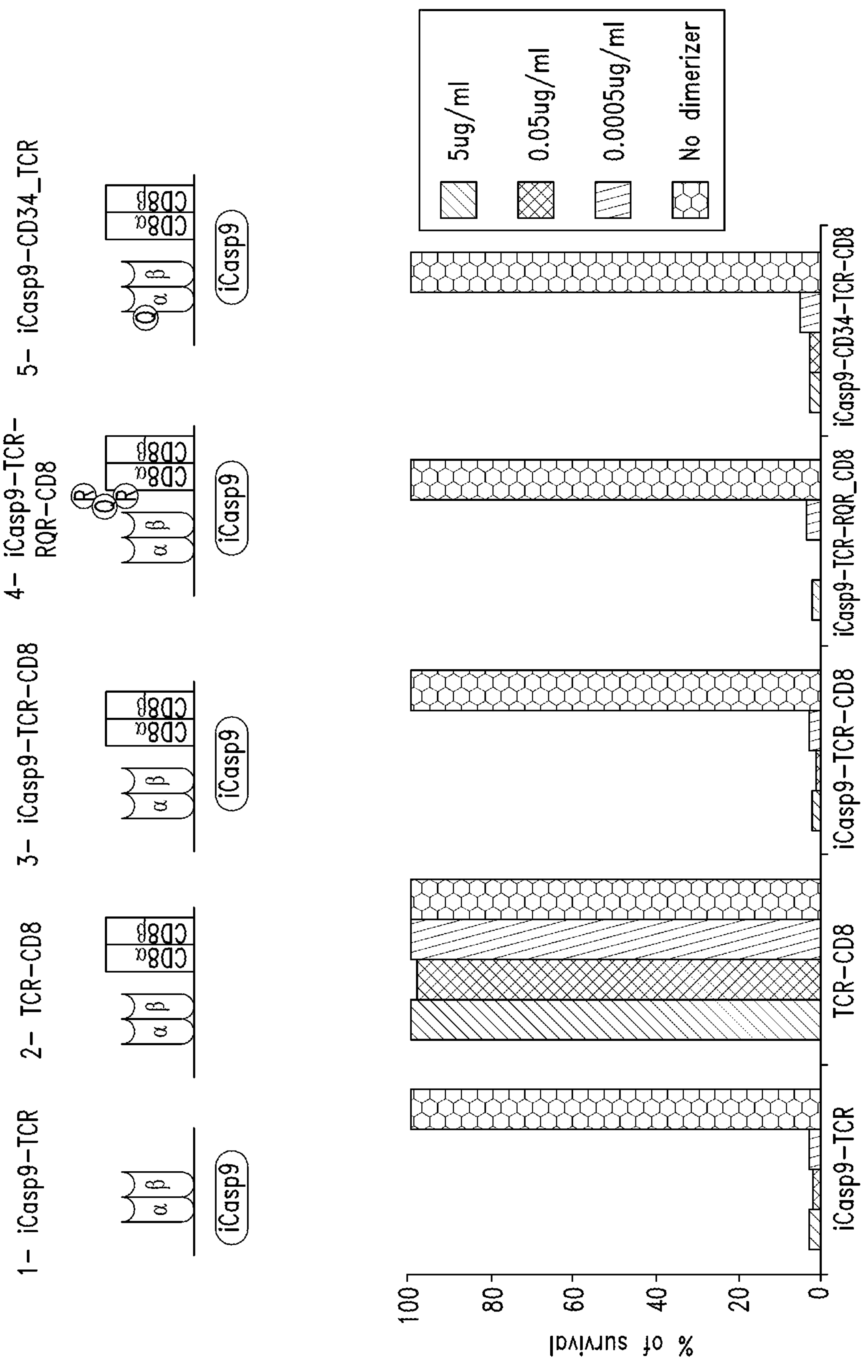

FIG. 26 shows survival (bottom) of T cells transduced with transgene constructs as shown (top) following introduction of the cognate suicide drug at the indicated concentrations.

Figure 27:
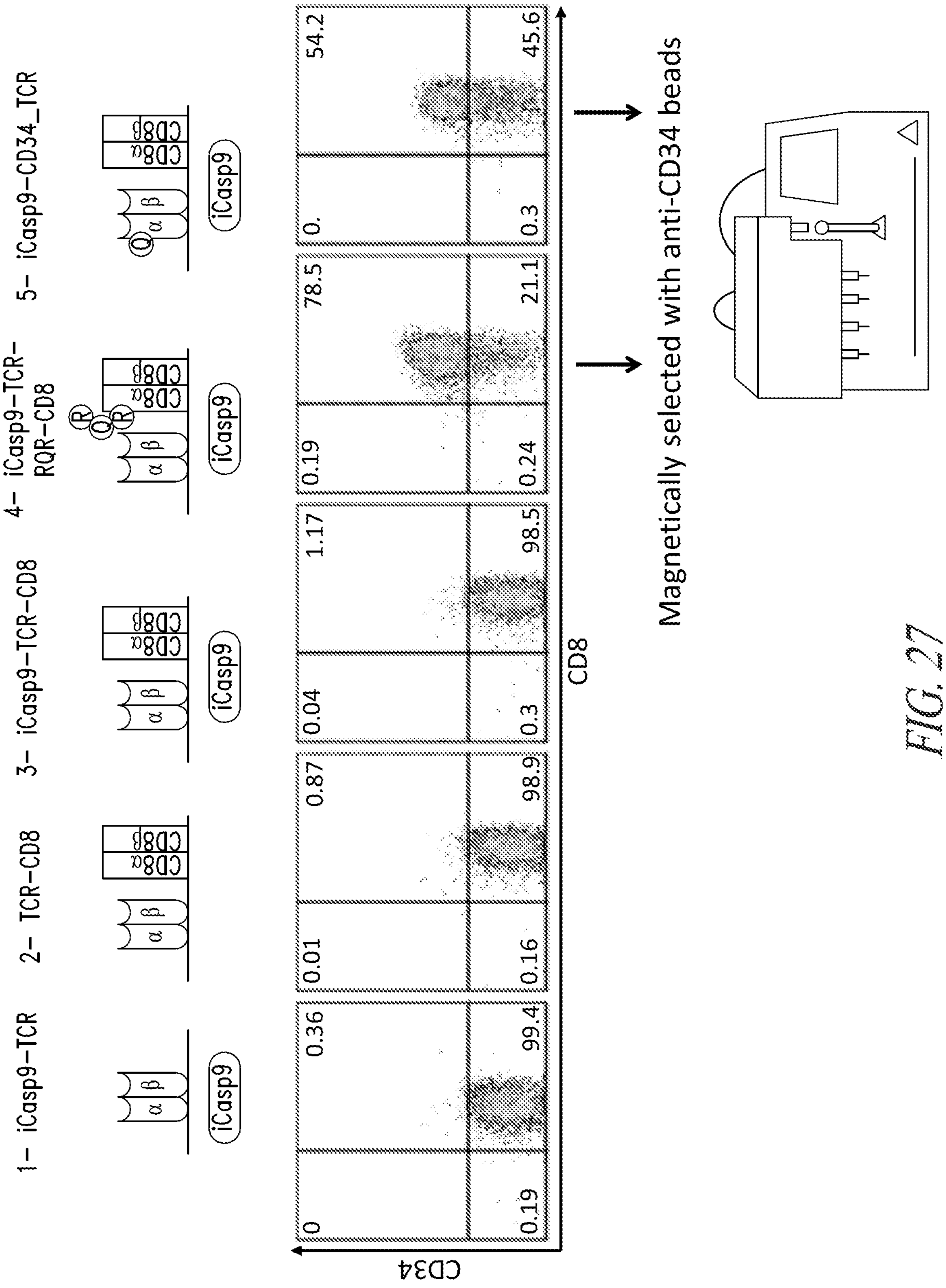

FIG. 27 shows an enrichment scheme for engineered T cells of the present disclosure. T cells are transduced with the indicated transgene constructs (top) and examined for expression (middle). Cells expressing a selectable transduction marker (CD34 epitope; two right-most scatter plots) are selected using magnetic beads with anti-CD34 antibody.

Figure 28A:
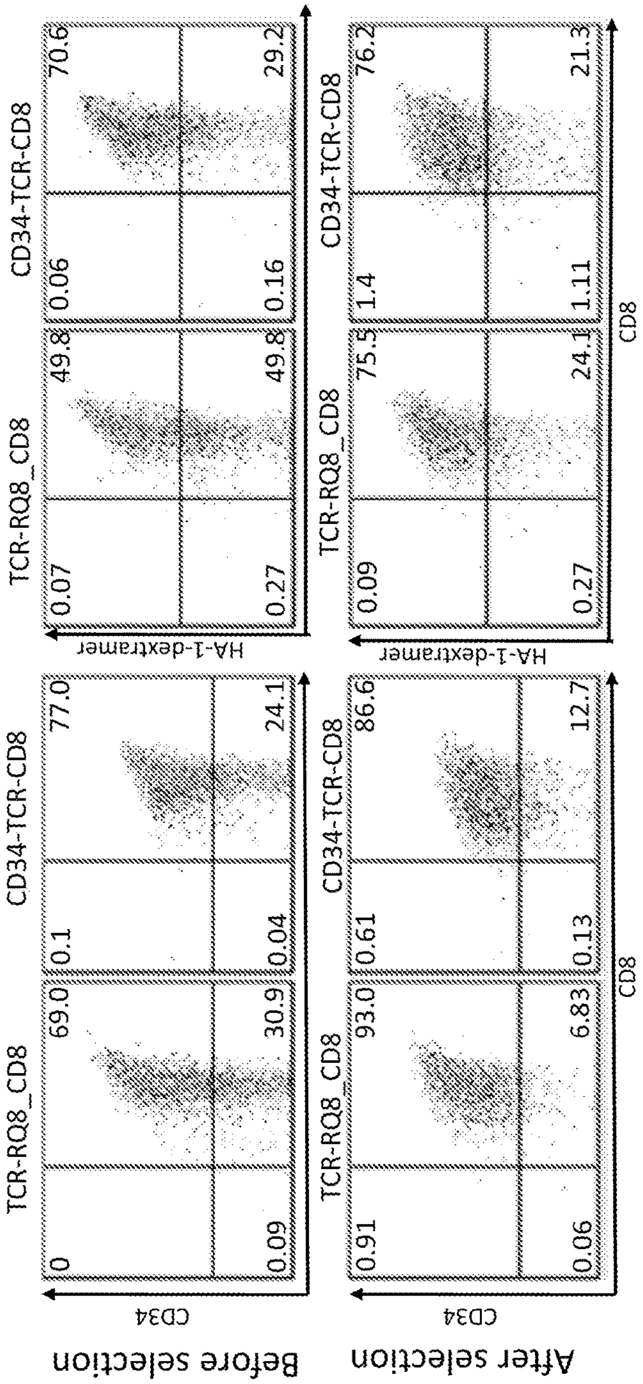
Figure 28B:
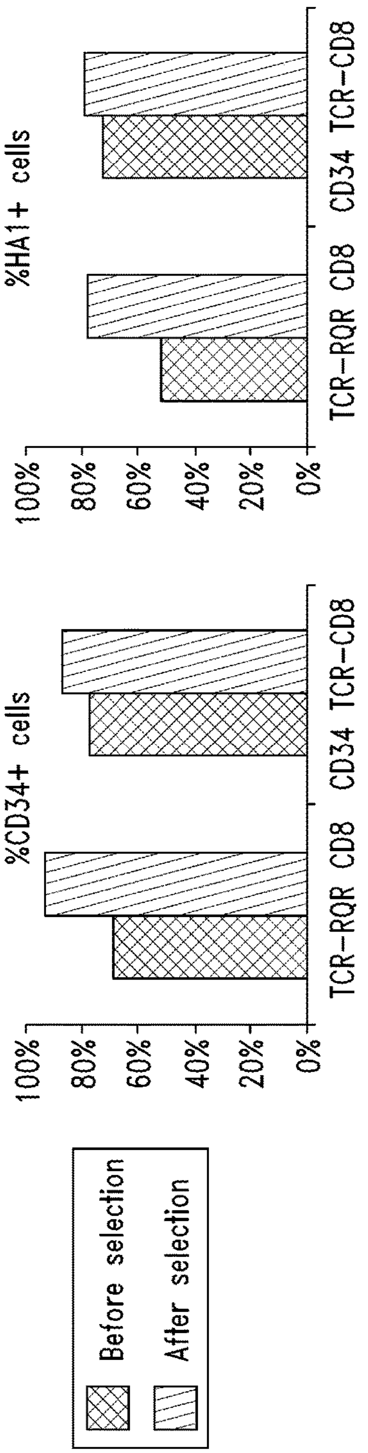

FIGS. 28A and 28B provide flow cytometry data (28A) showing frequency of transduced T cells before (top row) and after (bottom row) magnetic selection. Four scatter plots at left: staining for CD34 selection marker and CD8. Four scatter plots at right: staining for HA-$1^{H}$ dextramer and CD8. Also shown (28B) are cell counts of cells expressing the CD34 selection marker (left) or being specific for HA-$1^{H}$ (right) before and after selection.

Figure 29:
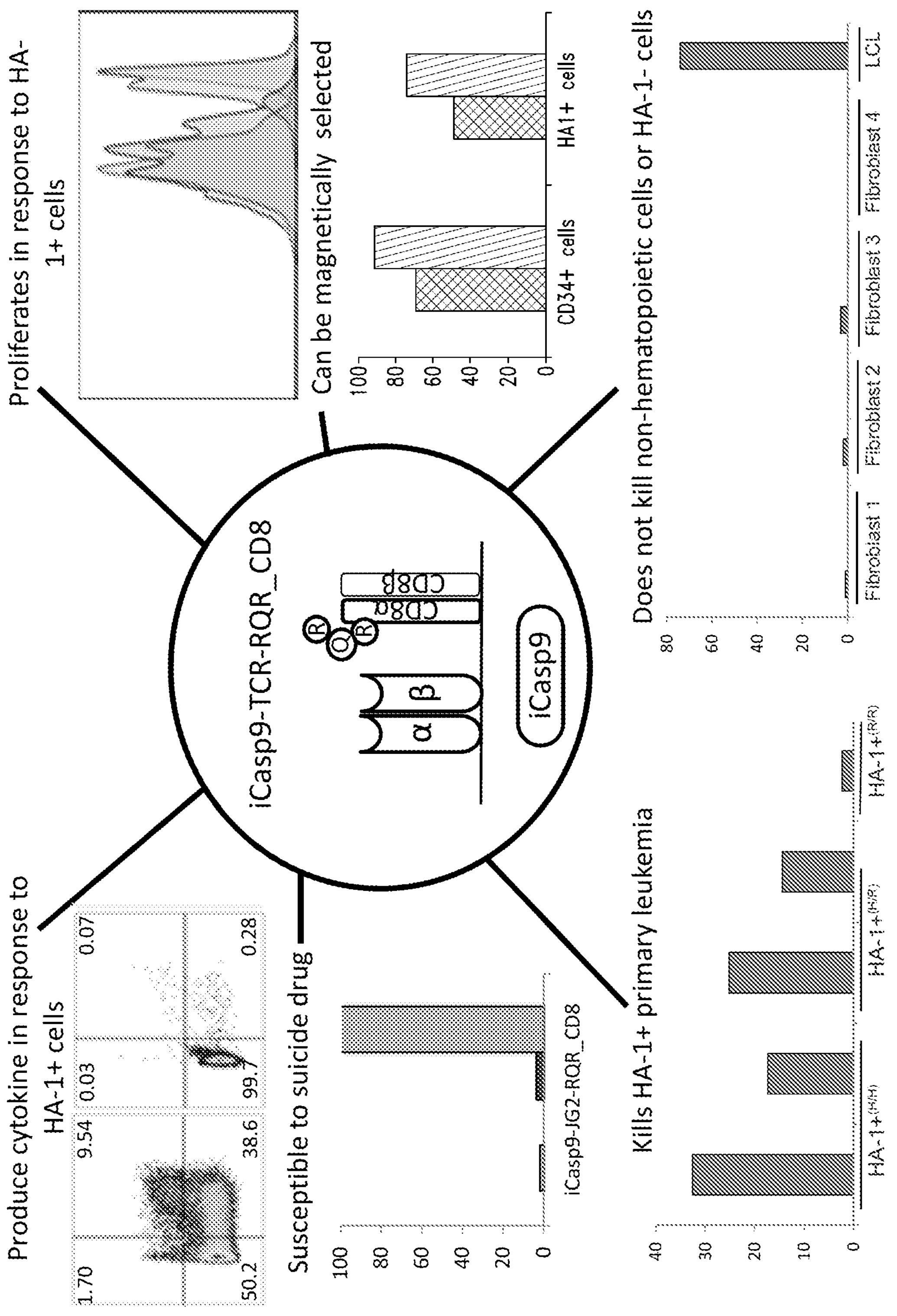

FIG. 29 provides a schematic showing various functionalities of a TCR-safety gene construct of the present disclosure.

Figure 30:
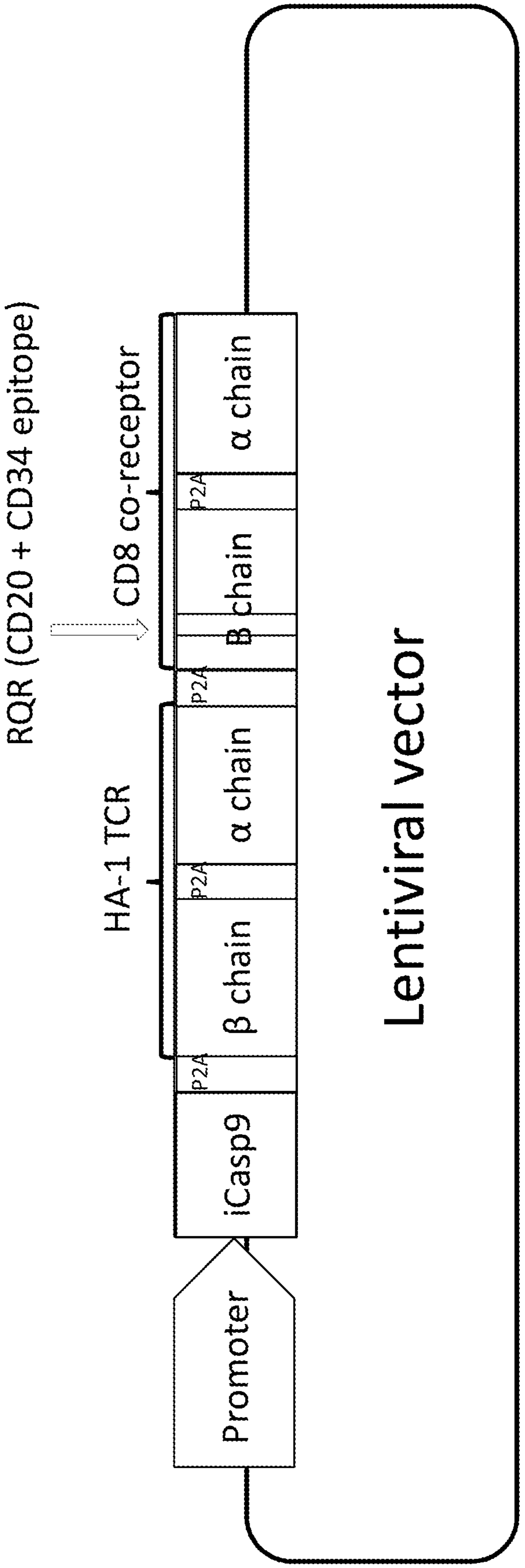

FIG. 30 provides a diagram of a lentiviral delivery vector encoding an exemplary iC9-HA-$1^{H}$-TCR-RQR-CD8 construct of the present disclosure.

Figure 31:
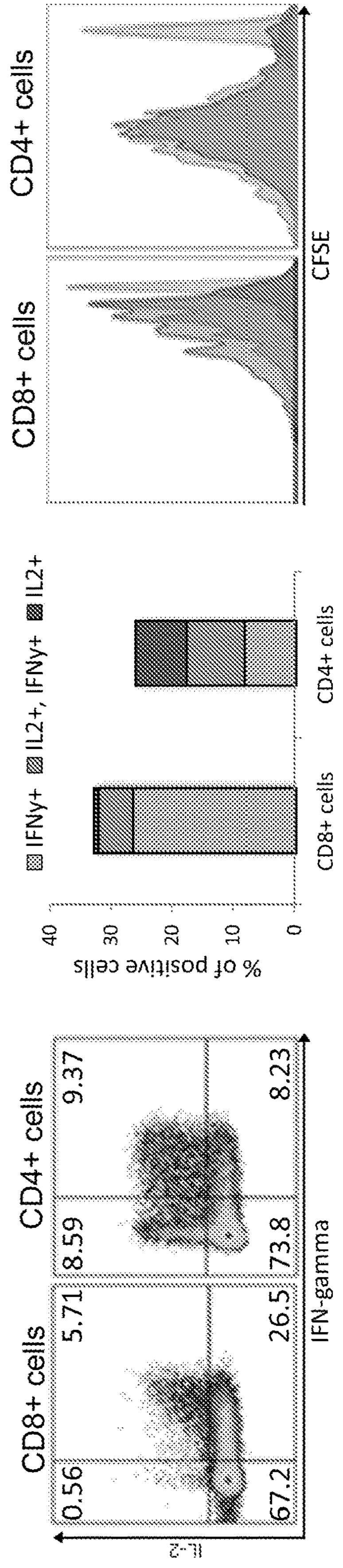

FIG. 31 shows the functional characterization of $CD8^{+}$ and $CD4^{+}$ cells transduced with a TCR2-CD8 transgene construct of the present disclosure. Left panel: flow cytometry data showing cytokine release (IL-2; IFN-γ) in response to HA-$1^{H}$ peptide antigen. Middle panel: quantification of the flow cytometry data. Right panels: proliferation of transduced cells in response to HA-$1^{H}$.

FIGS. 32A-32E show characterization of $CD4^{+}$ and $CD8^{+}$ T cells transduced with a (HA-$1^{H}$-specific TCR)-(RQR)-(CD8) and expanded to clinical scale. (A) Growth of transduced T cells. (B) HA-$1^{H}$ TCR multimer binding and CD34 expression on transduced T cells by flow cytometry with HA-1/HLA-A2 multimer staining. (C) Expression of co-stimulatory and homing molecules on T cells at the time of the apheresis, after CD45RA depletion and following transduction and expansion (N=5). (D, E) Expression of 'exhaustion' markers on HA-$1^{H}$ TCR $CD8^{+}$ and $CD4^{+}$ in the final cell product (N=3) (D) and a representative example (E).

FIGS. 33A-E show data from functional recognition assays in which the clinical-scale HA-$1^{H}$-TCR2-RQR-CD8-transduced T cells were incubated with target cells. (A) Lysis of target T2 cells pulsed with a range of VLH (solid lines, dark grey) and VLR (solid line, light grey) peptide concentrations by $CD8^{+}$ (solid lines) and $CD4^{+}$ T cells (dashed lines) in CRA at ET ratio 20:1. (B) Lysis of HA-$1^{H+}$ $A2^{+}$ LCL, HA-$1^{H-}$-A $2^{+}$ LCL and AML HA-$1^{H}$+$A2^{+}$ cell line (THP-1) by CD8+ (solid lines) in CRA (C) IL-2, IFN-γ, and TNFα production by T cells in response to stimulation by T2 cells pulsed with 10 ng/ml of HA-1 peptide. (D) Pie charts displaying the number of cytokine types secreted by T cells. (E) Concentration of cytokines and granzyme B in media 24 hours after stimulation of T cells by T2 cells pulsed with VLH or VLR peptides, as measured by multiplex immunoassay.

Figure 34A:
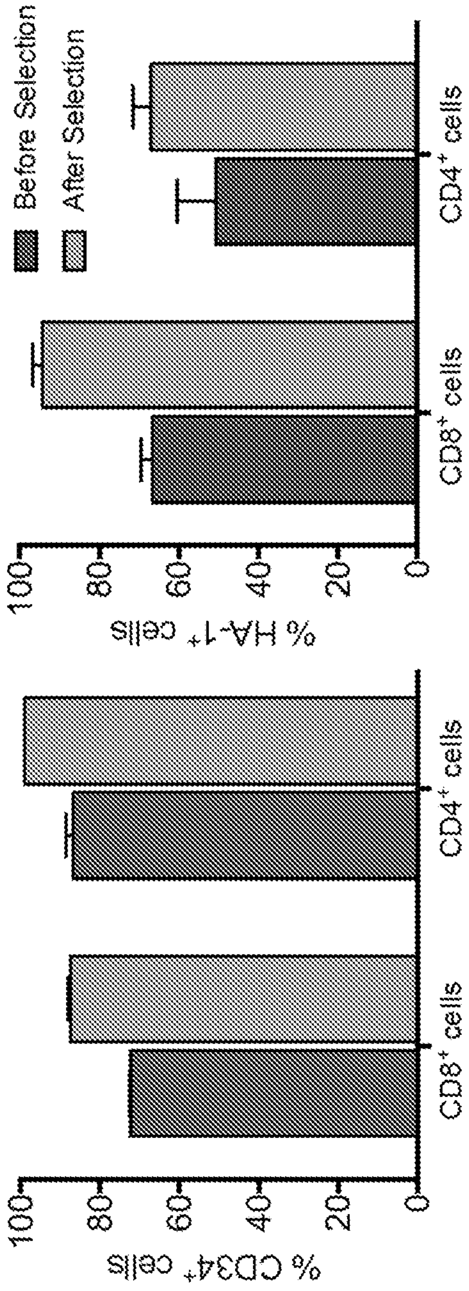
Figure 34B:
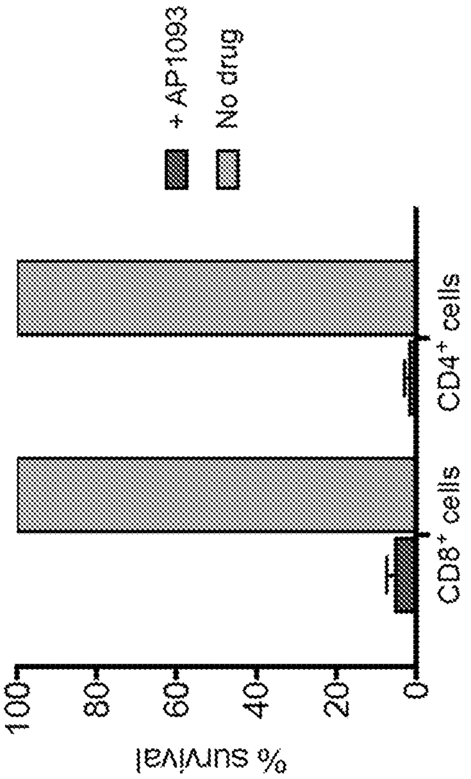

FIG. 34A shows (A) CD34 (left graph) and HA-$1^{H}$ TCR (right graph) expression on T cells in the final product before and after enrichment by CD34 immunomagnetic beads (N=3). FIG. 34B shows survival of T cells in the cell product after 24 hours of incubation with 5 ng/ml AP1903 or media control only.

Figure 35:
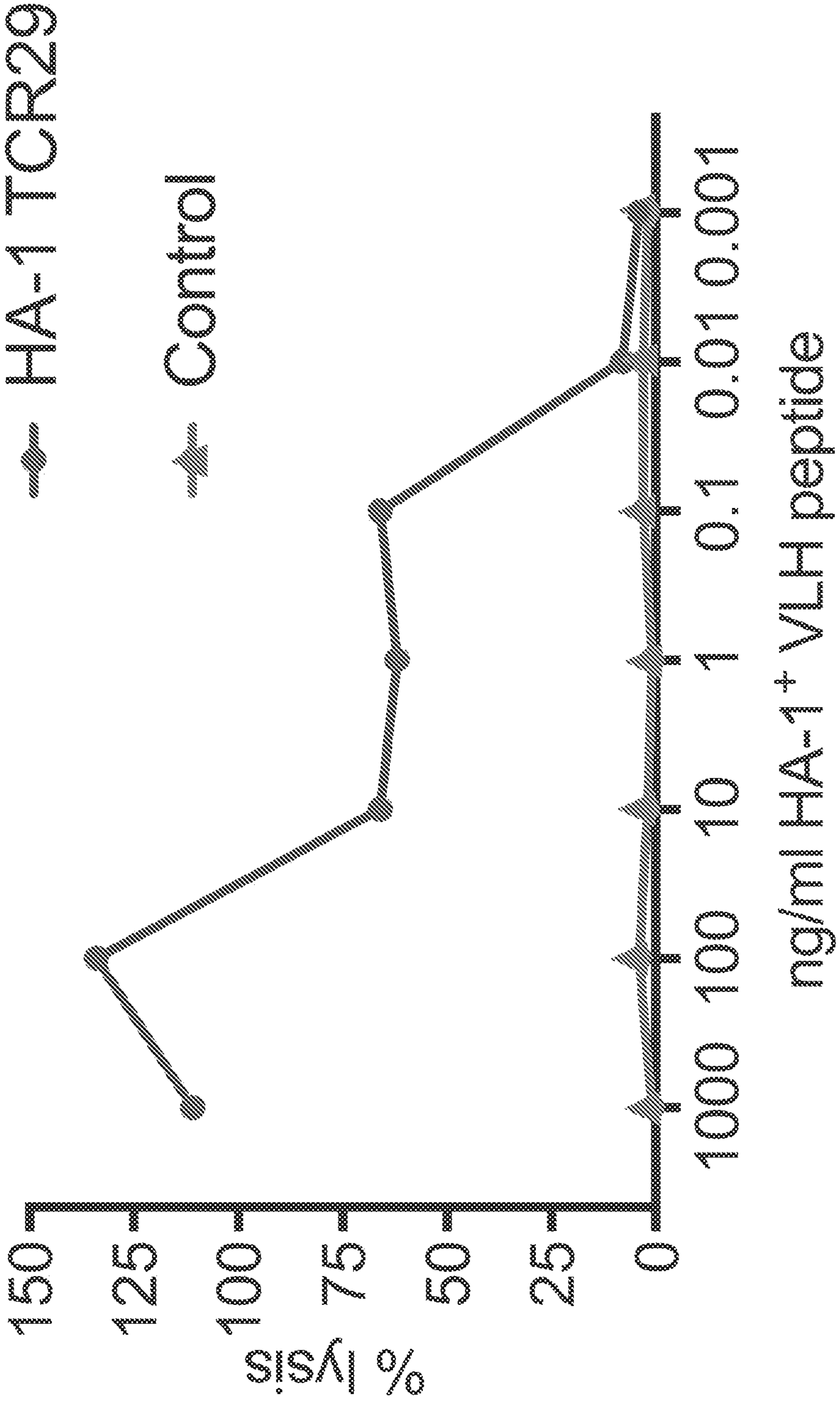

FIG. 35 shows cytolytic activity of T cells transduced with another HA-$1^{H}$ TCR of the present disclosure (circles) and of control cells (triangles) against T2 cells pulsed with the HA-$1^{H}$ antigen at the indicated concentrations.

DETAILED DESCRIPTION

In some aspects, the present disclosure provides compositions and methods for treating hyperproliferative diseases characterized by expression of minor histocompatibility antigen HA-$1^{H}$. By way of background, human leukocyte antigen (HLA) testing is typically used to match organ, cell, and tissue transplant recipients with compatible donors. HLA testing identifies the major HLA genes a person has inherited and the corresponding antigens, or proteins, which are present on the surface of their cells. These antigens help the body's immune system distinguish which cells are "self", and which are "foreign" or "non-self." Any cells that are recognized as "non-self" can trigger an immune response, such as T cell-mediated cytotoxicity or the production of antibodies. Of note, tests for major HLA genes do not identify the minor HLA genes, which give rise to further antigens. Accordingly, even "HLA-matched" donor cells may attack healthy recipient cells expressing a perceived "foreign" minor HLA protein or peptide. Minor H antigens that are expressed on epithelial tissues are targets of alloreactive T cells, leading to graft-versus-host disease. However, some minor H antigens are associated with genes that are expressed predominantly or exclusively in the hematopoietic system, including hematopoietic cells that can be affected by hematological malignancies. Thus, minor H antigens with restricted expression are potential targets for therapies that seek to augment the graft-versus-leukemia effect and thereby prevent relapse.

The minor histocompatibility antigen HA-$1^{H}$ is encoded by the polymeric HMHA1 gene (also called Rho GTPase-activating protein 45) and is highly expressed in leukemia cells and normal hematopoietic cells (see, e.g, Griffioen et al., *Front. Immunol.* 7:100, 2016; Spierings et al. *Biol. Blood Marrow Transpl.* 19:1244-1253, 2013, the HA-1 expression disclosure of which is incorporated herein by reference), but not in normal non-hematopoietic cells. HMHA1 variants (rs1801284 A/A or A/G) present in 52% of individuals give rise to an immunogenic peptide containing a histidine residue in place of an arginine (VLHDDLLEA; SEQ ID NO:66)

($R139^H$ polymorphism) and HLA presentation of this peptide occurs in individuals with the common HLA-A*0201 (A2) allele (den Haan et al., *Science* 279:1054-1057, 1998). T cell therapies targeting HA-$1^H$ are therefore applicable to approximately 25% of subjects transplanted for hematological malignancies and require a T cell donor who is either HLA-A2 negative or HA-$1^H$ negative ("HA-$1^R$"; rs1801284 G/G-VLRDDLLEA; SEQ ID NO: 65).

In some aspects, the present disclosure provides engineered immune cells expressing binding proteins, such as TCRs and CARs, specific for HA-$1^H$. Such engineered immune cells can be used as a standalone therapy to treat a hematologic malignancy or to prevent a relapse or recurrence thereof, or such cells can be used as part of a therapeutic regimen comprising additional therapies or agents (e.g., following, or in combination with, allogeneic HCT).

Prior to setting forth this disclosure in more detail, it may be helpful to an understanding thereof to provide definitions of certain terms to be used herein. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means ±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. As used herein, the terms "include", "have", and "comprise" are used synonymously, which terms and variants thereof are intended to be construed as non-limiting.

In addition, it should be understood that the individual compounds, or groups of compounds, derived from the various combinations of the structures and substituents described herein, are disclosed by the present application to the same extent as if each compound or group of compounds was set forth individually. Thus, selection of particular structures or particular substituents is within the scope of the present disclosure.

The term "consisting essentially of" is not equivalent to "comprising" and refers to the specified materials or steps of a claim, or to those that do not materially affect the basic characteristics of a claimed subject matter. For example, a protein domain, region, or module (e.g., a binding domain, hinge region, linker module) or a protein (which may have one or more domains, regions, or modules) "consists essentially of" a particular amino acid sequence when the amino acid sequence of a domain, region, module, or protein includes extensions, deletions, mutations, or a combination thereof (e.g., amino acids at the amino- or carboxy-terminus or between domains) that, in combination, contribute to at most 20% (e.g., at most 15%, 10%, 8%, 6%, 5%, 4%, 3%, 2% or 1%) of the length of a domain, region, module, or protein and do not substantially affect (i.e., do not reduce the activity by more than 50%, such as no more than 40%, 30%, 25%, 20%, 15%, 10%, 5%, or 1%) the activity of the domain(s), region(s), module(s), or protein (e.g., the target binding affinity of a binding protein).

As used herein, an "immune system cell" means any cell of the immune system that originates from a hematopoietic stem cell in the bone marrow, which gives rise to two major lineages, a myeloid progenitor cell (which give rise to myeloid cells such as monocytes, macrophages, dendritic cells, meagakaryocytes and granulocytes) and a lymphoid progenitor cell (which give rise to lymphoid cells such as T cells, B cells and natural killer (NK) cells). Exemplary immune system cells include a $CD4^+$ T cell, a $CD8^+$ T cell, a CD4−CD8− double negative T cell, a γδ T cell, a regulatory T cell, a natural killer cell, and a dendritic cell. Macrophages and dendritic cells can be referred to as "antigen presenting cells" or "APCs," which are specialized cells that can activate T cells when a major histocompatibility complex (MHC) receptor on the surface of the APC complexed with a peptide interacts with a TCR on the surface of a T cell.

A "T cell" or "T lymphocyte" is an immune system cell that matures in the thymus and produces T cell receptors (TCRs). T cells can be naïve ("$T_N$"; not exposed to antigen; increased expression of CD62L, CCR7, CD28, CD3, CD127, and CD45RA, and decreased or no expression of CD45RO as compared to $T_{CM}$ (described herein)), memory T cells ($T_M$) (antigen experienced and long-lived), and effector cells (antigen-experienced, cytotoxic). $T_M$ can be further divided into subsets of central memory T cells ($T_{CM}$ expresses CD62L, CCR7, CD28, CD45RO) and effector memory T cells ($T_{EM}$ express CD45RO, decreased expression of CD62L, CCR7, and CD28). Effector T cells ($T_E$) refers to antigen-experienced $CD8^+$ cytotoxic T lymphocytes that express CD45RA, have decreased expression of CD62L, CCR7, and CD28 as compared to $T_{CM}$, and are positive for granzyme and perforin. Helper T cells (TH) are $CD4^+$ cells that influence the activity of other immune cells by releasing cytokines. $CD4^+$ T cells can activate and suppress an adaptive immune response, and which of those two functions is induced will depend on presence of other cells and signals. T cells can be collected using known techniques, and the various subpopulations or combinations thereof can be enriched or depleted by known techniques, such as by affinity binding to antibodies, flow cytometry, or immunomagnetic selection. Other exemplary T cells include regulatory T cells, such as $CD4^+$ $CD25^+$ ($Foxp3^+$) regulatory T cells and Treg17 cells, as well as Tr1, Th3, $CD8^+$ $CD28^-$, and Qa-1 restricted T cells.

"T cell receptor" (TCR) refers to an immunoglobulin superfamily member (having a variable binding domain, a constant domain, a transmembrane region, and a short cytoplasmic tail; see, e.g., Janeway et al., Immunobiology: The Immune System in Health and Disease, 3rd Ed., Current Biology Publications, p. 433, 1997) capable of specifically binding to an antigen peptide bound to a MHC receptor. A TCR can be found on the surface of a cell or in soluble form and generally is comprised of a heterodimer having α and β chains (also known as TCR α and TCRβ, respectively), or γ and δ chains (also known as TCRγ and TCRδ, respectively).

Like other immunoglobulins (e.g., antibodies), the extracellular portion of TCR chains (e.g., α-chain, β-chain) contain two immunoglobulin domains, a variable domain (e.g., α-chain variable domain or $V_\alpha$ chain variable domain or $V_\beta$; typically amino acids 1 to 116 based on Kabat numbering (Kabat et al., "Sequences of Proteins of Immunological Interest, US Dept. Health and Human Services, Public Health Service National Institutes of Health, 1991, $5^{th}$ ed.) at the N-terminus, and one constant domain (e.g., α-chain constant domain or $C_\alpha$, typically 5 amino acids 117 to 259 based on Kabat, β-chain constant domain or $C_β$ typically amino acids 117 to 295 based on Kabat) adjacent the cell membrane. Also, like immunoglobulins, the variable domains contain complementary determining regions (CDRs) separated by frame work regions (FRs) (see, e.g., Jores et al., *Proc. Nat'l Acad. Sci. USA* 87:9138, 1990; Chothia et al., *EMBO J.* 7:3745, 1988; see also Lefranc et al., *Dev. Comp. Immunol.* 27:55, 2003).

"Antigen" or "Ag" as used herein refers to an immunogenic molecule that provokes an immune response. This immune response may involve antibody production, activation of specific immunologically-competent cells (e.g., T cells), or both. An antigen (immunogenic molecule) may be, for example, a peptide, glycopeptide, polypeptide, glycopolypeptide, polynucleotide, polysaccharide, lipid or the like. It is readily apparent that an antigen can be synthesized, produced recombinantly, or derived from a biological sample. Exemplary biological samples that can contain one or more antigens include tissue samples, tumor samples, cells, biological fluids, or combinations thereof. Antigens can be produced by cells that have been modified or genetically engineered to express an antigen, or that endogenously (e.g., without modification or genetic engineering by human intervention) express a mutation or polymorphism that is immunogenic.

"Major histocompatibility complex" (MHC) refers to glycoproteins that deliver peptide antigens to a cell surface of all nucleated cells. MHC class I molecules are heterodimers having a membrane spanning a chain (with three a domains) and a non-covalently associated 132 microglobulin. MHC class II molecules are composed of two transmembrane glycoproteins, α and β, both of which span the membrane. Each chain has two domains. MHC class I molecules deliver peptides originating in the cytosol to the cell surface, where a peptide:MHC complex is recognized by $CD8^+$ T cells. MHC class II molecules deliver peptides originating in the vesicular system to the cell surface, where they are recognized by $CD4^+$ T cells. Human MHC is referred to as human leukocyte antigen (HLA).

The term "epitope" or "antigenic epitope" includes any molecule, structure, amino acid sequence or protein determinant that is recognized and specifically bound by a cognate binding molecule, such as an immunoglobulin, T cell receptor (TCR), chimeric antigen receptor, or other binding molecule, domain or protein. Epitopic determinants generally contain chemically active surface groupings of molecules, such as amino acids or sugar side chains, and can have specific three dimensional structural characteristics, as well as specific charge characteristics.

As used herein "specifically binds" or "specific for" refers to an association or union of a binding protein (e.g., TCR receptor) or a binding domain (or fusion protein thereof) to a target molecule with an affinity or $K_a$ (i.e., an equilibrium association constant of a particular binding interaction with units of 1/M) equal to or greater than $10^5$ $M^{-1}$ (which equals the ratio of the on-rate [$k_{on}$] to the off-rate [$k_{off}$] for this association reaction), while not significantly associating or uniting with any other molecules or components in a sample. Binding proteins or binding domains (or fusion proteins thereof) may be classified as "high affinity" binding proteins or binding domains (or fusion proteins thereof) or as "low affinity" binding proteins or binding domains (or fusion proteins thereof). "High affinity" binding proteins or binding domains refer to those binding proteins or binding domains having a $K_a$ of at least $10^7$ $M^{-1}$, at least $10^8$ $M^{-1}$, at least $10^9$ $M^{-1}$, at least $10^{10}$ $M^{-1}$, at least $10^{11}$ $M^{-1}$, at least $10^{12}$ $M^{-1}$, or at least $10^{13}$ $M^{-1}$. "Low affinity" binding proteins or binding domains refer to those binding proteins or binding domains having a $K_a$ of up to $10^7$ $M^{-1}$, up to $10^6$ $M^{-1}$, up to $10^5$ $M^{-1}$. Alternatively, affinity can be defined as an equilibrium dissociation constant ($K_d$) of a particular binding interaction with units of M (e.g., $10^{-5}$ M to $10^{-13}$ M).

In certain embodiments, a receptor or binding domain may have "enhanced affinity," which refers to selected or engineered receptors or binding domains with stronger binding to a target antigen than a wild type (or parent) binding domain. For example, enhanced affinity may be due to a $K_a$ (equilibrium association constant) for the target antigen that is higher than the wild type binding domain, due to a $K_d$ (dissociation constant) for the target antigen that is less than that of the wild type binding domain, due to an off-rate ($k_{off}$) for the target antigen that is less than that of the wild type binding domain, or a combination thereof. In certain embodiments, enhanced affinity TCRs can be codon optimized to enhance expression in a particular host cell, such as a cell of the immune system, a hematopoietic stem cell, a T cell, a primary T cell, a T cell line, a NK cell, or a natural killer T cell (Scholten et al., *Clin. Immunol.* 119:135, 2006). The T cell can be a $CD4^+$ or a $CD8^+$ T cell.

A variety of assays are known for identifying binding domains of the present disclosure that specifically bind a particular target, as well as determining binding domain or fusion protein affinities, such as multimer/tetramer staining, Western blot, ELISA, analytical ultracentrifugation, spectroscopy and surface plasmon resonance (Biacore®) analysis (see, e.g., Dolton et al., *Immunology* 146:11-22, 2015, Scatchard et al., *Ann. NY Acad. Sci.* 51:660, 1949; Wilson, *Science* 20295:2103, 2002; Wolff et al., *Cancer Res.* 53:2560, 1993; and U.S. Pat. Nos. 5,283,173, 5,468,614, or the equivalent; all incorporated herein by reference).

The source of a TCR as used in the present disclosure can be from various animal species, such as a human, mouse, rat, rabbit or other mammal.

As used herein, the term "CD8 co-receptor" or "CD8" means the cell surface glycoprotein CD8, either as an alpha-alpha homodimer or an alpha-beta heterodimer. The CD8 co-receptor assists in the function of cytotoxic T cells ($CD8^+$) and functions through signaling via its cytoplasmic tyrosine phosphorylation pathway (Gao and Jakobsen, *Immunol. Today* 21:630-636, 2000*; Cole and Gao, Cell. Mol. Immunol.* 1:81-88, 2004). There are five (5) different CD8 beta chains (see UniProtKB identifier P10966) and a single CD8 alpha chain (see UniProtKB identifier P01732)

"CD4" is an immunoglobulin co-receptor glycoprotein that assists the TCR in communicating with antigen-presenting cells (see, Campbell & Reece, Biology 909 (Benjamin Cummings, Sixth Ed., 2002)). CD4 is found on the surface of immune cells such as T helper cells, monocytes, macrophages, and dendritic cells, and includes four immunoglobulin domains (D1 to D4) that are expressed at the cell surface. During antigen presentation, CD4 is recruited, along with the TCR complex, to bind to different regions of the MHCII molecule (CD4 binds MHCII β2, while the TCR complex binds MHCII α1/β1). Without wishing to be bound by theory, it is believed that close proximity to the TCR complex allows CD4-associated kinase molecules to phosphorylate the immunoreceptor tyrosine activation motifs (ITAMs) present on the cytoplasmic domains of CD3. This activity is thought to amplify the signal generated by the activated TCR in order to produce various types of T helper cells.

In certain embodiments, a TCR is found on the surface of T cells (or T lymphocytes) and associates with a CD3 complex. "CD3" is a multi-protein complex of six chains (see, Abbas and Lichtman, 2003; Janeway et al., p. 172 and 178, 1999) that is associated with antigen signaling in T cells. In mammals, the complex comprises a CD3γ chain, a CD3δ chain, two CD3ε chains, and a homodimer of CD3ζ chains. The CD3γ, CD31β, and CD3ε chains are highly related cell surface proteins of the immunoglobulin superfamily containing a single immunoglobulin domain. The transmembrane regions of the CD3γ, CD313, and CD3ε chains are negatively charged, which is a characteristic that allows these chains to associate with the positively charged T cell receptor chains. The intracellular tails of the CD3γ, CD31β, and CD3ε chains each contain a single conserved motif known as an immunoreceptor tyrosine based activation motif or ITAM, whereas each CD3ζ chain has three. Without wishing to be bound by theory, it is believed that the ITAMs are important for the signaling capacity of a TCR complex. CD3 as used in the present disclosure may be from various animal species, including human, mouse, rat, or other mammals.

As used herein, "TCR complex" refers to a complex formed by the association of CD3 with TCR. For example, a TCR complex can be composed of a CD3γ chain, a CD3β chain, two CD3ε chains, a homodimer of CD3ζ chains, a TCRα chain, and a TCRβ chain. Alternatively, a TCR complex can be composed of a CD3γ chain, a CD3β chain, two CD3ε chains, a homodimer of CD3ζ chains, a TCRγ chain, and a TCRβ chain.

A "component of a TCR complex", as used herein, refers to a TCR chain (i.e., TCRα, TCRβ, TCRγ or TCRδ), a CD3 chain (i.e., CD3γ, CD3δ, CD3ε or CD3ζ), or a complex formed by two or more TCR chains or CD3 chains (e.g., a complex of TCRα and TCRβ, a complex of TCRγ and TCRδ, a complex of CD3ε and CD3δ, a complex of CD3γ and CD3ε, or a sub-TCR complex of TCRα, TCRβ, CD3γ, CD3δ, and two CD3ε chains).

As used herein, the term "HA-$1^H$ antigen" or "HA-$1^H$ peptide antigen" or "HA-$1^H$-containing peptide antigen" (or "minor HA-$1^H$ antigen" or "minor HA-$1^H$ peptide antigen" or "minor HA-$1^H$-containing peptide antigen" or "minor Histocompatibility HA-$1^H$ antigen peptide") refers to a naturally or synthetically produced peptide portion of a HMHA1 protein ranging in length from about 7 amino acids, about 8 amino acids, about 9 amino acids, about 10 amino acids, up to about 20 amino acids, and comprising the R139H substitution polymorphism), which can form a complex with a MHC (e.g., HLA) molecule, and a binding protein of this disclosure specific for a HA-$1^H$ peptide:MHC (e.g., HLA) complex can specifically bind to such as complex. An exemplary HA-$1^H$ HA-1 peptide antigen comprises a peptide having the amino acid VLHDDLLEA (SEQ ID NO: 66), wherein the bolded histidine in the sequence represents the R$139^H$ polymorphism.

The term "HA-$1^H$-specific binding protein," as used herein, refers to a protein or polypeptide, such as a TCR or CAR, that specifically binds to an HA-$1^H$ peptide antigen (or to an HA-$1^H$ peptide antigen:HLA complex, e.g., on a cell surface), and does not bind an HMHA peptide that does not contain the HA-$1^H$ polymorphism (e.g., a peptide comprising the amino acid sequence shown in SEQ ID NO:65) and does not bind to an HLA complex containing such an HMHA peptide.

In certain embodiments, a HA-$1^H$-specific binding protein specifically binds to an HA-1-containing peptide (or an HA-$1^H$ peptide:HLA complex) with a $K_d$ of less than about $10^{-8}$ M, less than about $10^{-9}$ M, less than about $10^{-10}$ M, less than about $10^{-11}$ M, less than about $10^{-12}$ M, or less than about $10^{-13}$ M, or with an affinity that is about the same as, at least about the same as, or is greater than at or about the affinity exhibited by an exemplary HA-$1^H$-specific binding protein provided herein, such as any of the HA-$1^H$-specific TCRs provided herein, for example, as measured by the same assay. In certain embodiments, a HA-1-specific binding protein comprises a HA-1-specific immunoglobulin superfamily binding protein or binding portion thereof.

Principles of antigen processing by antigen presenting cells (APC) (such as dendritic cells, macrophages, lymphocytes or other cell types), and of antigen presentation by APC to T cells, including major histocompatibility complex (MHC)-restricted presentation between immunocompatible (e.g., sharing at least one allelic form of an MHC gene that is relevant for antigen presentation) APC and T cells, are well established (see, e.g., Murphy, Janeway's Immunobiology ($8^{th}$ Ed.) 2011 Garland Science, NY; chapters 6, 9 and 16). For example, processed antigen peptides originating in the cytosol (e.g., tumor antigen, intracellular pathogen) are generally from about 7 amino acids to about 11 amino acids in length and will associate with class I MHC (HLA) molecules, whereas peptides processed in the vesicular system (e.g., bacterial, viral) will vary in length from about 10 amino acids to about 25 amino acids and associate with class II MHC (HLA) molecules.

An"altered domain" or "altered protein" refers to a motif, region, domain, peptide, polypeptide, or protein with a non-identical sequence identity to a wild type motif, region, domain, peptide, polypeptide, or protein (e.g., a wild type TCRα chain, TCRβ chain, TCRα constant domain, TCRβ constant domain) of at least 85% (e.g., 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%).

Altered domains or altered proteins or derivatives can include those based on all possible codon choices for the same amino acid and codon choices based on conservative amino acid substitutions. For example, the following six group's each contain amino acids that are conservative substitutions for one another: 1) alanine (ala; A), serine (ser; S), threonine (thr; T); 2) aspartic acid (asp; D), glutamic acid (glu; E); 3) asparagine (asn; N), glutamine (gln; Q); 4) arginine (arg; R), lysine (lys; K); 5) Isoleucine (ile; I), leucine (L), methionine (met; M), valine (val; V); and 6) phenylalanine (phe; F), tyrosine (tyr; Y), tryptophan (trp; W). (See also WO97/09433 at page 10, Lehninger, Biochemistry, $2^{nd}$ Edition, Worth Publishers, Inc., NY, NY, pp. 71-77, 1975; Lewin Genes IV, Oxford University Press, NY and Cell Press, Cambridge, MA, p. 8, 1990; Creighton, Proteins, W.H. Freeman and Company 1984). In addition, individual substitutions, deletions or additions that alter, add or delete, a single amino acid or a small percentage of amino acids in an encoded sequence are also "conservative substitutions."

As used herein, "nucleic acid" or "nucleic acid molecule" refers to any of deoxyribonucleic acid (DNA), ribonucleic acid (RNA), oligonucleotides, polynucleotides, fragments thereof generated, for example, by the polymerase chain reaction (PCR) or by in vitro translation, and also to fragments generated by any of ligation, scission, endonuclease action, or exonuclease action. In certain embodiments, the nucleic acids of the present disclosure are produced by PCR. Nucleic acids can be composed of monomers that are naturally occurring nucleotides (such as deoxyribonucleotides and ribonucleotides), analogs of naturally occurring nucleotides (e.g., α-enantiomeric forms of naturally occurring nucleotides), or a combination of both. Modified nucleotides can have modifications in or replacement of sugar moieties, or pyrimidine or purine base moieties. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. Nucleic acid molecules can be either single stranded or double stranded.

The term "isolated" means that the material is removed from its original environment (e.g., the natural environment if it is naturally occurring). For example, a naturally occurring nucleic acid or polypeptide present in a living animal is not isolated, but the same nucleic acid or polypeptide, separated from some or all of the co-existing materials in the natural system, is isolated. Such a nucleic acid could be part of a vector and/or such nucleic acid or polypeptide could be part of a composition (e.g., a cell lysate), and still be isolated in that such vector or composition is not part of the natural environment for the nucleic acid or polypeptide. The term "gene" means the segment of DNA involved in producing a polypeptide chain; it includes regions preceding and following the coding region ("leader and trailer") as well as intervening sequences (introns) between individual coding segments (exons).

As used herein, the terms "recombinant" and "engineered" refer to a cell, microorganism, nucleic acid molecule, polypeptide, protein, plasmid, or vector that has been modified by introduction of an exogenous nucleic acid molecule, or refers to a cell or microorganism that has been genetically engineered by human intervention—that is, modified by introduction of of a heterologous nucleic acid molecule, or refers to a cell or microorganism that has been altered such that expression of an endogenous nucleic acid molecule or gene is controlled, deregulated or constitutive, where such alterations or modifications can be introduced by genetic engineering. Human-generated genetic alterations can include, for example, modifications introducing nucleic acid molecules (which may include an expression control element, such as a promoter) encoding one or more proteins or enzymes, or other nucleic acid molecule additions, deletions, substitutions, or other functional disruption of or addition to a cell's genetic material. Exemplary modifications include those in coding regions or functional fragments thereof of heterologous or homologous polypeptides from a reference or parent molecule.

As used herein, "mutation" refers to a change in the sequence of a nucleic acid molecule or polypeptide molecule as compared to a reference or wild-type nucleic acid molecule or polypeptide molecule, respectively. A mutation can result in several different types of change in sequence, including substitution, insertion or deletion of nucleotide(s) or amino acid(s). In certain embodiments, a mutation is a substitution of one or three codons or amino acids, a deletion of one to about 5 codons or amino acids, or a combination thereof.

A "conservative substitution" is recognized in the art as a substitution of one amino acid for another amino acid that has similar properties. Exemplary conservative substitutions are well known in the art (see, e.g., WO 97/09433 at page 10; Lehninger, Biochemistry, 2$^{nd}$ Edition; Worth Publishers, Inc. NY, NY, pp. 71-77, 1975; Lewin, Genes IV, Oxford University Press, NY and Cell Press, Cambridge, MA, p. 8, 1990).

The term "construct" refers to any polynucleotide that contains a recombinant nucleic acid molecule. A "transgene" or "transgene construct" refers to a construct that contains two or more genes operably linked in an arrangement that is not found in nature. The term "operably-linked" (or "operably linked" herein) refers to the association of two or more nucleic acid molecules on a single nucleic acid fragment so that the function of one is affected by the other. For example, a promoter is operably-linked with a coding sequence when it can affect the expression of that coding sequence (i.e., the coding sequence is under the transcriptional control of the promoter). "Unlinked" means that the associated genetic elements are not closely associated with one another and the function of one does not affect the other. In some embodiments, the genes present in a transgene are operably linked to an expression control sequence (e.g., a promoter).

A construct (e.g., a transgene) can be present in a vector (e.g., a bacterial vector, a viral vector) or can be integrated into a genome. A "vector" is a nucleic acid molecule that is capable of transporting another nucleic acid molecule. Vectors can be, for example, plasmids, cosmids, viruses, a RNA vector or a linear or circular DNA or RNA molecule that can include chromosomal, non-chromosomal, semi-synthetic or synthetic nucleic acid molecules. Exemplary vectors are those capable of autonomous replication (episomal vector) or expression of nucleic acid molecules to which they are linked (expression vectors). Vectors useful in the compositions and methods of this disclosure are described further herein.

The term "expression", as used herein, refers to the process by which a polypeptide is produced based on the encoding sequence of a nucleic acid molecule, such as a gene. The process can include transcription, post-transcriptional control, post-transcriptional modification, translation, post-translational control, post translational modification, or any combination thereof.

The term "introduced" in the context of inserting a nucleic acid molecule into a cell, means "transfection", or "transformation", or "transduction" and includes reference to the incorporation of a nucleic acid molecule into a eukaryotic or prokaryotic cell wherein the nucleic acid molecule can be incorporated into the genome of a cell (e.g., a chromosome, a plasmid, a plastid, or a mitochondrial DNA), converted into an autonomous replicon, or transiently expressed (e.g., transfected mRNA).

As used herein, "heterologous" or "exogenous" nucleic acid molecule, construct or sequence refers to a nucleic acid molecule or portion of a nucleic acid molecule that is not native to a host cell, but can be homologous to a nucleic acid molecule or portion of a nucleic acid molecule from the host cell. The source of the heterologous or exogenous nucleic acid molecule, construct or sequence can be from a different genus or species. In certain embodiments, a heterologous or exogenous nucleic acid molecule is added (i.e., not endogenous or native) to a host cell or host genome by, for example, conjugation, transformation, transfection, transduction, electroporation, or the like, wherein the added molecule can integrate into the host genome or exist as extra-chromosomal genetic material (e.g., as a plasmid or other form of self-replicating vector), and can be present in multiple copies. In addition, "heterologous" refers to a non-native enzyme, protein or other activity encoded by an exogenous nucleic acid molecule introduced into the host cell, even if the host cell encodes a homologous protein or activity.

As described herein, more than one heterologous or exogenous nucleic acid molecule can be introduced into a host cell as separate nucleic acid molecules, as a plurality of individually controlled genes, as a polycistronic nucleic acid molecule, as a single nucleic acid molecule encoding a fusion protein, or any combination thereof. For example, as disclosed herein, a host cell can be modified to express two or more heterologous or exogenous nucleic acid molecules encoding the desired TCR specific for a minor histocompatibility (H) antigen HA-$1^H$ peptide (e.g., TCR α and TCR β). When two or more exogenous nucleic acid molecules are introduced into a host cell, it is understood that the two or more exogenous nucleic acid molecules can be introduced as a single nucleic acid molecule (e.g., on a single vector), on separate vectors, integrated into the host chromosome at a single site or multiple sites, or any combination thereof. The number of referenced heterologous nucleic acid molecules or protein activities refers to the number of encoding nucleic acid molecules or the number of protein activities, not the number of separate nucleic acid molecules introduced into a host cell.

As used herein, the term "endogenous" or "native" refers to a gene, protein, or activity that is normally present in a host cell. Moreover, a gene, protein or activity that is mutated, overexpressed, shuffled, duplicated or otherwise altered as compared to a parent gene, protein or activity is still considered to be endogenous or native to that particular host cell. For example, an endogenous control sequence from a first gene (e.g., a promoter, translational attenuation sequences) can be used to alter or regulate expression of a second native gene or nucleic acid molecule, wherein the expression or regulation of the second native gene or nucleic acid molecule differs from normal expression or regulation in a parent cell.

The term "homologous" or "homolog" refers to a molecule or activity found in or derived from a host cell, species or strain. For example, a heterologous or exogenous nucleic acid molecule can be homologous to a native host cell gene, and can optionally have an altered expression level, a different sequence, an altered activity, or any combination thereof.

"Sequence identity," as used herein, refers to the percentage of amino acid residues in one sequence that are identical with the amino acid residues in another reference polypeptide sequence after aligning the sequences and introducing gaps, if necessary, to achieve the maximum percent sequence identity, and not considering any conservative substitutions as part of the sequence identity. The percentage sequence identity values can be generated using the NCBI BLAST 2.0 software as defined by Altschul et al. (1997), *Nucl. Acids Res.* 25:3389-3402, with the parameters set to default values.

HA-$1^H$-Specific Binding Proteins, Accessory Proteins, and Engineered Host Cells In certain aspects, the present disclosure provides engineered immune cells comprising a heterologous polynucleotide that encodes a binding protein that specifically binds to an HA-$1^H$ antigen. In certain embodiments, the encoded binding protein is an HA-$1^H$ antigen-specific T cell receptor (TCR) or an HA-$1^H$ antigen-specific chimeric antigen receptor (CAR). In further embodiments, a binding protein is expressed as part of a transgene construct that encodes additional accessory proteins, such as a safety switch protein, a tag, a selection marker, a CD8 co-receptor β-chain. α-chain or both, or any combination thereof.

In any of the embodiments described herein, an encoded polypeptide of this disclosure (e.g., iCasp9, TCR β-chain. TCR α-chain. CD8 β-chain. CD8 α-chain) can comprise a "signal peptide" (also known as a leader sequence, leader peptide, or transit peptide). Signal peptides target newly synthesized polypeptides to their appropriate location inside or outside the cell. A signal peptide may be removed from the polypeptide during or once localization or secretion is completed. Polypeptides that have a signal peptide are referred to herein as a "pre-protein" and polypeptides having their signal peptide removed are referred to herein as "mature" proteins or polypeptides. Representative signal peptides include the amino acids from position 1 to position 21 of any one of SEQ ID NOS: 1-3, 5-9, and 70-75, or the amino acids from position 1 to position 19 of any one of SEQ ID NOS:4, 10, and 12.

Binding proteins of this disclosure, such as TCRs and CARs, will contain a binding domain specific for a target (in this case, HA-$1^H$). A "binding domain" (also referred to as a "binding region" or "binding moiety"), as used herein, refers to a molecule or portion thereof (e.g., peptide, oligopeptide, polypeptide, protein) that possesses the ability to specifically and non-covalently associate, unite, or combine with a target (e.g., HA-$1^H$ peptide or HA-$1^H$ peptide:MHC complex). A binding domain includes any naturally occurring, synthetic, semi-synthetic, or recombinantly produced binding partner for a biological molecule, a molecular complex (i.e. complex comprising two or more biological molecules), or other target of interest. Exemplary binding domains include single chain immunoglobulin variable regions (e.g., single chain TCR (scTCR), single chain Fv (scFv)), receptor ectodomains, ligands (e.g., cytokines, chemokines), or synthetic polypeptides selected for their specific ability to bind to a biological molecule, a molecular complex or other target of interest.

In certain embodiments, an HA-$1^H$-specific binding domain alone (i.e., without any other portion of a HA-1-specific binding protein) can be soluble and can bind to HA-$1^H$ with a $K_d$ of less than about $10^{-8}$ M, less than about $10^{-9}$ M, less than about $10^{-10}$ M, less than about $10^{-11}$ M, less than about $10^{-12}$ M, or less than about $10^{-13}$ M. In particular embodiments, an HA-$1^H$-specific binding domain includes an HA-$1^H$-specific scTCR (e.g., single chain αβTCR proteins such as Vα-L-Vβ, Vβ-L-Vα, Vα-Cα-L-Vα, or Vα-L-Vβ-Cβ, wherein Vα and Vβ are TCRα and β variable domains respectively, Cα and Cβ are TCRα and β constant domains, respectively, and L is a linker).

The term "variable region" or "variable domain" refers to the domain of an immunoglobulin superfamily binding protein (e.g., a TCR α-chain or β-chain (or γ chain and β chain for γδ TCRs)) that is involved in binding of the immunoglobulin superfamily binding protein (e.g., TCR) to antigen. The variable domains of the α-chain and β-chain ($V_\alpha$, and $V_\beta$, respectively) of a native TCR generally have similar structures, with each domain comprising four conserved framework regions (FRs) and three CDRs. The $V_\alpha$, domain is encoded by two separate DNA segments, the variable gene segment and the joining gene segment (V-J); the $V_\beta$ domain is encoded by three separate DNA segments, the variable gene segment, the diversity gene segment, and the joining gene segment (V-D-J). A single $V_\alpha$, or $V_\beta$ domain may be sufficient to confer antigen-binding specificity. Furthermore, TCRs that bind a particular antigen may be isolated using a $V_\alpha$, or $V_\beta$ domain from a TCR that binds the antigen to screen a library of complementary $V_\alpha$, or $V_\beta$ domains, respectively.

The terms "complementarity determining region," and "CDR," are synonymous with "hypervariable region" or "HVR," and are known in the art to refer to non-contiguous sequences of amino acids within TCR variable regions, which confer antigen specificity and/or binding affinity. In general, there are three CDRs in each α-chain variable region (αCDR1, αCDR2, αCDR3) and three CDRs in each β-chain variable region (βCDR1, βCDR2, βCDR3). CDR3 is thought to be the main CDR responsible for recognizing processed antigen. CDR1 and CDR2 mainly interact with the MHC.

In certain embodiments, an encoded binding protein comprises: (a) a T cell receptor (TCR) α chain variable (Vα) domain having an amino acid sequence encoded by a TRAV17 gene, a TRAV21 gene, or a TRAV10 gene, and a TCR β-chain variable (Vβ) domain comprising a CDR3 amino acid sequence as shown in any one of SEQ ID NOS: 13-17 and 86; (b) a TCR Vα domain comprising a CDR3 amino acid sequence as shown in any one of SEQ ID NOS:87-92, and a TCR Vβ domain having an amino acid sequence encoded by a TRBV7-9 gene; or (c) a TCR Vα domain comprising a CDR3 amino acid sequence of any one of SEQ ID NOS:87-92, and a TCR Vβ domain comprising a CDR3 amino acid sequence of any one of SEQ ID NOS:13-17 and 86, wherein the encoded binding protein is capable of specifically binding to a peptide containing an HA-$1^H$ minor antigen and does not bind to a peptide that does not contain an HA-$1^H$ minor antigen.

In further embodiments, an encoded binding protein comprises a TCR $V_\alpha$, domain and a TCR Vp domain, wherein: (a) the encoded $V_\beta$ CDR3 comprises the amino acid sequence of SEQ ID NO: 13, and the encoded $V_\alpha$, CDR3 comprises the amino acid sequence of SEQ ID NO:87; (b) the encoded $V_\beta$ CDR3 comprises the amino acid sequence shown in SEQ ID NO: 14, and the encoded $V_\alpha$, CDR3 comprises the amino acid sequence of SEQ ID NO:88; (c) the encoded $V_\beta$ CDR3 comprises the amino acid sequence shown in SEQ ID NO: 15, and the encoded $V_\alpha$, CDR3 comprises the amino acid sequence of SEQ ID NO:89; (d) the encoded $V_\beta$ CDR3 comprises the amino acid sequence shown in SEQ ID NO: 16, and the encoded $V_\alpha$, CDR3 comprises the amino acid sequence of SEQ ID NO:90; (e) the encoded $V_\beta$ CDR3 comprises the amino acid sequence shown in SEQ ID NO: 17, and the encoded $V_\alpha$, CDR3 comprises the amino acid sequence of SEQ ID NO:91; or (f) the encoded $V_\beta$ CDR3 comprises the amino acid sequence shown in SEQ ID NO:86, and the encoded $V_\alpha$, CDR3 comprises the amino acid sequence of SEQ ID NO:92.

In further embodiments, an encoded binding protein comprises a $V_\alpha$ domain, wherein the encoded $V_\alpha$, domain comprises an amino acid sequence that has at least about 90% sequence identity to the amino acid sequence of any one of SEQ ID NOS:2, 4, 6, 8, 10, and 12. In additional embodiments, an encoded binding protein comprises a $V_\beta$ domain, wherein the encoded $V_\beta$ domain comprises an amino acid sequence that has at least about 90% sequence identity to the amino acid sequence of any one of SEQ ID NOS:1, 3, 5, 7, 9, and 11.

In some embodiments, the encoded $V_\alpha$, domain comprises no change in amino acid sequence of CDR1, the encoded $V_\beta$ domain comprises no change in amino acid sequence of CDR1, or the CDR1 of the encoded $V_\alpha$, domain and the CDR1 of the encoded $V_\beta$ domain comprise no change in amino acid sequence. In further embodiments, the encoded $V_\alpha$, domain comprises no change in amino acid sequence of CDR2, the encoded $V_\beta$ domain comprises no change in amino acid sequence of CDR2, or the CDR2 of the encoded $V_\alpha$, domain and the CDR2 of the encoded $V_\beta$ domain comprise no change in amino acid sequence.

In particular embodiments, an encoded binding protein comprises a TCR $V_\alpha$ domain and a TCR $V_\beta$ domain, wherein: (a) the encoded $V_\beta$ domain comprises or consists of the amino acid sequence of SEQ ID NO: 1, and the encoded $V_\alpha$ domain comprises or consists of the amino acid sequence of SEQ ID NO:2; (b) the encoded $V_\beta$ domain comprises or consists of the amino acid sequence of SEQ ID NO:3, and the encoded $V_\alpha$, domain comprises or consists of the amino acid sequence of SEQ ID NO:4; (c) the encoded $V_\beta$ domain comprises or consists of the amino acid sequence of SEQ ID NO:5, and the encoded $V_\alpha$ domain comprises or consists of the amino acid sequence of SEQ ID NO:6; (d) the encoded $V_\beta$ domain comprises or consists of the amino acid sequence of SEQ ID NO:7, and the encoded $V_\alpha$, domain comprises or consists of the amino acid sequence of SEQ ID NO:8; (e) the encoded $V_\beta$ domain comprises or consists of the amino acid sequence of SEQ ID NO:9, and the encoded $V_\alpha$ domain comprises or consists of the amino acid sequence of SEQ ID NO: 10; or (f) the encoded $V_\beta$ domain comprises or consists of the amino acid sequence of SEQ ID NO: 11, and the encoded $V_\alpha$, domain comprises or consists of the amino acid sequence of SEQ ID NO:12.

Exemplary binding proteins of this disclosure expressed by a cell may include a signal peptide (e.g., binding preproteins), and the cell may remove the signal peptide to generate a mature binding protein. In certain embodiments, a binding protein comprises two components, such as an α-chain and a β-chain, which can associate on the cell surface to form a functional binding protein. The two associated components may comprise mature proteins. In certain embodiments, a binding protein of this disclosure comprises a mature $V_\beta$ domain, wherein the mature $V_\beta$ domain comprises or consists of the amino acid sequence of any one of SEQ ID NOS:96, 98, 100, 102, 104, or 106. In further embodiments, a binding protein of this disclosure comprises a mature $V_\alpha$ domain, wherein the mature $V_\alpha$, domain comprises or consists of the amino acid sequence of any one of SEQ ID NOS:97, 99, 101, 103, 105, or 107. In still further embodiments, a binding protein of this disclosure comprises a mature $V_\beta$ domain and a mature $V_\alpha$, domain, wherein the mature $V_\beta$ domain comprises or consists of the amino acid sequence of any one of SEQ ID NOS:96, 98, 100, 102, 104, or 106, and the mature $V_\alpha$, domain comprises or consists of the amino acid sequence of any one of SEQ ID NOS:97, 99, 101, 103, 105, or 107. In certain embodiments, a binding protein of this disclosure comprises a mature TCR β-chain, wherein the mature TCR β-chain comprises or consists of the amino acid sequence of any one of SEQ ID NOS: 108, 110, 112, 114, 116, or 118. In further embodiments, a binding protein of this disclosure comprises a mature TCR α-chain, wherein the mature TCR α-chain comprises or consists of the amino acid sequence of any one of SEQ ID NOS:109, 111, 113, 115, 117, or 119. In yet further embodiments, a binding protein of this disclosure comprises a mature TCR β-chain and a mature TCR α-chain, wherein the mature TCR β-chain comprises or consists of the amino acid sequence of any one of SEQ ID NOS: 108, 110, 112, 114, 116, or 118, and the mature TCR α-chain comprises or consists of the amino acid sequence of any one of SEQ ID NOS:109, 111, 113, 115, 117, or 119. In certain embodiments, a binding protein of this disclosure is expressed with a CD8 β-chain and the CD8 β-chain comprises a mature CD8 β-chain, wherein the mature CD8 β-chain comprises or consists of the amino acid sequence shown in any one of SEQ ID NOS: 121-125. In further embodiments, a binding protein of this disclosure is expressed with a CD8 α-chain and the CD8 α-chain comprises a mature CD8 α-chain, wherein the mature CD8 α-chain comprises or consists of the amino acid sequence of SEQ ID NO: 120. In more embodiments, a binding protein of this disclosure is expressed with a CD8 β-chain and a CD8 α-chain, wherein the CD8 β-chain and α-chain comprises a mature CD8 β-chain and α-chain, wherein the mature CD8 β-chain comprises or consists of the amino acid sequence shown in any one of SEQ ID NOS:121-125, and the mature CD8 α-chain comprises or consists of the amino acid sequence of SEQ ID NO: 120.

In further embodiments, an encoded binding protein comprises a mature TCR $V_\alpha$, domain and a mature TCR $V_\beta$ domain, wherein: (a) the $V_\beta$ domain comprising or consisting of the amino acid sequence of SEQ ID NO:96, and the $V_\alpha$, domain comprising or consisting of the amino acid sequence of SEQ ID NO:97; (b) the $V_\beta$ domain comprising or consisting of the amino acid sequence of SEQ ID NO:98, and the $V_\alpha$, domain comprising or consisting of the amino acid sequence of SEQ ID NO:99; (c) the $V_\beta$ domain comprising or consisting of the amino acid sequence of SEQ ID NO: 100, and the $V_\alpha$ domain comprising or consisting of the amino acid sequence of SEQ ID NO: 101; (d) the $V_\beta$ domain comprising or consisting of the amino acid sequence of SEQ ID NO: 102, and the $V_\alpha$, domain comprising or consisting of the amino acid sequence of SEQ ID NO: 103; (e) the $V_\beta$ domain comprising or consisting of the amino acid sequence of SEQ ID NO: 104, and the $V_\alpha$, domain comprising or consisting of the amino acid sequence of SEQ ID NO: 105; or (f) the $V_\beta$ domain comprising or consisting of the amino acid sequence of SEQ ID NO: 106, and the $V_\alpha$, domain comprising or consisting of the amino acid sequence of SEQ ID NO: 107.

An encoded binding protein contained in an engineered immune cell of the present disclosure may, in some embodiments, comprise a TCR constant domain. In certain embodiments, a TCR constant domain is modified to enhance pairing of desired TCR chains. For example, enhanced pairing between a heterologous TCR α-chain and a heterologous TCR β-chain due to a modification results in the preferential assembly of a TCR comprising two heterologous chains over an undesired mispairing of a heterologous TCR chain with an endogenous TCR chain (see, e.g., Govers et al., *Trends Mol. Med.* 16(2):77 (2010), the TCR modifications of which are herein incorporated by reference). Exemplary modifications to enhance pairing of heterologous TCR chains include the introduction of complementary cysteine residues in each of the heterologous TCR α-chain and β-chain. In some embodiments, a polynucleotide encoding a heterologous TCR α-chain encodes a cysteine at amino acid position 48 (corresponding to the full-length, mature human TCR α-chain sequence) and a polynucleotide encoding a heterologous TCR β-chain encodes a cysteine at amino acid position 57 (corresponding to the full-length mature human TCR β-chain sequence).

In certain embodiments, the encoded binding protein comprises a TCR α-chain constant ($C_\alpha$) domain having at least about 90% sequence identity to the amino acid sequence of any one of SEQ ID NOS: 19, 22, 24 and 26. In further embodiments, the encoded binding protein comprises a TCR $C_\alpha$, domain having at least about 90% sequence identity to the amino acid sequence of any one of SEQ ID NOS: 19, 22, 24 and 26, provided that the TCR $C_\alpha$, domain retains the introduced cysteine residue at postion 48. In still further embodiments, the encoded binding protein comprises a TCR $C_\alpha$ domain comprising or consisting of the amino acid sequence of any one of SEQ ID NOS:19, 22, 24 and 26.

In certain embodiments, the encoded binding protein comprises a TCR β-chain constant ($C_\beta$) domain having at least about 90% sequence identity to the amino acid sequence of any one of SEQ ID NOS: 18, 23 and 25. In further embodiments, the encoded binding protein comprises a TCR $C_\beta$ domain having at least about 90% sequence identity to the amino acid sequence of any one of SEQ ID NOS: 18, 23 and 25, provided that the TCR $C_\beta$ domain retains the introduced cysteine residue at postion 57. In still further embodiments, the encoded binding protein comprises a TCR $C_\beta$ domain comprising or consisting of the amino acid sequence of any one of SEQ ID NOS: 18, 23 and 25.

In certain embodiments, an encoded binding protein comprises a TCR α-chain (e.g., a TCR $V_\alpha$, domain operatively associated with a TCR $C_\alpha$, domain) having an amino acid sequence that is at least about 90% identical to the amino acid sequence of any one of SEQ ID NOS:28, 30, 32, 34, 36 and 38, optionally wherein the TCR $C_\alpha$ domain retains the cysteine at position 47 (as counted from the beginning of the $C_\alpha$, domain). In further embodiments, an encoded binding protein comprises a TCR α-chain comprising or consisting of the amino acid sequence of any one of SEQ ID NOS:28, 30, 32, 34, 36 and 38. In other embodiments, an encoded binding protein comprises a TCR β-chain (e.g., a TCR $V_\beta$ domain operatively associated with a TCR $C_\beta$ domain) having an amino acid sequence that is at least about 90% identical to the amino acid sequence of any one of SEQ ID NOS:27, 29, 31, 33, 35, and 37, optionally wherein the TCR $C_\beta$ domain retains the cysteine at position 57 (as counted from the beginning of the Cp domain). In still further embodiments, the encoded binding protein comprises a TCR β-chain comprising or consisting of the amino acid sequence of any one of SEQ ID NOS:27, 29, 31, 33, 35, and 37.

A binding protein encoded by an engineered immune cell of this disclosure may comprise any of the presently disclosed TCR α-chains in association with any of the disclosed TCR β-chains. For example, in certain embodiments, an encoded binding protein comprises: (a) a TCR β-chain comprising or consisting of the amino acid sequence shown in SEQ ID NO:27, and a TCR α-chain comprising or consisting of the amino acid sequence shown in SEQ ID NO:28; (b) a TCR β-chain comprising or consisting of the amino acid sequence shown in SEQ ID NO:29, and a TCR α-chain comprising or consisting of the amino acid sequence shown in SEQ ID NO:30; (c) a TCR β-chain comprising or consisting of the amino acid sequence shown in SEQ ID NO:31, and the TCR α-chain comprising or consisting of the amino acid sequence shown in SEQ ID NO:32; (d) a TCR β-chain comprising or consisting of the amino acid sequence shown in SEQ ID NO:33, and a TCR α-chain comprising or consisting of the amino acid sequence shown in SEQ ID NO:34; (e) a TCR β-chain comprising or consisting of the amino acid sequence shown in SEQ ID NO:35, and a TCR-α chain comprising or consisting of the amino acid sequence shown in SEQ ID NO:36; or (f) a TCR β-chain comprising or consisting of the amino acid sequence shown in SEQ ID NO:37, and a TCR-α chain comprising or consisting of the amino acid sequence shown in SEQ ID NO:38.

An engineered immune cell of the present disclosure may comprise a single polynucleotide that encodes a binding protein as described herein, or the binding protein may be encoded by more than one polynucleotide. In other words, components or portions of a binding protein may be encoded by two or more polynucleotides, which may be contained on a single nucleic acid molecule or may be contained on two or more nucleic acid molecules.

In certain embodiments, a polynucleotide encoding two or more components or portions of a binding protein of the present disclosure comprises the two or more coding sequences operatively associated in a single open reading frame. Such an arrangement can advantageously allow coordinated expression of desired gene products, such as, for example, contemporaneous expression of alpha- and beta-chains of a TCR, such that they are produced in about a 1:1 ratio. In certain embodiments, two or more substituent gene products of a binding protein of this disclosure, such as a TCR (e.g., alpha- and beta-chains) or CAR, are expressed as separate molecules and associate post-translationally. In further embodiments, two or more substituent gene products of a binding protein of this disclosure are expressed as a single peptide with the parts separated by a cleavable or removable segment. For instance, self-cleaving peptides useful for expression of separable polypeptides encoded by a single polynucleotide or vector are known in the art and include, for example, a Porcine teschovirus-1 2A (P2A) peptide, such as a peptide encoded by a polynucleotide having the nucleotide sequence shown in any one of SEQ ID NOS:76-81, a Thoseaasigna virus 2A (T2A) peptide, such as a peptide encoded by a polynucleotide having the nucleotide sequence shown in SEQ ID NO:82, an Equine rhinitis A virus (ERAV) 2A (E2A) peptide, such as a peptide encoded by a polynucleotide having the nucleotide sequence shown in SEQ ID NO:83, and a Foot-and-Mouth disease virus 2A (F2A) peptide, such as a peptide encoded by a polynucleotide having the nucleotide sequence shown in SEQ ID NO:84.

In certain embodiments, a binding protein of the present disclosure comprises one or more junction amino acids. “Junction amino acids” or “junction amino acid residues” refer to one or more (e.g., 2 to about 10) amino acid residues between two adjacent motifs, regions or domains of a polypeptide, such as between a binding domain and an adjacent constant domain or between a TCR chain and an adjacent self-cleaving peptide. Junction amino acids can result from the design of a construct that encodes a fusion protein (e.g., amino acid residues resulting from the use of a restriction enzyme site during the construction of a nucleic acid molecule encoding a fusion protein), or from cleavage of, for example, a self-cleaving peptide adjacent one or more domains of an encoded binding protein of this disclosure (e.g., a P2A peptide disposed between a TCR α-chain and a TCR β-chain, the self-cleavage of which can leave one or more junction amino acids in the α-chain, the TCR β-chain, or both).

Binding proteins contained in engineered immune cells of this disclosure can, in certain embodiments, specifically bind to an HA-$1^H$ peptide:HLA complex. For example, in specific embodiments, a binding protein of this disclosure is capable of specifically binding to an HA-$1^H$ peptide:HLA complex, wherein the HLA can comprise HLA-A*0201. In particular embodiments, the HA-$1^H$ peptide comprises the amino acid sequence VLHDDLLEA (SEQ ID NO:66).

In any of the aforementioned embodiments, an encoded binding protein contained in an engineered immune cell can comprise a TCR, an antigen-binding fragment of a TCR (e.g., a single chain TCR (“scTCR”)), or a chimeric antigen receptor (‘CAR’).

In certain embodiments, an antigen-binding fragment of a TCR comprises a single chain TCR (scTCR), which comprises both the TCR $V_\alpha$, and TCR $V_\beta$ domains, but only a single TCR constant domain ($C_\alpha$, or $C_\beta$). In further embodiments, an antigen-binding fragment of a TCR or a chimeric antigen receptor is chimeric (e.g., comprises amino acid residues or motifs from more than one donor or species), humanized (e.g., comprises residues from a non-human organism that are altered or substituted so as to reduce the risk of immunogenicity in a human), or human.

“Chimeric antigen receptor” (CAR) refers to a fusion protein that is engineered to contain two or more naturally-occurring amino acid sequences linked together in a way that does not occur naturally or does not occur naturally in a host cell, which fusion protein can function as a receptor when present on a surface of a cell. CARs of the present disclosure include an extracellular portion comprising an antigen binding domain (i.e., obtained or derived from an immunoglobulin or immunoglobulin-like molecule, such as an scFv derived from an antibody or TCR specific for a cancer antigen, or an antigen binding domain derived or obtained from a killer immunoreceptor from an NK cell) linked to a transmembrane domain and one or more intracellular signaling domains (optionally containing co-stimulatory domain(s)) (see, e.g., Sadelain et al., *Cancer Discov.,* 3(4):388 (2013); see also Harris and Kranz, Trends *Pharmacol. Sci.,* 37(3):220 (2016), and Stone et al., *Cancer Immunol. Immunother.,* 63(11):1163 (2014)).

Methods for producing engineered TCRs are described in, for example, Bowerman et al., *Mol. Immunol.,* 46(15):3000 (2009), the techniques of which are herein incorporated by reference. Methods for making CARs are well known in the art and are described, for example, in U.S. Pat. Nos. 6,410,319; 7,446,191; U.S. Patent Publication No. 2010/065818; U.S. Pat. No. 8,822,647; PCT Publication No. WO 2014/031687; U.S. Pat. No. 7,514,537; and Brentjens et al., 2007, *Clin. Cancer Res.* 13:5426, the techniques of which are herein incorporated by reference.

Engineered immune cells of this disclosure can be administered as therapies for, e.g., cancer. In some circumstances, it may be desirable to reduce or stop the activity associated with a cellular immunotherapy. Thus, in certain embodiments, an engineered immune cell of the present disclosure comprises a heterologous polynucleotide encoding a binding protein and an accessory protein, such as a safety switch protein, which can be targeted using a cognate drug or other compound to selectively modulate the activity (e.g., lessen or ablate) of such cells when desirable. Safety switch proteins used in this regard include, for example, a truncated EGF receptor polypeptide (huEGFRt) that is devoid of extracellular N-terminal ligand binding domains and intracellular receptor tyrosine kinase activity but retains the native amino acid sequence, type I transmembrane cell surface localization, and a conformationally intact binding epitope for pharmaceutical-grade anti-EGFR monoclonal antibody, cetuximab (Erbitux) tEGF receptor (tEGFr; Wang et al., *Blood* 118:1255-1263, 2011), a caspase polypeptide (e.g., iCasp9; Straathof et al., *Blood* 105:4247-4254, 2005; Di Stasi et al., *N. Engl. J. Med.* 365:1673-1683, 2011; Zhou and Brenner, *Exp. Hematol.* pii:S0301-472X(16)30513-6. doi:10.1016/j.exphem.2016.07.011), RQR8 (Philip et al., *Blood* 124:1277-1287, 2014), a 10 amino acid tag of the human c-myc protein (Myc) (Kieback et al., *Proc. Natl. Acad. Sci. USA* 105:623-628, 2008), as discussed herein, and a marker/safety switch polypeptide, such as RQR (CD20+CD34; Philip et al., 2014).

Other accessory components useful for therapeutic cells comprise a tag or selection marker that allows the cells to be identified, sorted, isolated, enriched, or tracked. For example, marked immune cells having desired characteristics (e.g., an antigen-specific TCR and a safety switch protein) can be sorted away from unmarked cells in a sample and more efficiently activated and expanded for inclusion in a therapeutic product of desired purity.

As used herein, the term “selection marker” comprises a nucleic acid construct that confers an identifiable change to a cell permitting detection and positive selection of immune cells transduced with a polynucleotide comprising a selection marker. RQR is a selection marker that comprises a major extracellular loop of CD20 and two minimal CD34 binding sites. In some embodiments, an RQR-encoding polynucleotide comprises a polynucleotide that encodes the 16 amino acid CD34 minimal epitope. In some embodiments, such as certain embodiments provided in the examples herein, the CD34 minimal epitope is incorporated at the amino terminal position of the CD8 stalk domain (Q8). In further embodiments, the CD34 minimal binding site sequence can be combined with a target epitope for CD20 to form a compact marker/suicide gene for T cells (RQR8) (Philip et al., 2014, incorporated by reference herein). This construct allows for the selection of immune cells expressing the construct, with for example, CD34 specific antibody bound to magnetic beads (Miltenyi) and that utilizes clinically accepted pharmaceutical antibody, rituximab, that allows for the selective deletion of a transgene expressing engineered T cell (Philip et al., 2014).

Further exemplary selection markers also include several truncated type I transmembrane proteins normally not expressed on T cells: the truncated low-affinity nerve growth factor, truncated CD19, and truncated CD34 (see for example, Di Stasi et al., *N. Engl. J. Med.* 365:1673-1683, 2011; Mavilio et al., *Blood* 83:1988-1997, 1994; Fehse et al., *Mol. Ther.* 1:448-456, 2000; each incorporated herein in their entirety). A particularly attractive feature of CD19 and CD34 is the availability of the off-the-shelf Miltenyi CliniMACs™ selection system that can target these markers for clinical-grade sorting. However, CD19 and CD34 are relatively large surface proteins that may tax the vector packaging capacity and transcriptional efficiency of an integrating vector. Surface markers containing the extracellular, non-signaling domains or various proteins (e.g., CD19, CD34, LNGFR) also can be employed. Any selection marker may be employed and should be acceptable for Good Manufacturing Practices. In certain embodiments, selection markers are expressed with a polynucleotide that encodes a gene product of interest (e.g., a binding protein of the present disclosure, such as a TCR or CAR). Further examples of selection markers include, for example, reporters such as GFP, EGFP, β-gal or chloramphenicol acetyltransferase (CAT). In certain embodiments, a selection marker, such as, for example, CD34 is expressed by a cell and the CD34 can be used to select enrich for, or isolate (e.g., by immunomagnetic selection) the transduced cells of interest for use in the methods described herein. As used herein, a CD34 marker is distinguished from an anti-CD34 antibody, or, for example, a scFv, TCR, or other antigen recognition moiety that binds to CD34.

In certain embodiments, a selection marker comprises an RQR polypeptide, a truncated low-affinity nerve growth factor (tNGFR), a truncated CD19 (tCD19), a truncated CD34 (tCD34), or any combination thereof.

By way of background, inclusion of $CD4^+$ T cells in an immunotherapy cell product can provide antigen-induced IL-2 secretion and augment persistence and function of transferred cytotoxic $CD8^+$ T cells (see, e.g., Kennedy et al., *Immunol. Rev.* 222:129 (2008); Nakanishi et al., *Nature* 462(7272):510 (2009)). In certain circumstances, a class I restricted TCR in $CD4^+$ T cells may require the transfer of a CD8 co-receptor to enhance sensitivity of the TCR to class I HLA peptide complexes. CD4 co-receptors differ in structure to CD8 and cannot effectively substitute for CD8 co-receptors (see, e.g., Stone & Kranz, *Front. Immunol.* 4:244 (2013); see also Cole et al., *Immunology* 137(2):139 (2012). Thus, another accessory protein for use in the compositions and methods of this disclosure comprises a CD8 co-receptor or component thereof.

Engineered immune cells comprising a heterologous polynucleotide encoding a binding protein of the present disclosure may, in certain embodiments, further comprise a heterologous polynucleotide encoding a CD8 co-receptor protein, or a beta-chain or alpha-chain component thereof. An encoded CD8 co-receptor includes, in some embodiments, a β-chain comprising the amino acid sequence of any one of SEQ ID NOS:71-75. In further embodiments, the encoded CD8 co-receptor is a recombinant CD8 co-receptor further comprising a RQR polypeptide having the amino acid sequence of SEQ ID NO:69. Without wishing to be bound by theory, it is believed that distance from the host cell surface is important for RQR polypeptides to function as selection markers/safety switches (Philip et al., 2010 (supra)). In some embodiments, the encoded RQR polypeptide is contained in a β-chain, an α-chain, or both, of the encoded CD8 co-receptor. In specific embodiments, an engineered immune cell comprises a heterologous polynucleotide encoding iCasp9 and a heterologous polynucleotide encoding a recombinant CD8 co-receptor protein that comprises a β-chain containing a RQR polypeptide and further comprises a CD8 α-chain. In particular embodiments, the encoded CD8 α-chain comprises the amino acid sequence shown in SEQ ID NO:70.

In further embodiments, an engineered immune cell comprises a heterologous polynucleotide encoding iCasp9 and a heterologous polynucleotide encoding a recombinant CD8 co-receptor protein that comprises an α-chain containing a RQR polypeptide and further comprises a CD8 β-chain. In some embodiments, both of the encoded CD8 α-chain and the encoded CD8 β-chain contain a RQR polypeptide.

An engineered immune cell may be efficiently transduced to contain, and may efficiently express, a single polynucleotide that encodes the binding protein, safety switch protein, selection marker, and CD8 co-receptor protein. For example, in some embodiments, an engineered immune cell of the present disclosure comprises a heterologous polynucleotide that encodes, from 5' to 3', ([an iCasp9 polypeptide]-[a porcine teschovirus 2A (P2A) peptide]-[a TCR β-chain]-[a P2A peptide]-[a TCR α-chain]-[a P2A peptide]-[a CD8 β-chain comprising an RQR polypeptide]-[a P2A peptide]-[a CD8 α-chain]). In specific embodiments, the TCRβ-chain-encoding polynucleotide comprises or consists of the nucleotide sequence of SEQ ID NO:41, and the TCRα-chain-encoding polynucleotide comprises or consists of the nucleotide sequence of SEQ ID NO:42.

In particular embodiments, an engineered immune cell contains a heterologous polynucleotide that comprises or consists of the nucleotide sequence of SEQ ID NO:85.

Any suitable immune cell may be engineered to include a heterologous polynucleotide encoding a binding protein of this disclosure, including, for example, a T cell, a NK cell, or a NK-T cell. In some embodiments, an engineered immune cell comprises a $CD4^+$ T cell, a $CD8^+$ T cell, or both. Methods for transfecting/transducing T cells with desired nucleic acids have been described (e.g., U.S. Patent Application Pub. No. US 2004/0087025) as have adoptive transfer procedures using T cells of desired target-specificity (e.g., Schmitt et al., *Hum. Gen.* 20:1240, 2009; Dossett et al., *Mol. Ther.* 17:742, 2009; Till et al., *Blood* 112:2261, 2008; Wang et al., *Hum. Gene Ther.* 18:712, 2007; Kuball et al., *Blood* 109:2331, 2007; US 2011/0243972; US 2011/0189141; Leen et al., *Ann. Rev. Immunol.* 25:243, 2007), such that adaptation of these methodologies to the presently disclosed embodiments is contemplated, based on the teachings herein.

Any appropriate method can be used to transfect or transduce the cells, for example, the T cells, or to administer the polynucleotides or compositions of the present methods. Known methods for delivering polynucleotides to host cells include, for example, use of cationic polymers, lipid-like molecules, and certain commercial products such as, for example, IN-VIVO-JET PEI. Other methods include ex vivo transduction, injection, electroporation, DEAE-dextran, sonication loading, liposome-mediated transfection, receptor-mediated transduction, microprojectile bombardment, transposon-mediated transfer, and the like. Still further methods of transfecting or transducing host cells employ vectors, described in further detail herein.

In any of the foregoing embodiments, an engineered immune cell may be a "universal donor" cell that is modified to reduce or eliminate expression of one or more endogenous genes that encode a polypeptide involved in immune signaling or other related activities. Exemplary gene knockouts include those that encode PD-1, LAG-3, CTLA4, TIM3, an HLA molecule, a TCR molecule, or the like. Without wishing to be bound by theory, certain endogenously expressed immune cell proteins may be recognized as foreign by an allogeneic host receiving the engineered immune cells, which may result in elimination of the engineered immune cells (e.g., an HLA allele), or may downregulate the immune activity of the engineered immune cells (e.g., PD-1, LAG-3, CTLA4), or may interfere with the binding activity of a heterologously expressed binding protein of the present disclosure (e.g., an endogenous TCR that binds a non-HA-$1^{H}$ antigen and thereby interferes with the engineered immune cell binding a cell that expresses HA-$1^{H}$ antigen). Accordingly, decreasing or eliminating expression or activity of such endogenous genes or proteins can improve the activity, tolerance, and persistence of the engineered immune cells within an allogeneic host, and allows for universal, "off-the-shelf" cells for administration (e.g., to any recipient regardless of HLA type).

In certain embodiments, an engineered immune cell of this disclosure comprises a chromosomal gene knockout of one or more of a gene that encodes PD-1, LAG-3, CTLA4, TIM3, an HLA component (e.g., a gene that encodes an $\alpha$1 macroglobulin, an $\alpha$2 macroglobulin, an $\alpha$3 macroglobulin, a $\beta$1 microglobulin, or a $\beta$2 microglobulin), or a TCR component (e.g., a gene that encodes a TCR variable region or a TCR constant region) (see, e.g., Torikai et al., *Nature Sci. Rep.* 6:21757 (2016); Torikai et al., *Blood* 119(24):5697 (2012); and Torikai et al., *Blood* 122(8):1341 (2013), the gene editing techniques and compositions of which are herein incorporated by reference in their entirety). As used herein, the term "chromosomal gene knockout" refers to a genetic alteration in an engineered immune cell that prevents production, by the engineered immune cell, of a functionally active endogenous polypeptide product. Alterations resulting in a chromosomal gene knockout can include, for example, introduced nonsense mutations (including the formation of premature stop codons), missense mutations, gene deletion, and strand breaks, as well as the heterologous expression of inhibitory nucleic acid molecules that inhibit endogenous gene expression in the engineered immune cell.

A chromosomal gene knockout may be introduced by chromosomal editing of the immune cell. In certain embodiments, the chromosomal gene knockout is made by chromosomal editing of the immune cell. Chromosomal editing can be performed using, for example, endonucleases. As used herein "endonuclease" refers to an enzyme capable of catalyzing cleavage of a phosphodiester bond within a polynucleotide chain. In certain embodiments, an endonuclease is capable of cleaving a targeted gene thereby inactivating or "knocking out" the targeted gene. An endonuclease may be a naturally occurring, recombinant, genetically modified, or fusion endonuclease. The nucleic acid strand breaks caused by the endonuclease are commonly repaired through the distinct mechanisms of homologous recombination or non-homologous end joining (NHEJ). During homologous recombination, a donor nucleic acid molecule may be used for gene "knock-in" to inactivate a target gene. NHEJ is an error-prone repair process that often results in changes to the DNA sequence at the site of the cleavage, e.g., a substitution, deletion, or addition of at least one nucleotide. NHEJ may be used to "knock-out" a target gene. Methods of disrupting or knocking out genes or gene expression in immune cells using endonucleases are known in the art and described, for example, in PCT Publication Nos. WO 2015/066262; WO 2013/074916; and WO 2014/059173; methods from each of which is incorporated by reference. Examples of endonucleases include zinc finger nucleases, TALE-nucleases, CRISPR-Cas nucleases, and meganucleases.

As used herein, a "zinc finger nuclease" (ZFN) refers to a fusion protein comprising a zinc finger DNA-binding domain fused to a non-specific DNA cleavage domain, such as a Fokl endonuclease. Each zinc finger motif of about 30 amino acids binds to about 3 base pairs of DNA, and amino acids at certain residues can be changed to alter triplet sequence specificity (see, e.g., Desjarlais et al., *Proc. Natl. Acad. Sci.* 90:2256-2260, 1993; Wolfe et al., *J. Mol. Biol.* 285:1917-1934, 1999). Multiple zinc finger motifs can be linked in tandem to create binding specificity to desired DNA sequences, such as regions having a length ranging from about 9 to about 18 base pairs. By way of background, ZFNs mediate genome editing by catalyzing the formation of a site-specific DNA double strand break (DSB) in the genome, and targeted integration of a transgene comprising flanking sequences homologous to the genome at the site of DSB is facilitated by homology directed repair. Alternatively, a DSB generated by a ZFN can result in knock out of target gene via repair by non-homologous end joining (NHEJ), which is an error-prone cellular repair pathway that results in the insertion or deletion of nucleotides at the cleavage site. In certain embodiments, a gene knockout comprises an insertion, a deletion, a mutation or a combination thereof, made using a ZFN molecule.

As used herein, a "transcription activator-like effector nuclease" (TALEN) refers to a fusion protein comprising a TALE DNA-binding domain and a DNA cleavage domain, such as a FokI endonuclease. A "TALE DNA binding domain" or "TALE" is composed of one or more TALE repeat domains/units, each generally having a highly conserved 33-35 amino acid sequence with divergent $12^{th}$ and $13^{th}$ amino acids. The TALE repeat domains are involved in binding of the TALE to a target DNA sequence. The divergent amino acid residues, referred to as the Repeat Variable Diresidue (RVD), correlate with specific nucleotide recognition. The natural (canonical) code for DNA recognition of these TALEs has been determined such that an HD sequence at positions 12 and 13 leads to a binding to cytosine (C), NG binds to T, NI to A, NN binds to G or A, and NG binds to T and non-canonical (atypical) RVDs are also known (see, e.g., U.S. Patent Publication No. US 2011/0301073, which atypical RVDs are incorporated by reference herein in its entirety). TALENs can be used to direct site-specific double-strand breaks (DSB) in the genome of T cells. Non-homologous end joining (NHEJ) ligates DNA from both sides of a double-strand break in which there is little or no sequence overlap for annealing, thereby introducing errors that knock out gene expression. Alternatively, homology directed repair can introduce a transgene at the site of DSB providing homologous flanking sequences are present in the transgene. In certain embodiments, a gene knockout comprises an insertion, a deletion, a mutation or a combination thereof, and made using a TALEN molecule.

As used herein, a "clustered regularly interspaced short palindromic repeats/Cas" (CRISPR/Cas) nuclease system refers to a system that employs a CRISPR RNA (crRNA)-guided Cas nuclease to recognize target sites within a genome (known as protospacers) via base-pairing complementarity and then to cleave the DNA if a short, conserved protospacer associated motif (PAM) immediately follows 3' of the complementary target sequence. CRISPR/Cas systems are classified into three types (i.e., type I, type II, and type III) based on the sequence and structure of the Cas nucleases. The crRNA-guided surveillance complexes in types I and III need multiple Cas subunits. Type II system, the most studied, comprises at least three components: an RNA-guided Cas9 nuclease, a crRNA, and a trans-acting crRNA (tracrRNA). The tracrRNA comprises a duplex forming region. A crRNA and a tracrRNA form a duplex that is capable of interacting with a Cas9 nuclease and guiding the Cas9/crRNA:tracrRNA complex to a specific site on the target DNA via Watson-Crick base-pairing between the spacer on the crRNA and the protospacer on the target DNA upstream from a PAM. Cas9 nuclease cleaves a double-stranded break within a region defined by the crRNA spacer. Repair by NHEJ results in insertions and/or deletions which disrupt expression of the targeted locus. Alternatively, a transgene with homologous flanking sequences can be introduced at the site of DSB via homology directed repair. The crRNA and tracrRNA can be engineered into a single guide RNA (sgRNA or gRNA) (see, e.g., Jinek et al., *Science* 337:816-21, 2012). Further, the region of the guide RNA complementary to the target site can be altered or programed to target a desired sequence (Xie et al., PLOS One 9:e100448, 2014; U.S. Pat. Appl. Pub. No. US 2014/0068797, U.S. Pat. Appl. Pub. No. US 2014/0186843; U.S. Pat. No. 8,697,359, and PCT Publication No. WO 2015/071474; the techniques and compositions of each of which are incorporated by reference). In certain embodiments, a gene knockout comprises an insertion, a deletion, a mutation or a combination thereof, and made using a CRISPR/Cas nuclease system.

As used herein, a "meganuclease," also referred to as a "homing endonuclease," refers to an endodeoxyribonuclease characterized by a large recognition site (double stranded DNA sequences of about 12 to about 40 base pairs). Meganucleases can be divided into five families based on sequence and structure motifs: LAGLIDADG (SEQ ID NO: 131), GIY-YIG, HNH, His-Cys box and PD-(D/E)XK (SEQ ID NO: 132). Exemplary meganucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII, whose recognition sequences are known (see, e.g., U.S. Pat. Nos. 5,420,032 and 6,833,252; Belfort et al., *Nucleic Acids Res.* 25:3379-3388, 1997; Dujon et al., *Gene* 82:115-118, 1989; Perler et al., *Nucleic Acids Res.* 22:1125-1127, 1994; *Jasin, Trends Genet.* 12:224-228, 1996; Gimble et al., *J. Mol. Biol.* 263:163-180, 1996; Argast et al., *J. Mol. Biol.* 280:345-353, 1998).

In certain embodiments, naturally-occurring meganucleases may be used to promote site-specific genome modification of a target selected from PD-1, LAG3, TIM3, CTLA4, an HLA-encoding gene, or a TCR component-encoding gene. In other embodiments, an engineered meganuclease having a novel binding specificity for a target gene is used for site-specific genome modification (see, e.g., Porteus et al., *Nat. Biotechnol.* 23:967-73, 2005; Sussman et al., *J. Mol. Biol.* 342:31-41, 2004; Epinat et al., *Nucleic Acids Res.* 31:2952-62, 2003; Chevalier et al., *Molec. Cell* 10:895-905, 2002; Ashworth et al., *Nature* 441:656-659, 2006; Paques et al., *Curr. Gene Ther.* 7:49-66, 2007; U.S. Patent Publication Nos. US 2007/0117128; US 2006/0206949; US 2006/0153826; US 2006/0078552; and US 2004/0002092).

In certain embodiments, a chromosomal gene knockout comprises an inhibitory nucleic acid molecule that is introduced into an engineered immune cell comprising a heterologous polynucleotide encoding an antigen-specific receptor that specifically binds to a tumor associated antigen, wherein the inhibitory nucleic acid molecule encodes a target-specific inhibitor and wherein the encoded target-specific inhibitor inhibits endogenous gene expression (i.e., of PD-1, TIM3, LAG3, CTLA4, an HLA component, a TCR component, or any combination thereof) in the engineered immune cell.

A chromosomal gene knockout can be confirmed directly by DNA sequencing of the engineered immune cell following use of the knockout procedure or agent. Chromosomal gene knockouts can also be inferred from the absence of gene expression (e.g., the absence of an mRNA or polypeptide product encoded by the gene) following the knockout.

In another aspect, compositions are provided herein that comprise an engineered immune cell of the present disclosure and a pharmaceutically acceptable carrier, diluent, or excipient. Also provided herein are unit doses that comprise an effective amount of an engineered immune cell or of a composition comprising the engineered immune cell. In certain embodiments, a unit dose comprises (i) a composition comprising at least about 30%, at least about 40%, at least about 50%, at least about 60%, at least about 70%, at least about 80%, at least about 85%, at least about 90%, or at least about 95% engineered $CD4^+$ T cells, combined with (ii) a composition comprising at least about 30%, at least about 40%, at least about 50%, at least about 60%, at least about 70%, at least about 80%, at least about 85%, at least about 90%, or at least about 95% engineered $CD8^+$ T cells, in about a 1:1 ratio, wherein the unit dose contains a reduced amount or substantially no naïve T cells (i.e., has less than about 50%, less than about 40%, less than about 30%, less then about 20%, less than about 10%, less than about 5%, or less then about 1% the population of naïve T cells present in a unit dose as compared to a patient sample having a comparable number of PBMCs).

In some embodiments, a unit dose comprises (i) a composition comprising at least about 50% engineered $CD4^+$ T cells, combined with (ii) a composition comprising at least about 50% engineered $CD8^+$ T cells, in about a 1:1 ratio, wherein the unit dose contains a reduced amount or substantially no naïve T cells. In further embodiments, a unit dose comprises (i) a composition comprising at least about 60% engineered $CD4^+$ T cells, combined with (ii) a composition comprising at least about 60% engineered $CD8^+$ T cells, in about a 1:1 ratio, wherein the unit dose contains a reduced amount or substantially no naïve T cells. In still further embodiments, a unit dose comprises (i) a composition comprising at least about 70% engineered $CD4^+$ T cells, combined with (ii) a composition comprising at least about 70% engineered $CD8^+$ T cells, in about a 1:1 ratio, wherein the unit dose contains a reduced amount or substantially no naïve T cells. In some embodiments, a unit dose comprises (i) a composition comprising at least about 80% engineered $CD4^+$ T cells, combined with (ii) a composition comprising at least about 80% engineered $CD8^+$ T cells, in about a 1:1 ratio, wherein the unit dose contains a reduced amount or substantially no naïve T cells. In some embodiments, a unit dose comprises (i) a composition comprising at least about 85% engineered $CD4^+$ T cells, combined with (ii) a composition comprising at least about 85% engineered $CD8^+$ T cells, in about a 1:1 ratio, wherein the unit dose contains a reduced amount or substantially no naïve T cells. In some embodiments, a unit dose comprises (i) a composition comprising at least about 90% engineered $CD4^+$ T cells, combined with (ii) a composition comprising at least about 90% engineered $CD8^+$ T cells, in about a 1:1 ratio, wherein the unit dose contains a reduced amount or substantially no naïve T cells.

In any of the embodiments described herein, a unit dose comprises equal, or approximately equal numbers of engineered $CD45RA^-$ $CD3^+$ $CD8^+$ and engineered $CD45RA^-$ $CD3^+CD4^+$ $T_M$ cells.

Polynucleotides, Transgenes and Vectors

In further aspects, the present disclosure provides an isolated polynucleotide that encodes a binding protein as described herein (e.g., an HA-$1^H$-specific TCR, scTCR, or CAR that comprises TCR $V_\alpha$, and $V_\beta$ domains as described herein (and optionally further comprises constant domains or other components as described herein)), and may additionally encoded a safety switch protein, a selection marker, a CD8 co-receptor β-chain, or a CD8 co-receptor α-chain, or any combination thereof, provided that at least a portion of the isolated polynucleotide is codon-optimized for expression in a host cell (e.g., an engineered immune cell as disclosed herein).

In particular, any of the aforementioned heterologous polynucleotides comprised in the engineered immune cells (e.g., encoding any of the binding proteins of the present disclosure) may also or alternatively be provided in an isolated form, wherein the polynucleotide is codon-optimized for expression in a host cell. For example, in certain embodiments, an isolated polynucleotide encodes a TCR β-chain of an HA-$1^H$-specific binding protein and comprises or consists of the nucleotide sequence of any one of SEQ ID NOS:39, 41, 43, 45, 47, 49, or 51. In further embodiments, an isolated polynucleotide encodes a TCR α-chain of an HA-$1^H$-specific binding protein and comprises or consists of the nucleotide sequence of any one of SEQ ID NOS:40, 42, 46, 48, 50, or 52.

In certain embodiments, a heterologous polynucleotide encoding a TCR α-chain and a heterologous polynucleotide encoding a TCR β-chain are contained in a single open reading frame comprised in the engineered immune cell, wherein the single open reading frame further comprises a polynucleotide encoding a self-cleaving peptide disposed between the α-chain-encoding polynucleotide and the β-chain-encoding polynucleotide. In some embodiments, the polynucleotide encoding the self-cleaving peptide comprises or consists of the nucleotide sequence of any one of SEQ ID NOS:76-84.

In further embodiments, the single open reading frame comprises a nucleotide sequence that is at least about 80% identical to the nucleotide sequence of any one of SEQ ID NOS:59-63. In specific embodiments, the single open reading frame comprises or consists of the nucleotide sequence of any one of SEQ ID NOS: 59-63. In still further embodiments, the encoded ([TCR β-chain]-[self-cleaving-peptide]-[TCR α-chain]) comprises or consists of the amino acid sequence of any one of SEQ ID NOS: 53-57, which exists before the cell removes the signal peptide, and before the β-chain and α-chains are separated by the self cleaving peptide.

An isolated polynucleotide of this disclosure may further comprise a polynucleotide encoding a safety switch protein, a selection marker, a CD8 co-receptor beta chain (e.g., SEQ ID NOs:71-75), or a CD8 co-receptor alpha chain (e.g., SEQ ID NO:70) as disclosed herein, or may comprise a polynucleotide encoding any combination thereof. In specific embodiments, an isolated comprising a heterologous polynucleotide encoding iCasp9 and a heterologous polynucleotide encoding a recombinant CD8 co-receptor protein that comprises a β-chain or α-chain that contains a RQR polypeptide.

In some embodiments, an isolated polynucleotide comprises a single open reading frame containing, from 5' to 3', ([a polynucleotide encoding a safety switch protein]-[a polynucleotide encoding a self-cleaving peptide]-[the polynucleotide encoding a TCR β-chain]-[a polynucleotide encoding a self-cleaving polypeptide]-[a polynucleotide encoding a TCR α-chain]-[a polynucleotide encoding a self-cleaving polypeptide]-[a polynucleotide encoding a CD8 β-chain that contains an RQR polypeptide]-[a polynucleotide encoding a self-cleaving polypeptide]-[a polynucleotide encoding a CD8 α-chain]).

In further embodiments, an isolated polynucleotide comprises a single open reading frame that encodes, from 5' to 3', ([an iCasp9 polypeptide]-[a porcine teschovirus 2A (P2A) peptide]-[a TCR β chain]-[a P2A peptide]-[a TCR α-chain]-[a P2A peptide]-[a CD8 β-chain comprising an RQR polypeptide]-[a P2A peptide]-[a CD8 α-chain]). In certain embodiments, the TCR β-chain-encoding polynucleotide comprises or consists of the nucleotide sequence of SEQ ID NO:41, and wherein the TCR α-chain-encoding polynucleotide comprises or consists of the nucleotide sequence of SEQ ID NO:42.

In specific embodiments, an isolated polynucleotide comprises or consists of the nucleotide sequence of SEQ ID NO:85.

In any of the embodiments described herein, an isolated polynucleotide is codon-optimized for expression in an immune cell, such as a T cell.

In another aspect, transgene constructs are provided herein, wherein a transgene construct comprises an expression control sequence (e.g., a promoter sequence) operatively linked to a single open reading frame comprising (a) a polynucleotide encoding a safety switch protein; (b) a polynucleotide encoding a TCR β-chain; (c) a polynucleotide encoding a TCR α-chain; (b) a polynucleotide encoding a selection marker; (c) a polynucleotide encoding a CD8 co-receptor β-chain; and (d) a polynucleotide encoding a CD8 co-receptor α-chain.

Construction of an transgene construct for genetically engineering and producing a polypeptide of interest can be accomplished by using any suitable molecular biology engineering technique known in the art. To obtain efficient transcription and translation, a polynucleotide in each transgene construct of the present disclosure includes, in certain embodiments, at least one appropriate expression control sequence (also called a regulatory sequence), such as a leader sequence and particularly a promoter operably (i.e., operatively) linked to the nucleotide sequence encoding the polypeptide of interest. In certain embodiments, a transgene construct comprises a polynucleotide that encodes a safety switch protein, wherein the encoded safety switch protein comprises: (i) a truncated EGF receptor (tEGFR); (ii) iCasp9; (iii) a RQR polypeptide; (iv) a myc epitope; or (v) any combination thereof.

In further embodiments, the encoded selection marker comprises: (i) a RQR polypeptide; (ii) a truncated low-affinity nerve growth factor (tNGFR); (iii) a truncated CD19 (tCD19); (iv) a truncated CD34 (tCD34); or (v) any combination thereof.

In some embodiments, the encoded CD8 co-receptor is a recombinant CD8 co-receptor comprising a RQR polypeptide having the amino acid sequence shown in SEQ ID NO:69. In particular embodiments, a transgene construct includes a polynucleotide that encodes an RQR polypeptide that is contained in an encoded CD8 β-chain. In further embodiments, a transgene construct includes a polynucleotide that encodes an RQR polypeptide that is contained in an encoded CD8 α-chain.

For example, a transgene construct of the present disclosure comprises, in certain embodiments, an open reading frame containing (a) a polynucleotide encoding a safety switch protein; (b) a polynucleotide encoding a TCRβ-chain; (c) a polynucleotide encoding a TCRα-chain; (d) a polynucleotide encoding a CD8 β-chain that contains an RQR polypeptide; and (e) a polynucleotide encoding a CD8 α-chain. Any arrangement of the component polynucleotides is contemplated herein, including, for example, a single open reading frame that comprises, from 5' to 3', ([the polynucleotide encoding a safety switch protein]-[a polynucleotide encoding a self-cleaving peptide]-[the polynucleotide encoding a TCR β-chain]-[the polynucleotide encoding a self-cleaving polypeptide]-[the polynucleotide encoding a TCR α-chain]-[a polynucleotide encoding a self-cleaving polypeptide]-[the polynucleotide encoding a CD8 β-chain that contains an RQR polypeptide]-[a polynucleotide encoding a self-cleaving polypeptide]-[the polynucleotide encoding a CD8 α-chain]).

In specific embodiments, a transgene construct of the instant disclosure comprises a single open reading frame that encodes, from 5' to 3', ([an iCasp9 polypeptide]-[a P2A peptide]-[a TCR β-chain]-[a P2A peptide]-[a TCR α-chain]-[a P2A peptide]-[a CD8 β-chain comprising an RQR polypeptide]-[a P2A peptide]-[a CD8 α-chain]).

In further embodiments, a transgene construct can comprise an expression control sequence operatively linked to a polynucleotide as described herein. For example, a transgene construct can comprise an expression control sequence operatively linked to a polynucleotide that encodes a binding protein of the present disclosure, wherein the binding protein includes (a) a T cell receptor (TCR) a chain variable ($V_\alpha$) domain having an amino acid sequence encoded by a TRAV17 gene, a TRAV21 gene, or a TRAV10 gene, and a TCR β-chain variable (Vp) domain comprising a CDR3 amino acid sequence as shown in any one of SEQ ID NOS: 13-17 and 86; (b) a TCR $V_\alpha$, domain comprising a CDR3 amino acid sequence as shown in any one of SEQ ID NOS:87-92, and a TCR $V_\beta$ domain having an amino acid sequence encoded by a TRBV7-9 gene; or (c) a TCR $V_\alpha$, domain comprising a CDR3 amino acid sequence of any one of SEQ ID NOS:87-92, and a TCR $V_\beta$ domain comprising a CDR3 amino acid sequence of any one of SEQ ID NOS: 13-17 and 86, wherein the encoded binding protein is capable of specifically binding to a peptide containing an HA-$1^H$ antigen and does not bind to a peptide that does not contain an HA-$1^H$ antigen.

Also provided herein are vectors that comprise a transgene construct of the instant disclosure. Some examples of vectors include plasmids, viral vectors, cosmids, and others. Some vectors may be capable of autonomous replication in a host cell into which they are introduced (e.g., bacterial vectors having a bacterial origin of replication and episomal mammalian vectors), whereas other vectors may be integrated into the genome of a host cell or promote integration of the polynucleotide insert upon introduction into the host cell and thereby replicate along with the host genome (e.g., lentiviral vector, retroviral vector). Additionally, some vectors are capable of directing the expression of genes to which they are operatively linked (these vectors may be referred to as "expression vectors"). According to related embodiments, it is further understood that, if one or more agents (e.g., polynucleotides encoding binding proteins as described herein) are co administered to a subject, that each agent may reside in separate or the same vectors, and multiple vectors (each containing a different agent or the same agent) may be introduced to a cell or cell population or administered to a subject.

In certain embodiments, polynucleotides of the present disclosure may be operatively linked to certain elements of a vector. For example, polynucleotide sequences that are needed to effect the expression and processing of coding sequences to which they are ligated may be operatively linked. Expression control sequences may include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequences); sequences that enhance protein stability; and possibly sequences that enhance protein secretion. Expression control sequences may be operatively linked if they are contiguous with the gene of interest and expression control sequences that act in trans or at a distance to control the gene of interest.

In certain embodiments, the vector comprises a plasmid vector or a viral vector (e.g., a vector selected from lentiviral vector or a γ-retroviral vector). Viral vectors include retrovirus, adenovirus, parvovirus (e.g., adeno-associated viruses), coronavirus, negative strand RNA viruses such as ortho-myxovirus (e.g., influenza virus), rhabdovirus (e.g., rabies and vesicular stomatitis virus), paramyxovirus (e.g., measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegailovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include avian leukosis-sarcoma, mammalian C-type, B-type viruses, D type viruses, HTLV-BLV group, lentivirus, and spumavirus (Coffin, J. M., Retroviridae: The viruses and their replication, In Fundamental Virology, Third Edition, B. N. Fields et al., Eds., Lippincott-Raven Publishers, Philadelphia, 1996).

"Retroviruses" are viruses having an RNA genome, which is reverse-transcribed into DNA using a reverse transcriptase enzyme, the reverse-transcribed DNA is then incorporated into the host cell genome. "Gammaretrovirus" refers to a genus of the retroviridae family. Examples of gammaretroviruses include mouse stem cell virus, murine leukemia virus, feline leukemia virus, feline sarcoma virus, and avian reticuloendotheliosis viruses. "Lentiviral vector," as used herein, means HIV-based lentiviral vectors for gene delivery, which can be integrative or non-integrative, have relatively large packaging capacity, and can transduce a range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration into the DNA of infected cells.

In certain embodiments, the viral vector can be a gammaretrovirus, e.g., Moloney murine leukemia virus (MLV)-derived vectors. In other embodiments, the viral vector can be a more complex retrovirus-derived vector, e.g., a lentivirus-derived vector. HIV-1-derived vectors belong to this category. Other examples include lentivirus vectors derived from HIV-2, FIV, equine infectious anemia virus, SIV, and Maedi-Visna virus (ovine lentivirus). Methods of using retroviral and lentiviral viral vectors and packaging cells for transducing mammalian host cells with viral particles containing TCR or CAR transgenes are known in the art and have been previous described, for example, in: U.S. Pat. No. 8,119,772; Walchli et al., *PLoS One* 6:327930, 2011; Zhao et al., *J. Immunol.* 174:4415, 2005; Engels et al., *Hum. Gene Ther.* 14:1155, 2003; Frecha et al., *Mol. Ther.* 18:1748, 2010; and Verhoeyen et al., *Methods Mol. Biol.* 506:97, 2009. Retroviral and lentiviral vector constructs and expression systems are also commercially available. Other viral vectors also can be used for polynucleotide delivery including DNA viral vectors, including, for example adenovirus-based vectors and adeno-associated virus (AAV)-based vectors; vectors derived from herpes simplex viruses (HSVs), including amplicon vectors, replication-defective HSV and attenuated HSV (Krisky et al., Gene Ther. 5:1517, 1998).

Other vectors recently developed for gene therapy uses can also be used with the compositions and methods of this disclosure. Such vectors include those derived from baculoviruses and α-viruses. (Jolly, D J. 1999. Emerging Viral Vectors. pp 209-40 in Friedmann T. ed. The Development of Human Gene Therapy. New York: Cold Spring Harbor Lab), or plasmid vectors (such as Sleeping Beauty or other transposon vectors).

When a viral vector genome comprises a plurality of polynucleotides to be expressed in a host cell as separate transcripts, the viral vector may also comprise additional sequences between the two (or more) transcripts allowing for bicistronic or multicistronic expression. Examples of such sequences used in viral vectors include internal ribosome entry sites (IRES), furin cleavage sites, viral 2A peptide, or any combination thereof.

In certain embodiments, a vector is capable of delivering the transgene construct to a host cell (e.g., a hematopoietic progenitor cell or a human immune system cell). In specific embodiments, a vector is capable of delivering a transgene construct to human immune system cell, such as, for example, a $CD4^+$ T cell, a $CD8^+$ T cell, a $CD4^-$ $CD8^-$ double negative T cell, a γδ T cell, a natural killer cell, a dendritic cell, or any combination thereof. In further embodiments, a vector is capable of delivering a transgene construct to a naïve T cell, a central memory T cell, an effector memory T cell, or any combination thereof. In some embodiments, a vector that encodes a polynucleotide or transgene construct of the present disclosure may further comprise a polynucleotide that encodes a nuclease that can be used to perform a chromosomal knockout in a host cell (e.g., a CRISPR-Cas endonuclease or another endonuclease as disclosed herein) or that can be used to to deliver a therapeutic transgene or portion thereof to a host cell in a gene therapy replacement or gene repair therapy. Alternatively, a nuclease used for a chromosomal knockout or a gene replacement or gene repair therapy can be delivered to a host cell independent of a vector that encodes a polynucleotide or transgene construct of this disclosure.

Uses

In still other aspects, the present disclosure provides methods for treating or for preventing a relapse of a hyperproliferative disorder characterized by expression of an HA-1 antigen in a subject, the method comprising administering to the subject a unit dose comprising an engineered immune cell of this disclosure (or a composition comprising an engineered immune cell), thereby treating the hyperproliferative disorder.

"Treat" or "treatment" or "ameliorate" refers to medical management of a disease, disorder, or condition of a subject (e.g., a human or non-human mammal, such as a primate, horse, cat, dog, goat, mouse, or rat). In general, an appropriate dose or treatment regimen comprising an engineered immune cell of the present disclosure, and optionally an adjuvant, is administered in an amount sufficient to elicit a therapeutic or prophylactic benefit. Therapeutic or prophylactic/preventive benefit includes improved clinical outcome; lessening or alleviation of symptoms associated with a disease; decreased occurrence of symptoms; improved quality of life; longer disease-free status; diminishment of extent of disease, stabilization of disease state; delay of disease progression; remission; survival; prolonged survival; or any combination thereof.

A "therapeutically effective amount" or "effective amount", as used herein, refers to an amount of engineered immune cells sufficient to result in a therapeutic effect, including improved clinical outcome; lessening or alleviation of symptoms associated with a disease; decreased occurrence of symptoms; improved quality of life; longer disease-free status; diminishment of extent of disease, stabilization of disease state; delay of disease progression; remission; survival; or prolonged survival in a statistically significant manner. When referring to an individual active ingredient or a cell expressing a single active ingredient, administered alone, a therapeutically effective amount refers to the effects of that ingredient or cell expressing that ingredient alone. When referring to a combination, a therapeutically effective amount refers to the combined amounts of active ingredients or combined adjunctive active ingredient with a cell expressing an active ingredient that results in a therapeutic effect, whether administered serially or simultaneously. A combination may also be a cell expressing more than one active ingredient.

The term "pharmaceutically acceptable excipient or carrier" or "physiologically acceptable excipient or carrier" refer to biologically compatible vehicles, e.g., physiological saline, which are described in greater detail herein, that are suitable for administration to a human or other non-human mammalian subject and generally recognized as safe or not causing a serious adverse event.

As used herein, "statistically significant" refers to a p value of 0.050 or less when calculated using the Students t-test and indicates that it is unlikely that a particular event or result being measured has arisen by chance.

The presently disclosed methods may be useful to, for example, treat or prevent a relapse of a hyperproliferative disorder characterized by expression of HA-1 antigen in a subject, wherein the HA-$1^H$ antigen is present in an HLA complex expressed by hyperproliferating cells in the subject.

Examples of hyperproliferative disorders characterized by HA-$1^H$:HLA complexes include hematological malignancies. In certain embodiments, the hematological malignancy comprises a leukemia (e.g., an acute leukemia or a chronic leukemia). In specific embodiments, the leukemia comprises acute myeloid leukemia (AML), acute lymphocytic leukemia (ALL), mixed phenotype acute leukemia (MPAL), chronic myeloid leukemia (CML), B cell prolymphocytic leukemia, hairy cell leukemia, or chronic lymphocytic leukemia (CLL). In certain embodiments, the hematological malignancy comprises a lymphoma. In certain embodiments, the lymphoma comprises Hodgkin's lymphoma (HL), non-Hodgkin's lymphoma (NHL), a central nervous system lymphoma, small lymphocytic lymphoma (SLL), CD37+ dendritic cell lymphoma, lymphoplasmacytic lymphoma, splenic marginal zone lymphoma, plasma cell myeloma, extraosseous plasmacytoma, extra-nodal marginal zone B-cell lymphoma of mucosa-associated (MALT) lymphoid tissue, nodal marginal zone B-cell lymphoma, follicular lymphoma, mantle cell lymphoma, diffuse large B-cell lymphoma, mediastinal (thymic) large B-cell lymphoma, precursor B-lymphoblastic lymphoma, immunoblastic large cell lymphoma, intravascular large B-cell lymphoma, primary effusion lymphoma, Burkitt's lymphoma/leukemia, B-cell proliferations of uncertain malignant potential, lymphomatoid granulomatosis, and post-transplant lymphoproliferative disorder. In certain embodiments, the hematological malignancy comprises a myelodysplastic disorder, such as, for example, refractory cytopenia with unilineage dysplasia (refractory anemia, refractory neutropenia, and refractory thrombocytopenia), refractory anemia with ring sideroblasts (RARS), refractory anemia with ring sideroblasts—thrombocytosis (RARS-t), refractory cytopenia with multinieage dysplasia (RCMD), refractory cytopenia with multinieage dysplasia and ring sideroblasts (RCMD-RS), refractory anemia with excess blasts (RAEB), myelodysplasia unclassifiable, and refractory cytopenia of childhood. In further embodiments, the hematological malignancy comprises a myeloma. Subjects that can be treated by the present invention are, in general, human and other primate subjects, such as monkeys and apes for veterinary medicine purposes. In any of the aforementioned embodiments, the subject may be a human subject. The subjects can be male or female and can be any suitable age, including infant, juvenile, adolescent, adult, and geriatric subjects. Cells according to the present disclosure may be administered in a manner appropriate to the disease, condition, or disorder to be treated as determined by persons skilled in the medical art. In any of the above embodiments, an engineered immune cell or unit dose as described herein is administered intravenously, intraperitoneally, intratumorally, into the bone marrow, into a lymph node, or into the cerebrospinal fluid so as to encounter target cells (e.g., leukemia cells). An appropriate dose, suitable duration, and frequency of administration of the compositions will be determined by such factors as a condition of the patient; size, type, and severity of the disease, condition, or disorder; the particular form of the active ingredient; and the method of administration.

The amount of cells in a composition or unit dose is at least one cell (for example, one engineered $CD8^+$ T cell subpopulation; one engineered $CD4^+$ T cell subpopulation) or is more typically greater than $10^2$ cells, for example, up to $10^6$, up to $10^7$, up to $10^8$ cells, up to $10^9$ cells, or more than $10^{10}$ cells. In certain embodiments, the cells are administered in a range from about 106 to about $10^{10}$ cells/$m^2$, preferably in a range of about $10^5$ to about $10^9$ cells/$m^2$. The number of cells will depend upon the ultimate use for which the composition is intended as well the type of cells included therein. For example, cells modified to contain a fusion protein specific for a particular antigen will comprise a cell population containing at least 30%, 35%, 40%, 45%, 50%, 55%, 60%, 65%, 70%, 75%, 80%, 85%, 90%, 95% or more of such cells. For uses provided herein, cells are generally in a volume of a liter or less, 500 mls or less, 250 mls or less, or 100 mls or less. In embodiments, the density of the desired cells is typically greater than 104 cells/ml and generally is greater than 107 cells/ml, generally $10^8$ cells/ml or greater. The cells may be administered as a single infusion or in multiple infusions over a range of time. A clinically relevant number of immune cells can be apportioned into multiple infusions that cumulatively equal or exceed $10^6$, $10^7$, $10^8$, $10^9$, $10^{10}$, or $10^{11}$ cells. In certain embodiments, a unit dose of the engineered immune cells can be co-administered with (e.g., simultaneously or contemporaneously) hematopoietic stem cells from an allogeneic donor (e.g., a donor that is $HA1^R$-negative, HLA-A2-negative, or both).

Also contemplated are pharmaceutical compositions (i.e., compositions) that engineered immune cells as disclosed herein and a pharmaceutically acceptable carrier, diluents, or excipient. Suitable excipients include water, saline, dextrose, glycerol, or the like and combinations thereof. In embodiments, compositions comprising fusion proteins or host cells as disclosed herein further comprise a suitable infusion media. Suitable infusion media can be any isotonic medium formulation, typically normal saline, Normosol R (Abbott) or Plasma-Lyte A (Baxter), 5% dextrose in water, Ringer's lactate can be utilized. An infusion medium can be supplemented with human serum albumin or other human serum components.

Pharmaceutical compositions may be administered in a manner appropriate to the disease or condition to be treated (or prevented) as determined by persons skilled in the medical art. An appropriate dose and a suitable duration and frequency of administration of the compositions will be determined by such factors as the health condition of the patient, size of the patient (i.e., weight, mass, or body area), the type and severity of the patient's condition, the particular form of the active ingredient, and the method of administration. In general, an appropriate dose and treatment regimen provide the composition(s) in an amount sufficient to provide therapeutic and/or prophylactic benefit (such as described herein, including an improved clinical outcome, such as more frequent complete or partial remissions, or longer disease-free and/or overall survival, or a lessening of symptom severity).

An effective amount of a pharmaceutical composition refers to an amount sufficient, at dosages and for periods of time needed, to achieve the desired clinical results or beneficial treatment, as described herein. An effective amount may be delivered in one or more administrations. If the administration is to a subject already known or confirmed to have a disease or disease-state, the term "therapeutic amount" may be used in reference to treatment, whereas "prophylactically effective amount" may be used to describe administrating an effective amount to a subject that is susceptible or at risk of developing a disease or disease-state (e.g., recurrence) as a preventative course.

The pharmaceutical compositions described herein may be presented in unit-dose or multi-dose containers, such as sealed ampoules or vials. Such containers may be frozen to preserve the stability of the formulation until infusion into the patient. In certain embodiments, a unit dose comprises an engineered immune cell as described herein at a dose of about $10^7$ cells/$m^2$ to about $10^{11}$ cells/$m^2$. The development of suitable dosing and treatment regimens for using the particular compositions described herein in a variety of treatment regimens, including e.g., parenteral or intravenous administration or formulation.

If the subject composition is administered parenterally, the composition may also include sterile aqueous or oleaginous solution or suspension. Suitable non-toxic parenterally acceptable diluents or solvents include water, Ringer's solution, isotonic salt solution, 1,3-butanediol, ethanol, propylene glycol or polythethylene glycols in mixtures with water. Aqueous solutions or suspensions may further comprise one or more buffering agents, such as sodium acetate, sodium citrate, sodium borate or sodium tartrate. Of course, any material used in preparing any dosage unit formulation should be pharmaceutically pure and substantially non-toxic in the amounts employed. In addition, the active compounds may be incorporated into sustained-release preparation and formulations. Dosage unit form, as used herein, refers to physically discrete units suited as unitary dosages for the subject to be treated; each unit may contain a predetermined quantity of engineered immune cells or active compound calculated to produce the desired effect in association with an appropriate pharmaceutical carrier.

In general, an appropriate dosage and treatment regimen provides the active molecules or cells in an amount sufficient to provide a benefit. Such a response can be monitored by establishing an improved clinical outcome (e.g., more frequent remissions, complete or partial, or longer disease-free survival) in treated subjects as compared to non-treated subjects. Increases in preexisting immune responses to a tumor protein generally correlate with an improved clinical outcome. Such immune responses may generally be evaluated using standard proliferation, cytotoxicity or cytokine assays, which are routine.

For prophylactic use, a dose should be sufficient to prevent, delay the onset of, or diminish the severity of a disease associated with disease or disorder. Prophylactic benefit of the immunogenic compositions administered according to the methods described herein can be determined by performing pre-clinical (including in vitro and in vivo animal studies) and clinical studies and analyzing data obtained therefrom by appropriate statistical, biological, and clinical methods and techniques, all of which can readily be practiced by a person skilled in the art.

As used herein, administration of a composition refers to delivering the same to a subject, regardless of the route or mode of delivery. Administration may be effected continuously or intermittently, and parenterally. Administration may be for treating a subject already confirmed as having a recognized condition, disease or disease state, or for treating a subject susceptible to or at risk of developing such a condition, disease or disease state. Co-administration with an adjunctive therapy may include simultaneous and/or sequential delivery of multiple agents in any order and on any dosing schedule (e.g., engineered immune cells with one or more cytokines; immunosuppressive therapy such as calcineurin inhibitors, corticosteroids, microtubule inhibitors, low dose of a mycophenolic acid prodrug, or any combination thereof).

In certain embodiments, a plurality of doses of an engineered immune cell described herein is administered to the subject, which may be administered at intervals between administrations of about two to about four weeks.

Treatment or prevention methods of this disclosure may be administered to a subject as part of a treatment course or regimen, which may comprise additional treatments prior to, or after, administration of the instantly disclosed unit doses, cells, or compositions. For example, in certain embodiments, a subject receiving a unit dose of the engineered immune cell is receiving or had previously received a hematopoietic cell transplant (HCT; including myeloablative and non-myeloablative HCT). In specific embodiments, the HCT comprises donor cells that are HA-$1^{-}$, HLA-$A2^{-}$, or both, and the subject receiving the HCT donor cells is HA-$1^{+}$/HLA-$A2^{+}$. In any of the foregoing embodiments, a hematopoietic cell used in an HCT may be a "universal donor" cell that is modified to reduce or eliminate expression of one or more endogenous genes that encode a polypeptide product selected from an HLA molecule or a TCR molecule (e.g., by a chromosomal gene knockout according to the methods described herein). Techniques and regimens for performing HCT are known in the art and can comprise transplantation of any suitable donor cell, such as a cell derived from umbilical cord blood, bone marrow, or peripheral blood, a hematopoietic stem cell, a mobilized stem cell, or a cell from amniotic fluid. Accordingly, in certain embodiments, an engineered immune cell of the present disclosure can be administered with or shortly after hematopoietic stem cells in a modified HCT therapy.

In further embodiments, the subject had previously received lymphodepleting chemotherapy prior to receiving the engineered immune cells or HCT. In certain embodiments, a lymphodepleting chemotherapy comprises a conditioning regimen comprising cyclophosphamide, fludarabine, anti-thymocyte globulin, or a combination thereof.

Methods according to this disclosure may further include administering one or more additional agents to treat the disease or disorder in a combination therapy. For example, in certain embodiments, a combination therapy comprises administering an engineered immune cell with (concurrently, simultaneously, or sequentially) an immune checkpoint inhibitor. In some embodiments, a combination therapy comprises administering an engineered immune cell with an agonist of a stimulatory immune checkpoint agent. In further embodiments, a combination therapy comprises administering an engineered immune cell with a secondary therapy, such as chemotherapeutic agent, a radiation therapy, a surgery, an antibody, or any combination thereof.

As used herein, the term "immune suppression agent" or "immunosuppression agent" refers to one or more cells, proteins, molecules, compounds or complexes providing inhibitory signals to assist in controlling or suppressing an immune response. For example, immune suppression agents include those molecules that partially or totally block immune stimulation; decrease, prevent or delay immune activation; or increase, activate, or up regulate immune suppression. Exemplary immunosuppression agents to target (e.g., with an immune checkpoint inhibitor) include PD-1, PD-L1, PD-L2, LAG3, CTLA4, B7-H3, B7-H4, CD244/2B4, HVEM, BTLA, CD160, TIM3, GAL9, KIR, PVR1G (CD112R), PVRL2, adenosine, A2aR, immunosuppressive cytokines (e.g., IL-10, IL-4, IL-1RA, IL-35), IDO, arginase, VISTA, TIGIT, LAIR1, CEACAM-1, CEACAM-3, CEACAM-5, Treg cells, or any combination thereof.

An immune suppression agent inhibitor (also referred to as an immune checkpoint inhibitor) may be a compound, an antibody, an antibody fragment or fusion polypeptide (e.g., Fc fusion, such as CTLA4-Fc or LAG3-Fc), an antisense molecule, a ribozyme or RNAi molecule, or a low molecular weight organic molecule. In any of the embodiments disclosed herein, a method may comprise an engineered immune cell with one or more inhibitor of any one of the following immune suppression components, singly or in any combination.

In certain embodiments, an engineered immune cell is used in combination with a PD-1 inhibitor, for example a PD-1-specific antibody or binding fragment thereof, such as pidilizumab, nivolumab, pembrolizumab, MEDI0680 (formerly AMP-514), AMP-224, BMS-936558 or any combination thereof. In further embodiments, an engineered immune cell of the present disclosure (or an engineered host cell expressing the same) is used in combination with a PD-L1 specific antibody or binding fragment thereof, such as BMS-936559, durvalumab (MEDI4736), atezolizumab (RG7446), avelumab (MSB0010718C), MPDL3280A, or any combination thereof.

In certain embodiments, an engineered immune cell of the present disclosure is used in combination with a LAG3 inhibitor, such as LAG525, IMP321, IMP701, 9H12, BMS-986016, or any combination thereof.

In certain embodiments, an engineered immune cell is used in combination with an inhibitor of CTLA4. In particular embodiments, an engineered immune cell is used in combination with a CTLA4 specific antibody or binding fragment thereof, such as ipilimumab, tremelimumab, CTLA4-Ig fusion proteins (e.g., abatacept, belatacept), or any combination thereof.

In certain embodiments, an engineered immune cell is used in combination with a B7-H3 specific antibody or binding fragment thereof, such as enoblituzumab (MGA271), 376.96, or both. A B7-H4 antibody binding fragment may be a scFv or fusion protein thereof, as described in, for example, Dangaj et al., *Cancer Res.* 73:4820, 2013, as well as those described in U.S. Pat. No. 9,574,000 and PCT Patent Publication Nos. WO/201640724A1 and WO 2013/025779A1.

In certain embodiments, an engineered immune cell is used in combination with an inhibitor of CD244.

In certain embodiments, an engineered immune cell is used in combination with an inhibitor of BLTA, HVEM, CD160, or any combination thereof. Anti CD-160 antibodies are described in, for example, PCT Publication No. WO 2010/084158.

In certain embodiments, an engineered immune cell is used in combination with an inhibitor of TIM3.

In certain embodiments, an engineered immune cell is used in combination with an inhibitor of Gal9.

In certain embodiments, an engineered immune cell is used in combination with an inhibitor of adenosine signaling, such as a decoy adenosine receptor.

In certain embodiments, an engineered immune cell is used in combination with an inhibitor of A2aR.

In certain embodiments, an engineered immune cell is used in combination with an inhibitor of KIR, such as lirilumab (BMS-986015).

In certain embodiments, an engineered immune cell is used in combination with an inhibitor of an inhibitory cytokine (typically, a cytokine other than TGFβ) or Treg development or activity.

In certain embodiments, an engineered immune cell is used in combination with an IDO inhibitor, such as levo-1-methyl tryptophan, epacadostat (INCB024360; Liu et al., *Blood* 115:3520-30, 2010), ebselen (Terentis et al., *Biochem.* 49:591-600, 2010), indoximod, NLG919 (Mautino et al., American Association for Cancer Research 104th Annual Meeting 2013; Apr. 6-10, 2013), 1-methyl-tryptophan (1-MT)-tira-pazamine, or any combination thereof.

In certain embodiments, an engineered immune cell is used in combination with an arginase inhibitor, such as N(omega)-Nitro-L-arginine methyl ester (L-NAME), N-omega-hydroxy-nor-1-arginine (nor-NOHA), L-NOHA, 2(S)-amino-6-boronohexanoic acid (ABH), S-(2-boronoethyl)-L-cysteine (BEC), or any combination thereof.

In certain embodiments, an engineered immune cell is used in combination with an inhibitor of VISTA, such as CA-170 (Curis, Lexington, Mass.).

In certain embodiments, an engineered immune cell is used in combination with an inhibitor of TIGIT such as, for example, COM902 (Compugen, Toronto, Ontario Canada), an inhibitor of CD155, such as, for example, COM701 (Compugen), or both.

In certain embodiments, an engineered immune cell is used in combination with an inhibitor of PVRIG, PVRL2, or both. Anti-PVRIG antibodies are described in, for example, PCT Publication No. WO 2016/134333. Anti-PVRL2 antibodies are described in, for example, PCT Publication No. WO 2017/021526.

In certain embodiments, an engineered immune cell is used in combination with a LAIR1 inhibitor.

In certain embodiments, an engineered immune cell is used in combination with an inhibitor of CEACAM-1, CEACAM-3, CEACAM-5, or any combination thereof.

In certain embodiments, an engineered immune cell is used in combination with an agent that increases the activity (i.e., is an agonist) of a stimulatory immune checkpoint molecule. For example an engineered immune cell can be used in combination with a CD137 (4-1BB) agonist (such as, for example, urelumab), a CD134 (OX-40) agonist (such as, for example, MEDI6469, MEDI6383, or MEDI0562), lenalidomide, pomalidomide, a CD27 agonist (such as, for example, CDX-1127), a CD28 agonist (such as, for example, TGN1412, CD80, or CD86), a CD40 agonist (such as, for example, CP-870,893, rhuCD40L, or SGN-40), a CD122 agonist (such as, for example, IL-2) an agonist of GITR (such as, for example, humanized monoclonal antibodies described in PCT Patent Publication No. WO 2016/054638), an agonist of ICOS (CD278) (such as, for example, GSK3359609, mAb 88.2, JTX-2011, Icos 145-1, Icos 314-8, or any combination thereof). In any of the embodiments disclosed herein, a method may comprise administering an engineered immune cell with one or more agonist of a stimulatory immune checkpoint molecule, including any of the foregoing, singly or in any combination.

In certain embodiments, a combination therapy comprises an engineered immune cell and a secondary therapy comprising one or more of: an antibody or antigen binding-fragment thereof that is specific for a cancer antigen expressed by the non-inflamed solid tumor, a radiation treatment, a surgery, a chemotherapeutic agent, a cytokine, RNAi, or any combination thereof.

In certain embodiments, a combination therapy method comprises administering a fusion protein and further administering a radiation treatment or a surgery. Radiation therapy is well-known in the art and includes X-ray therapies, such as gamma-irradiation, and radiopharmaceutical therapies. Surgeries and surgical techniques appropriate to treating a given cancer in a subject are well-known to those of ordinary skill in the art.

In certain embodiments, a combination therapy method comprises administering an engineered immune cell and further administering a chemotherapeutic agent. A chemotherapeutic agent includes, but is not limited to, an inhibitor of chromatin function, a topoisomerase inhibitor, a microtubule inhibiting drug, a DNA damaging agent, an antimetabolite (such as folate antagonists, pyrimidine analogs, purine analogs, and sugar-modified analogs), a DNA synthesis inhibitor, a DNA interactive agent (such as an intercalating agent), and a DNA repair inhibitor. Illustrative chemotherapeutic agents include, without limitation, the following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as *vinca* alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, Cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, temozolamide, teniposide, triethylenethiophosphoramide and etoposide (VP 16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates—busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP470, genistein) and growth factor inhibitors (vascular endothelial growth factor (VEGF) inhibitors, fibroblast growth factor (FGF) inhibitors); angiotensin receptor blocker; nitric oxide donors; antisense oligonucleotides; antibodies (trastuzumab, rituximab); chimeric antigen receptors; cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers, toxins such as Cholera toxin, ricin, *Pseudomonas* exotoxin, *Bordetella pertussis* adenylate cyclase toxin, or diphtheria toxin, and caspase activators; and chromatin disruptors.

Cytokines are increasingly used to manipulate host immune response towards anticancer activity. See, e.g., Floros & Tarhini, *Semin. Oncol.* 42(4):539-548, 2015. Cytokines useful for promoting immune anticancer or antitumor response include, for example, IFN-α, IL-2, IL-3, IL-4, IL-10, IL-12, IL-13, IL-15, IL-16, IL-17, IL-18, IL-21, IL-24, and GM-CSF, singly or in any combination with an engineered immune cell of this disclosure.

Also provided herein are methods for modulating an adoptive immunotherapy, wherein the methods comprise administering, to a subject who has previously received an engineered immune cell of the present disclosure that comprises a heterologous polynucleotide encoding a safety switch protein, a cognate compound of the safety switch protein in an amount effective to ablate in the subject the previously administered engineered immune cell.

As used herein, the term "adoptive immune therapy" or "adoptive immunotherapy" refers to administration of naturally occurring or genetically engineered, disease- or antigen-specific immune cells (e.g., T cells). Adoptive cellular immunotherapy may be autologous (immune cells are from the recipient), allogeneic (immune cells are from a donor of the same species) or syngeneic (immune cells are from a donor genetically identical to the recipient).

In certain embodiments, the safety switch protein comprises tEGFR and the cognate compound is cetuximab, or the safety switch protein comprises iCasp9 and the cognate compound is AP1903 (e.g., dimerized AP1903), or the safety switch protein comprises a RQR polypeptide and the cognate compound is rituximab, or the safety switch protein comprises a myc binding domain and the cognate compound is an antibody specific for the myc binding domain.

In still further aspects, methods are provided for manufacturing a composition, or unit dose of the present disclosure. In certain embodiments, the methods comprise combining (i) an aliquot of a host cell transduced with a vector of the present disclosure with (ii) a pharmaceutically acceptable carrier. In certain embodiments, vectors of the present disclosure are used to transfect/transduce a host cell (e.g., a T cell) for use in adoptive transfer therapy (e.g., targeting a cancer antigen).

In some embodiments, the methods further comprise, prior to the aliquotting, culturing the transduced host cell and selecting the transduced cell as having incorporated (i.e., expressing) the vector. In further embodiments, the methods comprise, following the culturing and selection and prior to the aliquotting, expanding the transduced host cell. In any of the embodiments of the instant methods, the manufactured composition or unit dose may be frozen for later use. Any appropriate host cell can be used for manufacturing a composition or unit dose according to the instant methods, including, for example, a hematopoietic stem cell, a T cell, a primary T cell, a T cell line, a NK cell, or a NK-T cell. In specific embodiments, the methods comprise a host cell which is a $CD4^+$ T cell or a $CD8^+$ T cell.

EXAMPLES

Example 1

Isolation and Cloning of HA-$1^H$-Specific TCRs

Figure 1:
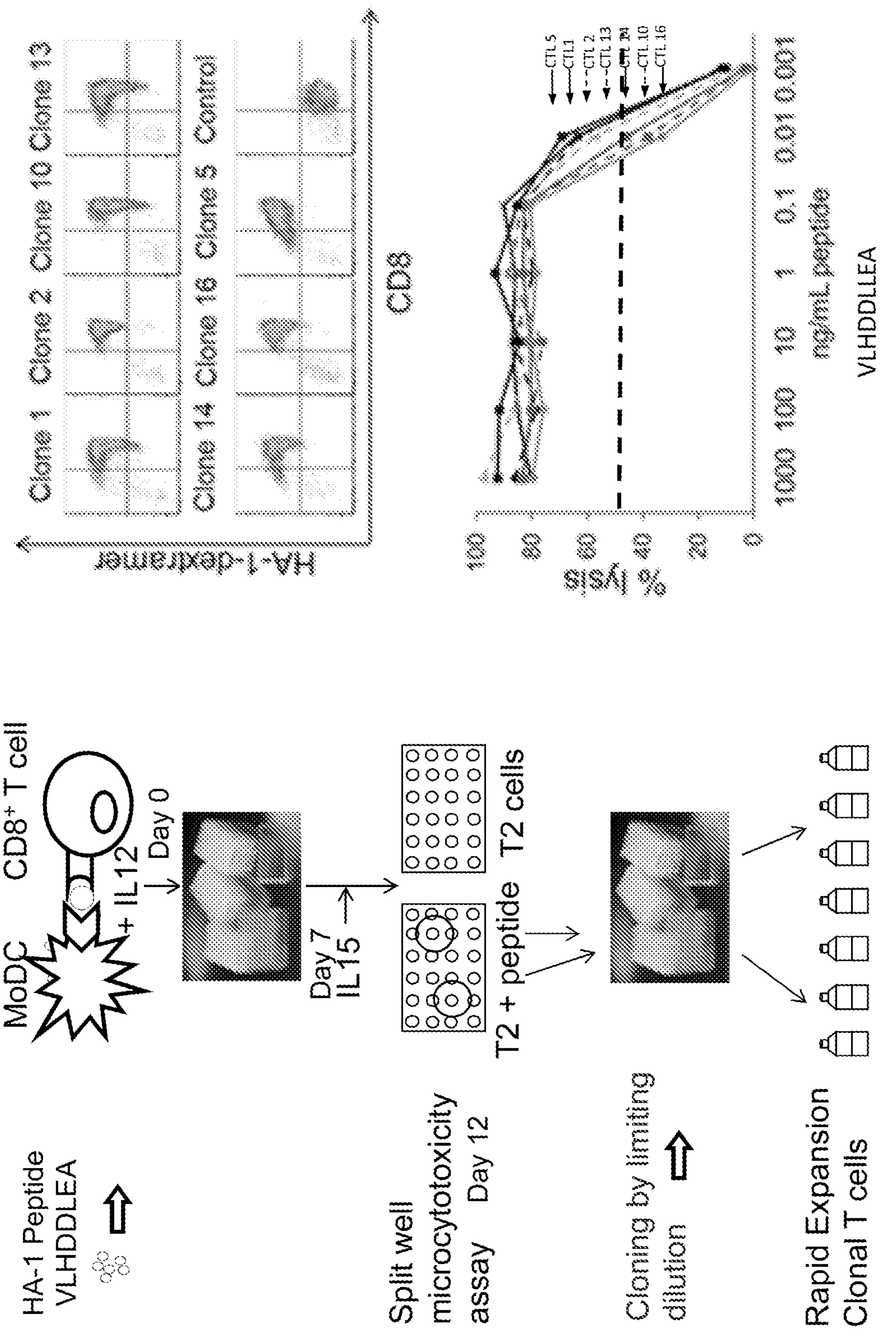
FIG. 1 depicts a process used to isolate and characterize HA-$1^H$-specific T cell clones of the present disclosure. (Top left of FIG. 1) To isolate HA-$1^H$-specific T cells, $CD8^+$ cells were primed with dendritic cells (DCs) pulsed with HA$1^H$ peptide (VLHDDLLEA; SEQ ID NO: 1) and expanded in microcultures. (Middle left) Following 12 days of incubation in CTL media containing IL-12 and IL-15, aliquots of the T cells were evaluated in a split well microcytotoxicity assay, where T2 cells were pulsed with the VLHDDLLEA peptide or not. (Bottom left) Cells that specifically reacted against the $T2^+$ VLHDDLLEA were cloned by limiting dilution, reassessed for cytotoxicity, and rapidly expended for further evaluation (8 clones). (Top right) Flow cytometry data showing HA-$1^H$ specificity of the indicated seven (7) clones. Staining for HLA-A2-HA-$1^H$ dextramer staining (y-axis) and CD8 (x-axis). (Bottom right) Data from a chromium release assay (CRA) experiment wherein the indicated CTL clones were tested for specific lysis of $^{51}$CR-labeled T2 cells pulsed with the cognate peptide at the indicated titrations.

HA-$1^H$-specific $CD8^+$ T cell clones were isolated using in vitro methods previously described (Bleakley et al., *Blood* 115:4923-4933, 2010 (FIG. 1). Specifically, $CD8^+$ T cells were isolated from HLA-$A2^+$ donor (2 donors) peripheral blood mononuclear cells (PBMC), using a $CD8^+$ T cell isolation kit and anti-CD45RO immunomagnetic beads (Miltenyi Biotec). Autologous dendritic cells (DCs) were pulsed with 1 μg/mL HA-$1^H$ peptide (VLHDDLLEA) for 3-6 hours at 37° C. Purified $CD8^+$ $T_N$ were combined in complete T lymphocyte (CTL) medium with peptide-pulsed DCs at a $T_N$ to DC ratio of 30:1, and co-cultured in 96-well plates at $6\times10^4$ T cells/well, supplemented with 10 ng/mL IL-12 from initiation and 10 ng/mL IL-15 from day 7. On day 11-13, cells were evaluated for HA-$1^H$-specific cytotoxicity in split-well micro-chromium release assays (CRA; μCRA). T cell lines that lysed T2 cells pulsed with 1 ug/mL HA-$1^H$ peptide (>20% lysis and >5 fold more lysis of peptide-pulsed versus unpulsed targets) were subsequently cloned by limiting dilution using anti-CD3 monoclonal antibody (mAb), interleukin-2 (IL-2) and feeder cells.

Figure 2A:
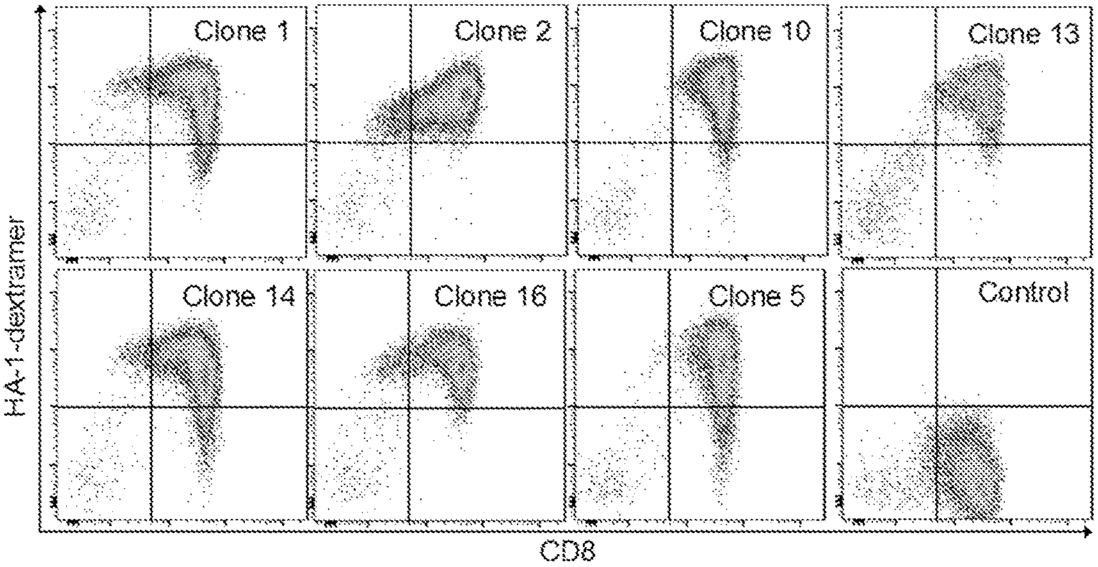
FIGS. 2A-2C show characterization of isolated cytotoxic T cell clones that were obtained using the method shown in FIG. 1. (A) HLA-A2/HA-$1^H$ multimer and $CD8^+$ monoclonal antibody staining of seven (7) representative HA-$1^H$ specific clones (1, 2, 10, 13, 4, 16, and 5) and a control clone specific for another tumor antigen. (B) Data from a chromium release assay in which the seven HA-$1^H$-specific clones were tested for killing HA-1 peptide-pulsed target cells. (C) Data from cytotoxicity assays in which the HA-$1^H$-specific CTL clones were incubated with peptide-pulsed T2 cells, HA-$1^{H+}$ AML cell line THP-1, HA-$1^{H+}$ primary AML, or HA-$1^-$ AML.

Clones were screened by μCRA on day 11-13. T cell clones from wells showing specific cytotoxicity, using the above criteria, were expanded using anti-CD3 mAb, IL-2 and feeder cells, by the Rapid Expansion Protocol (REP). The specificity of expanded clones was evaluated by CRA, HA-1/HLA-A2 multimer staining, and intracellular cytokine staining (ICC). The HA-$1^H$ specificity of the CTL clones was verified with HA-$1^H$/HLA A2 multimers. In particular, HLA-A2/HA-$1^H$ multimer and $CD8^+$ monoclonal antibody (mAb) were used to stain HA-1 specific clones (clones 1, 2, 10, 13, 14, 16, and 5) and a control clone specific for another tumor antigen (FIG. 2A).

Figure 2B:
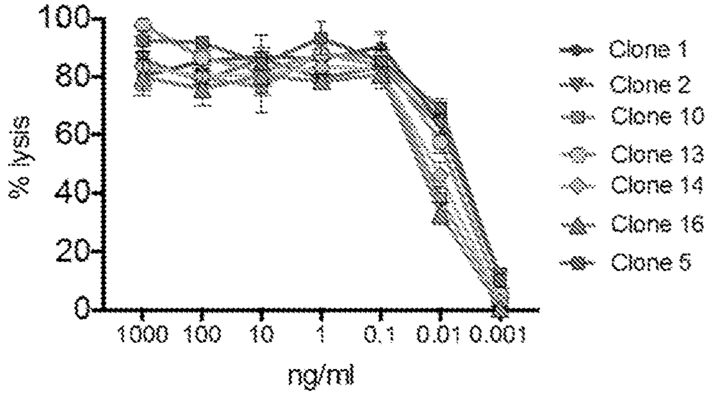
Figure 2C:
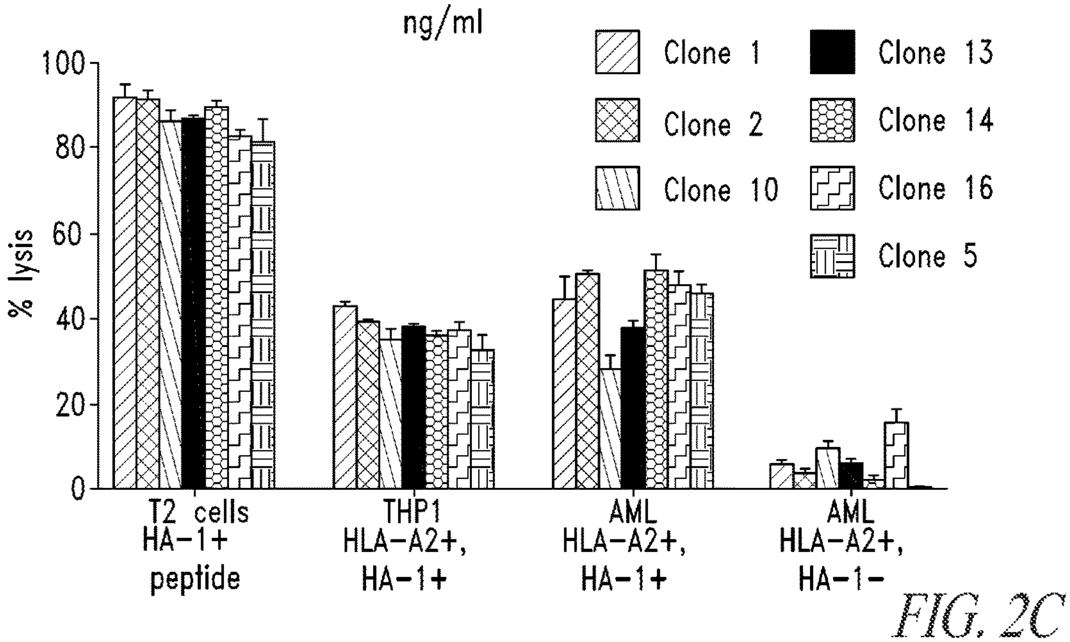
Figure 3:
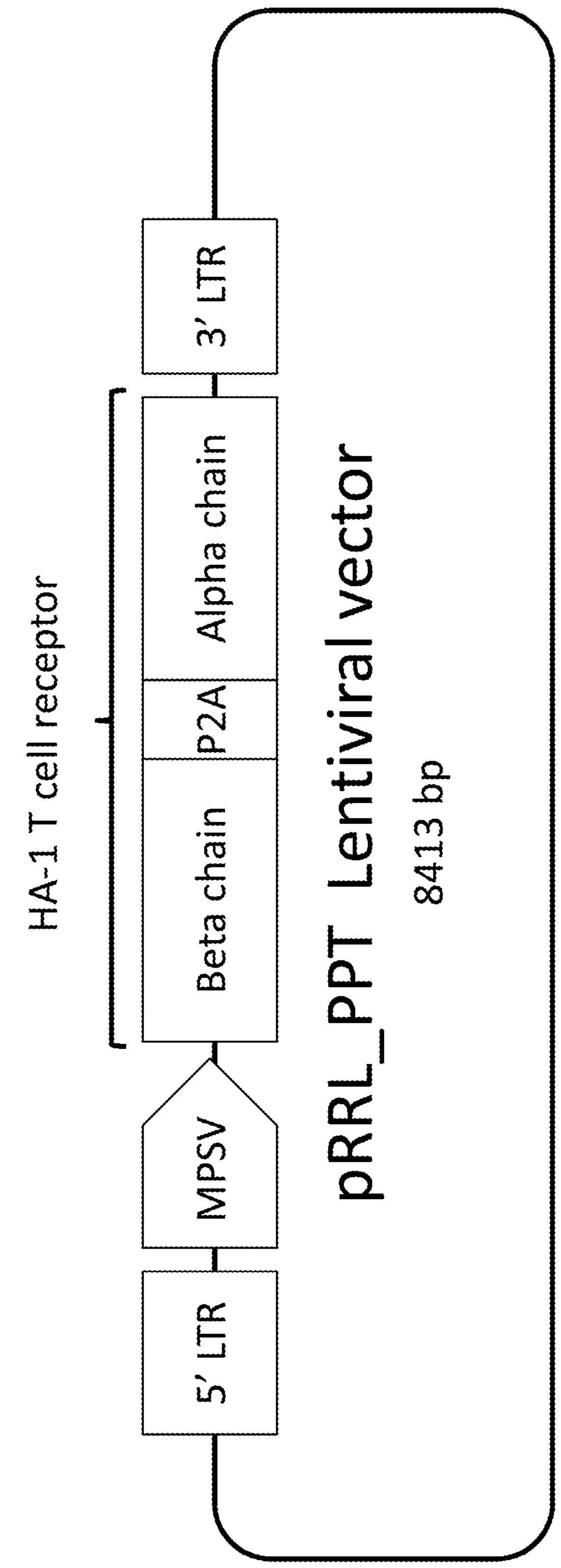
FIG. 3 depicts a representative HA-$1^H$ TCR-encoding lentiviral construct of the present disclosure.

In addition, a chromium release assay (CRA) was used to test 7 of the HA-1-specific CTL clones (1, 2, 10, 13, 14, 16 and 5) for killing of HA-$1^H$ peptide-pulsed targets. The T cell clones recognized HA-$1^H$ peptide (VLHDDLLEA)-pulsed target cells at very low peptide concentrations and half-maximal lysis is seen at a peptide concentration of 10 pM. (FIG. 2B) (ICC data not shown). Cytotoxicity of the isolated clones against cells with or without endogenous HA-$1^H$ expression was also examined. The assays show 7 HA-$1^H$-specific CTL clones (TCR1, TCR2, TCR10, TCR13, TCR14, TCR16 and TCR5) lysing HA-$1^{H+}$ acute myeloid leukemia (AML) cell line (THP-1) and HA-$1^{H+}$ primary AML but not HA-$1^{H-}$ AML (FIG. 2C).

Next, the isolated HA-$1^H$ TCRs were cloned. The TCR $V_\beta$ and $V_\alpha$, genes of the 8 CTL were sequenced and 6 distinct TCRs were identified (TCR1 and TCR13 were found to be identical, as were TCR2 and TCR14). The genes (and specific alleles) encoding the 6 TCRs, as well as the $V_\beta$ CDR3 amino acid sequences of the TCRs, are shown in Table 1:

A seventh TCR, "TCR29" was also identified and sequenced. After sequencing, the genes encoding the HA-$1^H$ TCRs (except for TCR24, which had poor function in transduced $CD8^+$ T cells) were codon optimized to maximize expression and cysteine modifications were introduced and to reduce the risk of mispairing with endogenous TCR chains, as described below. The nucleotide sequences of the CTL clone TCRβ and TCRα genes after codon optimization and cysteine modification are provided in SEQ ID NOs 39-48 and 51-52.

RNA was extracted from each HA-$1^H$-specific T cell clone. 5'-first-strand cDNA amplification and Rapid Amplification of cDNA Ends (RACE) PCR were performed to identify full-length TCR regions, using a SMARTer RACE cDNA Amplification Kit (Clontech Laboratories). cDNA was synthesized from RNA using 5' CDS Primer A, SMARTer IIA oligo and SMARTScribe Reverse Transcriptase. Subsequently, the cDNA was used to perform a RACE PCR reaction, using Phusion® High Fidelity DNA polymerase, and Gene-Specific Primers for the TCR alpha (α)-(5'-GGTGAATAGGCAGACAGACTT-3') (SEQ ID NO:93) or TCR beta (β)-chain (GTGGCCAGGCACACCAGTGT) (SEQ ID NO:94). The RACE PCR product was purified and sequenced to identify the TCR α- and β-chains. IMGT/V-QUEST was used to define the TCR variable (V), diversity (D) and joining (J) regions.

Complementary cysteine residues at positions 48 (Thr to Cys) and 57 (Ser to Cys) were incorporated into the constant domains of the TCR α and β genes to increase exogenous TCR pairing and decrease mispairing with the endogenous TCR. To ensure coordinated gene expression, the TCR chains were separated by 2A elements from the porcine teschovirus (P2A). The transgenes were codon-optimized to enhance expression and synthesized by GeneArt (Life Technologies), and were cloned into the pRRLSIN-.cPPT.MSCV.WPRE LV vector by restriction digestion and ligation. The amino acid sequences of the encoded TCR constructs are provided in SEQ ID NOS: 53-57.

TABLE 1

Genes and βCDR3 sequences of isolated TCRs

| | Alpha | | Beta | | | |
|---|---|---|---|---|---|---|
| | V gene | J gene | V gene | D gene | J gene | CDR3 (aa) |
| TCR 1 | TRAV17*01 F | TRAJ28*01 F | TRVB7-9*03 | TRBD1*01 | TRBJ21*01 | CASSSTGGHNEQFF |
| TCR 13 | TRAV17*01 F | TRAJ28*01 F | TRVB7-9*03 | TRBD1*01 | TRBJ21*01 | CASSSTGGHNEQFF |
| TCR 2 | TRAV21*02 F | TRAJ40*01 F | TRVB7-9*03 | TRBD1*01 | TRBJ1-4*01 | CASSLVKGEKLFF |
| TCR 14 | TRAV21*02 F | TRAJ40*01 F | TRVB7-9*03 | TRBD1*01 | TRBJ1-4*01 | CASSLVKGEKLFF |
| TCR 10 | TRAV10*01F | TRAG45*01 F | TRVB7-9*03 | TRBD2*01 | TRBJ27*01 | CASSMLTNYEQYF |
| TCR 16 | TRAV21*01 or *02 | TRAF20*01 F | TRVB7-9*03 | TRBD1*01 F | TRBJ21*01 | CASSLVVGNEQFF |
| TCR 5 | TRAV17 | TRAJ29 | TRVB7-9*03 | TRBD1/2 | TRBJ2-7 | CASSLTTLDEQY |
| TCR 24 | TRAV8-3 | TRAJ27 | TRBV15 | TRBD1*01 | TRBJ2-5 | ATSKTRIAQETQYF |

Example 2

Heterologous Expression and Activity of HA-$1^H$-Specific TCRs

Next, codon-optimized and cysteine modified TCRs were tested for expression and activity.

Figure 4:
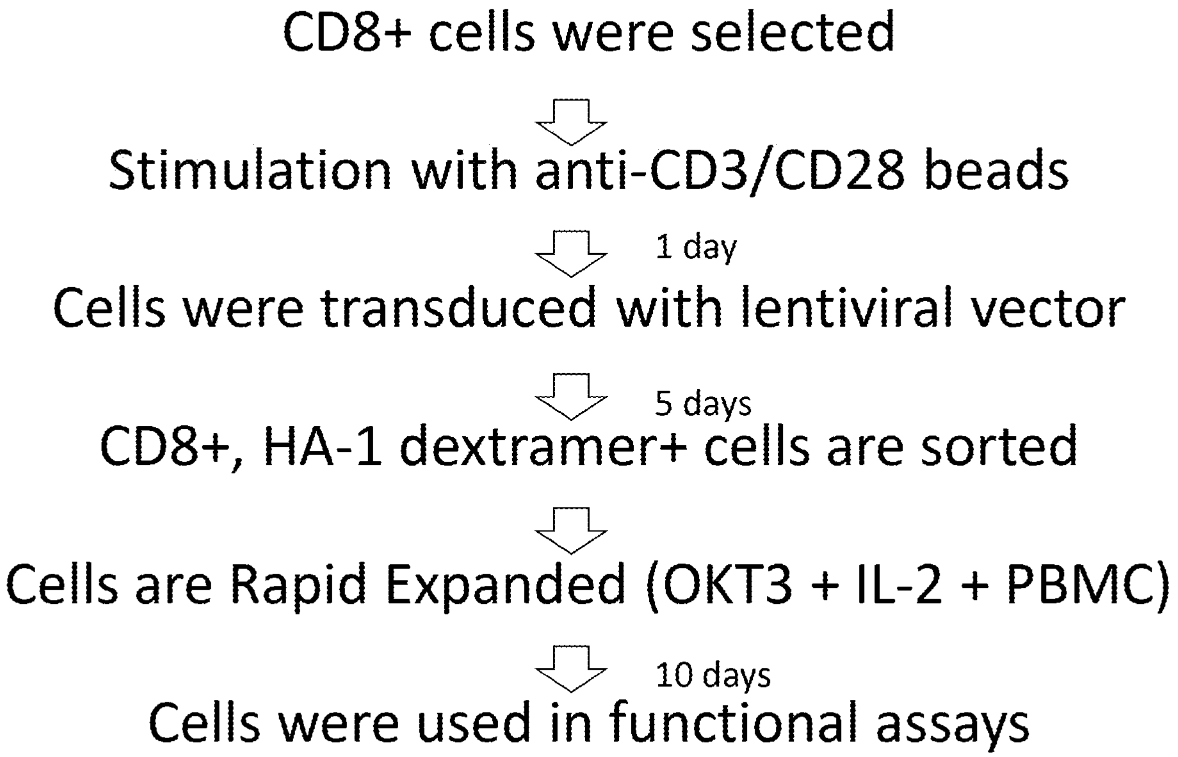
FIG. 4 shows a procedure for evaluating T cells transduced to express HA-1 TCRs.
Figure 5A:
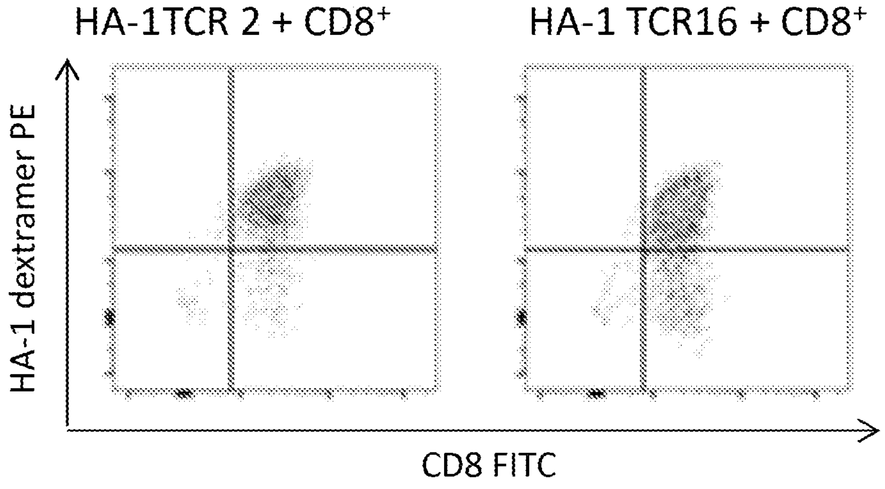
FIGS. 5A-5C show expression and activity of HA-$1^H$-transduced $CD8^+$ T cells. (A) Flow cytometry data showing HA-$1^H$ dextramer binding and CD8 expression of T cells transduced with TCR2 or TCR16. (B) Killing activity of $CD8^+$ T cells transduced with TCR2 or TCR16, as well as of the corresponding 'parental clones', i.e., the T cell clones from which TCR2 and TCR16 were isolated and of a control clone specific for a control a different antigen (SMCY). Left, lysis of HA-$1^H$-pulsed T2 cells. Right, T2 cells pulsed with irrelevant SMCY peptide. (C) Specific lysis of T2 cells pulsed with the indicated amount of HA-$1^H$ peptide (x-axis) by HA-$1^H$ TCR2 (dashed line with circles), HA-$1^H$ TCR16 (dashed line with squares), parental TCR2 clone (solid line with circles), parental TCR16 clone (solid line with squares), and a heterologous or parent clone specific for SMCY peptide (lower two lines on graph).
Figure 5B:
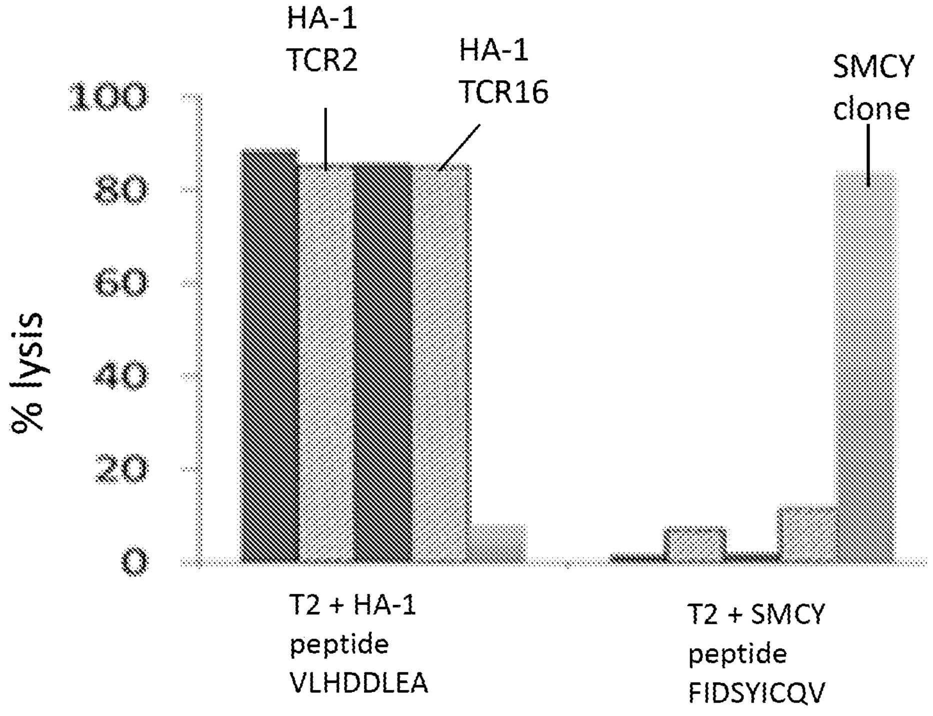
Figure 5C:
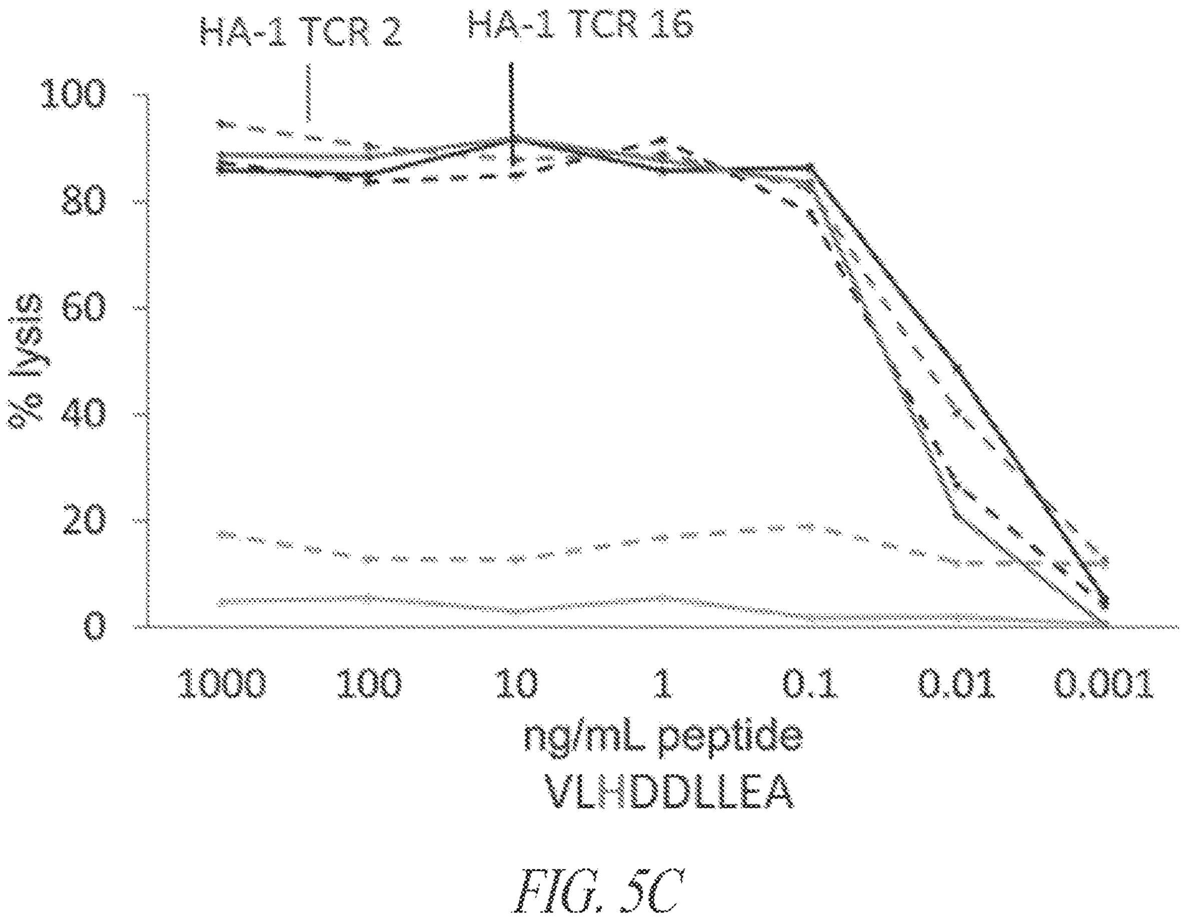
Figure 6A:
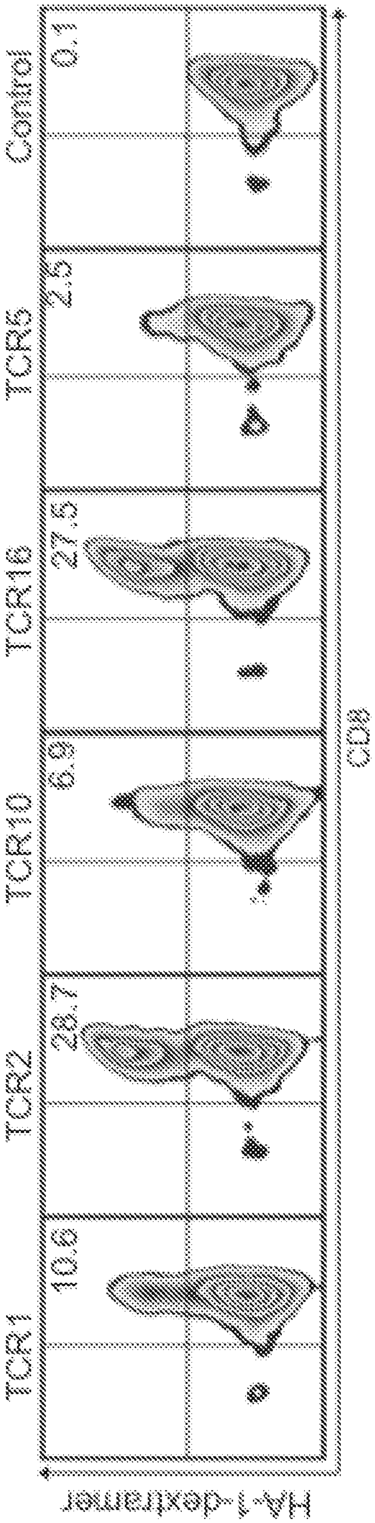
FIGS. 6A-6E show transduction and activity of the HA-$1^H$ TCRs into $CD8^+$ T cells using a lentiviral vector. (A) Flow cytometry showing HLA-A2/HA-$1^H$ multimer staining of $CD8^+$ T cells transduced to contain a polynucleotide encoding a HA-$1^H$ specific TCR (specifically, TCR clones 1, 2, 10, 16, and 5), which were delivered with a lentiviral vector (LV), or with a TCR specific for a different minor H antigen (control). (B-E) A chromium release assay (CRA) was used to evaluate specific lytic activity. (B) Lysis of T2 target cells pulsed with HA-1 peptide antigen at various concentrations by TCR-transduced $CD8^+$ T cells (solid lines and symbols-TCR2 circles, TCR16 squares), HA-$1^H$-specific T cell clones (dashed lines, open symbols-clone 2=circles, clone 16=squares), or T cell clone control (diamonds). (C) Lysis of HLA-A2$^+$HA-$1^{H+}$ LCL by $CD8^+$ T cells transduced with HA-$1^H$-specific TCR2 (circles) or HA-$1^H$-specific TCR16 (squares) at the indicated effector: target (E:T) ratios. (D) Lysis of HLA-A2$^+$/HA-$1^+$ homozygous (H/H) (circles n=7), HLA-A2$^+$/HA1$^{H+}$ heterozygous (H/R) (square n=22), HLA-A2$^+$/HA-$1^{H-}$ (R/R) (triangles n=17) or HLA-A2 negative (inverted triangles n=41) hematopoietic cell (LCL) targets by HA-$1^H$ TCR2 transduced $CD8^+$ T cells. (E) Lysis of LCL with common HLA alleles by HA-$1^H$ TCR2 transduced $CD8^+$ T cells. An E:T ratio of 20:1 was used unless otherwise specified. Data comparable to that shown in (D) and (E) were also obtained with HA-$1^H$ TCR16 (not shown).
Figure 6B:
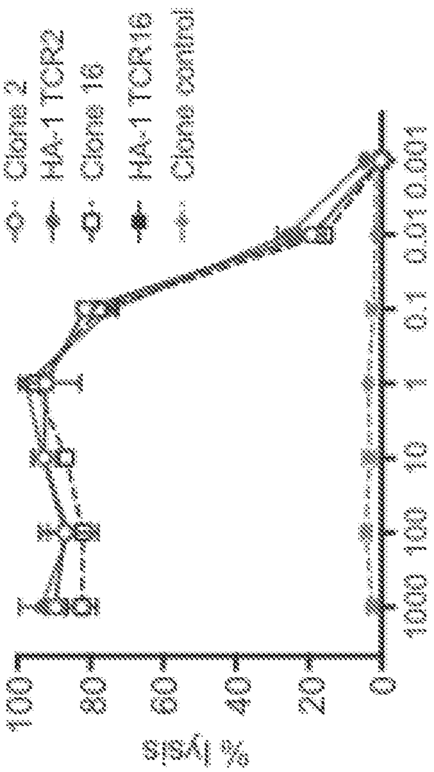
Figure 6C:
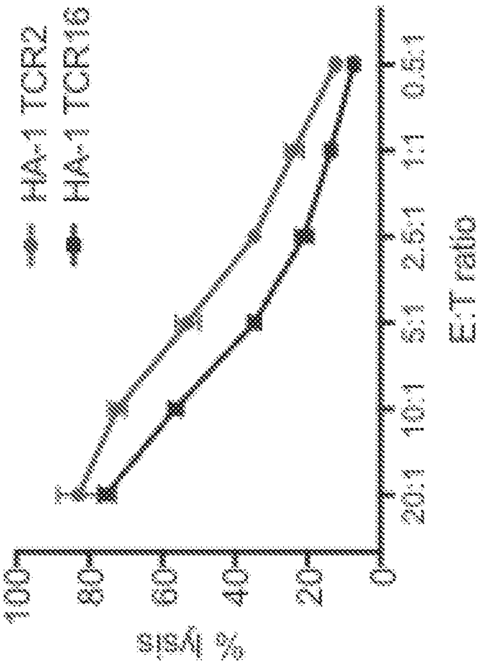
Figure 6D:
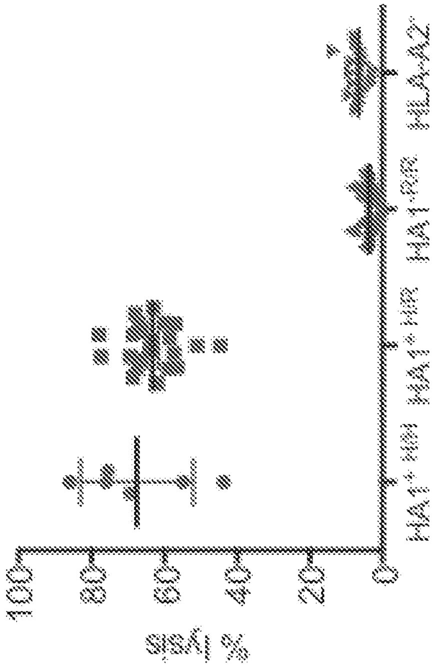
Figure 6E:
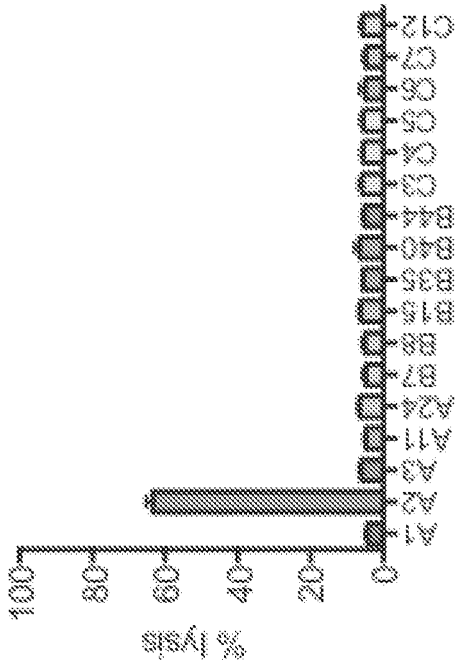
Figure 7:
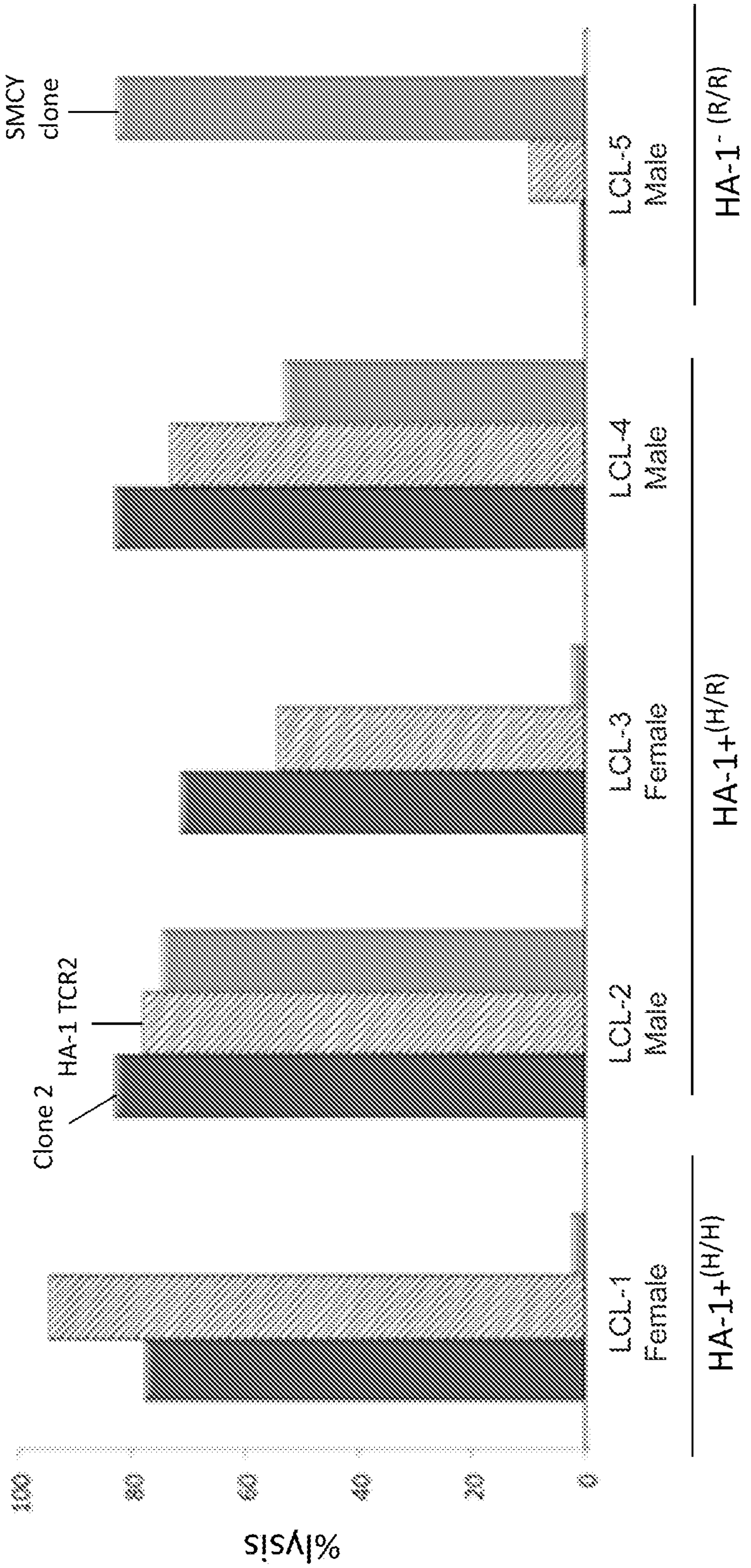
FIG. 7 provides data from cytotoxicity experiments in which target cells that endogenously express HA-1 (HA-$1^{H+}$ LCL (H/H or H/R) and HA-$1^{H-}$LCL (R/R) by were incubated with TCR2 transduced cells or with 'parental' clone 2 cells. Also shown is a control clone specific for a Y chromosome-associated minor H antigen (FIDSYICQV) (SEQ ID NO: 128).
Figure 8A:
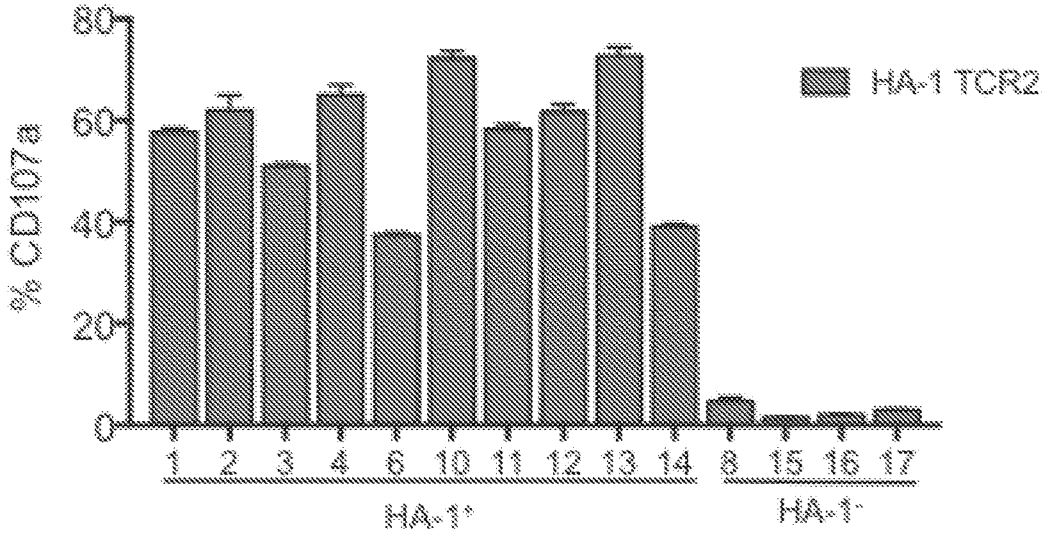
FIGS. 8A-8E show specific killing of HA-$1^+$ leukemia cells by HA-$1^H$-TCR2-transduced $CD8^+$ T cells. (A) HA-$1^H$-specific expression of CD107a on HA-$1^H$-TCR2 transduced $CD8^+$ T cells showing degranulation after 5 h co-culture (1:1) with a panel of primary AML samples. (B-E) CRA showing lysis of leukemia and lymphoma targets by HA-1 TCR-transduced $CD8^+$ T cells; (B) Lysis of primary HA-$1^{H+}$ AML or HA-$1^-$ AML by HA-$1^H$TCR-transduced $CD8^+$ T cells (dark grey bars) and HA-$1^H$-specific T cell clone 2 (light grey bars); (C) HLA-A2$^+$/HA-$1^{H+}$ primary AML (AML1) at various E:T ratios; (D) B-ALL lines (1) BALL-1, (2) RS4; 11, T-ALL lines (1) MOLT4, (2) CEM (3) RPMI-8402 (4) HSB-2 and AML line NB-4; (E) T cell lymphoma (SUP-M2 HLA-A2$^+$, HA-$1^+$; SU-DHL-1 HLA-A2$^+$ HA-$1^-$) cell lines. In (D) HLA-A2$^-$ and/or HA-$1^{H-}$ (WT) cell lines were transduced (TD) with LV encoding *HLA-A2 or **HLA-A2 and HA-$1^H$minigene if the WT was HLA-A2− or had a HA-$1^H$− genotoype. An E:T ratio of 20:1 was used, unless otherwise specified.
Figure 8B:
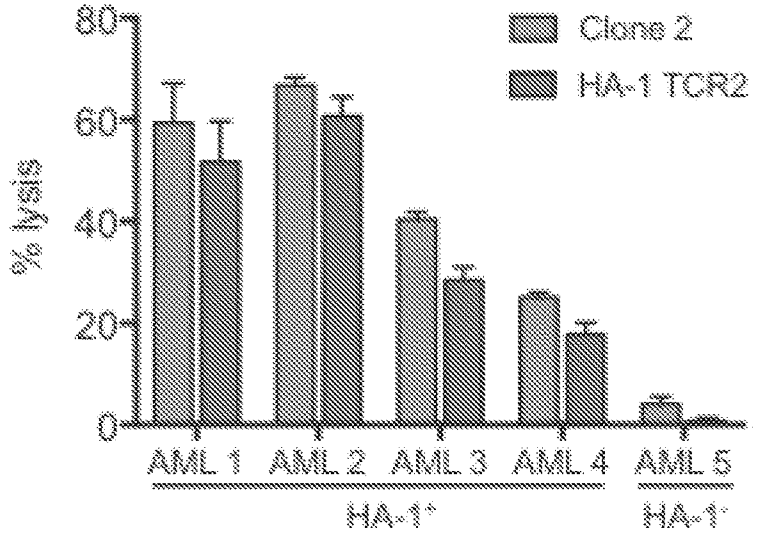
Figure 8C:
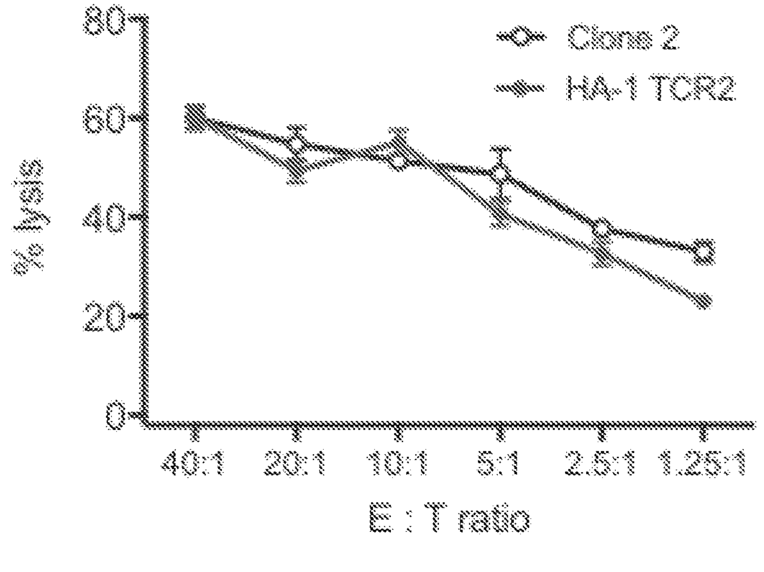
Figure 8E:
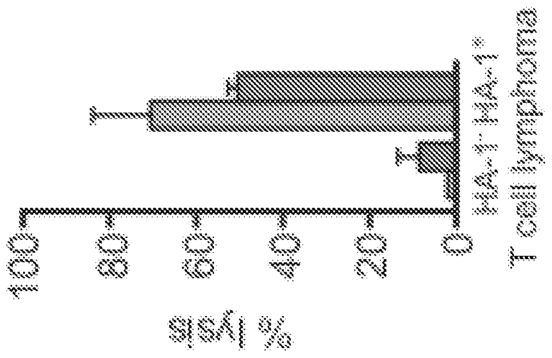
Figure 8D:
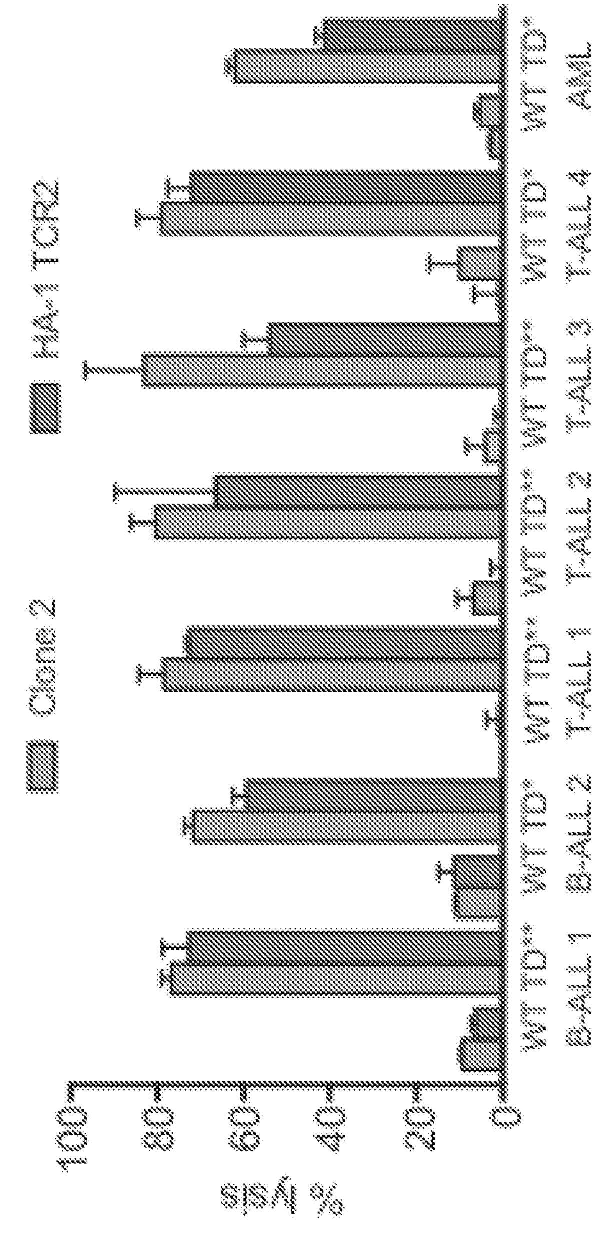
Figure 9A:
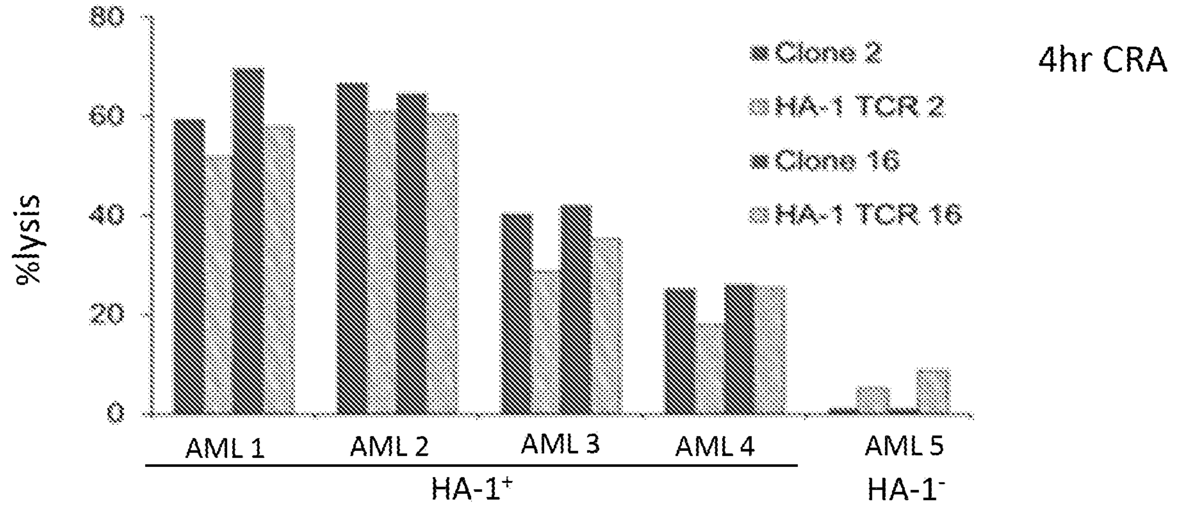
FIGS. 9A and 9B show cytotoxicity of T cells transduced with TCR2 or TCR16 (as well as of the corresponding parental clones) against HA-$1^{H+}$ or HA-$1^{H-}$ primary leukemia cells. 9A: specific lysis (4 h CRA) of the indicated cell lines. 9B: specific lysis of target cells at the indicated effector:target ratios.
Figure 9B:
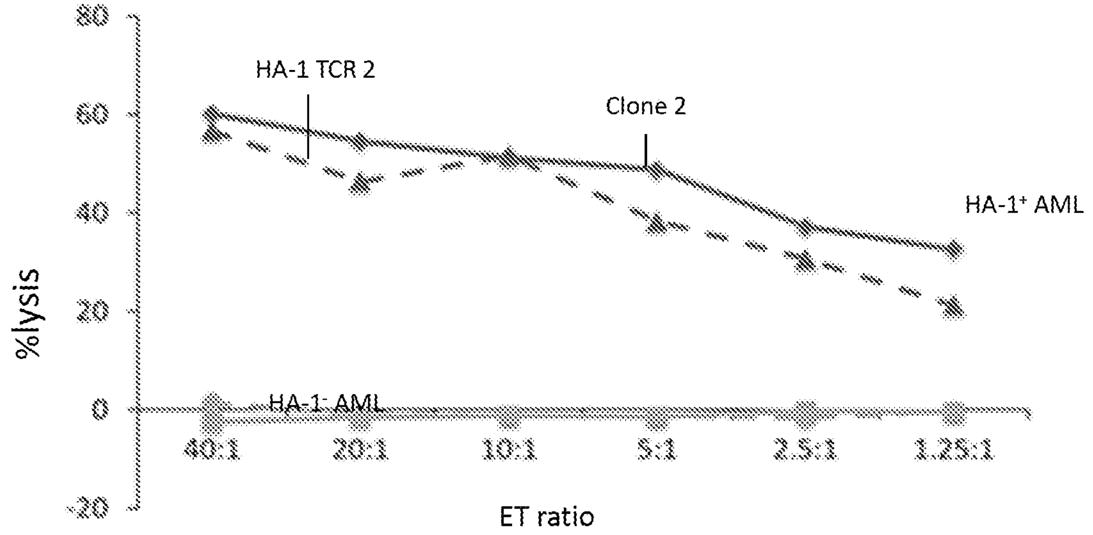
Figure 10:
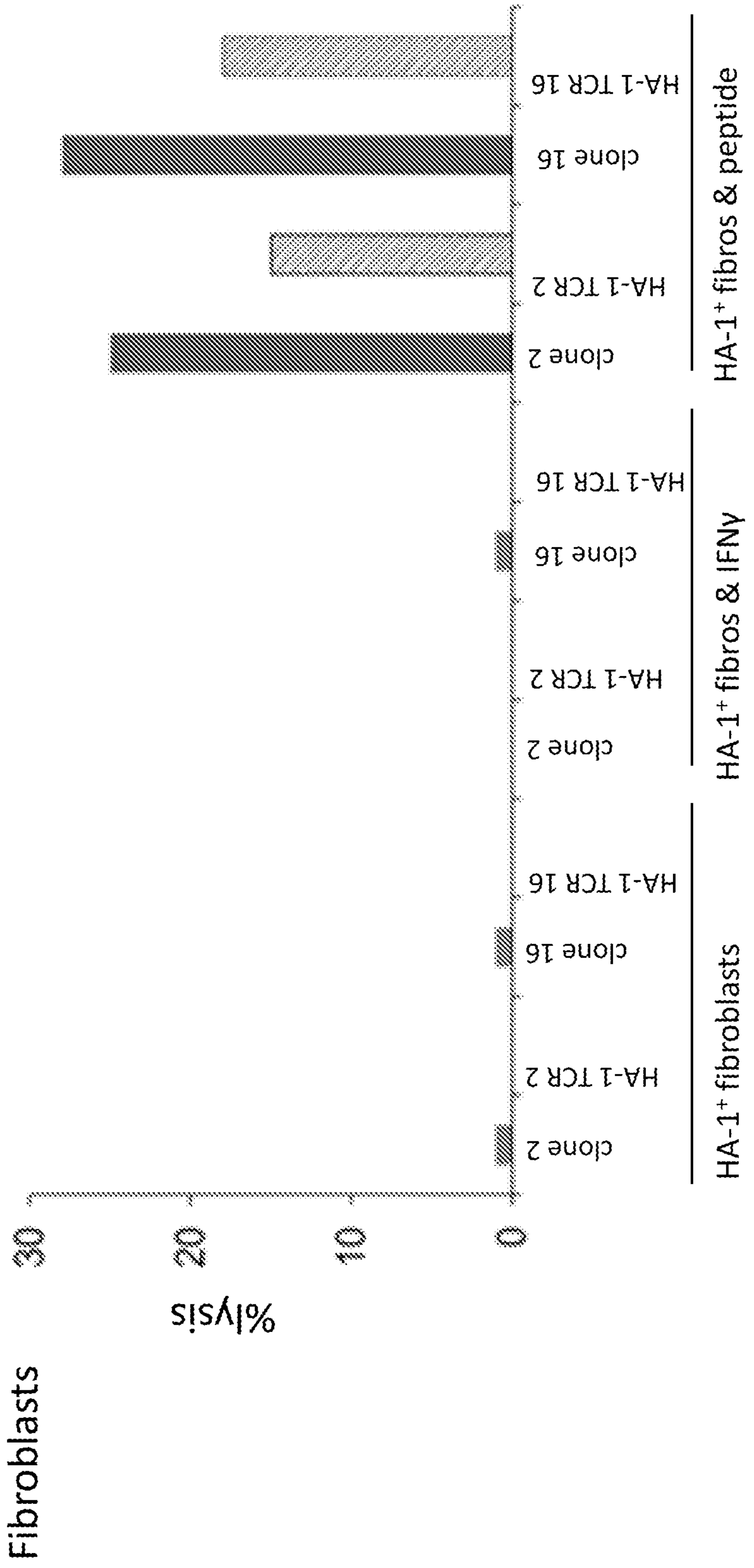
FIG. 10 shows data from a cytotoxicity assay in which TCR2- and TCR16-transduced cells (and parental clones) were incubated with HA-$1^H$ genotypically positive dermal fibroblasts, with or without exposure of the fibroblasts to interferon gamma (IFNγ).

Lentiviral (LV) vectors were used to transduce primary T cells to deliver a polynucleotide encoding the engineered HA-$1^H$ specific TCR constructs. The transduced T cells were sorted, expanded, and tested for HA-$1^H$ specificity (FIG. 4). Five of six HA-$1^H$ TCR LVs efficiently transduced primary $CD8^+$ and $CD4^+$ T cells (FIGS. 5A and 6A), and conferred specific recognition of HLA-$A2^+$ cells pulsed with low amounts of HA-$1^H$ peptide. TCR2 and TCR16 showed the strongest cytotoxic activity and were selected for further experiments. T cells transduced with these TCRs killed HA-$1^H$-pulsed cells (FIGS. 5B, 5C, 6B, and 35), cell lines with endogenous HA-$1^H$ expression (FIGS. 6C-6E and FIG. 7) and primary leukemia cells with endogenous HA-$1^H$ (FIGS. 8A-8E, FIG. 9), but these engineered cells were not activated by, and did not kill, HA-$1^H$-negative cells (FIG. 7), primary leukemia cells (FIGS. 8A, 8B and 9) or fibroblasts (FIG. 10). In addition, $CD8^+$ and $CD4^+$ HA-$1^H$ TCR T cells secreted IFNγ and IL-2 in response to HA-$1^H$ peptide stimulation (data not shown). HA-$1^H$ TCR $CD4^+$ cells killed target cells pulsed with high peptide concentrations, although LV transduction with the HA-$1^H$ TCR alone did not make $CD4^+$ T cells responsive to primary leukemia cells with native levels of antigen (data not shown).

In sum, these data demonstrate that T cells effectively express transduced HA-$1^H$ TCRs and have antigen-specific killing activity against lymphoid cells.

Example 3

CD8 Co-Receptor Function in $CD4^+$ HA-$1^H$ TCR Cells

Inclusion of $CD4^+$ T cells in an immunotherapy cell product can provide antigen-induced IL-2 secretion and augment persistence and function of transferred cytotoxic $CD8^+$ T cells (see, e.g., Kennedy et al., *Immunol. Rev.* 222:129 (2008); Nakanishi et al., *Nature* 462(7272):510 (2009)). However, optimal function of many class I restricted TCR in $CD4^+$ T cells requires the transfer of a CD8 co-receptor to enhance sensitivity of the TCR to class I HLA peptide complexes. CD4 co-receptors differ in structure to CD8 and cannot effectively substitute for CD8 co-receptors (see, e.g., Stone & Kranz, *Front. Immunol.* 4:244 (2013); see also Cole et al., *Immunology* 137(2):139 (2012). Relatively high HA-$1^H$ peptide concentrations were required to induce cytolytic activity in $CD4^+$ T cells transduced with an HA-$1^H$ TCR alone, and HA-1 TCR $CD4^+$ T cells did not recognize cell lines or leukemia, implying CD8 co-receptor dependency of the TCR (data not shown).

Various options for including a CD8 co-receptor in the transgene construct were explored. CD8 co-receptors exist on the surface of human conventional αβ TCR T cells, typically as dimers of CD8α- and β-chains, and there are five β-chain variants with different intracytoplasmic tail sequences (13M1-5) (see, e.g., Thakral et al., *J. Immunol.* 180(11):7431 (2008); see also Thakral et al., *PLoS One* 8(3):e59374 (2013)). The amino acid sequences of the CD8 co-receptor chains are provided in SEQ ID NOs: 48-53.

Figure 11A:
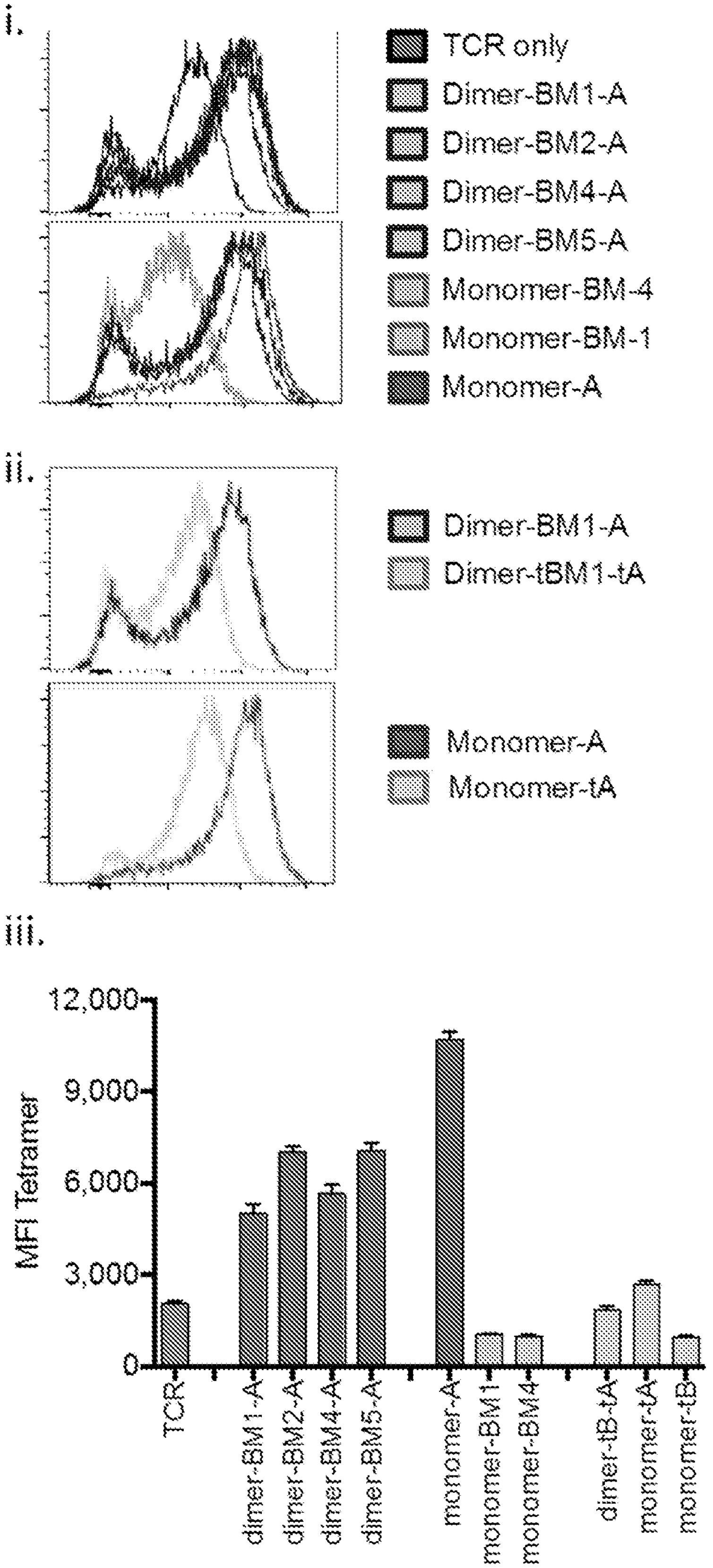
FIGS. 11A-11C show characterization of $CD4^+$ T cells transduced with the HA-$1^H$ TCR2 and CD8 co-receptor variants. (A) (i, ii) Mean fluorescence intensity (MFI) of HA-$1^H$/HLA-A2 multimer staining of $CD4^+$ T cells transduced with CD8α and/or βM1-M5 chains as indicated. (iii) MFI of the various CD8 co-receptor constructs is summarized in the graph. (B) CRA showing lysis of T2 pulsed with HA-$1^H$ peptide at various concentrations by HA-$1^H$-specific $CD8^+$ T cells (solid circles), CD4+ T cells transduced with the CD8α and β chains (squares, diamonds, downward triangles), CD8α chains alone (upward triangles), or HA-$1^H$ TCR only (open circle). (C) Proliferation assay showing dilution of the carboxyfluorescein (CFSE) dye with cell division in $CD4^+$ T cells transduced with (top to bottom) the HA-$1^H$ TCR alone, with CD8 α chain, CD8 α and βM1 chain, or CD8α and βM4 chain, in response to stimulation with HLA-A2$^+$ HA-$1^{H+}$ LCL, HA-$1^{H-}$ LCL, or media only.
Figure 11B:
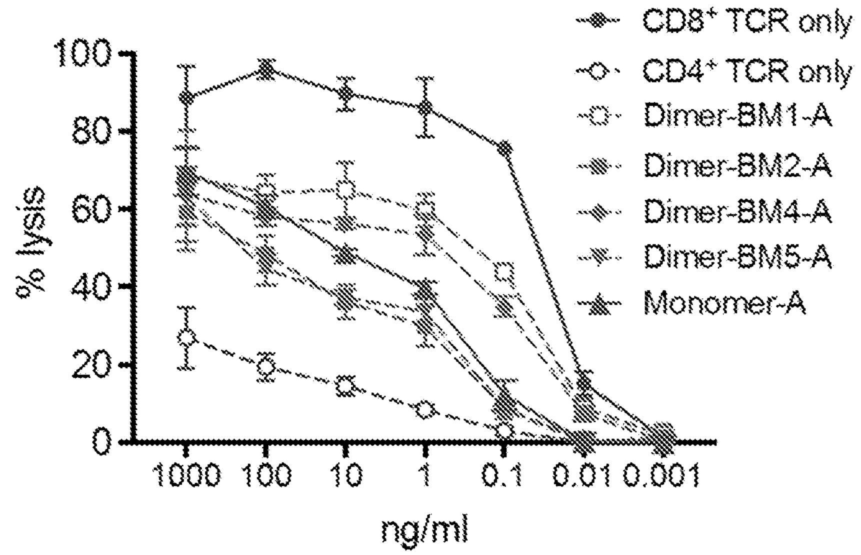
Figure 11C:
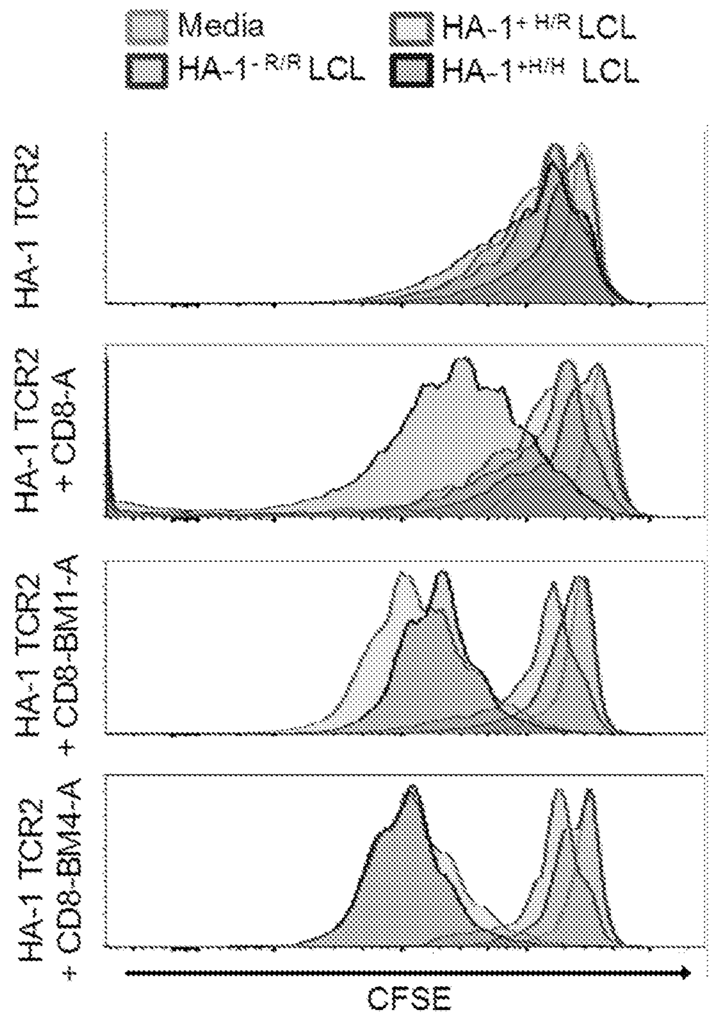
Figure 12A:
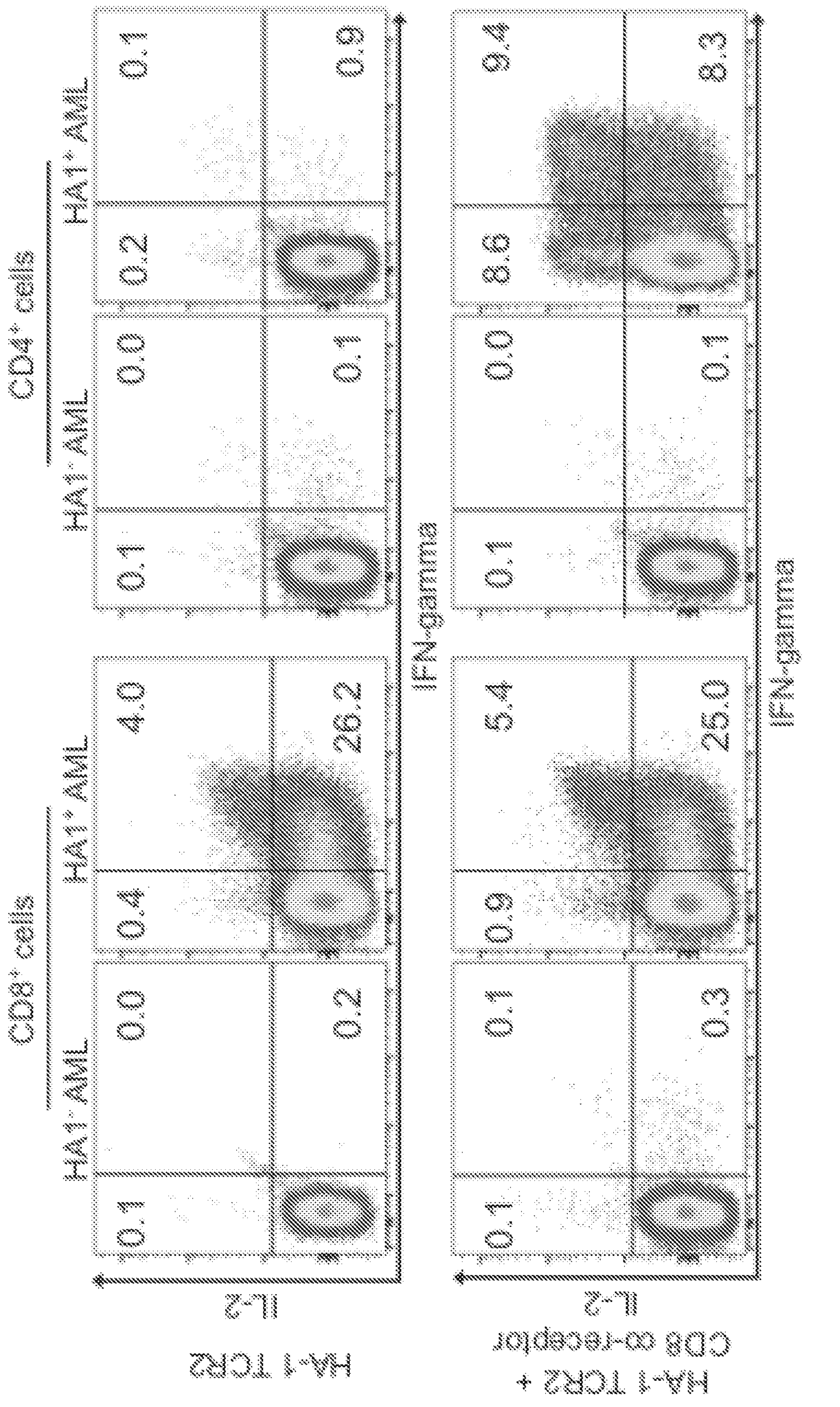
FIGS. 12A and 12B show further functional characterization of $CD4^+$ T cells transduced with the HA-$1^H$-TCR2 and a CD8 co-receptor. (A) Intracellular cytokine assay showing IL-2 and IFN-γ production by $CD8^+$ T cells (left) and $CD4^+$ T cells (right) transduced with HA-$1^H$TCR2 LV (upper panels) or HA-$1^H$TCR2-CD8 co-receptor LV (lower panels) in response to HLA-A2'/HA-$1^{H+}$ AML or HLA-A2'/HA-$1^{H-}$ AML; (B) CFSE assay showing proliferation of $CD8^+$ T cells (left) and $CD4^+$ T cells (right) transduced with HA-$1^H$-specific TCR2 LV (upper panels) or HA-$1^H$TCR2-CD8 co-receptor LV (lower panels) in response to HLA-A2$^+$/HA-$1^{H+}$ primary AML, HLA-A2$^+$/HA-$1^{H-}$ AML or media control.
Figure 12B:
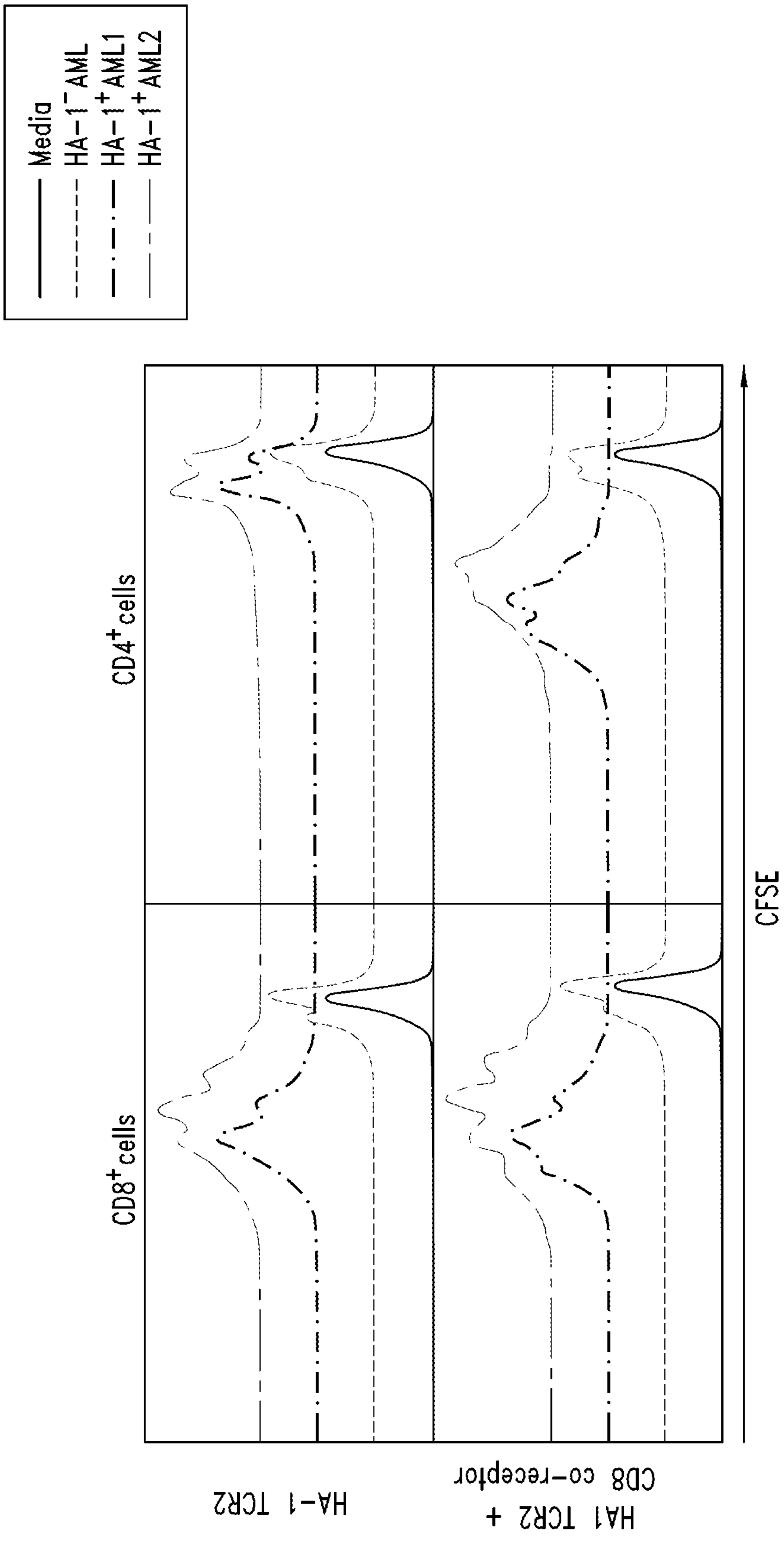
Figure 13:
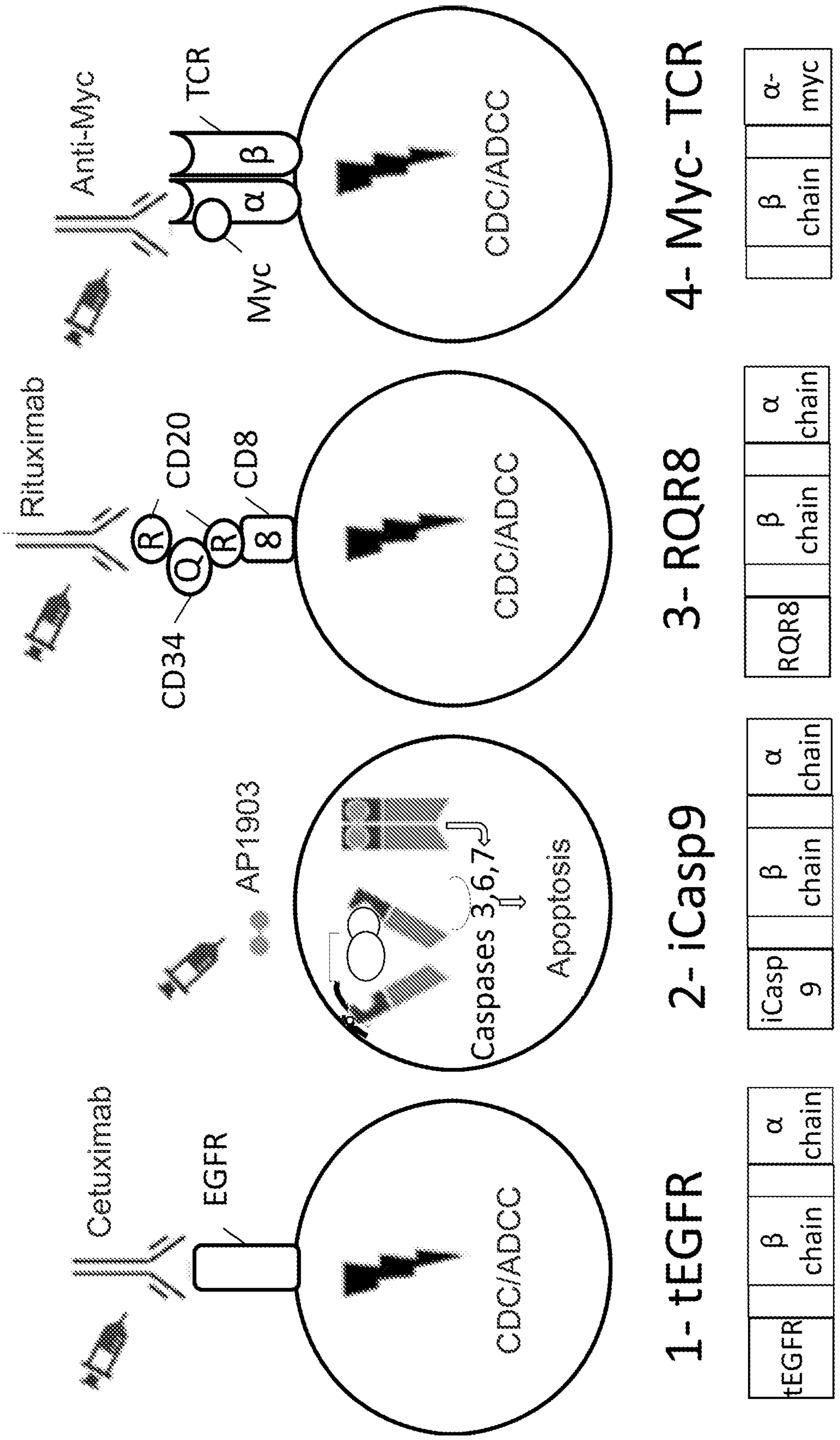
FIG. 13 provides representative diagrams of safety switch gene constructs of the present disclosure (bottom) and schema using the safety switch gene constructs to kill T cells (top).

HA-$1^H$ TCR2 constructs were generated that included one or both of the CD8 α-chain and the CD8 β-chain as full-length or truncated variants. When used to transduce primary $CD4^+$ T cells, the α- and β-chains were expressed on the cell surface; αβ dimers and a monomers increased HA-$1^H$/HLA-A2 multimer binding by TCR-transduced T cells to a greater extent than did β monomers (FIG. 11A(i-ii)). CD8 α- and β-chains with truncations of the intracellular chain components did not increase multimer binding above the TCR alone (FIG. 11A(iii)). Transduction with the CD8α and 13M1 or βM4 variants improved HA-$1^H$ TCR function in $CD4^+$ T cells more than did the CD8 α and βM2 or βM5 chains (FIG. 11B). In functional assays, incorporation of the βM1 or βM4 chain improved the $CD4^+$ T cell function to a greater extent than CD8 α monomers (FIGS. 11B and 11C). βM1 provided greater specificity of response than did βM4. The βM1 variant was therefore selected and used in a multi-cistronic LV that included CD8α and βM1 sequences as well as the HA-$1^H$ TCR. $CD4^+$ T cells transduced with the vector secreted IL-2 and interferon gamma (IFNγ) (FIG. 12A) and proliferated when co-cultured with HA-$1^{H+}$ AML cells (FIG. 12B).

Example 4

Introduction of a Safety Switch into the HA-$1^H$ TCR Constructs

To ensure that HA-$1^H$ TCR-transduced T cells can be rapidly depleted in case of any unexpected toxicity, four codon-optimized "safety switch" HA-$1^H$ TCR constructs were generated: (1) The inducible caspase 9 (iCasp9) is based on the fusion of human caspase 9 to a modified human FK-binding protein, allowing conditional dimerization; when exposed to a synthetic dimerizing drug, iCasp9 becomes activated and initiates rapid death of cells expressing this construct (see, e.g., Straathof et al., *Blood* 105(11): 4247 (2005)); (2) The truncated human EGFR ("tEGFR") is a polypeptide devoid of extracellular N-terminal ligand binding domains and intracellular receptor tyrosine kinase activity, but retains type I transmembrane cell surface localization and a binding epitope for pharmaceutical-grade anti-EGFR mAb, cetuximab (see Wang et al., *Blood* 118(5): 4255 (2011)); (3) RQR8 is a compact combined marker and safety switch for T cells, combining target epitopes from both CD34 (a marker recognized by antibody QBEnd10) and CD20 antigens (extracellular loop mimotopes) presented on a truncated CD8 co-receptor stalk; RQR8 is bound by the pharmaceutical-grade anti-CD20 mAb, rituximab (see Philip et al., *Blood* 124(8):1255 (2011)); (4) Myc-tagged TCR incorporate a 10-amino acid tag of the human c-Myc protein that is bound by a tag-specific mAb (see Kieback et al., *PNAS* 105(2):623 (2008)).

Figure 14:
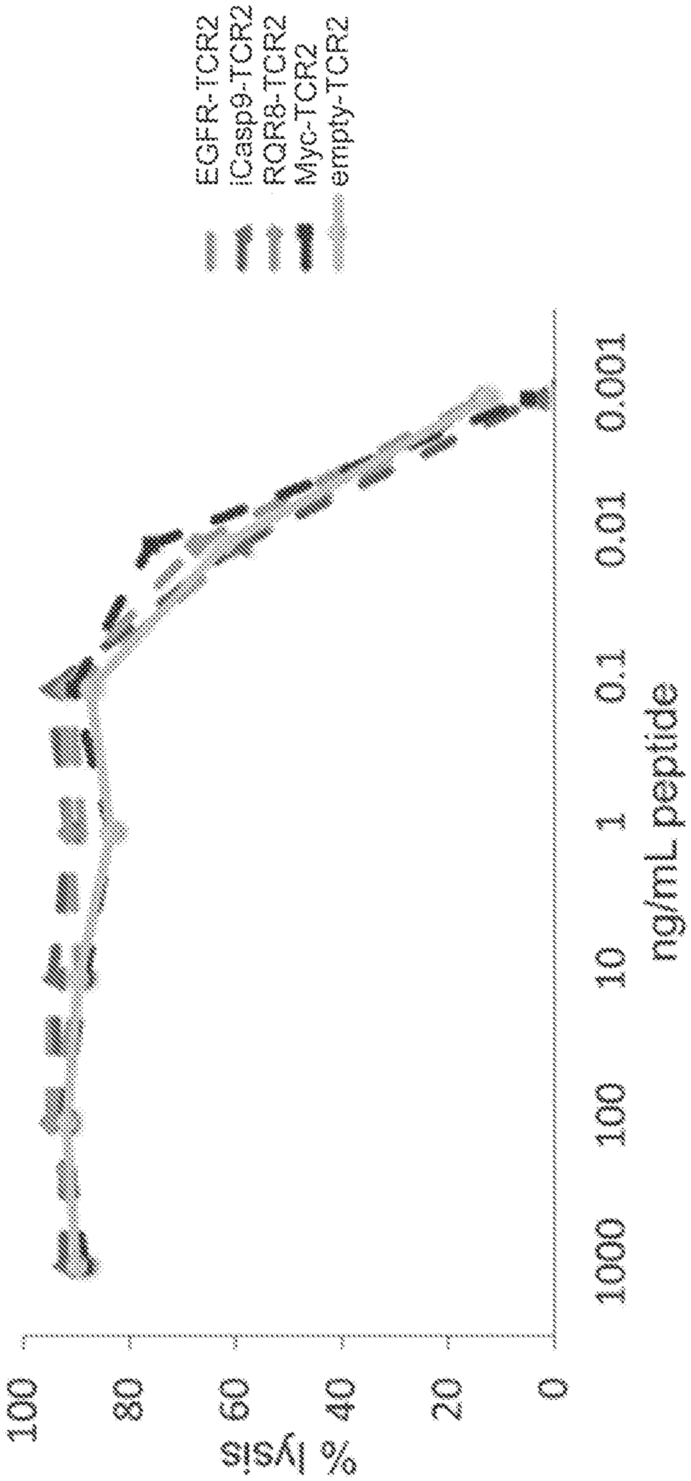
FIG. 14 provides data from a cytotoxicity assay in which primary T cells were transduced with transgene constructs expressing safety switch genes and the HA-$1^H$ specific TCR2 (or were transduced with TCR2 alone) and incubated with T2 cells pulsed with HA-$1^H$ peptide.

Binding of the respective mAbs to tEGFR, RQR8 or myc-tag provides a target for complement-dependent or antibody-dependent cellular cytotoxicity and elimination of transduced cells. The safety switch molecules were cloned into TCR2 LV constructs upstream of, and operatively associated with, the TCRβ and TCRα coding sequences. The TCRβ and TCRα sequences were separated by P2A elements from the porcine teschovirus to ensure coordinated gene expression. T cells transduced with iCasp9-HA-$1^H$ TCR, tEGFR-HA-$1^H$ TCR, RQR8-HA-$1^H$ TCR or Myc-tagged HA-$1^H$-TCR all demonstrated HA-$1^H$ TCR expression and HA-$1^{H+}$ target cell recognition similar to recognition by T cells transduced with the HA-$1^H$ TCR alone (FIG. 14).

Figure 15:
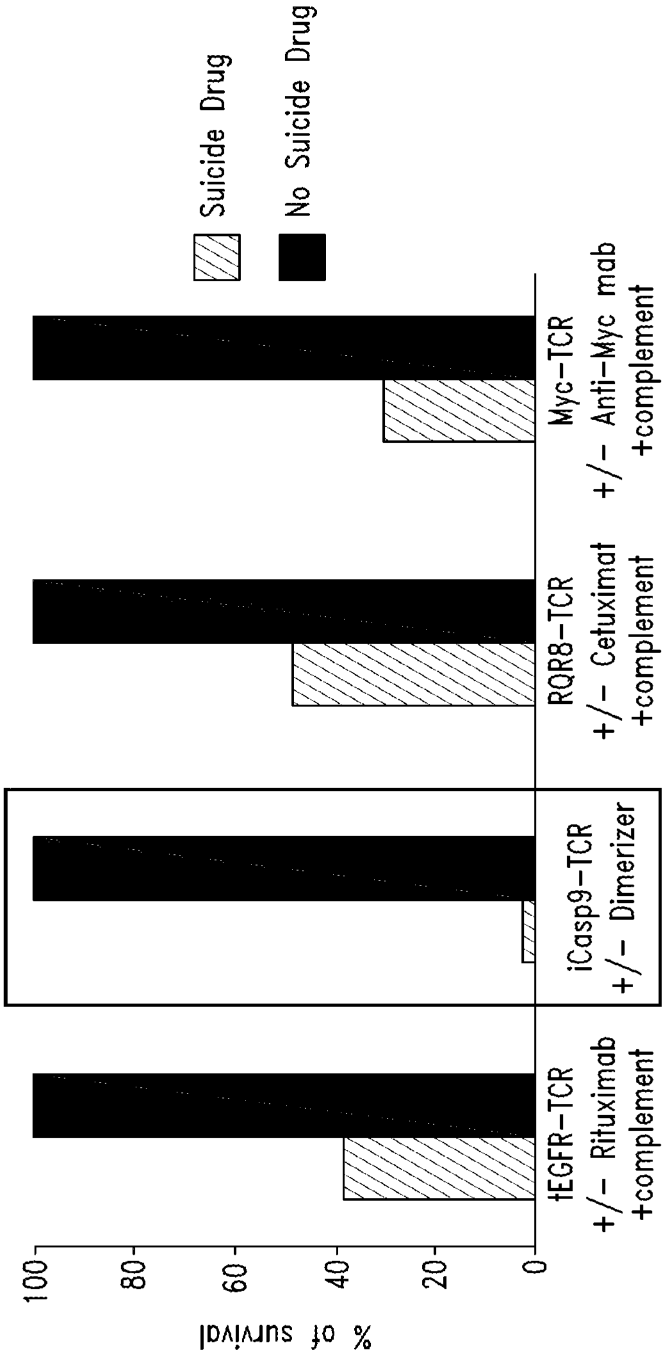
FIG. 15 shows percent survival of the transduced TCRs in the presence or absence of a "suicide drug" that activates the encoded safety switch.
Figure 16:
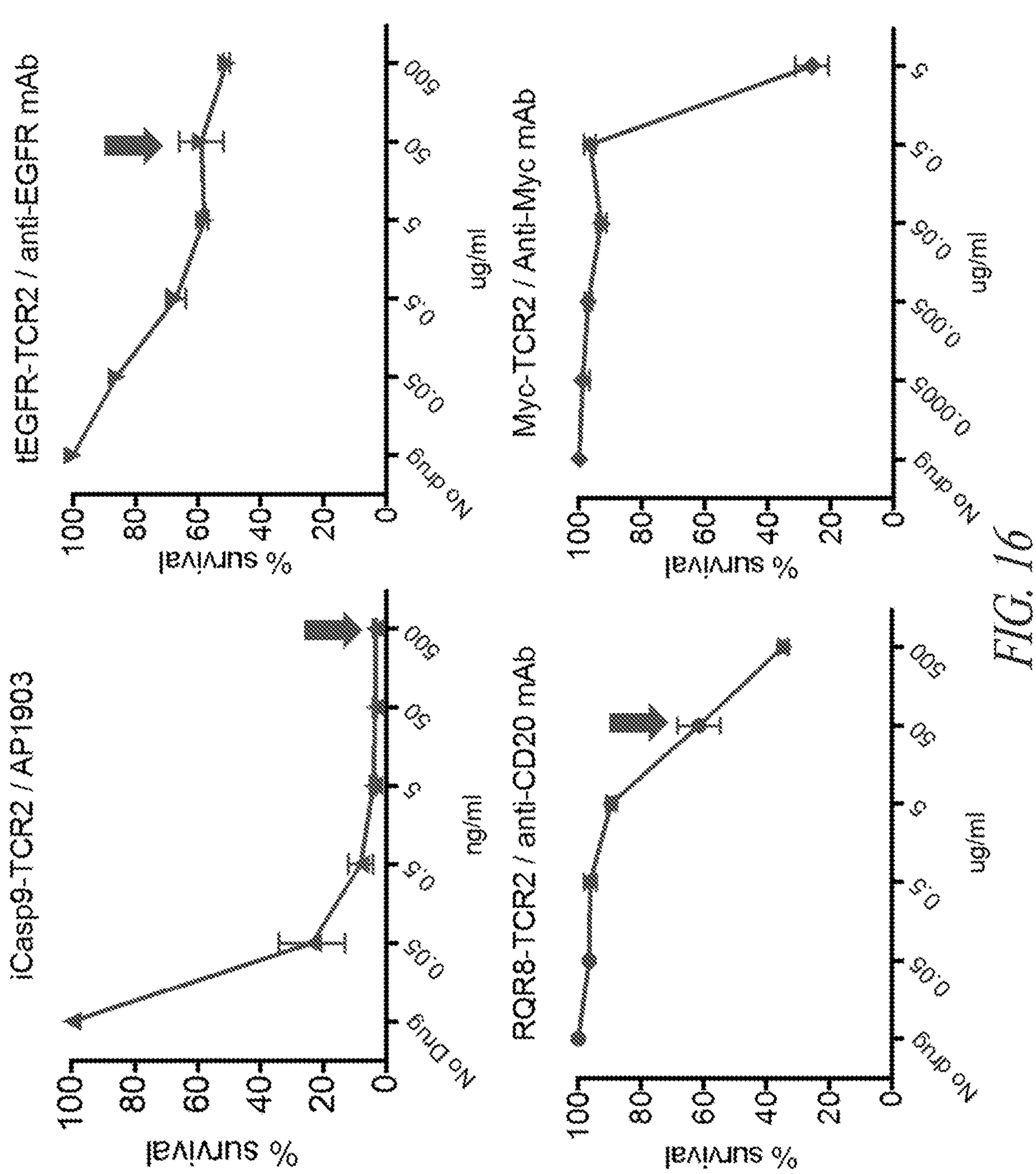
FIG. 16 shows survival of $CD8^+$ T cells transduced with HA-$1^H$ TCR2 plus safety genes after exposure to the cognate safety-switch activating drug at the indicated concentrations. Survival of iCasp9-TCR2, tEGFR-TCR2, RQR8-TCR2 and Myc-TCR2 $CD8^+$-transduced T cells was measured after 24 hours of incubation with the indicated concentrations of the respective safety switch activating drug: AP1903; anti-EGFR mAb (Cetuximab)+complement; anti-CD20Mab (Rituximab)+complement; anti-myc mAb+complement. Residual HA-1 TCR2 transduced T cells were quantified by flow cytometry. The arrows indicate the drug concentrations that can be achieved and tolerated in humans in vivo.

To test the ability of the safety switches to eliminate T cells, transduced T cells were incubated for 24 hours with the optimal concentration (FIG. 16) of the respective cognate drug (the dimerizer AP1903 for iCasp9/HA-$1^H$ TCR; complement plus appropriate mAb (anti-EGFR mAb for tEGFR-HA-$1^H$ TCR; anti-CD20 mAb plus for RQR8-HA- $1^H$ TCR; and anti-Myc tag mAb for Myc-tagged HA-$1^H$-TCR in all other constructs). All of the safety switch transduced T cells were susceptible to their respective trigger (FIG. 16, see also FIG. 15). However, iCasp9 with AP1903 consistently provided the most rapid and complete elimination of transduced T cells and was selected for further evaluation.

Example 5

Design and Selection of a Transgene Construct

Figure 17:
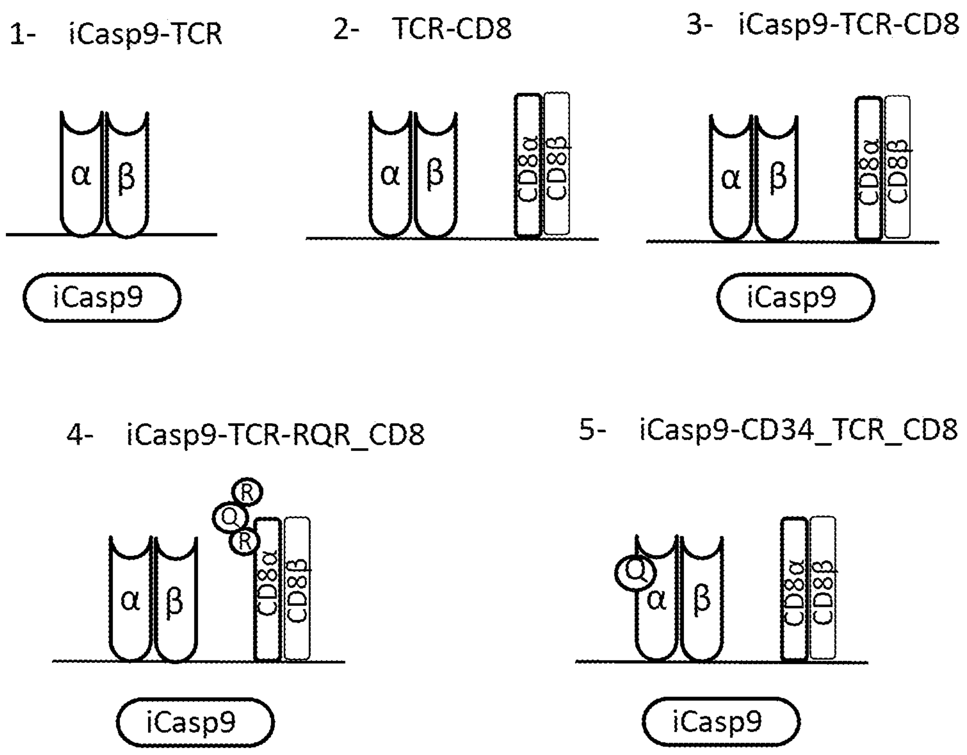
FIG. 17 shows five (5) different types of constructs for the evaluation of iCasp 9-HA-$1^H$ TCR-CD8+ expression constructs: (i) iCasp 9 and TCR2; (ii) TCR 2 and CD8 co-receptor; (iii) iCasp 9, TCR 2 and CD8 co-receptor; (iv) iCasp 9, TCR 2 and CD8 co-receptor with RQR tag on the CD8 co-receptor; and (v) iCasp 9, TCR 2 and CD8 co-receptor with Q (CD34) tag on the alpha chain of the TCR.
Figure 18:
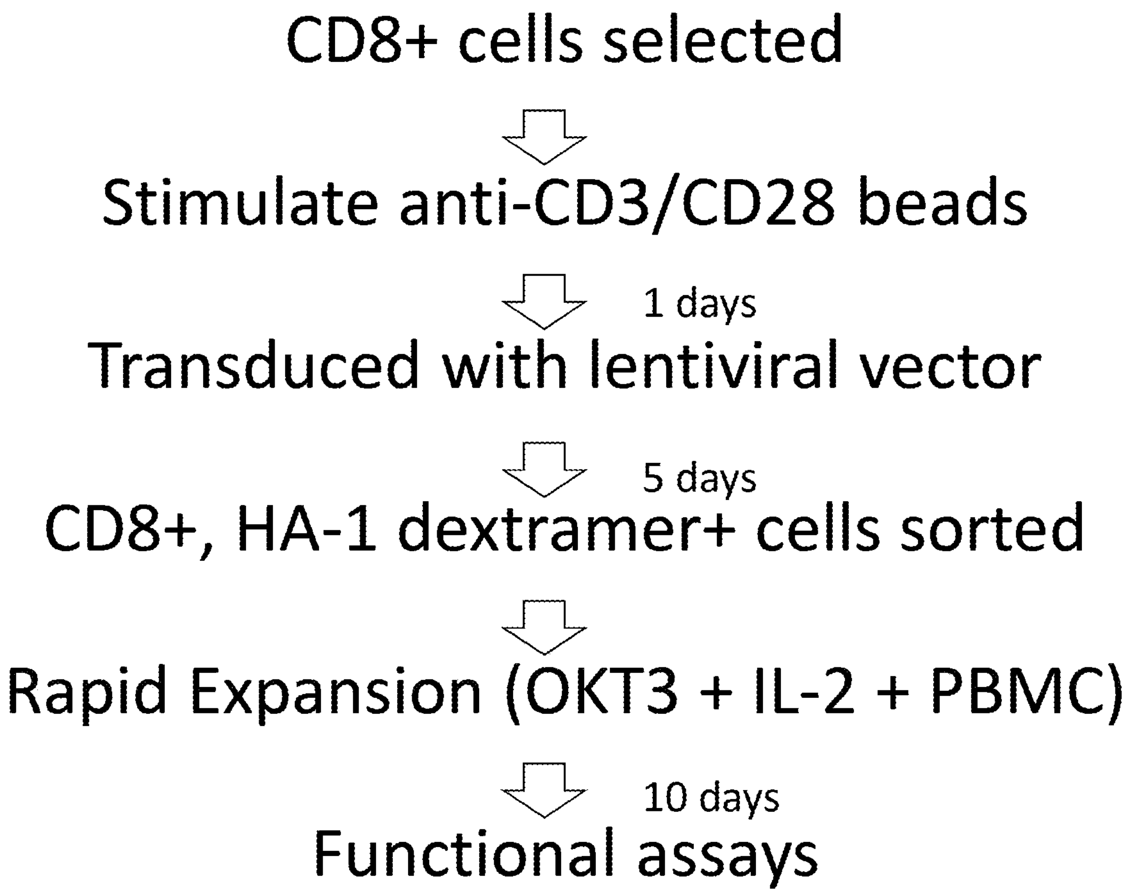
FIG. 18 depicts a flow chart for evaluating TCR-transduced cells of the present disclosure.
Figure 19:
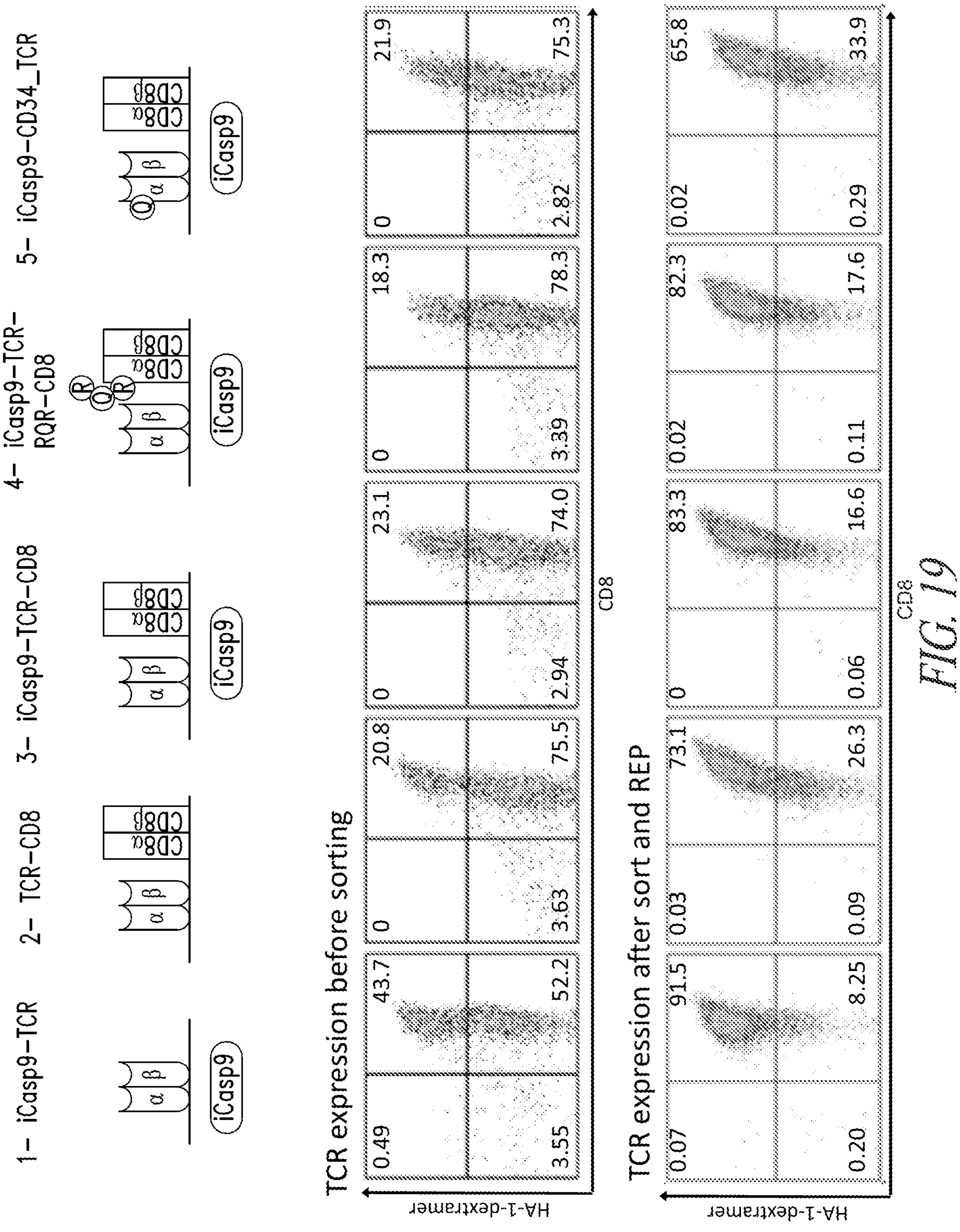
FIG. 19 provides flow cytometry data showing expression of the engineered TCR in each of the indicated transgene constructs before (top row) and after (bottom row) enrichment with an HA-1 dextramer.
Figure 20A:
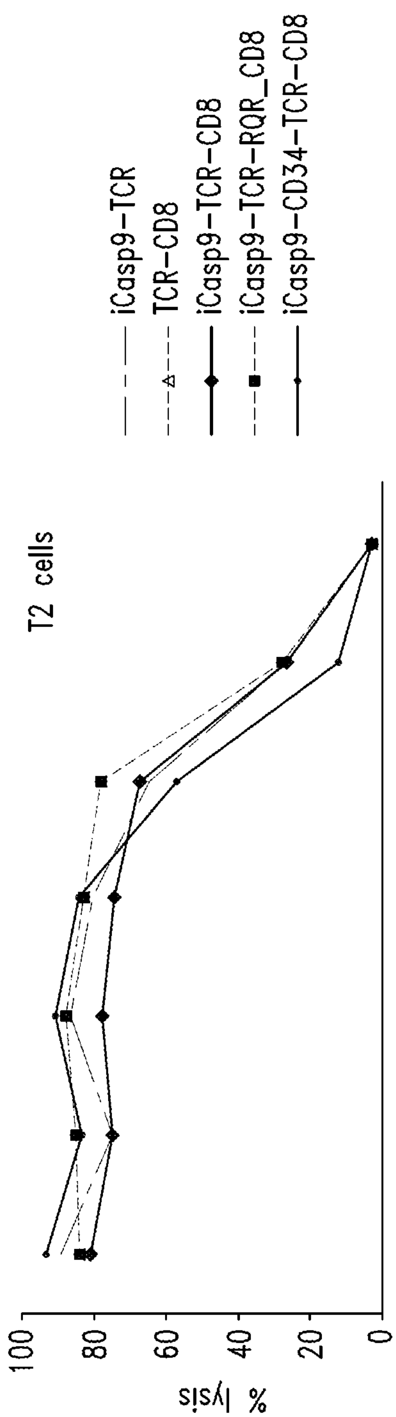
FIGS. 20A and 20B show specific lysis of peptide-pulsed target cells (20A) and LCL lines (20B) by T cells transduced with transgene constructs: iCasp-9-TCR (- -; first bar); TCR and CD8 co-receptor (-▲-; second bar); iCasp-9-TCR-CD8 co-receptor (-◆-; third bar); iCasp9-TCR-RQR-CD8 co-receptor (-■-; fourth bar); and iCas9-CD 34tag-TCR-CD8 co-receptor (-•-; fifth bar).
Figure 20B:
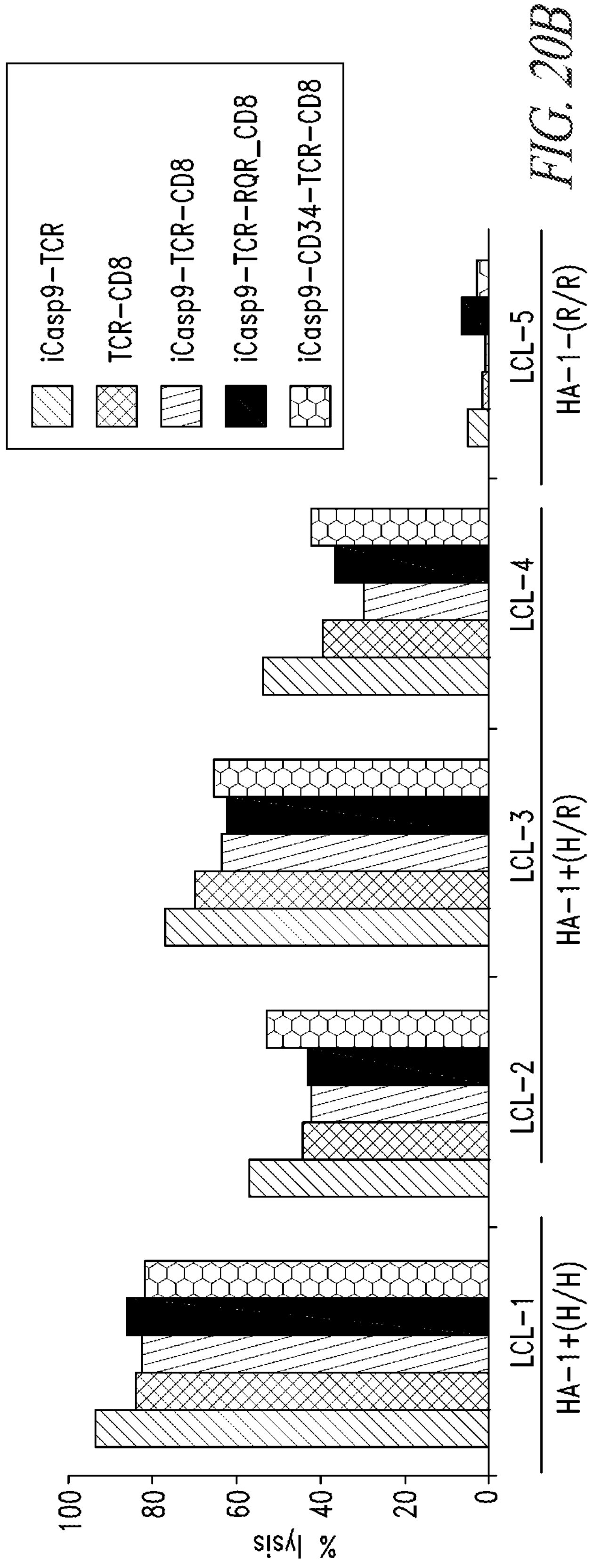

Next, the HA-$1^H$ TCR transgenes incorporating both iCasp9 and the CD8αβM1 co-receptor were analyzed for functionality. To assist in the selection and tracking of transduced T cells, two marker configurations were designed. In one, the minimal CD34 epitope ("Q") of the RQR polypeptide was nested into the α-chain of the HA-$1^H$ TCR. In the other, the RQR polypeptide was incorporated into the β-chain of the full-length functional CD8 αβM1 co-receptor. Five LV transgene constructs were then created, used to transduce $CD8^+$ T cells, and compared: (1) iCasp9-HA-$1^H$ TCR2; (2) HA-$1^H$-TCR2-CD8 co-receptor; (3) iCasp9-HA-$1^H$ TCR2-CD8; (4) iCasp9-HA-$1^H$ TCR2-RQR-CD8; and (5) iCasp9-CD34-HA-$1^H$ TCR2-CD8 (see FIGS. 17 and 18).

All of the constructs produced T cells that specifically secreted cytokines and killed HA-$1^{H+}$, but not HA-$1^{H-}$ AML cells or fibroblasts, and had similar function (see FIGS. 19-26), except the iCasp9-CD34-HA-$1^H$ TCR2-CD8 construct (with the CD34 epitope embedded in the TCR α-chain), which performed poorly. The iCasp9-HA-$1^H$ TCR2-RQR-CD8 transgene, which contains all of the desired elements (including the capacity for immunomagnetic selection; see FIGS. 27-29) and functioned as well as the less complex constructs, was selected for further studies. A schematic diagram of this construct is shown in FIG. 30, and the nucleotide sequence of the construct is provided in SEQ ID NO:85.

Example 6

Clinical-Scale Production and Testing of HA-$1^H$ TCR T Cells

The cellular composition of T cell immunotherapy products can have important downstream effects on the persistence and function of antigen-specific T cells after adoptive T cell transfer (see, e.g., Sommermeyer et al., Leukemia 30(2):492 (2016); see also Wang et al., Blood 117(6):1888 (2011) and Hinrichs et al., PNAS 106*41):17469 (2009)). In general, infusion of antigen-specific T cells derived from "younger" T cell subsets, including $T_N$, T memory stem cells ($T_{SCM}$) and central memory T cells ($T_{CM}$), appears advantageous. In the context of post-HCT T cell immunotherapy, it is also important to consider the potential for GVHD mediated by the native TCR of donor T cells. $T_N$ cause severe GVHD in murine models and depletion of $CD45RA^+$ $T_N$ from PBSC grafts reduces the risk of severe and/or chronic GVHD in humans (see, e.g., Bleakley et al., J. Clin. Invest. 125(7):2677 (2015). It is also desirable to include both $CD4^+$ and $CD8^+$ cells specific for the same antigen, as $CD4^+$ T helper cells can enhance anti-tumor CTL responses by enhancing clonal expansion at the tumor site and preventing activation-induced cell death (see, e.g., Giuntoli et al., Clin. Cancer Res. 8(3):922 (2002); see also Kennedy and Celis, J. Immunol. 177(5):2862 (2006)). Therefore, the T cell product ($1\text{-}2\times10^9$ PBSC/PBMC) was first depleted of $CD45RA^+$ $T_N$ cells to minimize the risk of serious GVHD, and depleted of $CD14^+$ monocytes to optimize LV transduction efficiency, prior to separating $CD8^+$ and $CD4^+$ enriched fractions to ensure a consistent CD4:CD8 composition (approx. $3\times10^6$ cells of each cell type), and stimulating (CD3/CD28 microbeads beads) and transducing the T cells with the iCasp9-HA1 TCR2-RQR-CD8 LV.

Figure 32B:
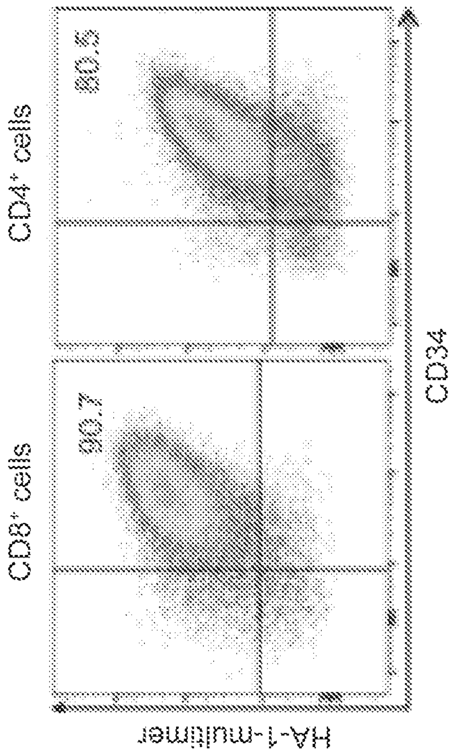
Figure 32A:
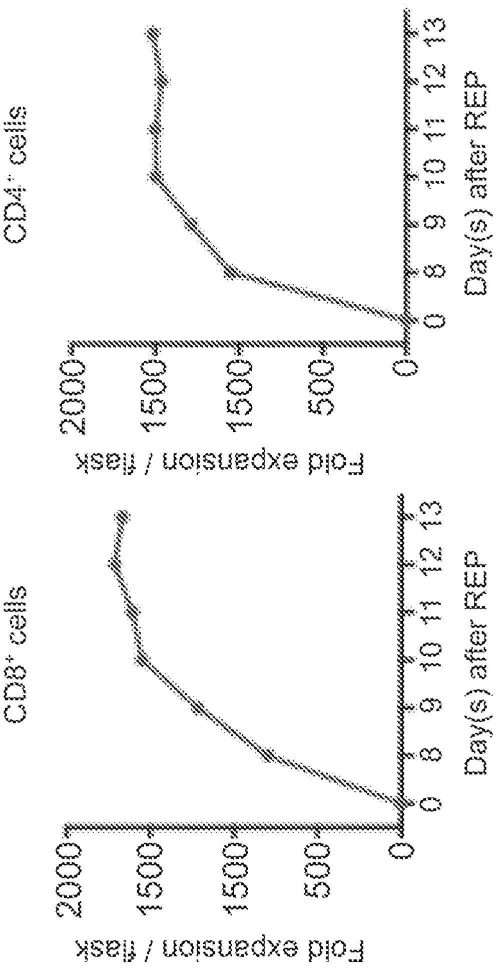
Figure 32C:
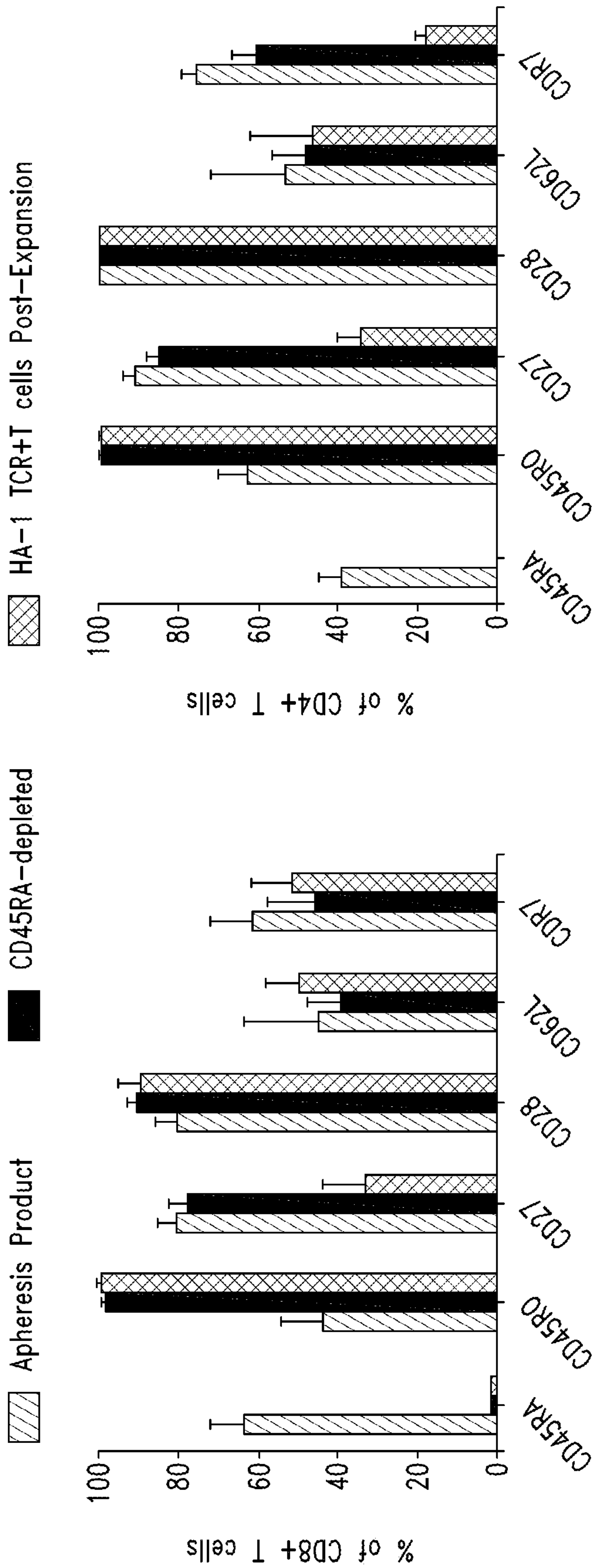
Figure 32E:
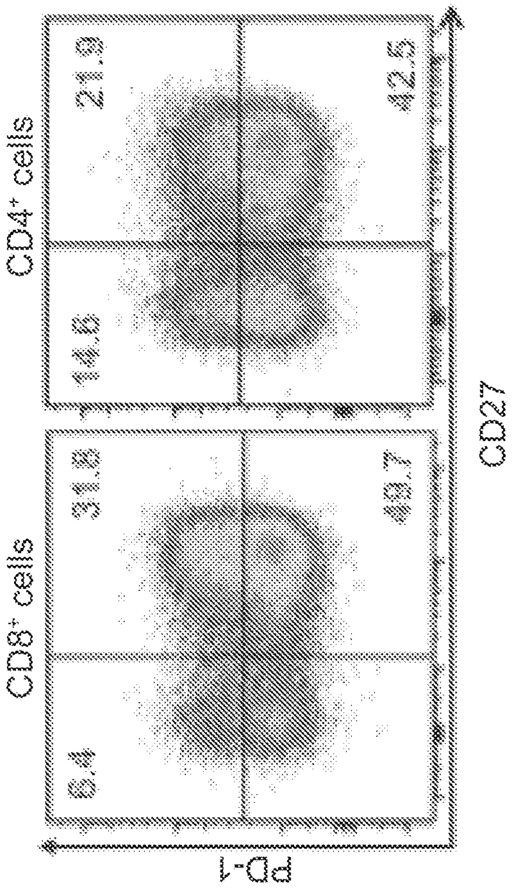
Figure 32D:
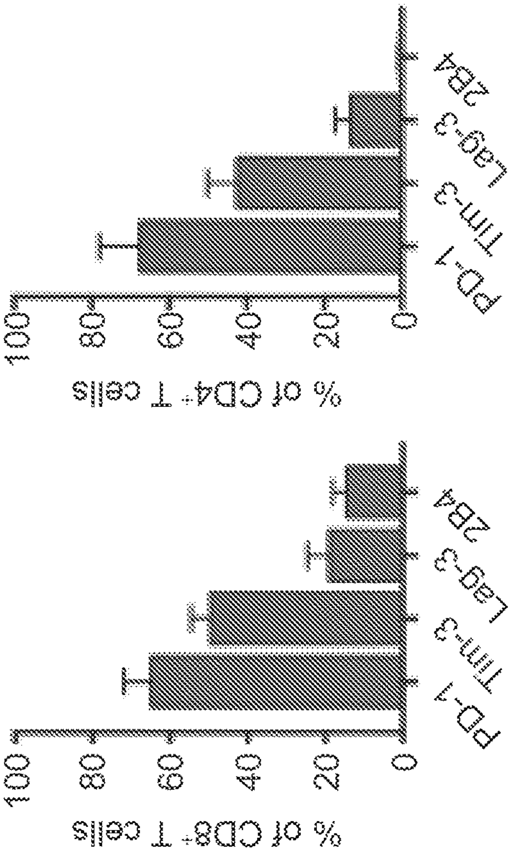

The transduced cells were flow-sorted using HA-$1^H$/HLA-A2 multimers and CD34 mAb 4-5 days later, and cultured in G-Rex flasks using REP (Rapid Expansion Protocol) comprising OKT3 cells, PBMC, HA-$1^+$ LCL, and IL-2. The $CD4^+$ and CD8+HA-$1^H$TCR memory T cells expanded efficiently, with an average 2000-fold expansion (FIG. 32A; see also FIG. 31, left-most panels). The $CD4^+$ and $CD8^+$-transduced T cells were harvested and combined (total $3\text{-}6\times10^9$ cells at days 16-20), then enriched via selection for CD34 to produce an enriched population of $\geq1.5\times10^9$ cells. Release assays were then performed to test for purity (>75%), viability, function, specificity, presence or absence of virus, and sterility. The final T cell product retained expression of the HA-$1^H$ TCR (FIG. 32B), had a predominantly $CD45RO^+CD28^+$ phenotype with variable expression of CD62L, CCR7 and CD27 (FIG. 32C), and included cells that did not express exhaustion markers such as PD-1 (FIGS. 32D, 32E).

Figure 33A:
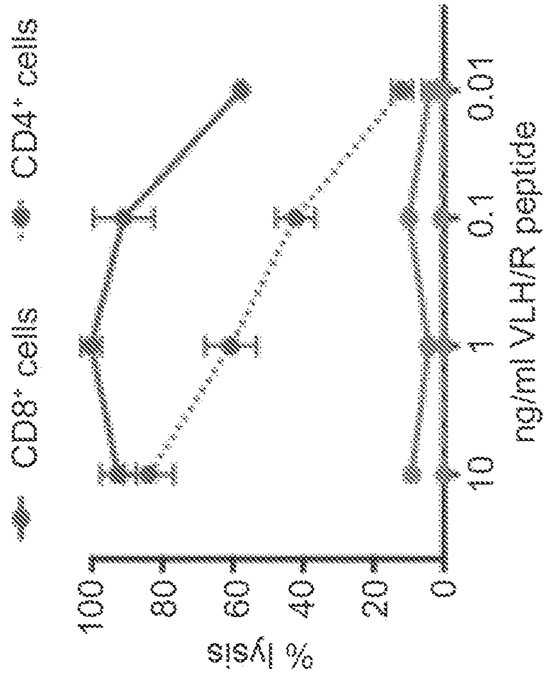
Figure 33B:
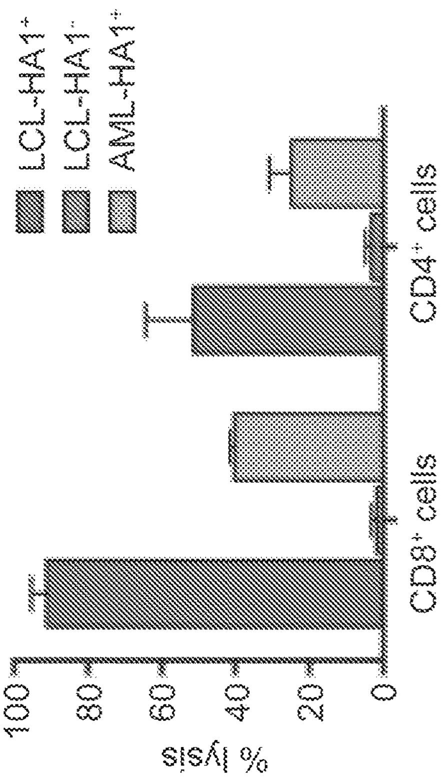
Figure 33C:
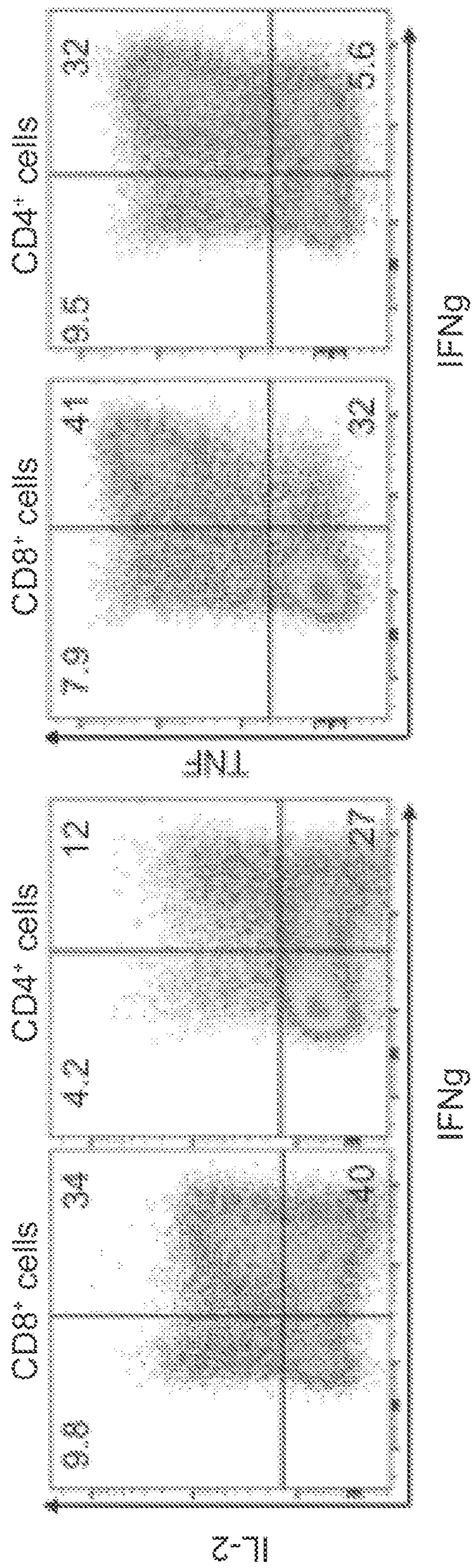
Figure 33D:
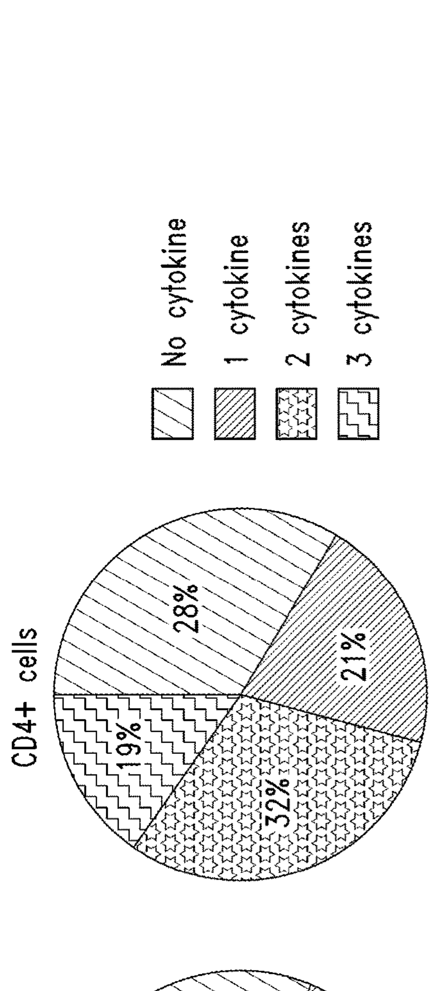
Figure 33E:
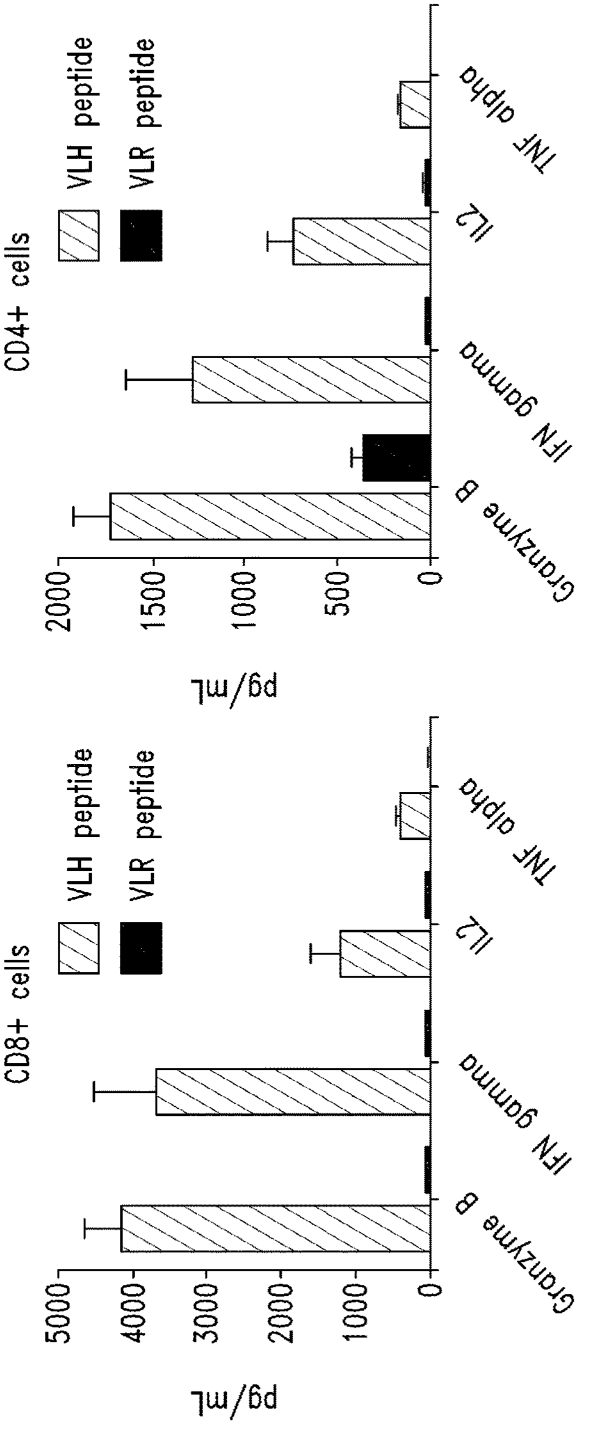

The expanded $CD8^+$ and $CD4^+$ HA-$1^H$ TCR T cells retained their ability to specifically kill and secrete cytokines in response to stimulation with HA-$1^H$-pulsed cells (FIG. 33A) or HA-$1^{H+}$ leukemia cell lines (FIG. 33B), and many HA-$1^H$ TCR $CD8^+$ and $CD4^+$ cells secreted multiple cytokines (FIG. 33C; see also FIG. 31 middle and right-hand panels). Further, the cells could be enriched using anti-CD34 immunomagnetic beads (FIG. 34A) and were efficiently eliminated by exposure to the AP1903 dimerizer drug (FIG. 34B). Finally, the native TCR in HA-$1^H$ TCR $CD4^+$ and $CD8^+$ T cells in the cell product was evaluated using TCR immunosequencing (Adaptive Biotechnologies) and a diverse polyclonal population was bserved (data not shown). Moreover, the product contained numerous very-low-frequency TCR, a finding that has recently been associated with the potential for persistence and expansion after adoptive T cell transfer (Chapuis et al., *Sci. Immunol.* 2(8) (2017).

Example 7

Clinical Study Using the HA-$1^H$ T Cell Therapy Product

A feasibility and safety study is conducted using the HA-$1^H$ cell therapy product described in Example 5 ($CD8^+$ and $CD4^+$ memory T cells transduced with pRRLSIN iC9-HA-$1^H$-TCR2-RQR-CD8; abbreviated hereafter as "HA-$1^H$ TCR LV"). The patient sample comprises children, adolescents and adults with recurrent leukemia (AML, ALL, another acute leukemia, or CML). Specifically, patients aged 0-70 are enrolled into two age groups of approximately 12 subjects each: one group aged ≥16 years, and one group aged <16 years. group. All patients express HLA-A*0201 and have the HA-1(H) genotype (RS_1801284: A/G, A/A). The patients also have an adult donor for HCT who is adequately HLA-matched by institutional standards, and are currently undergoing or have previously undergone allogeneic HCT for AML, ALL, another type of acute leukemia, or chronic myeloid leukemia.

Bone marrow samples are taken subsequent to a suspected relapse. Patients then generally receive lymphodepleting chemotherapy (fludarabine) prior to infusion with the T cell product. Thereafter, patients are administered a single dose of HA-$1^H$ TCR LV-T cells (approx. 1:1 $CD4^+$:$CD8^+$ $T_M$) when three criteria are satisfied: (1) there is evidence of recurrent or refractory disease after HCT; (2) HA-$1^H$ TCR T cells have been generated; and (3) lymphodepleting chemotherapy has been administered (if indicated). HA-$1^H$ TCR LV-T cells are administered by infusion (as rapidly as tolerated through a central venous catheter via gravity or a syringe pump) according to the dosage schedule provided in Table 2.

TABLE 2

| Clinical Dosing Schedule | | |
|---|---|---|
| Dose level | Dose (HA-$1^H$ TCR T cells) | |
| −1 | Up to 3 × $10^5$/kg | |
| 0 | Up to 1 × $10^6$/kg | |
| 1 | Up to 3 × $10^6$/kg | Starting dose |
| 2 | Up to 10 × $10^6$/kg | |
| 3 | Up to 30 × $10^6$/kg | |

At least 1-2 subjects ≥16 y.o. are treated prior to treatment of a subject in the younger cohort. In each age group (≥16 and <16 years old), patients are treated in cohorts of three or more patients at one of five dose levels of HA-$1^H$ TCR T cells, starting at dose level 1 ($3\times10^6$ HA-$1^H$ TCR T cells/kg). A 28-day period between administration of the investigational agent to consecutive subjects within each age group is observed. Bone marrow samples are taken at days 4, 18, and 32 following infusion of the T cell product. Other aspects of the study include monitoring: the in vivo persistence of transferred HA-$1^H$ TCR T cells in peripheral blood; the ability of HA-$1^H$ TCR T cells to migrate to bone marrow; the function of HA-$1^H$ TCR T cells before and, if possible, after adoptive T cell transfer; whether infusion of HA-$1^H$ TCR T cells is followed by a reduction of leukemia burden; whether infusion of HA-$1^H$ TCR T cells is followed by a reduction of recipient hematopoietic chimerism; and whether infusion of HA-$1^H$ TCR T cells is followed by the appearance or recurrence of signs or symptoms of graft-versus-host disease (GVHD).

U.S. Provisional Patent Application No. 62/399,291, filed Sep. 23, 2016, to which the present application claims priority, is hereby incorporated herein by reference in its entirety.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

SEQUENCE LISTING

```
Sequence total quantity: 136
SEQ ID NO: 1            moltype = AA  length = 133
FEATURE                 Location/Qualifiers
REGION                  1..133
                        note = Synthetic sequence TCR1,13 beta chain variable
                         region with signal peptide
source                  1..133
                        mol_type = protein
                        organism = synthetic construct
SEQUENCE: 1
MGTSLLCWMA LCLLGADHAD TGVSQDPRHK ITKRGQNVTF RCDPISEHNR LYWYRQTLGQ  60
GPEFLTYFQN EAQLEKSRLL SDRFSAERPK GSFSTLEIQR TEQGDSAMYL CASSSTGGHN  120
EQFFGPGTRL TVL                                                     133

SEQ ID NO: 2            moltype = AA  length = 134
FEATURE                 Location/Qualifiers
REGION                  1..134
                        note = Synthetic sequence TCR1,13 alpha chain variable
                         region with signal peptide
source                  1..134
                        mol_type = protein
                        organism = synthetic construct
SEQUENCE: 2
METLLGVSLV ILWLQLARVN SQQGEEDPQA LSIQEGENAT MNCSYKTSIN NLQWYRQNSG  60
RGLVHLILIR SNEREKHSGR LRVTLDTSKK SSSLLITASR AADTASYFCA TKRDSGAGSY  120
QLTFGKGTKL SVIP                                                    134

SEQ ID NO: 3            moltype = AA  length = 132
FEATURE                 Location/Qualifiers
REGION                  1..132
                        note = Synthetic sequence TCR2,14 beta chain variable
                         region with signal peptide
source                  1..132
                        mol_type = protein
                        organism = synthetic construct
SEQUENCE: 3
MGTSLLCWMA LCLLGADHAD TGVSQDPRHK ITKRGQNVTF RCDPISEHNR LYWYRQTLGQ  60
GPEFLTYFQN EAQLEKSRLL SDRFSAERPK GSFSTLEIQR TEQGDSAMYL CASSLVKGEK  120
LFFGSGTQLS VL                                                      132
```

```
SEQ ID NO: 4            moltype = AA  length = 132
FEATURE                 Location/Qualifiers
REGION                  1..132
                        note = Synthetic sequence TCR2,14 alpha chain variable
                         region with signal peptide
source                  1..132
                        mol_type = protein
                        organism = synthetic construct
SEQUENCE: 4
METLLGLLIL WLQLQWVSSK QEVTQIPAAL SVPEGENLVL NCSFTDSAIY NLQWFRQDPG  60
KGLTSLLLIQ SSQREQTSGR LNASLDKSSG RSTLYIAASQ PGDSATYLCA VIGLGGTYKY  120
IFGTGTRLKV LA                                                      132

SEQ ID NO: 5            moltype = AA  length = 132
FEATURE                 Location/Qualifiers
REGION                  1..132
                        note = Synthetic sequence TCR5 beta chain variable region
                         with signal peptide
source                  1..132
                        mol_type = protein
                        organism = synthetic construct
SEQUENCE: 5
MGTSLLCWMA LCLLGADHAD TGVSQDPRHK ITKRGQNVTF RCDPISEHNR LYWYRQTLGQ  60
GPEFLTYFQN EAQLEKSRLL SDRFSAERPK GSFSTLEIQR TEQGDSAMYL CASSLTTLDE  120
QYVGPGTRLT VT                                                      132

SEQ ID NO: 6            moltype = AA  length = 130
FEATURE                 Location/Qualifiers
REGION                  1..130
                        note = Synthetic sequence TCR5 alpha chain variable region
                         with signal peptide
source                  1..130
                        mol_type = protein
                        organism = synthetic construct
SEQUENCE: 6
METLLGVSLV ILWLQLARVN SQQGEEDPQA LSIQEGENAT MNCSYKTSIN NLQWYRQNSG  60
RGLVHLILIR SNEREKHSGR LRVTLDTSKK SSSLLITASR AADTASYFCA TNSGNTPLVF  120
GKGTRLSVIA                                                         130

SEQ ID NO: 7            moltype = AA  length = 132
FEATURE                 Location/Qualifiers
REGION                  1..132
                        note = Synthetic sequence TCR10 beta chain variable region
                         with signal peptide
source                  1..132
                        mol_type = protein
                        organism = synthetic construct
SEQUENCE: 7
MGTSLLCWMA LCLLGADHAD TGVSQDPRHK ITKRGQNVTF RCDPISEHNR LYWYRQTLGQ  60
GPEFLTYFQN EAQLEKSRLL SDRFSAERPK GSFSTLEIQR TEQGDSAMYL CASSMLTNYE  120
QYFGPGTRLT VT                                                      132

SEQ ID NO: 8            moltype = AA  length = 134
FEATURE                 Location/Qualifiers
REGION                  1..134
                        note = Synthetic sequence TCR10 alpha chain variable region
                         with signal peptide
source                  1..134
                        mol_type = protein
                        organism = synthetic construct
SEQUENCE: 8
MKKHLTTFLV ILWLYFYRGN GKNQVEQSPQ SLIILEGKNC TLQCNYTVSP FSNLRWYKQD  60
TGRGPVSLTI MTFSENTKSN GRYTATLDAD TKQSSLHITA SQLSDSASYI CVVDSGGGAD  120
GLTFGKGTHL IIQP                                                    134

SEQ ID NO: 9            moltype = AA  length = 132
FEATURE                 Location/Qualifiers
REGION                  1..132
                        note = Synthetic sequence TCR16 beta chain variable region
                         with signal peptide
source                  1..132
                        mol_type = protein
                        organism = synthetic construct
SEQUENCE: 9
MGTSLLCWMA LCLLGADHAD TGVSQDPRHK ITKRGQNVTF RCDPISEHNR LYWYRQTLGQ  60
GPEFLTYFQN EAQLEKSRLL SDRFSAERPK GSFSTLEIQR TEQGDSAMYL CASSLVVGNE  120
QFFGPGTRLT VL                                                      132
```

```
SEQ ID NO: 10          moltype = AA  length = 131
FEATURE                Location/Qualifiers
REGION                 1..131
                       note = Synthetic sequence TCR16 alpha chain variable region
                        with signal peptide
source                 1..131
                       mol_type = protein
                       organism = synthetic construct
SEQUENCE: 10
METLLGLLIL WLQLQWVSSK QEVTQIPAAL SVPEGENLVL NCSFTDSAIY NLQWFRQDPG  60
KGLTSLLLIQ SSQREQTSGR LNASLDKSSG RSTLYIAASQ PGDSATYLCA VHLLNDYKLS  120
FGAGTTVTVR A                                                       131

SEQ ID NO: 11          moltype = AA  length = 132
FEATURE                Location/Qualifiers
REGION                 1..132
                       note = Synthetic sequence TCR29 beta chain variable region
                        with signal peptide
source                 1..132
                       mol_type = protein
                       organism = synthetic construct
SEQUENCE: 11
MGTSLLCWMA LCLLGADHAD TGVSQDPRHK ITKRGQNVTF RCDPISEHNR LYWYRQTLGQ  60
GPEFLTYFQN EAQLEKSRLL SDRFSAERPK GSFSTLEIQR TEQGDSAMYL CASSLVSGNT  120
IYFGEGSWLT VV                                                      132

SEQ ID NO: 12          moltype = AA  length = 134
FEATURE                Location/Qualifiers
REGION                 1..134
                       note = Synthetic sequence TCR29 alpha chain variable region
                        with signal peptide
source                 1..134
                       mol_type = protein
                       organism = synthetic construct
SEQUENCE: 12
METLLGLLIL WLQLQWVSSK QEVTQIPAAL SVPEGENLVL NCSFTDSAIY NLQWFRQDPG  60
KGLTSLLLIQ SSQREQTSGR LNASLDKSSG RSTLYIAASQ PGDSATYLCA VRGGTTSGTY  120
KYIFGTGTRL KVLA                                                    134

SEQ ID NO: 13          moltype = AA  length = 14
FEATURE                Location/Qualifiers
REGION                 1..14
                       note = Synthetic sequence TCR1 beta chain CDR3
source                 1..14
                       mol_type = protein
                       organism = synthetic construct
SEQUENCE: 13
CASSSTGGHN EQFF                                                    14

SEQ ID NO: 14          moltype = AA  length = 12
FEATURE                Location/Qualifiers
REGION                 1..12
                       note = Synthetic sequence TCR2 beta chain CDR3
source                 1..12
                       mol_type = protein
                       organism = synthetic construct
SEQUENCE: 14
CASSLVKGEK LF                                                      12

SEQ ID NO: 15          moltype = AA  length = 13
FEATURE                Location/Qualifiers
REGION                 1..13
                       note = Synthetic sequence TCR5 beta chain CDR3
source                 1..13
                       mol_type = protein
                       organism = synthetic construct
SEQUENCE: 15
CASSLTTLDE QYV                                                     13

SEQ ID NO: 16          moltype = AA  length = 13
FEATURE                Location/Qualifiers
REGION                 1..13
                       note = Synthetic sequence TCR10 beta chain CDR3
source                 1..13
                       mol_type = protein
                       organism = synthetic construct
SEQUENCE: 16
CASSMLTNYE QYF                                                     13
```

-continued

```
SEQ ID NO: 17          moltype = AA  length = 13
FEATURE                Location/Qualifiers
REGION                 1..13
                       note = Synthetic sequence TCR16 beta chain CDR3
source                 1..13
                       mol_type = protein
                       organism = synthetic construct
SEQUENCE: 17
CASSLVVGNE QFF                                                    13

SEQ ID NO: 18          moltype = AA  length = 177
FEATURE                Location/Qualifiers
REGION                 1..177
                       note = Synthetic sequence TCR1,5,10,13,16 beta chain
                        constant region (Cys modified)
source                 1..177
                       mol_type = protein
                       organism = synthetic construct
SEQUENCE: 18
EDLKNVFPPE VAVFEPSEAE ISHTQKATLV CLATGFYPDH VELSWWVNGK EVHSGVCTDP  60
QPLKEQPALN DSRYCLSSRL RVSATFWQNP RNHFRCQVQF YGLSENDEWT QDRAKPVTQI  120
VSAEAWGRAD CGFTSESYQQ GVLSATILYE ILLGKATLYA VLVSALVLMA MVKRKDS     177

SEQ ID NO: 19          moltype = AA  length = 141
FEATURE                Location/Qualifiers
REGION                 1..141
                       note = Synthetic sequence TCR1,13 alpha chain constant
                        region
source                 1..141
                       mol_type = protein
                       organism = synthetic construct
SEQUENCE: 19
NIQNPDPAVY QLRDSKSSDK SVCLFTDFDS QTNVSQSKDS DVYITDKCVL DMRSMDFKSN  60
SAVAWSNKSD FACANAFNNS IIPEDTFFPS PESSCDVKLV EKSFETDTNL NFQNLSVIGF  120
RILLLKVAGF NLLMTLRLWS S                                           141

SEQ ID NO: 20          moltype = AA  length = 201
FEATURE                Location/Qualifiers
REGION                 1..201
                       note = Synthetic sequence TCR5 alpha chain constant region
                        (Cys modified)
source                 1..201
                       mol_type = protein
                       organism = synthetic construct
SEQUENCE: 20
NIQNPDPAVY QLRDSKSSDK SVCLFTDFDS QTNVSQSKDS DVYITDKCVL DMRSMDFKSN  60
SAVAWSNKSD FACANAFNNS IIPEDTFFPS PESSCDVKLV EKSFETDTNL NFQNLSVIGF  120
RILLLKVAGF NLLMTLRLWS SFACANAFNN SIIPEDTFFP SPESSCDVKL VEKSFETDTN  180
LNFQNLSVIG FRILLLKVAG F                                           201

SEQ ID NO: 21          moltype = AA  length = 81
FEATURE                Location/Qualifiers
REGION                 1..81
                       note = Synthetic sequence TCR10 alpha chain constant region
source                 1..81
                       mol_type = protein
                       organism = synthetic construct
SEQUENCE: 21
YIQNPDPAVY QLRDSKSSDK SVCLFTDFDS QTNVSQSKDS DVYITDKCVL DMRSMDFKSN  60
SAVAWSNKSD NLLMTLRLWS S                                           81

SEQ ID NO: 22          moltype = AA  length = 141
FEATURE                Location/Qualifiers
REGION                 1..141
                       note = Synthetic sequence TCR16 alpha chain constant region
                        (Cys modified)
source                 1..141
                       mol_type = protein
                       organism = synthetic construct
SEQUENCE: 22
NIQNPDPAVY QLRDSKSSDK SVCLFTDFDS QTNVSQSKDS DVYITDKCVL DMRSMDFKSN  60
SAVAWSNKSD FACANAFNNS IIPEDTFFPS PESSCDVKLV EKSFETDTNL NFQNLSVIGF  120
RILLLKVAGF NLLMTLRLWS S                                           141

SEQ ID NO: 23          moltype = AA  length = 176
FEATURE                Location/Qualifiers
REGION                 1..176
                       note = Synthetic sequence TCR2,14 beta chain constant
                        region (Cys modified)
```

-continued

```
source                  1..176
                        mol_type = protein
                        organism = synthetic construct
SEQUENCE: 23
EDLNKVFPPE VAVFEPSEAE ISHTQKATLV CLATGFFPDH VELSWWVNGK EVHSGVCTDP  60
QPLKEQPALN DSRYCLSSRL RVSATFWQNP RNHFRCQVQF YGLSENDEWT QDRAKPVTQI  120
VSAEAWGRAD CGFTSVSYQQ GVLSATILYE ILLGKATLYA VLVSALVLMA MVKRKD      176

SEQ ID NO: 24           moltype = AA  length = 141
FEATURE                 Location/Qualifiers
REGION                  1..141
                        note = Synthetic sequence TCR2,14 alpha chain constant
                         region (Cys modified)
source                  1..141
                        mol_type = protein
                        organism = synthetic construct
SEQUENCE: 24
NIQNPDPAVY QLRDSKSSDK SVCLFTDFDS QTNVSQSKDS DVYITDKCVL DMRSMDFKSN  60
SAVAWSNKSD FACANAFNNS IIPEDTFFPS PESSCDVKLV EKSFETDTNL NFQNLSVIGF  120
RILLLKVAGF NLLMTLRLWS S                                           141

SEQ ID NO: 25           moltype = AA  length = 177
FEATURE                 Location/Qualifiers
REGION                  1..177
                        note = Synthetic sequence TCR29 beta chain constant region
source                  1..177
                        mol_type = protein
                        organism = synthetic construct
SEQUENCE: 25
EDLNKVFPPE VAVFEPSEAE ISHTQKATLV CLATGFFPDH VELSWWVNGK EVHSGVSTDP  60
QPLKEQPALN DSRYCLSSRL RVSATFWQNP RNHFRCQVQF YGLSENDEWT QDRAKPVTQI  120
VSAEAWGRAD CGFTSVSYQQ GVLSATILYE ILLGKATLYA VLVSALVLMA MVKRKDF     177

SEQ ID NO: 26           moltype = AA  length = 141
FEATURE                 Location/Qualifiers
REGION                  1..141
                        note = Synthetic sequence TCR29 alpha chain constant region
source                  1..141
                        mol_type = protein
                        organism = synthetic construct
SEQUENCE: 26
NIQNPDPAVY QLRDSKSSDK SVCLFTDFDS QTNVSQSKDS DVYITDKTVL DMRSMDFKSN  60
SAVAWSNKSD FACANAFNNS IIPEDTFFPS PESSCDVKLV EKSFETDTNL NFQNLSVIGF  120
RILLLKVAGF NLLMTLRLWS S                                           141

SEQ ID NO: 27           moltype = AA  length = 310
FEATURE                 Location/Qualifiers
REGION                  1..310
                        note = Synthetic sequence TCR1,13 beta chain (full length)
                         (Cys modified)
source                  1..310
                        mol_type = protein
                        organism = synthetic construct
SEQUENCE: 27
MGTSLLCWMA LCLLGADHAD TGVSQDPRHK ITKRGQNVTF RCDPISEHNR LYWYRQTLGQ  60
GPEFLTYFQN EAQLEKSRLL SDRFSAERPK GSFSTLEIQR TEQGDSAMYL CASSSTGGHN  120
EQFFGPGTRL TVLEDLKNVF PPEVAVFEPS EAEISHTQKA TLVCLATGFY PDHVELSWWV  180
NGKEVHSGVC TDPQPLKEQP ALNDSRYCLS SRLRVSATFW QNPRNHFRCQ VQFYGLSEND  240
EWTQDRAKPV TQIVSAEAWG RADCGFTSES YQQGVLSATI LYEILLGKAT LYAVLVSALV  300
LMAMVKRKDS                                                        310

SEQ ID NO: 28           moltype = AA  length = 275
FEATURE                 Location/Qualifiers
REGION                  1..275
                        note = Synthetic sequence TCR1,13 alpha chain (full length)
                         (Cys modified) with signal peptide
source                  1..275
                        mol_type = protein
                        organism = synthetic construct
SEQUENCE: 28
METLLGVSLV ILWLQLARVN SQQGEEDPQA LSIQEGENAT MNCSYKTSIN NLQWYRQNSG  60
RGLVHLILIR SNEREKHSGR LRVTLDTSKK SSSLLITASR AADTASYFCA TKRDSGAGSY  120
QLTFGKGTKL SVIPNIQNPD PAVYQLRDSK SSDKSVCLFT DFDSQTNVSQ SKDSDVYITD  180
KCVLDMRSMD FKSNSAVAWS NKSDFACANA FNNSIIPEDT FFPSPESSCD VKLVEKSFET  240
DTNLNFQNLS VIGFRILLLK VAGFNLLMTL RLWSS                            275

SEQ ID NO: 29           moltype = AA  length = 308
FEATURE                 Location/Qualifiers
REGION                  1..308
```

```
                        note = Synthetic sequence TCR2,14 beta chain (full length)
                         (Cys modified) with signal peptide
source                  1..308
                        mol_type = protein
                        organism = synthetic construct
SEQUENCE: 29
MGTSLLCWMA LCLLGADHAD TGVSQDPRHK ITKRGQNVTF RCDPISEHNR LYWYRQTLGQ  60
GPEFLTYFQN EAQLEKSRLL SDRFSAERPK GSFSTLEIQR TEQGDSAMYL CASSLVKGEK  120
LFFGSGTQLS VLEDLNKVFP PEVAVFEPSE AEISHTQKAT LVCLATGFFP DHVELSWWVN  180
GKEVHSGVCT DPQPLKEQPA LNDSRYCLSS RLRVSATFWQ NPRNHFRCQV QFYGLSENDE  240
WTQDRAKPVT QIVSAEAWGR ADCGFTSVSY QQGVLSATIL YEILLGKATL YAVLVSALVL  300
MAMVKRKD                                                           308

SEQ ID NO: 30           moltype = AA  length = 273
FEATURE                 Location/Qualifiers
REGION                  1..273
                        note = Synthetic sequence TCR2,14 alpha chain (full length)
                         (Cys modified) with signal peptide
source                  1..273
                        mol_type = protein
                        organism = synthetic construct
SEQUENCE: 30
METLLGLLIL WLQLQWVSSK QEVTQIPAAL SVPEGENLVL NCSFTDSAIY NLQWFRQDPG  60
KGLTSLLLIQ SSQREQTSGR LNASLDKSSG RSTLYIAASQ PGDSATYLCA VIGLGGTYKY  120
IFGTGTRLKV LANIQNPDPA VYQLRDSKSS DKSVCLFTDF DSQTNVSQSK DSDVYITDKC  180
VLDMRSMDFK SNSAVAWSNK SDFACANAFN NSIIPEDTFF PSPESSCDVK LVEKSFETDT  240
NLNFQNLSVI GFRILLLKVA GFNLLMTLRL WSS                               273

SEQ ID NO: 31           moltype = AA  length = 309
FEATURE                 Location/Qualifiers
REGION                  1..309
                        note = Synthetic sequence TCR5 beta chain (full length)
                         (Cys modified) with signal peptide
source                  1..309
                        mol_type = protein
                        organism = synthetic construct
SEQUENCE: 31
MGTSLLCWMA LCLLGADHAD TGVSQDPRHK ITKRGQNVTF RCDPISEHNR LYWYRQTLGQ  60
GPEFLTYFQN EAQLEKSRLL SDRFSAERPK GSFSTLEIQR TEQGDSAMYL CASSLTTLDE  120
QYVGPGTRLT VTEDLKNVFP PEVAVFEPSE AEISHTQKAT LVCLATGFYP DHVELSWWVN  180
GKEVHSGVCT DPQPLKEQPA LNDSRYCLSS RLRVSATFWQ NPRNHFRCQV QFYGLSENDE  240
WTQDRAKPVT QIVSAEAWGR ADCGFTSESY QQGVLSATIL YEILLGKATL YAVLVSALVL  300
MAMVKRKDS                                                          309

SEQ ID NO: 32           moltype = AA  length = 271
FEATURE                 Location/Qualifiers
REGION                  1..271
                        note = Synthetic sequence TCR5 alpha chain (full length)
                         (Cys modified) with signal peptide
source                  1..271
                        mol_type = protein
                        organism = synthetic construct
SEQUENCE: 32
METLLGVSLV ILWLQLARVN SQQGEEDPQA LSIQEGENAT MNCSYKTSIN NLQWYRQNSG  60
RGLVHLILIR SNEREKHSGR LRVTLDTSKK SSSLLITASR AADTASYFCA TNSGNTPLVF  120
GKGTRLSVIA NIQNPDPAVY QLRDSKSSDK SVCLFTDFDS QTNVSQSKDS DVYITDKCVL  180
DMRSMDFKSN SAVAWSNKSD FACANAFNNS IIPEDTFFPS PESSCDVKLV EKSFETDTNL  240
NFQNLSVIGF RILLLKVAGF NLLMTLRLWS S                                 271

SEQ ID NO: 33           moltype = AA  length = 309
FEATURE                 Location/Qualifiers
REGION                  1..309
                        note = Synthetic sequence TCR10 beta chain (full length)
                         (Cys modified) with signal peptide
source                  1..309
                        mol_type = protein
                        organism = synthetic construct
SEQUENCE: 33
MGTSLLCWMA LCLLGADHAD TGVSQDPRHK ITKRGQNVTF RCDPISEHNR LYWYRQTLGQ  60
GPEFLTYFQN EAQLEKSRLL SDRFSAERPK GSFSTLEIQR TEQGDSAMYL CASSMLTNYE  120
QYFGPGTRLT VTEDLKNVFP PEVAVFEPSE AEISHTQKAT LVCLATGFYP DHVELSWWVN  180
GKEVHSGVCT DPQPLKEQPA LNDSRYCLSS RLRVSATFWQ NPRNHFRCQV QFYGLSENDE  240
WTQDRAKPVT QIVSAEAWGR ADCGFTSESY QQGVLSATIL YEILLGKATL YAVLVSALVL  300
MAMVKRKDS                                                          309

SEQ ID NO: 34           moltype = AA  length = 275
FEATURE                 Location/Qualifiers
REGION                  1..275
                        note = Synthetic sequence TCR10 alpha chain (full length)
```

```
                         (Cys modified) with signal peptide
source                  1..275
                        mol_type = protein
                        organism = synthetic construct
SEQUENCE: 34
MKKHLTTFLV ILWLYFYRGN GKNQVEQSPQ SLIILEGKNC TLQCNYTVSP FSNLRWYKQD  60
TGRGPVSLTI MTFSENTKSN GRYTATLDAD TKQSSLHITA SQLSDSASYI CVVDSGGGAD  120
GLTFGKGTHL IIQPYIQNPD PAVYQLRDSK SSDKSVCLFT DFDSQTNVSQ SKDSDVYITD  180
KCVLDMRSMD FKSNSAVAWS NKSDFACANA FNNSIIPEDT FFPSPESSCD VKLVEKSFET  240
DTNLNFQNLS VIGFRILLLK VAGFNLLMTL RLWSS                             275

SEQ ID NO: 35           moltype = AA  length = 308
FEATURE                 Location/Qualifiers
REGION                  1..308
                        note = Synthetic sequence TCR16 beta chain (full length)
                         (Cys modified) with signal peptide
source                  1..308
                        mol_type = protein
                        organism = synthetic construct
SEQUENCE: 35
MGTSLLCWMA LCLLGADHAD TGVSQDPRHK ITKRGQNVTF RCDPISEHNR LYWYRQTLGQ  60
GPEFLTYFQN EAQLEKSRLL SDRFSAERPK GSFSTLEIQR TEQGDSAMYL CASSLVVGNE  120
QFFGPGTRLT VLEDLKNVFP PEVAVFEPSE AEISHTQKAT LVCLATGFYP DHVELSWWVN  180
GKEVHSGVCT DPQPLKEQPA LNDSRYCLSS RLRVSATFWQ NPRNHFRCQV QFYGLSENDE  240
WTQDRAKPVT QIVSAEAWGR ADCGFTSESY QQGVLSATIL YEILLGKATL YAVLVSALVL  300
MAMVKRKD                                                           308

SEQ ID NO: 36           moltype = AA  length = 272
FEATURE                 Location/Qualifiers
REGION                  1..272
                        note = Synthetic sequence TCR16 alpha chain (full length)
                         (Cys modified) with signal peptide
source                  1..272
                        mol_type = protein
                        organism = synthetic construct
SEQUENCE: 36
METLLGLLIL WLQLQWVSSK QEVTQIPAAL SVPEGENLVL NCSFTDSAIY NLQWFRQDPG  60
KGLTSLLLIQ SSQREQTSGR LNASLDKSSG RSTLYIAASQ PGDSATYLCA VHLLNDYKLS  120
FGAGTTVTVR ANIQNPDPAV YQLRDSKSSD KSVCLFTDFD SQTNVSQSKD SDVYITDKCV  180
LDMRSMDFKS NSAVAWSNKS DFACANAFNN SIIPEDTFFP SPESSCDVKL VEKSFETDTN  240
LNFQNLSVIG FRILLLKVAG FNLLMTLRLW SS                                272

SEQ ID NO: 37           moltype = AA  length = 309
FEATURE                 Location/Qualifiers
REGION                  1..309
                        note = Synthetic sequence TCR29 beta chain (full length)
                         with signal peptide
source                  1..309
                        mol_type = protein
                        organism = synthetic construct
SEQUENCE: 37
MGTSLLCWMA LCLLGADHAD TGVSQDPRHK ITKRGQNVTF RCDPISEHNR LYWYRQTLGQ  60
GPEFLTYFQN EAQLEKSRLL SDRFSAERPK GSFSTLEIQR TEQGDSAMYL CASSLVSGNT  120
IYFGEGSWLT VVEDLNKVFP PEVAVFEPSE AEISHTQKAT LVCLATGFFP DHVELSWWVN  180
GKEVHSGVST DPQPLKEQPA LNDSRYCLSS RLRVSATFWQ NPRNHFRCQV QFYGLSENDE  240
WTQDRAKPVT QIVSAEAWGR ADCGFTSVSY QQGVLSATIL YEILLGKATL YAVLVSALVL  300
MAMVKRKDF                                                          309

SEQ ID NO: 38           moltype = AA  length = 275
FEATURE                 Location/Qualifiers
REGION                  1..275
                        note = Synthetic sequence TCR29 alpha chain (full length)
                         with signal peptide
source                  1..275
                        mol_type = protein
                        organism = synthetic construct
SEQUENCE: 38
METLLGLLIL WLQLQWVSSK QEVTQIPAAL SVPEGENLVL NCSFTDSAIY NLQWFRQDPG  60
KGLTSLLLIQ SSQREQTSGR LNASLDKSSG RSTLYIAASQ PGDSATYLCA VRGGTTSGTY  120
KYIFGTGTRL KVLANIQNPD PAVYQLRDSK SSDKSVCLFT DFDSQTNVSQ SKDSDVYITD  180
KTVLDMRSMD FKSNSAVAWS NKSDFACANA FNNSIIPEDT FFPSPESSCD VKLVEKSFET  240
DTNLNFQNLS VIGFRILLLK VAGFNLLMTL RLWSS                             275

SEQ ID NO: 39           moltype = DNA  length = 930
FEATURE                 Location/Qualifiers
misc_feature            1..930
                        note = Synthetic sequence TCR1,13 beta chain (codon
                         optimized, Cys modified)
source                  1..930
```

```
                        mol_type = other DNA
                        organism = synthetic construct
SEQUENCE: 39
atgggcacct ccctgctgtg ttggatggcc ctgtgtctgc tgggagccga ccatgccgat  60
acaggggtgt cccaggaccc ccggcacaag attaccaagc ggggccagaa cgtgaccttc  120
agatgcgacc ccatcagcga gcacaaccgg ctgtactggt acaggcagac cctgggccag  180
ggccccgagt tcctgaccta ctttcagaac gaggcccagc tggaaaagtc ccggctgctg  240
agcgacagat tcagcgccga aagacccaag ggcagcttca gcaccctgga aatccagcgg  300
accgagcagg gcgatagcgc catgtacctg tgtgccagca gcagcacagg cggccacaac  360
gagcagttct ttggccctgg cacccggctg accgtgctgg aagatctgaa gaacgtgttc  420
cccccagagg tggccgtgtt cgagccttct gaggccgaga tcagccacac ccagaaagcc  480
accctcgtgt gtctggccac cggcttctac cccgaccacg tggaactgtc ttggtgggtc  540
aacggcaaag aggtgcactc cggcgtgtgc accgatcccc agcctctgaa agaacagccc  600
gccctgaacg acagccggta ctgcctgagc agcagactga gagtgtccgc caccttctgg  660
cagaaccccc ggaaccactt cagatgccag gtgcagttct acggcctgag cgagaacgac  720
gagtggaccc aggacagagc caagcccgtg acccagatcg tgtctgccga agcctggggc  780
agagccgatt gcggctttac cagcgagagc taccagcagg gcgtgctgag cgccaccatc  840
ctgtacgaga tcctgctggg caaggccacc ctgtacgccg tgctggtgtc tgccctggtg  900
ctgatggcca tggtcaagcg gaaggacagc                                  930

SEQ ID NO: 40           moltype = DNA  length = 828
FEATURE                 Location/Qualifiers
misc_feature            1..828
                        note = Synthetic sequence TCR1,13 alpha chain (codon
                         optimized; Cys modified)
source                  1..828
                        mol_type = other DNA
                        organism = synthetic construct
SEQUENCE: 40
atggaaacac tgctgggcgt gtccctcgtg atcctgtggc tgcagctggc cagagtgaac  60
agccagcagg gggaagagga tccccaggcc ctgagcattc aggaaggcga gaacgccacc  120
atgaactgca gctacaagac cagcatcaac aacctgcagt ggtacagaca gaacagcggc  180
agaggcctgg tgcacctgat cctgatcaga agcaacgaga gagagaagca cagcggacgg  240
ctgagagtga ccctggacac ctccaagaag tccagctccc tgctgatcac cgccagcaga  300
gccgccgata ccgccagcta cttctgtgcc accaagcggg attctggcgc cggatcctac  360
cagctgacct tcggcaaggg caccaagctg agcgtgatcc ccaacatcca gaaccccgac  420
cccgccgtgt atcagctgag agacagcaag agcagcgaca agagcgtgtg cctgttcacc  480
gacttcgaca gccagaccaa cgtgtcccag agcaaggaca gcgacgtgta catcaccgat  540
aagtgcgtgc tggacatgcg gagcatggac ttcaagagca acagcgccgt ggcctggtcc  600
aacaagagcg acttcgcctg cgccaacgcc ttcaacaaca gcatcatccc cgaggacacc  660
tttttcccca gccccgagag cagctgcgac gtgaaactgg tggagaagtc cttcgagaca  720
gacaccaatc tgaactttca gaacctgagc gtgatcggct tccggatcct gctgctgaaa  780
gtggccggct tcaatctgct gatgaccctg cggctgtgga gcagctga              828

SEQ ID NO: 41           moltype = DNA  length = 930
FEATURE                 Location/Qualifiers
misc_feature            1..930
                        note = Synthetic sequence TCR2,14 beta chain (codon
                         optimized; Cys modified)
source                  1..930
                        mol_type = other DNA
                        organism = synthetic construct
SEQUENCE: 41
atgggcacct ccctgctgtg ttggatggcc ctgtgtctgc tgggagccga ccatgccgat  60
acaggggtgt cccaggaccc ccggcacaag attaccaagc ggggccagaa cgtgaccttc  120
agatgcgacc ccatcagcga gcacaaccgg ctgtactggt acaggcagac cctgggccag  180
ggccccgagt tcctgaccta ctttcagaac gaggcccagc tggaaaagtc ccggctgctg  240
agcgacagat tcagcgccga aagacccaag ggcagcttca gcaccctgga aatccagcgg  300
accgagcagg gcgatagcgc catgtacctg tgtgccagca gcctcgtgaa gggcgagaag  360
ctgttcttcg gcagcggcac ccagctgagc gtgctggaag atctgaacaa ggtgttcccc  420
ccagaggtgg ccgtgttcga gccttctgag gccgagatca gccacaccca gaaagccacc  480
ctcgtgtgcc tggccaccgg ctttttcccc gaccacgtgg aactgtcttg gtgggtcaac  540
ggcaaagagg tgcactccgg cgtgtgcacc gatccccagc ctctgaaaga acagcccgcc  600
ctgaacgaca gccggtactg cctgagcagc agactgagag tgtccgccac cttctggcag  660
aacccccgga accacttcag atgccaggtg cagttctacg gcctgagcga gaacgacgag  720
tggacccagg acagagccaa gcccgtgacc cagatcgtgt ctgccgaagc ctggggcaga  780
gccgattgcg gctttaccag cgtgtcctat cagcagggcg tgctgagcgc caccatcctg  840
tacgagatcc tgctgggcaa ggccaccctg tacgccgtgc tggtgtctgc cctggtgctg  900
atggccatgg tcaagcggaa ggactttggc                                  930

SEQ ID NO: 42           moltype = DNA  length = 820
FEATURE                 Location/Qualifiers
misc_feature            1..820
                        note = Synthetic sequence TCR2,14 alpha chain (codon
                         optimized; Cys modified)
source                  1..820
                        mol_type = other DNA
                        organism = synthetic construct
SEQUENCE: 42
```

```
atggaaacac tgctgggcct gctgatcctg tggctgcagc tgcagtgggt gtccagcaag  60
caggaagtga cacagatccc tgccgccctg tctgtgcccg agggcgaaaa tctggtgctg  120
aactgcagct tcaccgacag cgccatctac aacctgcagt ggttcagaca ggaccccggc  180
aagggcctga caagcctgct gctgattcag agcagccaga gagagcagac cagcggcaga  240
ctgaacgcca gcctggataa gagcagcggc cgcagcaccc tgtatatcgc cgcttctcag  300
cctggcgact ctgccacata tctgtgcgcc gtgatcggcc tgggcggcac ctacaagtac  360
atctttggca ccggcaccag actgaaagtg ctggccaaca tccagaaccc cgaccccgcc  420
gtgtaccagc tgagagacag caagtccagc gacaagagcg tgtgtctgtt caccgacttc  480
gacagccaga ccaacgtgtc ccagagcaag gacagcgacg tgtacatcac cgataagtgc  540
gtgctggaca tgcggagcat ggacttcaag agcaacagcg ccgtggcctg gtccaacaag  600
agcgacttcg cctgcgccaa cgccttcaac aacagcatca tccccgagga cacctttttc  660
cccagccccg agagcagctg cgacgtgaaa ctggtggaga agtccttcga gacagacacc  720
aatctgaact ttcagaacct gagcgtgatc ggcttccgga tcctgctgct gaaagtggcc  780
ggcttcaatc tgctgatgac cctgcggctg tggagcagcg                       820

SEQ ID NO: 43           moltype = DNA  length = 933
FEATURE                 Location/Qualifiers
misc_feature            1..933
                        note = Synthetic sequence TCR5 beta chain (codon optimized;
                         Cys modified)
source                  1..933
                        mol_type = other DNA
                        organism = synthetic construct
SEQUENCE: 43
atgggcacct ccctgctgtg ttggatggcc ctgtgtctgc tgggagccga ccatgccgat  60
acaggggtgt cccaggaccc ccggcacaag attaccaagc ggggccagaa cgtgaccttc  120
agatgcgacc ccatcagcga gcacaaccgg ctgtactggt acaggcagac cctgggccag  180
ggccccgagt tcctgaccta ctttcagaac gaggcccagc tggaaaagtc ccggctgctg  240
agcgacagat tcagcgccga aagacccaag ggcagcttca gcaccctgga aatccagcgg  300
accgagcagg gggacagcgc catgtatctg tgtgccagct ccctgaccac cctggacgag  360
cagtatgtgg gcccaggcac cagactgacc gtgaccgagg acctgaagaa cgtgttcccc  420
ccagaggtgg ccgtgttcga gccttctgag gccgagatca gccacaccca gaaagccacc  480
ctcgtgtgtc tggccaccgg cttctacccc gatcacgtgg agctgtcttg gtgggtgaac  540
ggcaaagagg tgcacagcgg cgtctgcacc gacccccagc ccctgaaaga gcagcccgcc  600
ctgaacgaca gccggtactg cctgagcagc cggctgagag tgagcgccac cttctggcag  660
aacccccgga accacttccg gtgccaggtg cagttctacg gcctgagcga gaacgacgag  720
tggacccagg acagagccaa gcccgtgacc cagatcgtga gcgccgaggc ctggggcaga  780
gccgactgcg gcttcaccag cgagagctac cagcagggcg tgctgtccgc cacaatcctg  840
tacgagatcc tgctgggcaa ggccaccctg tacgccgtgc tggtgtccgc cctggtgctg  900
atggccatgg tgaagcggaa ggacagccgg ggc                              933

SEQ ID NO: 44           moltype = DNA  length = 816
FEATURE                 Location/Qualifiers
misc_feature            1..816
                        note = Synthetic sequence TCR5 alpha chain (codon
                         optimized; Cys modified)
source                  1..816
                        mol_type = other DNA
                        organism = synthetic construct
SEQUENCE: 44
atggaaaccc tgctgggcgt gtccctcgtg atcctgtggc tgcagctggc cagagtgaac  60
agccagcagg gcgaagaaga tccccaggcc ctgagcatcc aggaaggcga gaacgccaca  120
atgaactgca gctacaagac cagcatcaac aacctgcagt ggtacagaca gaacagcggc  180
agaggcctgg tgcacctgat cctgatcaga agcaacgaga gagagaagca ctccggcaga  240
ctgagagtga ccctggacac cagcaagaag tccagcagcc tgctgatcac cgccagcaga  300
gccgccgata ccgccagcta cttctgcgcc accaactccg gcaacacccc cctggtgttt  360
ggcaagggca cccggctgag cgtgatcgcc aacatccaga accccgaccc cgccgtgtac  420
cagctgagag acagcaagag cagcgacaag agcgtgtgcc tgttcaccga cttcgacagc  480
cagaccaacg tgtcccagag caaggacagc gacgtgtaca tcaccgataa gtgcgtgctg  540
gacatgcgga gcatggactt caagagcaac agcgccgtgg cctggtccaa caagagcgac  600
ttcgcctgcg ccaacgcctt caacaacagc atcatccccg aggacacctt tttccccagc  660
cccgagagca gctgcgacgt gaaactggtg gagaagtcct tcgagacaga caccaatctg  720
aactttcaga acctgagcgt gatcggcttc cggatcctgc tgctgaaagt ggccggcttc  780
aatctgctga tgaccctgcg gctgtggagc agctga                           816

SEQ ID NO: 45           moltype = DNA  length = 933
FEATURE                 Location/Qualifiers
misc_feature            1..933
                        note = Synthetic sequence TCR10 beta chain (codon
                         optimized; Cys modified)
source                  1..933
                        mol_type = other DNA
                        organism = synthetic construct
SEQUENCE: 45
atgggcacct ccctgctgtg ttggatggcc ctgtgtctgc tgggagccga ccatgccgat  60
acaggggtgt cccaggaccc ccggcacaag attaccaagc ggggccagaa cgtgaccttc  120
agatgcgacc ccatcagcga gcacaaccgg ctgtactggt acaggcagac cctgggccag  180
ggccccgagt tcctgaccta ctttcagaac gaggcccagc tggaaaagtc ccggctgctg  240
agcgacagat tcagcgccga aagacccaag ggcagcttca gcaccctgga aatccagcgg  300
```

```
accgagcagg gcgatagcgc catgtacctg tgcgccagct ccatgctgac caactacgag  360
cagtacttcg gccctggcac ccggctgacc gtgaccgagg atctgaagaa cgtgttcccc  420
ccagaggtgg ccgtgttcga gccttctgag gccgagatca gccacaccca gaaagccacc  480
ctcgtgtgtc tggccaccgg cttctacccc gaccacgtgg aactgtcttg gtgggtcaac  540
ggcaaagagg tgcactccgg cgtgtgcacc gatccccagc ctctgaaaga acagcccgcc  600
ctgaacgaca gccggtactg cctgagcagc agactgagag tgtccgccac cttctggcag  660
aacccccgga accacttcag atgccaggtg cagttctacg gcctgagcga gaacgacgag  720
tggacccagg acagagccaa gcccgtgacc cagatcgtgt ctgccgaagc ctggggcaga  780
gccgattgcg gctttaccag cgagagctac cagcagggcg tgctgagcgc caccatcctg  840
tacgagatcc tgctgggcaa ggccaccctg tacgccgtgc tggtgtctgc cctggtgctg  900
atggccatgg tcaagcggaa ggacagcaga ggc                              933

SEQ ID NO: 46          moltype = DNA  length = 828
FEATURE                Location/Qualifiers
misc_feature           1..828
                       note = Synthetic sequence TCR10 alpha chain (codon
                        optimized; Cys modified)
source                 1..828
                       mol_type = other DNA
                       organism = synthetic construct
SEQUENCE: 46
atgaagaagc acctgaccac ctttctcgtg atcctgtggc tgtacttcta ccggggcaac  60
ggcaagaacc aggtggaaca gagcccccag agcctgatca tcctggaagg caagaattgc  120
accctgcagt gcaactacac cgtgtccccc ttcagcaacc tgcggtggta caagcaggac  180
accggcagag gccctgtgtc cctgaccatc atgaccttca gcgagaacac caagagcaac  240
ggccggtaca ccgccaccct ggatgccgat acaaagcaga gcagcctgca catcaccgcc  300
agccagctga gcgattccgc cagctacatc tgcgtggtgg attctggcgg cggagccgat  360
ggcctgacat ttggcaaggg cacccacctg atcattcagc cctacatcca gaaccccgac  420
cccgccgtgt accagctgag agacagcaag tccagcgaca agagcgtgtg cctgttcacc  480
gacttcgaca gccagaccaa cgtgtcccag agcaaggaca gcgacgtgta catcaccgat  540
aagtgcgtgc tggacatgcg gagcatggac ttcaagagca acagcgccgt ggcctggtcc  600
aacaagagcg acttcgcctg cgccaacgcc ttcaacaaca gcatcatccc cgaggacacc  660
tttttcccca gccccgagag cagctgcgac gtgaaactgg tggagaagtc cttcgagaca  720
gacaccaatc tgaactttca gaacctgagc gtgatcggct tccggatcct gctgctgaaa  780
gtggccggct tcaatctgct gatgaccctg cggctgtgga gcagctga              828

SEQ ID NO: 47          moltype = DNA  length = 933
FEATURE                Location/Qualifiers
misc_feature           1..933
                       note = Synthetic sequence TCR16 beta chain (codon
                        optimized; Cys modified)
source                 1..933
                       mol_type = other DNA
                       organism = synthetic construct
SEQUENCE: 47
atgggcacct ccctgctgtg ttggatggcc ctgtgtctgc tgggagccga ccatgccgat  60
acaggggtgt cccaggaccc ccggcacaag attaccaagc ggggccagaa cgtgaccttc  120
agatgcgacc ccatcagcga gcacaaccgg ctgtactggt acaggcagac cctgggccag  180
ggccccgagt tcctgaccta ctttcagaac gaggcccagc tggaaaagtc ccggctgctg  240
agcgacagat tcagcgccga aagacccaag ggcagcttca gcaccctgga aatccagcgg  300
accgagcagg gcgatagcgc catgtacctg tgtgccagca gcctggtcgt gggcaacgag  360
cagtttttcg gccctggcac cagactgacc gtgctggaag atctgaagaa cgtgttcccc  420
ccagaggtgg ccgtgttcga gccttctgag gccgagatca gccacaccca gaaagccacc  480
ctcgtgtgtc tggccaccgg cttctacccc gaccacgtgg aactgtcttg gtgggtcaac  540
ggcaaagagg tgcactccgg cgtgtgcacc gatccccagc ctctgaaaga acagcccgcc  600
ctgaacgaca gccggtactg cctgagcagc agactgagag tgtccgccac cttctggcag  660
aacccccgga accacttcag atgccaggtg cagttctacg gcctgagcga gaacgacgag  720
tggacccagg acagagccaa gcccgtgacc cagatcgtgt ctgccgaagc ctggggcaga  780
gccgattgcg gctttaccag cgagagctac cagcagggcg tgctgagcgc caccatcctg  840
tacgagatcc tgctgggcaa ggccaccctg tacgccgtgc tggtgtctgc cctggtgctg  900
atggccatgg tcaagcggaa ggacagcaga ggc                              933

SEQ ID NO: 48          moltype = DNA  length = 819
FEATURE                Location/Qualifiers
misc_feature           1..819
                       note = Synthetic sequence TCR16 alpha chain (codon
                        optimized; Cys modified)
source                 1..819
                       mol_type = other DNA
                       organism = synthetic construct
SEQUENCE: 48
atggaaacac tgctgggcct gctgatcctg tggctgcagc tgcagtgggt gtccagcaag  60
caggaagtga cacagatccc tgccgccctg tctgtgcccg agggcgaaaa tctggtgctg  120
aactgcagct tcaccgacag cgccatctac aacctgcagt ggttcagaca ggaccccggc  180
aagggcctga caagcctgct gctgattcag agcagccaga gagagcagac cagcggcaga  240
ctgaacgcca gcctggataa gagcagcggc cgcagcaccc tgtatatcgc cgcttctcag  300
cctggcgact ctgccacata tctgtgcgcc gtgcatctgc tgaacgacta caagctgagc  360
ttcggagccg gcaccaccgt gacagtgcgg gccaacatcc agaaccccga ccctgccgtg  420
taccagctga gagacagcaa gtccagcgac aagagcgtgt gcctgttcac cgacttcgac  480
```

```
agccagacca acgtgtccca gagcaaggac agcgacgtgt acatcaccga taagtgcgtg  540
ctggacatgc ggagcatgga cttcaagagc aacagcgccg tggcctggtc caacaagagc  600
gacttcgcct gcgccaacgc cttcaacaac agcatcatcc ccgaggacac ctttttcccc  660
agccccgaga gcagctgcga cgtgaaactg gtggagaagt ccttcgagac agacaccaat  720
ctgaactttc agaacctgag cgtgatcggc ttccggatcc tgctgctgaa agtggccggc  780
ttcaatctgc tgatgaccct gcggctgtgg agcagctga                        819

SEQ ID NO: 49          moltype = DNA  length = 939
FEATURE                Location/Qualifiers
misc_feature           1..939
                       note = Synthetic sequence TCR24 beta chain (wild type)
source                 1..939
                       mol_type = other DNA
                       organism = synthetic construct
SEQUENCE: 49
atgggtcctg ggcttctcca ctggatggcc ctttgtctcc ttggaacagg tcatggggat  60
gccatggtca tccagaaccc aagataccag gttacccagt ttggaaagcc agtgaccctg  120
agttgttctc agactttgaa ccataacgtc atgtactggt accagcagaa gtcaagtcag  180
gccccaaagc tgctgttcca ctactatgac aaagatttta acaatgaagc agacacccct  240
gataacttcc aatccaggag gccgaacact tctttctgct ttcttgacat ccgctcacca  300
ggcctggggg acgcagccat gtacctgtgt gccaccagca agacacggat agctcaagag  360
acccagtact tcgggccagg cacgcggctc ctggtgctcg aggacctgaa aaacgtgttc  420
ccacccgagg tcgctgtgtt tgagccatca gaagcagaga tctcccacac ccaaaaggcc  480
acactggtgt gcctggccac aggcttctac cccgaccacg tggagctgag ctggtgggtg  540
aatgggaagg aggtgcacag tggggtcagc acagacccgc agcccctcaa ggagcagccc  600
gccctcaatg actccagata ctgcctgagc agccgcctga gggtctcggc caccttctgg  660
cagaaccccc gcaaccactt ccgctgtcaa gtccagttct acgggctctc ggagaatgac  720
gagtggaccc aggatagggc caaacctgtc acccagatcg tcagcgccga ggcctggggt  780
agagcagact gtggcttcac ctccgagtct taccagcaag ggtcctgtc tgccaccatc  840
ctctatgaga tcttgctagg gaaggccacc ttgtatgccg tgctggtcag tgccctcgtg  900
ctgatggcca tggtcaagag aaaggattcc agaggctag                        939

SEQ ID NO: 50          moltype = DNA  length = 825
FEATURE                Location/Qualifiers
misc_feature           1..825
                       note = Synthetic sequence TCR24 alpha chain (wild type)
source                 1..825
                       mol_type = other DNA
                       organism = synthetic construct
SEQUENCE: 50
atgctcctgg agcttatccc actgctgggg atacattttg tcctgagaac tgccagagcc  60
cagtcagtga cccagcctga catccacatc actgtctctg aaggagcctc actggagttg  120
agatgtaact attcctatgg ggcaacacct tatctcttct ggtatgtcca gtcccccggc  180
caaggcctcc agctgctcct gaagtacttt tcaggagaca ctctggttca aggcattaaa  240
ggctttgagg ctgaatttaa gaggagtcaa tcttccttca acctgaggaa accctctgtg  300
cattggagtg atgctgctga gtacttctgt gctgtgggtt ataacaccaa tgcaggcaaa  360
tcaacctttg gggatgggac tacgctcact gtgaagccaa atatccagaa ccctgaccct  420
gccgtgtacc agctgagaga ctctaaatcc agtgacaagt ctgtctgcct attcaccgat  480
tttgattctc aaacaaatgt gtcacaaagt aaggattctg atgtgtatat cacagacaaa  540
actgtgctag acatgaggtc tatggacttc aagagcaaca gtgctgtggc ctggagcaac  600
aaatctgact ttgcatgtgc aaacgccttc aacaacagca ttattccaga agacaccttc  660
ttccccagcc cagaaagttc ctgtgatgtc aagctggtcg agaaaagctt tgaaacagat  720
acgaacctaa actttcaaaa cctgtcagtg attgggttcc gaatcctcct cctgaaagtg  780
gccgggttta atctgctcat gacgctgcgg ctgtggtcca gctga                 825

SEQ ID NO: 51          moltype = DNA  length = 929
FEATURE                Location/Qualifiers
misc_feature           1..929
                       note = Synthetic sequence TCR29 beta chain (codon
                        optimized; Cys modified)
source                 1..929
                       mol_type = other DNA
                       organism = synthetic construct
SEQUENCE: 51
atgggcacaa gcctgctgtg ttggatggcc ctgtgtctgc tgggagccga tcatgccgat  60
acgggagtgt cccaggatcc tcggcacaag attaccaagc ggggccagaa cgtgaccttc  120
agatgcgacc ctatcagcga gcacaaccgg ctgtactggt acagacagac actcggccag  180
ggacctgagt tcctgaccta cttccagaac gaggcccagc tggaaaagag cagactgctg  240
agcgacagat tcagcgccga aagacccaag ggcagcttca gcaccctgga aatccagaga  300
accgagcagg gcgacagcgc catgtatctg tgtgccagct ctctggtgtc cggcaacacc  360
atctacttcg gcgaaggcag ctggctgaca gtggttaaga tctgaacaag gtgttccccc  420
cagaggtggc cgtgttcgag ccttctgagg ccgagatcag ccacacccag aaagccaccc  480
tcgtgtgcct ggccaccggc tttttccccg accacgtgga actgtcttgg tgggtcaacg  540
gcaaagaggt gcactccggc gtgtgcaccg atccccagcc tctgaaagaa cagcccgccc  600
tgaacgacag ccggtactgc ctgagcagca gactgagagt gtccgccacc ttctggcaga  660
acccccggaa ccacttcaga tgccaggtgc agttctacgg cctgagcgag aacgacgagt  720
ggacccagga cagagccaag cccgtgaccc agatcgtgtc tgccgaagcc tggggcagag  780
ccgattgcgg ctttaccagc gtgtcctatc agcagggcgt gctgagcgcc accatcctgt  840
acgagatcct gctgggcaag gccaccctgt acgccgtgct ggtgtctgcc ctggtgctga  900
```

```
tggccatggt caagcggaag gactttggc                                929

SEQ ID NO: 52          moltype = DNA  length = 828
FEATURE                Location/Qualifiers
misc_feature           1..828
                       note = Synthetic sequence TCR29 alpha chain (codon
                        optimized; Cys modified)
source                 1..828
                       mol_type = other DNA
                       organism = synthetic construct
SEQUENCE: 52
atggaaacac tgctgggcct gctgatcctg tggctgcaac tgcaatgggt gtccagcaag  60
caagaagtga cacagatccc tgccgctctg tctgtgcctg agggcgaaaa cctggtgctg  120
aactgcagct tcaccgacag cgccatctac aacctgcagt ggttcagaca ggaccccggc  180
aagggactga caagcctgct gctgattcag agcagccaga gagagcagac cagcggcaga  240
ctgaatgcca gcctggataa gtcctccggc agaagcaccc tgtatatcgc cgcttctcag  300
cctggcgata gcgccacata tctgtgtgcc gttagaggcg gcaccacctc cggcacctac  360
aagtacatct ttggcaccgg caccagactg aaggtgctgg ccaatatcca gaaccccgac  420
cccgccgtgt accagctgag agacagcaag tccagcgaca agagcgtgtg tctgttcacc  480
gacttcgaca gccagaccaa cgtgtcccag agcaaggaca gcgacgtgta catcaccgat  540
aagtgcgtgc tggacatgcg gagcatggac ttcaagagca acagcgccgt ggcctggtcc  600
aacaagagcg acttcgcctg cgccaacgcc ttcaacaaca gcatcatccc cgaggacacc  660
tttttcccca gccccgagag cagctgcgac gtgaaactgg tggagaagtc cttcgagaca  720
gacaccaatc tgaactttca gaacctgagc gtgatcggct tccggatcct gctgctgaaa  780
gtggccggct tcaatctgct gatgaccctg cggctgtgga gcagctga            828

SEQ ID NO: 53          moltype = AA  length = 609
FEATURE                Location/Qualifiers
REGION                 1..609
                       note = Synthetic sequence TCR1/13 beta-P2A-alpha (Cys
                        modified) with signal peptide
source                 1..609
                       mol_type = protein
                       organism = synthetic construct
SEQUENCE: 53
MGTSLLCWMA LCLLGADHAD TGVSQDPRHK ITKRGQNVTF RCDPISEHNR LYWYRQTLGQ  60
GPEFLTYFQN EAQLEKSRLL SDRFSAERPK GSFSTLEIQR TEQGDSAMYL CASSSTGGHN  120
EQFFGPGTRL TVLEDLKNVF PPEVAVFEPS EAEISHTQKA TLVCLATGFY PDHVELSWWV  180
NGKEVHSGVC TDPQPLKEQP ALNDSRYCLS SRLRVSATFW QNPRNHFRCQ VQFYGLSEND  240
EWTQDRAKPV TQIVSAEAWG RADCGFTSES YQQGVLSATI LYEILLGKAT LYAVLVSALV  300
LMAMVKRKDS RGGSGATNFS LLKQAGDVEE NPGPMETLLG VSLVILWLQL ARVNSQQGEE  360
DPQALSIQEG ENATMNCSYK TSINNLQWYR QNSGRGLVHL ILIRSNEREK HSGRLRVTLD  420
TSKKSSSLLI TASRAADTAS YFCATKRDSG AGSYQLTFGK GTKLSVIPNI QNPDPAVYQL  480
RDSKSSDKSV CLFTDFDSQT NVSQSKDSDV YITDKCVLDM RSMDFKSNSA VAWSNKSDFA  540
CANAFNNSII PEDTFFPSPE SSCDVKLVEK SFETDTNLNF QNLSVIGFRI LLLKVAGFNL  600
LMTLRLWSS                                                      609

SEQ ID NO: 54          moltype = AA  length = 604
FEATURE                Location/Qualifiers
REGION                 1..604
                       note = Synthetic sequence TCR2/14 beta-P2A-alpha (Cys
                        modified) with signal peptide
source                 1..604
                       mol_type = protein
                       organism = synthetic construct
SEQUENCE: 54
MGTSLLCWMA LCLLGADHAD TGVSQDPRHK ITKRGQNVTF RCDPISEHNR LYWYRQTLGQ  60
GPEFLTYFQN EAQLEKSRLL SDRFSAERPK GSFSTLEIQR TEQGDSAMYL CASSLVKGEK  120
LFFGSGTQLS VLEDLNKVFP PEVAVFEPSE AEISHTQKAT LVCLATGFFP DHVELSWWVN  180
GKEVHSGVCT DPQPLKEQPA LNDSRYCLSS RLRVSATFWQ NPRNHFRCQV QFYGLSENDE  240
WTQDRAKPVT QIVSAEAWGR ADCGFTSVSY QQGVLSATIL YEILLGKATL YAVLVSALVL  300
MAMVKRKDFG SGATNFSLLK QAGDVEENPG PMETLLGLLI LWLQLQWVSS KQEVTQIPAA  360
LSVPEGENLV LNCSFTDSAI YNLQWFRQDP GKGLTSLLLI QSSQREQTSG RLNASLDKSS  420
GRSTLYIAAS QPGDSATYLC AVIGLGGTYK YIFGTGTRLK VLANIQNPDP AVYQLRDSKS  480
SDKSVCLFTD FDSQTNVSQS KDSDVYITDK CVLDMRSMDF KSNSAVAWSN KSDFACANAF  540
NNSIIPEDTF FPSPESSCDV KLVEKSFETD TNLNFQNLSV IGFRILLLKV AGFNLLMTLR  600
LWSS                                                           604

SEQ ID NO: 55          moltype = AA  length = 604
FEATURE                Location/Qualifiers
REGION                 1..604
                       note = Synthetic sequence TCR5 beta-P2A-alpha (Cys
                        modified) with signal peptide
source                 1..604
                       mol_type = protein
                       organism = synthetic construct
SEQUENCE: 55
MGTSLLCWMA LCLLGADHAD TGVSQDPRHK ITKRGQNVTF RCDPISEHNR LYWYRQTLGQ  60
GPEFLTYFQN EAQLEKSRLL SDRFSAERPK GSFSTLEIQR TEQGDSAMYL CASSLTTLDE  120
```

```
QYVGPGTRLT VTEDLKNVFP PEVAVFEPSE AEISHTQKAT LVCLATGFYP DHVELSWWVN  180
GKEVHSGVCT DPQPLKEQPA LNDSRYCLSS RLRVSATFWQ NPRNHFRCQV QFYGLSENDE  240
WTQDRAKPVT QIVSAEAWGR ADCGFTSESY QQGVLSATIL YEILLGKATL YAVLVSALVL  300
MAMVKRKDSR GGSGATNFSL LKQAGDVEEN PGPMETLLGV SLVILWLQLA RVNSQQGEED  360
PQALSIQEGE NATMNCSYKT SINNLQWYRQ NSGRGLVHLI LIRSNEREKH SGRLRVTLDT  420
SKKSSSLLIT ASRAADTASY FCATNSGNTP LVFGKGTRLS VIANIQNPDP AVYQLRDSKS  480
SDKSVCLFTD FDSQTNVSQS KDSDVYITDK CVLDMRSMDF KSNSAVAWSN KSDFACANAF  540
NNSIIPEDTF FPSPESSCDV KLVEKSFETD TNLNFQNLSV IGFRILLLKV AGFNLLMTLR  600
LWSS                                                               604

SEQ ID NO: 56          moltype = AA  length = 608
FEATURE                Location/Qualifiers
REGION                 1..608
                       note = Synthetic sequence TCR10 beta-P2A-alpha (Cys
                        modified) with signal peptide
source                 1..608
                       mol_type = protein
                       organism = synthetic construct
SEQUENCE: 56
MGTSLLCWMA LCLLGADHAD TGVSQDPRHK ITKRGQNVTF RCDPISEHNR LYWYRQTLGQ  60
GPEFLTYFQN EAQLEKSRLL SDRFSAERPK GSFSTLEIQR TEQGDSAMYL CASSMLTNYE  120
QYFGPGTRLT VTEDLKNVFP PEVAVFEPSE AEISHTQKAT LVCLATGFYP DHVELSWWVN  180
GKEVHSGVCT DPQPLKEQPA LNDSRYCLSS RLRVSATFWQ NPRNHFRCQV QFYGLSENDE  240
WTQDRAKPVT QIVSAEAWGR ADCGFTSESY QQGVLSATIL YEILLGKATL YAVLVSALVL  300
MAMVKRKDSR GGSGATNFSL LKQAGDVEEN PGPMKKHLTT FLVILWLYFY RGNGKNQVEQ  360
SPQSLIILEG KNCTLQCNYT VSPFSNLRWY KQDTGRGPVS LTIMTFSENT KSNGRYTATL  420
DADTKQSSLH ITASQLSDSA SYICVVDSGG GADGLTFGKG THLIIQPYIQ NPDPAVYQLR  480
DSKSSDKSVC LFTDFDSQTN VSQSKDSDVY ITDKCVLDMR SMDFKSNSAV AWSNKSDFAC  540
ANAFNNSIIP EDTFFPSPES SCDVKLVEKS FETDTNLNFQ NLSVIGFRIL LLKVAGFNLL  600
MTLRLWSS                                                           608

SEQ ID NO: 57          moltype = AA  length = 605
FEATURE                Location/Qualifiers
REGION                 1..605
                       note = Synthetic sequence TCR16 beta-P2A-alpha (Cys
                        modified) with signal peptide
source                 1..605
                       mol_type = protein
                       organism = synthetic construct
SEQUENCE: 57
MGTSLLCWMA LCLLGADHAD TGVSQDPRHK ITKRGQNVTF RCDPISEHNR LYWYRQTLGQ  60
GPEFLTYFQN EAQLEKSRLL SDRFSAERPK GSFSTLEIQR TEQGDSAMYL CASSLVVGNE  120
QFFGPGTRLT VLEDLKNVFP PEVAVFEPSE AEISHTQKAT LVCLATGFYP DHVELSWWVN  180
GKEVHSGVCT DPQPLKEQPA LNDSRYCLSS RLRVSATFWQ NPRNHFRCQV QFYGLSENDE  240
WTQDRAKPVT QIVSAEAWGR ADCGFTSESY QQGVLSATIL YEILLGKATL YAVLVSALVL  300
MAMVKRKDSR GGSGATNFSL LKQAGDVEEN PGPMETLLGL LILWLQLQWV SSKQEVTQIP  360
AALSVPEGEN LVLNCSFTDS AIYNLQWFRQ DPGKGLTSLL LIQSSQREQT SGRLNASLDK  420
SSGRSTLYIA ASQPGDSATY LCAVHLLNDY KLSFGAGTTV TVRANIQNPD PAVYQLRDSK  480
SSDKSVCLFT DFDSQTNVSQ SKDSDVYITD KCVLDMRSMD FKSNSAVAWS NKSDFACANA  540
FNNSIIPEDT FFPSPESSCD VKLVEKSFET DTNLNFQNLS VIGFRILLLK VAGFNLLMTL  600
RLWSS                                                              605

SEQ ID NO: 58          moltype = AA  length = 585
FEATURE                Location/Qualifiers
REGION                 1..585
                       note = Synthetic sequence Consensus sequence of the TCR
                        beta-P2A-alpha
source                 1..585
                       mol_type = protein
                       organism = synthetic construct
SEQUENCE: 58
MGTSLLCWMA LCLLGADHAD TGVSQDPRHK ITKRGQNVTF RCDPISEHNR LYWYRQTLGQ  60
GPEFLTYFQN EAQLEKSRLL SDRFSAERPK GSFSTLEIQR TEQGDSAMYL CASSLVGEQF  120
FGPGTRLTVL EDLKNVFPPE VAVFEPSEAE ISHTQKATLV CLATGFYPDH VELSWWVNGK  180
EVHSGVCTDP QPLKEQPALN DSRYCLSSRL RVSATFWQNP RNHFRCQVQF YGLSENDEWT  240
QDRAKPVTQI VSAEAWGRAD CGFTSESYQQ GVLSATILYE ILLGKATLYA VLVSALVLMA  300
MVKRKDSRGG SGATNFSLLK QAGDVEENPG PMETLLGLVI LWLQLRVNSK QQPQALSIEG  360
ENTLNCSYTS INLQWYRQDS GRGLVSLLLI SSEREKTSGR LATLDSSKSS LITASQGDSA  420
SYLCAVSGGG YLTFGKGTRL SVLANIQNPD PAVYQLRDSK SSDKSVCLFT DFDSQTNVSQ  480
SKDSDVYITD KCVLDMRSMD FKSNSAVAWS NKSDFACANA FNNSIIPEDT FFPSPESSCD  540
VKLVEKSFET DTNLNFQNLS VIGFRILLLK VAGFNLLMTL RLWSS                  585

SEQ ID NO: 59          moltype = DNA  length = 1830
FEATURE                Location/Qualifiers
misc_feature           1..1830
                       note = Synthetic sequence TCR1/13 beta-P2A-alpha (codon
                        optimized; Cys modified)
source                 1..1830
                       mol_type = other DNA
```

```
                        organism = synthetic construct
SEQUENCE: 59
atgggcacct ccctgctgtg ttggatggcc ctgtgtctgc tgggagccga ccatgccgat  60
acaggggtgt cccaggaccc ccggcacaag attaccaagc ggggccagaa cgtgaccttc  120
agatgcgacc ccatcagcga gcacaaccgg ctgtactggt acaggcagac cctgggccag  180
ggccccgagt tcctgaccta ctttcagaac gaggcccagc tggaaaagtc ccggctgctg  240
agcgacagat tcagcgccga aagacccaag ggcagcttca gcaccctgga aatccagcgg  300
accgagcagg gcgatagcgc catgtacctg tgtgccagca gcagcacagg cggccacaac  360
gagcagttct ttggccctgg cacccggctg accgtgctgg aagatctgaa gaacgtgttc  420
cccccagagg tggccgtgtt cgagccttct gaggccgaga tcagccacac ccagaaagcc  480
accctcgtgt gtctggccac cggcttctac cccgaccacg tggaactgtc ttggtgggtc  540
aacggcaaag aggtgcactc cggcgtgtgc accgatcccc agcctctgaa agaacagccc  600
gccctgaacg acagccggta ctgcctgagc agcagactga gagtgtccgc caccttctgg  660
cagaaccccc ggaaccactt cagatgccag gtgcagttct acggcctgag cgagaacgac  720
gagtggaccc aggacagagc caagcccgtg acccagatcg tgtctgccga agcctggggc  780
agagccgatt gcggctttac cagcgagagc taccagcagg gcgtgctgag cgccaccatc  840
ctgtacgaga tcctgctggg caaggccacc ctgtacgccg tgctggtgtc tgccctggtg  900
ctgatggcca tggtcaagcg gaaggacagc agaggcggaa gcggcgccac caacttcagc  960
ctgctgaaac aggccggcga cgtggaagag aaccctggcc ctatggaaac actgctgggc  1020
gtgtccctcg tgatcctgtg gctgcagctg gccagagtga acagccagca gggggaagag  1080
gatccccagg ccctgagcat tcaggaaggc gagaacgcca ccatgaactg cagctacaag  1140
accagcatca acaacctgca gtggtacaga cagaacagcg gcagaggcct ggtgcacctg  1200
atcctgatca gaagcaacga gagagagaag cacagcggac ggctgagagt gaccctggac  1260
acctccaaga agtccagctc cctgctgatc accgccagca gagccgccga taccgccagc  1320
tacttctgtg ccaccaagcg ggattctggc gccggatcct accagctgac cttcggcaag  1380
ggcaccaagc tgagcgtgat ccccaacatc cagaaccccg accccgccgt gtatcagctg  1440
agagacagca agagcagcga caagagcgtg tgcctgttca ccgacttcga cagccagacc  1500
aacgtgtccc agagcaagga cagcgacgtg tacatcaccg ataagtgcgt gctggacatg  1560
cggagcatgg acttcaagag caacagcgcc gtggcctggt ccaacaagag cgacttcgcc  1620
tgcgccaacg ccttcaacaa cagcatcatc cccgaggaca ccttttttccc cagccccgag  1680
agcagctgcg acgtgaaact ggtggagaag tccttcgaga cagacaccaa tctgaacttt  1740
cagaacctga gcgtgatcgg cttccggatc ctgctgctga aagtggccgg cttcaatctg  1800
ctgatgaccc tgcggctgtg gagcagctga                                 1830

SEQ ID NO: 60           moltype = DNA  length = 1813
FEATURE                 Location/Qualifiers
misc_feature            1..1813
                        note = Synthetic sequence TCR2/14 beta-P2A-alpha (codon
                         optimized; Cys modified)
source                  1..1813
                        mol_type = other DNA
                        organism = synthetic construct
SEQUENCE: 60
atgggcacct ccctgctgtg ttggatggcc ctgtgtctgc tgggagccga ccatgccgat  60
acaggggtgt cccaggaccc ccggcacaag attaccaagc ggggccagaa cgtgaccttc  120
agatgcgacc ccatcagcga gcacaaccgg ctgtactggt acaggcagac cctgggccag  180
ggccccgagt tcctgaccta ctttcagaac gaggcccagc tggaaaagtc ccggctgctg  240
agcgacagat tcagcgccga aagacccaag ggcagcttca gcaccctgga aatccagcgg  300
accgagcagg gcgatagcgc catgtacctg tgtgccagca gcctcgtgaa gggcgagaag  360
ctgttcttcg gcagcggcac ccagctgagc gtgctggaag atctgaacaa ggtgttcccc  420
ccagaggtgg ccgtgttcga gccttctgag gccgagatca gccacaccca gaaagccacc  480
ctcgtgtgcc tggccaccgg cttttcccc gaccacgtgg aactgtcttg gtgggtcaac  540
ggcaaagagg tgcactccgg cgtgtgcacc gatccccagc ctctgaaaga acagcccgcc  600
ctgaacgaca gccggtactg cctgagcagc agactgagag tgtccgccac cttctggcag  660
aacccccgga accacttcag atgccaggtg cagttctacg gcctgagcga gaacgacgag  720
tggacccagg acagagccaa gcccgtgacc cagatcgtgt ctgccgaagc ctggggcaga  780
gccgattgcg gctttaccag cgtgtcctat cagcagggcg tgctgagcgc caccatcctg  840
tacgagatcc tgctgggcaa ggccaccctg tacgccgtgc tggtgtctgc cctggtgctg  900
atggccatgg tcaagcggaa ggactttggc agcggcgcca ccaacttcag cctgctgaaa  960
caggccggcg acgtggaaga gaaccctggc cctaatctga actttcagaa cctgagcgtg  1020
atcggcttcc ggatcctgct gctgaaagtg gccggcttca atctgctgat gaccctgcgg  1080
ctgtggagca gcgatggaaa cactgctggg cctgctgatc ctgtggctgc agctgcagtg  1140
ggtgtccagc aagcaggaag tgacacagat ccctgccgcc ctgtctgtgc ccgagggcga  1200
aaatctggtg ctgaactgca gcttcaccga cagcgccatc tacaacctgc agtggttcag  1260
acaggacccc ggcaagggcc tgacaagcct gctgctgatt cagagcagcc agagagagca  1320
gaccagcggc agactgaacg ccagcctgga taagagcagc ggccgcagca ccctgtatat  1380
cgccgcttct cagcctggcg actctgccac atatctgtgc gccgtgatcg gcctgggcgg  1440
cacctacaag tacatctttg gcaccggcac cagactgaaa gtgctggcca acatccagaa  1500
ccccgacccc gccgtgtacc agctgagaga cagcaagtcc agcgacaaga gcgtgtgtct  1560
gttcaccgac ttcgacagcc agaccaacgt gtcccagagc aaggacagcg acgtgtacat  1620
caccgataag tgcgtgctgg acatgcggag catggacttc aagagcaaca gcgccgtggc  1680
ctggtccaac aagagcgact tcgcctgcgc caacgccttc aacaacagca tcatccccga  1740
ggacaccttt ttccccagcc ccgagagcag ctgcgacgtg aaactggtgg agaagtcctt  1800
cgagacagac acc                                                   1813

SEQ ID NO: 61           moltype = DNA  length = 1815
FEATURE                 Location/Qualifiers
misc_feature            1..1815
                        note = Synthetic sequence TCR5 beta-P2A-alpha (codon
```

-continued

```
                      optimized; Cys modified)
source                1..1815
                      mol_type = other DNA
                      organism = synthetic construct
SEQUENCE: 61
atgggcacct ccctgctgtg ttggatggcc ctgtgtctgc tgggagccga ccatgccgat  60
acaggggtgt cccaggaccc ccggcacaag attaccaagc ggggccagaa cgtgaccttc  120
agatgcgacc ccatcagcga gcacaaccgg ctgtactggt acaggcagac cctgggccag  180
ggccccgagt tcctgaccta ctttcagaac gaggcccagc tggaaaagtc ccggctgctg  240
agcgacagat tcagcgccga aagacccaag ggcagcttca gcaccctgga aatccagcgg  300
accgagcagg gggacagcgc catgtatctg tgtgccagct ccctgaccac cctggacgag  360
cagtatgtgg gcccaggcac cagactgacc gtgaccgagg acctgaagaa cgtgttcccc  420
ccagaggtgg ccgtgttcga gccttctgag gccgagatca gccacaccca gaaagccacc  480
ctcgtgtgtc tggccaccgg cttctacccc gatcacgtgg agctgtcttg gtgggtgaac  540
ggcaaagagg tgcacagcgg cgtctgcacc gacccccagc ccctgaaaga gcagcccgcc  600
ctgaacgaca gccggtactg cctgagcagc cggctgagag tgagcgccac cttctggcag  660
aacccccgga accacttccg gtgccaggtg cagttctacg gcctgagcga gaacgacgag  720
tggacccagg acagagccaa gcccgtgacc cagatcgtga gcgccgaggc ctggggcaga  780
gccgactgcg gcttcaccag cgagagctac cagcagggcg tgctgtccgc cacaatcctg  840
tacgagatcc tgctgggcaa ggccaccctg tacgccgtgc tggtgtccgc cctggtgctg  900
atggccatgg tgaagcggaa ggacagccgg ggcggcagcg gcgccaccaa cttcagcctg  960
ctgaagcagg ccggcgacgt ggaggaaaac cctggcccca tggaaaccct gctgggcgtg  1020
tccctcgtga tcctgtggct gcagctggcc agagtgaaca gccagcaggg cgaagaagat  1080
ccccaggccc tgagcatcca ggaaggcgag aacgccacaa tgaactgcag ctacaagacc  1140
agcatcaaca acctgcagtg gtacagacag aacagcggca gaggcctggt gcacctgatc  1200
ctgatcagaa gcaacgagag agagaagcac tccggcagac tgagagtgac cctggacacc  1260
agcaagaagt ccagcagcct gctgatcacc gccagcagag ccgccgatac cgccagctac  1320
ttctgcgcca ccaactccgg caacaccccc ctggtgtttg gcaagggcac ccggctgagc  1380
gtgatcgcca acatccagaa ccccgacccc gccgtgtacc agctgagaga cagcaagagc  1440
agcgacaaga gcgtgtgcct gttcaccgac ttcgacagcc agaccaacgt gtcccagagc  1500
aaggacagcg acgtgtacat caccgataag tgcgtgctgg acatgcggag catggacttc  1560
aagagcaaca gcgccgtggc ctggtccaac aagagcgact tcgcctgcgc caacgccttc  1620
aacaacagca tcatccccga ggacaccttt ttccccagcc ccgagagcag ctgcgacgtg  1680
aaactggtgg agaagtcctt cgagacagac accaatctga actttcagaa cctgagcgtg  1740
atcggcttcc ggatcctgct gctgaaagtg gccggcttca atctgctgat gaccctgcgg  1800
ctgtggagca gctga                                                   1815

SEQ ID NO: 62         moltype = DNA  length = 1827
FEATURE               Location/Qualifiers
misc_feature          1..1827
                      note = Synthetic sequence TCR10 beta P2A-alpha (codon
                      optimized; Cys modified)
source                1..1827
                      mol_type = other DNA
                      organism = synthetic construct
SEQUENCE: 62
atgggcacct ccctgctgtg ttggatggcc ctgtgtctgc tgggagccga ccatgccgat  60
acaggggtgt cccaggaccc ccggcacaag attaccaagc ggggccagaa cgtgaccttc  120
agatgcgacc ccatcagcga gcacaaccgg ctgtactggt acaggcagac cctgggccag  180
ggccccgagt tcctgaccta ctttcagaac gaggcccagc tggaaaagtc ccggctgctg  240
agcgacagat tcagcgccga aagacccaag ggcagcttca gcaccctgga aatccagcgg  300
accgagcagg gcgatagcgc catgtacctg tgcgccagct ccatgctgac caactacgag  360
cagtacttcg gccctggcac ccggctgacc gtgaccgagg atctgaagaa cgtgttcccc  420
ccagaggtgg ccgtgttcga gccttctgag gccgagatca gccacaccca gaaagccacc  480
ctcgtgtgtc tggccaccgg cttctacccc gaccacgtgg aactgtcttg gtgggtcaac  540
ggcaaagagg tgcactccgg cgtgtgcacc gatccccagc ctctgaaaga acagcccgcc  600
ctgaacgaca gccggtactg cctgagcagc agactgagag tgtccgccac cttctggcag  660
aacccccgga accacttcag atgccaggtg cagttctacg gcctgagcga gaacgacgag  720
tggacccagg acagagccaa gcccgtgacc cagatcgtgt ctgccgaagc ctggggcaga  780
gccgattgcg gctttaccag cgagagctac cagcagggcg tgctgagcgc caccatcctg  840
tacgagatcc tgctgggcaa ggccaccctg tacgccgtgc tggtgtctgc cctggtgctg  900
atggccatgg tcaagcggaa ggacagcaga ggcggaagcg gcgccaccaa cttcagcctg  960
ctgaaacagg ccggcgacgt ggaagagaac cctggcccca tgaagaagca cctgaccacc  1020
tttctcgtga tcctgtggct gtacttctac cggggcaacg gcaagaacca ggtggaacag  1080
agcccccaga gcctgatcat cctggaaggc aagaattgca ccctgcagtg caactacacc  1140
gtgtccccct tcagcaacct gcggtggtac aagcaggaca ccggcagagg ccctgtgtcc  1200
ctgaccatca tgaccttcag cgagaacacc aagagcaacg gccggtacac cgccaccctg  1260
gatgccgata caaagcagag cagcctgcac atcaccgcca gccagctgag cgattccgcc  1320
agctacatct gcgtggtgga ttctggcggc ggagccgatg gcctgacatt tggcaagggc  1380
acccacctga tcattcagcc ctacatccag aaccccgacc ccgccgtgta ccagctgaga  1440
gacagcaagt ccagcgacaa gagcgtgtgc ctgttcaccg acttcgacag ccagaccaac  1500
gtgtcccaga gcaaggacag cgacgtgtac atcaccgata agtgcgtgct ggacatgcgg  1560
agcatggact tcaagagcaa cagcgccgtg gcctggtcca acaagagcga cttcgcctgc  1620
gccaacgcct tcaacaacag catcatcccc gaggacacct tttccccag ccccgagagc  1680
agctgcgacg tgaaactggt ggagaagtcc ttcgagacag acaccaatct gaactttcag  1740
aacctgagcg tgatcggctt ccggatcctg ctgctgaaag tggccggctt caatctgctg  1800
atgaccctgc ggctgtggag cagctga                                      1827

SEQ ID NO: 63         moltype = DNA  length = 1818
```

```
FEATURE                 Location/Qualifiers
misc_feature            1..1818
                        note = Synthetic sequence TCR16 beta-P2A-alpha (codon
                         optimized; Cys modified)
source                  1..1818
                        mol_type = other DNA
                        organism = synthetic construct
SEQUENCE: 63
atgggcacct ccctgctgtg ttggatggcc ctgtgtctgc tgggagccga ccatgccgat  60
acaggggtgt cccaggaccc ccggcacaag attaccaagc ggggccagaa cgtgaccttc  120
agatgcgacc ccatcagcga gcacaaccgg ctgtactggt acaggcagac cctgggccag  180
ggccccgagt tcctgaccta ctttcagaac gaggcccagc tggaaaagtc ccggctgctg  240
agcgacagat tcagcgccga aagacccaag ggcagcttca gcaccctgga aatccagcgg  300
accgagcagg gcgatagcgc catgtacctg tgtgccagca gcctggtcgt gggcaacgag  360
cagtttttcg gccctggcac cagactgacc gtgctggaag atctgaagaa cgtgttcccc  420
ccagaggtgg ccgtgttcga gccttctgag gccgagatca gccacaccca gaaagccacc  480
ctcgtgtgtc tggccaccgg cttctacccc gaccacgtgg aactgtcttg gtgggtcaac  540
ggcaaagagg tgcactccgg cgtgtgcacc gatccccagc ctctgaaaga acagcccgcc  600
ctgaacgaca gccggtactg cctgagcagc agactgagag tgtccgccac cttctggcag  660
aacccccgga accacttcag atgccaggtg cagttctacg gcctgagcga gaacgacgag  720
tggacccagg acagagccaa gcccgtgacc cagatcgtgt ctgccgaagc ctggggcaga  780
gccgattgcg gctttaccag cgagagctac cagcagggcg tgctgagcgc caccatcctg  840
tacgagatcc tgctgggcaa ggccaccctg tacgccgtgc tggtgtctgc cctggtgctg  900
atggccatgg tcaagcggaa ggacagcaga ggcggaagcg gcgccaccaa cttcagcctg  960
ctgaaacagg ccggcgacgt ggaagagaac cctggcccta tggaaacact gctgggcctg  1020
ctgatcctgt ggctgcagct gcagtgggtg tccagcaagc aggaagtgac acagatccct  1080
gccgccctgt ctgtgcccga gggcgaaaat ctggtgctga actgcagctt caccgacagc  1140
gccatctaca acctgcagtg gttcagacag gaccccggca agggcctgac aagcctgctg  1200
ctgattcaga gcagccagag agagcagacc agcggcagac tgaacgccag cctggataag  1260
agcagcggcc gcagcaccct gtatatcgcc gcttctcagc ctggcgactc tgccacatat  1320
ctgtgcgccg tgcatctgct gaacgactac aagctgagct tcggagccgg caccaccgtg  1380
acagtgcggg ccaacatcca gaaccccgac cctgccgtgt accagctgag agacagcaag  1440
tccagcgaca agagcgtgtg cctgttcacc gacttcgaca gccagaccaa cgtgtcccag  1500
agcaaggaca gcgacgtgta catcaccgat aagtgcgtgc tggacatgcg gagcatggac  1560
ttcaagagca acagcgccgt ggcctggtcc aacaagagcg acttcgcctg cgccaacgcc  1620
ttcaacaaca gcatcatccc cgaggacacc tttttcccca gccccgagag cagctgcgac  1680
gtgaaactgg tggagaagtc cttcgagaca gacaccaatc tgaactttca gaacctgagc  1740
gtgatcggct tccggatcct gctgctgaaa gtggccggct tcaatctgct gatgaccctg  1800
cggctgtgga gcagctga                                               1818

SEQ ID NO: 64           moltype = AA  length = 1135
FEATURE                 Location/Qualifiers
REGION                  1..1135
                        note = Synthetic sequence HMHA1 (wt)
source                  1..1135
                        mol_type = protein
                        organism = synthetic construct
SEQUENCE: 64
MFSRKKRELM KTPSISKKNR AGSPSPQPSG ELPRKDGADA VFPGPSLEPP AGSSGVKATG  60
TLKRPTSLSR HASAAGFPLS GAASWTLGRS HRSPLTAASP GELPTEGAGP DVVEDISHLL  120
ADVARFAEGL EKLKECVLRD DLLEARRPRA HECLGEALRV MHQIISKYPL LNTVETLTAA  180
GTLIAKVKAF HYESNNDLEK QEFEKALETI AVAFSSTVSE FLMGEVDSST LLAVPPGDSS  240
QSMESLYGPG SEGTPPSLED CDAGCLPAEE VDVLLQRCEG GVDAALLYAK NMAKYMKDLI  300
SYLEKRTTLE MEFAKGLQKI AHNCRQSVMQ EPHMPLLSIY SLALEQDLEF GHSMVQAVGT  360
LQTQTFMQPL TLRRLEHEKR RKEIKEAWHR QRKLQEAESN LRKAKQGYVQ RCEDHDKARF  420
LVAKAEEEQA GSAPGAGSTA TKTLDKRRRL EEEAKNKAEE AMATYRTCVA DAKTQKQELE  480
DTKVTALRQI QEVIRQSDQT IKSATISYYQ MMHMQTAPLP VHFQMLCESS KLYDPGQQYA  540
SHVRQLQRDQ EPDVHYDFEP HVSANAWSPV MRARKSSFNV SDVARPEAAG SPPEEGGCTE  600
GTPAKDHRAG RGHQVHKSWP LSISDSDSGL DPGPGAGDFK KFERTSSSGT MSSTEELVDP  660
DGGAGASAFE QADLNGMTPE LPVAVPSGPF RHEGLSKAAR THRLRKLRTP AKCRECNSYV  720
YFQGAECEEC CLACHKKCLE TLAIQCGHKK LQGRLQLFGQ DFSHAARSAP DGVPFIVKKC  780
VCEIERRALR TKGIYRVNGV KTRVEKLCQA FENGKELVEL SQASPHDISN VLKLYLRQLP  840
EPLISFRLYH ELVGLAKDSL KAEAEAKAAS RGRQDGSESE AVAVALAGRL RELLRDLPPE  900
NRASLQYLLR HLRRIVEVEQ DNKMTPGNLG IVFGPTLLRP RPTEATVSLS SLVDYPHQAR  960
VIETLIVHYG LVFEEEPEET PGGQDESSNQ RAEVVVQVPY LEAGEAVVYP LQEAAADGCR  1020
ESRVVSNDSD SDLEEASELL SSSEASALGH LSFLEQQQSE ASLEVASGSH SGSEEQLEAT  1080
AREDGDGDED GPAQQLSGFN TNQSNNVLQA PLPPMRLRGG RMTLGSCRER QPEFV       1135

SEQ ID NO: 65           moltype = AA  length = 9
FEATURE                 Location/Qualifiers
REGION                  1..9
                        note = Synthetic sequence HA-1 non-immunogenic peptide wild
                         type
source                  1..9
                        mol_type = protein
                        organism = synthetic construct
SEQUENCE: 65
VLRDDLLEA                                                          9
```

```
SEQ ID NO: 66          moltype = AA  length = 9
FEATURE                Location/Qualifiers
REGION                 1..9
                       note = Synthetic sequence HA-1H antigen polymorphism
source                 1..9
                       mol_type = protein
                       organism = synthetic construct
SEQUENCE: 66
VLHDDLLEA                                                            9

SEQ ID NO: 67          moltype = DNA  length = 1206
FEATURE                Location/Qualifiers
misc_feature           1..1206
                       note = Synthetic sequence Inducible Caspase9 (codon
                        optimized)
source                 1..1206
                       mol_type = other DNA
                       organism = synthetic construct
SEQUENCE: 67
atgctggaag gcgtgcaggt ggaaaccatc agccctggcg acggcagaac cttccctaag  60
aggggccaga cctgcgtggt gcactacacc ggaatgctgg aagatggcaa gaaggtggac  120
agcagccggg accggaacaa gcccttcaag ttcatgctgg gcaagcagga agtgatccgg  180
ggctgggaag agggcgtggc ccagatgtct gtgggccaga gagccaagct gaccatctcc  240
cccgattacg cctacggcgc cacaggccac cctggcatca ttcctccaca cgccacactg  300
gtgttcgacg tggaactgct gaagctggaa agcggcggag gcagcggagt ggatggcttt  360
ggagatgtgg gcgccctgga aagcctgaga ggcaatgccg acctggccta catcctgagc  420
atggaacctt gcggccactg cctgattatc aacaacgtga acttctgcag agagagcggc  480
ctgcggacca gaaccggcag caacatcgac tgcgagaagc tgcggcggag attcagcagc  540
ctgcacttca tggtggaagt gaagggcgac ctgaccgcca agaaaatggt gctggccctg  600
ctggaactgg cccagcagga tcatggcgct ctggactgct gtgtggtcgt gatcctgagc  660
cacggctgcc aggccagcca tctgcagttc cctggcgccg tgtatggcac cgatggctgt  720
cctgtgtccg tggaaaagat cgtgaacatc ttcaacggca ccagctgccc cagcctgggc  780
ggaaagccca agctgttctt tattcaagcc tgcggaggcg agcagaagga ccacggattt  840
gaggtggcct ccaccagccc cgaggatgag agccctggaa gcaaccctga gcccgacgcc  900
accccatttc aggaaggcct gagaaccttc gaccagctgg acgccatcag ctccctgccc  960
acccccagcg atatcttcgt gtcctacagc accttccccg gctttgtgtc ctggcgggat  1020
cccaagtccg gctcttggta cgtggaaacc ctggacgaca tcttcgagca gtgggcccat  1080
agcgaggacc tgcagagcct gctgctgaga gtggccaatg ccgtgtccgt gaagggcatc  1140
tacaagcaga tgcctggctg cttcaacttc ctgcggaaga agctgttttt caagaccagc  1200
gccagc                                                            1206

SEQ ID NO: 68          moltype = DNA  length = 159
FEATURE                Location/Qualifiers
misc_feature           1..159
                       note = Synthetic sequence RQR (codon optimized)
source                 1..159
                       mol_type = other DNA
                       organism = synthetic construct
SEQUENCE: 68
gcctgcccct acagcaaccc tagcctgtgt tctggcggcg gaggcagcga actgcctacc  60
cagggcacct tcagcaacgt gtccaccaat gtgtctggcg gaggcggctc tgcctgccct  120
tactccaatc catccctgtg cagcggaggg ggcggaagc                        159

SEQ ID NO: 69          moltype = AA  length = 53
FEATURE                Location/Qualifiers
REGION                 1..53
                       note = Synthetic sequence RQR
source                 1..53
                       mol_type = protein
                       organism = synthetic construct
SEQUENCE: 69
ACPYSNPSLC SGGGGSELPT QGTFSNVSTN VSGGGGSACP YSNPSLCSGG GGS         53

SEQ ID NO: 70          moltype = AA  length = 235
FEATURE                Location/Qualifiers
REGION                 1..235
                       note = Synthetic sequence CD8 co-receptor alpha chain with
                        signal peptide
source                 1..235
                       mol_type = protein
                       organism = synthetic construct
SEQUENCE: 70
MALPVTALLL PLALLLHAAR PSQFRVSPLD RTWNLGETVE LKCQVLLSNP TSGCSWLFQP  60
RGAAASPTFL LYLSQNKPKA AEGLDTQRFS GKRLGDTFVL TLSDFRRENE GYYFCSALSN  120
SIMYFSHFVP VFLPAKPTTT PAPRPPTPAP TIASQPLSLR PEACRPAAGG AVHTRGLDFA  180
CDIYIWAPLA GTCGVLLLSL VITLYCNHRN RRRVCKCPRP VVKSGDKPSL SARYV       235

SEQ ID NO: 71          moltype = AA  length = 210
FEATURE                Location/Qualifiers
```

```
REGION                  1..210
                        note = Synthetic sequence CD8 co-receptor beta chain
                         isoform 1 with signal peptide
source                  1..210
                        mol_type = protein
                        organism = synthetic construct
SEQUENCE: 71
MRPRLWLLLA AQLTVLHGNS VLQQTPAYIK VQTNKMVMLS CEAKISLSNM RIYWLRQRQA  60
PSSDSHHEFL ALWDSAKGTI HGEEVEQEKI AVFRDASRFI LNLTSVKPED SGIYFCMIVG  120
SPELTFGKGT QLSVVDFLPT TAQPTKKSTL KKRVCRLPRP ETQKGPLCSP ITLGLLVAGV  180
LVLLVSLGVA IHLCCRRRRA RLRFMKQFYK                                  210

SEQ ID NO: 72           moltype = AA  length = 221
FEATURE                 Location/Qualifiers
REGION                  1..221
                        note = Synthetic sequence CD8 co-receptor beta chain
                         isoform 2 with signal peptide
source                  1..221
                        mol_type = protein
                        organism = synthetic construct
SEQUENCE: 72
MRPRLWLLLA AQLTVLHGNS VLQQTPAYIK VQTNKMVMLS CEAKISLSNM RIYWLRQRQA  60
PSSDSHHEFL ALWDSAKGTI HGEEVEQEKI AVFRDASRFI LNLTSVKPED SGIYFCMIVG  120
SPELTFGKGT QLSVVDFLPT TAQPTKKSTL KKRVCRLPRP ETQKGPLCSP ITLGLLVAGV  180
LVLLVSLGVA IHLCCRRRRA RLRFMKQLRL HPLEKCSRMD Y                     221

SEQ ID NO: 73           moltype = AA  length = 246
FEATURE                 Location/Qualifiers
REGION                  1..246
                        note = Synthetic sequence CD8 co-receptor beta chain
                         isoform 3 with signal peptide
source                  1..246
                        mol_type = protein
                        organism = synthetic construct
SEQUENCE: 73
MRPRLWLLLA AQLTVLHGNS VLQQTPAYIK VQTNKMVMLS CEAKISLSNM RIYWLRQRQA  60
PSSDSHHEFL ALWDSAKGTI HGEEVEQEKI AVFRDASRFI LNLTSVKPED SGIYFCMIVG  120
SPELTFGKGT QLSVVDFLPT TAQPTKKSTL KKRVCRLPRP ETQKGPLCSP ITLGLLVAGV  180
LVLLVSLGVA IHLCCRRRRA RLRFMKQKFN IVCLKISGFT TCCCFQILQI SREYGFGVLL  240
QKDIGQ                                                            246

SEQ ID NO: 74           moltype = AA  length = 246
FEATURE                 Location/Qualifiers
REGION                  1..246
                        note = Synthetic sequence CD8 co-receptor beta chain
                         isoform 4 with signal peptide
source                  1..246
                        mol_type = protein
                        organism = synthetic construct
SEQUENCE: 74
MRPRLWLLLA AQLTVLHGNS VLQQTPAYIK VQTNKMVMLS CEAKISLSNM RIYWLRQRQA  60
PSSDSHHEFL ALWDSAKGTI HGEEVEQEKI AVFRDASRFI LNLTSVKPED SGIYFCMIVG  120
SPELTFGKGT QLSVVDFLPT TAQPTKKSTL KKRVCRLPRP ETQKGPLCSP ITLGLLVAGV  180
LVLLVSLGVA IHLCCRRRRA RLRFMKQKFN IVCLKISGFT TCCCFQILQI SREYGFGVLL  240
QKDIGQ                                                            246

SEQ ID NO: 75           moltype = AA  length = 243
FEATURE                 Location/Qualifiers
REGION                  1..243
                        note = Synthetic sequence CD8 co-receptor beta chain
                         isoform 5 with signal peptide
source                  1..243
                        mol_type = protein
                        organism = synthetic construct
SEQUENCE: 75
MRPRLWLLLA AQLTVLHGNS VLQQTPAYIK VQTNKMVMLS CEAKISLSNM RIYWLRQRQA  60
PSSDSHHEFL ALWDSAKGTI HGEEVEQEKI AVFRDASRFI LNLTSVKPED SGIYFCMIVG  120
SPELTFGKGT QLSVVDFLPT TAQPTKKSTL KKRVCRLPRP ETQKGPLCSP ITLGLLVAGV  180
LVLLVSLGVA IHLCCRRRRA RLRFMKQPQG EGISGTFVPQ CLHGYYSNTT TSQKLLNPWI  240
LKT                                                               243

SEQ ID NO: 76           moltype = DNA  length = 66
FEATURE                 Location/Qualifiers
misc_feature            1..66
                        note = Synthetic sequence P2A-1 (codon-optimized)
source                  1..66
                        mol_type = other DNA
                        organism = synthetic construct
SEQUENCE: 76
```

```
ggaagtggag ctacgaattt ttctttatta aaacaagcag gagatgttga ggagaatccc  60
ggtcca                                                             66

SEQ ID NO: 77          moltype = DNA  length = 63
FEATURE                Location/Qualifiers
misc_feature           1..63
                       note = Synthetic sequence P2A-2 (codon-optimized)
source                 1..63
                       mol_type = other DNA
                       organism = synthetic construct
SEQUENCE: 77
agcggcgcca ccaacttcag cctgctgaaa caggccggcg acgtggaaga gaaccctggc  60
cct                                                                63

SEQ ID NO: 78          moltype = DNA  length = 65
FEATURE                Location/Qualifiers
misc_feature           1..65
                       note = Synthetic sequence P2A-3 (codon-optimized)
source                 1..65
                       mol_type = other DNA
                       organism = synthetic construct
SEQUENCE: 78
gaagcggcgc cacaaatttc agcctgctga agcaggccgg cgacgtggaa gagaaccctg  60
gccct                                                              65

SEQ ID NO: 79          moltype = DNA  length = 66
FEATURE                Location/Qualifiers
misc_feature           1..66
                       note = Synthetic sequence P2A-4 (codon-optimized)
source                 1..66
                       mol_type = other DNA
                       organism = synthetic construct
SEQUENCE: 79
ggctccggcg ccaccaactt ttcactgctg aaacaggctg ggatgtgga agaaaatccc  60
ggccca                                                             66

SEQ ID NO: 80          moltype = DNA  length = 66
FEATURE                Location/Qualifiers
misc_feature           1..66
                       note = Synthetic sequence P2A-5
source                 1..66
                       mol_type = other DNA
                       organism = synthetic construct
SEQUENCE: 80
ggcagcggcg ccaccaactt tagcctgctg aaacaggctg gcgacgtgga agagaacccc  60
ggacct                                                             66

SEQ ID NO: 81          moltype = DNA  length = 66
FEATURE                Location/Qualifiers
misc_feature           1..66
                       note = Synthetic sequence P2A-6
source                 1..66
                       mol_type = other DNA
                       organism = synthetic construct
SEQUENCE: 81
ggctctggcg ccaccaactt tagcctgctg aaacaggctg gcgacgtgga agagaacccc  60
ggacct                                                             66

SEQ ID NO: 82          moltype = DNA  length = 63
FEATURE                Location/Qualifiers
misc_feature           1..63
                       note = Synthetic sequence T2A
source                 1..63
                       mol_type = other DNA
                       organism = synthetic construct
SEQUENCE: 82
ggaagcggag agggcagagg aagtctgcta acatgcggtg acgtcgagga gaatcctgga  60
cct                                                                63

SEQ ID NO: 83          moltype = DNA  length = 69
FEATURE                Location/Qualifiers
misc_feature           1..69
                       note = Synthetic sequence E2A
source                 1..69
                       mol_type = other DNA
                       organism = synthetic construct
SEQUENCE: 83
ggaagcggac agtgtactaa ttatgctctc ttgaaattgg ctggagatgt tgagagcaac  60
cctggacct                                                          69
```

```
SEQ ID NO: 84           moltype = DNA  length = 75
FEATURE                 Location/Qualifiers
misc_feature            1..75
                        note = Synthetic sequence F2A
source                  1..75
                        mol_type = other DNA
                        organism = synthetic construct
SEQUENCE: 84
ggaagcggag tgaaacagac tttgaatttt gaccttctca agttggcggg agacgtggag  60
tccaaccctg gacct                                                   75

SEQ ID NO: 85           moltype = DNA  length = 4713
FEATURE                 Location/Qualifiers
misc_feature            1..4713
                        note = Synthetic sequence iC9-HA1-TCR2-RQR-CD8
source                  1..4713
                        mol_type = other DNA
                        organism = synthetic construct
SEQUENCE: 85
atgctggaag gcgtgcaggt ggaaaccatc agccctggcg acggcagaac cttccctaag  60
aggggccaga cctgcgtggt gcactacacc ggaatgctgg aagatggcaa gaaggtggac  120
agcagccggg accggaacaa gcccttcaag ttcatgctgg gcaagcagga agtgatccgg  180
ggctgggaag agggcgtggc ccagatgtct gtgggccaga gagccaagct gaccatctcc  240
cccgattacg cctacggcgc cacaggccac cctggcatca ttcctccaca cgccacactg  300
gtgttcgacg tggaactgct gaagctggaa agcggcggag gcagcggagt ggatggcttt  360
ggagatgtgg gcgccctgga aagcctgaga ggcaatgccg acctggccta catcctgagc  420
atggaacctt gcggccactg cctgattatc aacaacgtga acttctgcag agagagcggc  480
ctgcggacca gaaccggcag caacatcgac tgcgagaagc tgcggcggag attcagcagc  540
ctgcacttca tggtggaagt gaagggcgac ctgaccgcca agaaaatggt gctggccctg  600
ctggaactgg cccagcagga tcatggcgct ctggactgct gtgtggtcgt gatcctgagc  660
cacggctgcc aggccagcca tctgcagttc cctggcgccg tgtatggcac cgatggctgt  720
cctgtgtccg tggaaaagat cgtgaacatc ttcaacggca ccagctgccc cagcctgggc  780
ggaaagccca agctgttctt tattcaagcc tgcggaggcg agcagaagga ccacggattt  840
gaggtggcct ccaccagccc cgaggatgag agccctggaa gcaaccctga gcccgacgcc  900
accccatttc aggaaggcct gagaaccttc gaccagctgg acgccatcag ctccctgccc  960
acccccagcg atatcttcgt gtcctacagc accttccccg gctttgtgtc ctggcgggat  1020
cccaagtccg gctcttggta cgtggaaacc ctggacgaca tcttcgagca gtgggcccat  1080
agcgaggacc tgcagagcct gctgctgaga gtggccaatg ccgtgtccgt gaagggcatc  1140
tacaagcaga tgcctggctg cttcaacttc ctgcggaaga agctgttttt caagaccagc  1200
gccagcggaa gtggagctac gaatttttct ttattaaaac aagcaggaga tgttgaggag  1260
aatcccggtc caatgggcac ctccctgctg tgttggatgg ccctgtgtct gctgggagcc  1320
gaccatgccg atacaggggt gtcccaggac ccccggcaca agattaccaa gcggggccag  1380
aacgtgacct tcagatgcga ccccatcagc gagcacaacc ggctgtactg gtacaggcag  1440
accctgggcc agggccccga gttcctgacc tactttcaga acgaggccca gctggaaaag  1500
tcccggctgc tgagcgacag attcagcgcc gaaagaccca agggcagctt cagcaccctg  1560
gaaatccagc ggaccgagca gggcgatagc gccatgtacc tgtgtgccag cagcctcgtg  1620
aagggcgaga agctgttctt cggcagcggc acccagctga gcgtgctgga agatctgaac  1680
aaggtgttcc ccccagaggt ggccgtgttc gagccttctg aggccgagat cagccacacc  1740
cagaaagcca ccctcgtgtg cctggccacc ggcttttttcc ccgaccacgt ggaactgtct  1800
tggtgggtca acggcaaaga ggtgcactcc ggcgtgtgca ccgatcccca gcctctgaaa  1860
gaacagcccg ccctgaacga cagccggtac tgcctgagca gcagactgag agtgtccgcc  1920
accttctggc agaacccccg gaaccacttc agatgccagg tgcagttcta cggcctgagc  1980
gagaacgacg agtggaccca ggacagagcc aagcccgtga cccagatcgt gtctgccgaa  2040
gcctggggca gagccgattg cggctttacc agcgtgtcct atcagcaggg cgtgctgagc  2100
gccaccatcc tgtacgagat cctgctgggc aaggccaccc tgtacgccgt gctggtgtct  2160
gccctggtgc tgatggccat ggtcaagcgg aaggactttg gcagcggcgc caccaacttc  2220
agcctgctga aacaggccgg cgacgtggaa gagaaccctg gccctatgga aacactgctg  2280
ggcctgctga tcctgtggct gcagctgcag tgggtgtcca gcaagcagga agtgacacag  2340
atccctgccg ccctgtctgt gcccgagggc gaaaatctgg tgctgaactg cagcttcacc  2400
gacagcgcca tctacaacct gcagtggttc agacaggacc ccggcaaggg cctgacaagc  2460
ctgctgctga ttcagagcag ccagagagag cagaccagcg gcagactgaa cgccagcctg  2520
gataagagca gcggccgcag caccctgtat atcgccgctt ctcagcctgg cgactctgcc  2580
acatatctgt gcgccgtgat cggcctgggc ggcacctaca agtacatctt tggcaccggc  2640
accagactga aagtgctggc caacatccag aaccccgacc ccgccgtgta ccagctgaga  2700
gacagcaagt ccagcgacaa gagcgtgtgt ctgttcaccg acttcgacag ccagaccaac  2760
gtgtcccaga gcaaggacag cgacgtgtac atcaccgata agtgcgtgct ggacatgcgg  2820
agcatggact tcaagagcaa cagcgccgtg gcctggtcca acaagagcga cttcgcctgc  2880
gccaacgcct tcaacaacag catcatcccc gaggacacct ttttccccag ccccgagagc  2940
agctgcgacg tgaaactggt ggagaagtcc ttcgagacag acaccaatct gaactttcag  3000
aacctgagcg tgatcggctt ccggatcctg ctgctgaaag tggccggctt caatctgctg  3060
atgaccctgc ggctgtggag cagcggaagc ggcgccacaa atttcagcct gctgaagcag  3120
gccggcgacg tggaagagaa ccctggccct atgaggccca gactgtggct gctgctggcc  3180
gctcagctga cagtgctgca cggcaatagc gtggcctgcc cctacagcaa ccctagcctg  3240
tgttctggcg gcggaggcag cgaactgcct acccagggca ccttcagcaa cgtgtccacc  3300
aatgtgtctg gcggaggcgg ctctgcctgc ccttactcca atccatccct gtgcagcgga  3360
gggggcggaa gcctgcagca gacaccagcc tacatcaagg tgcagaccaa caagatggtc  3420
atgctgagct gcgaggccaa gatcagcctg agcaacatgc ggatctactg gctgcggcag  3480
agacaggccc ctagcagcga tagccaccac gagtttctgg ccctgtggga cagcgccaag  3540
```

-continued

```
ggcaccattc acggcgagga agtggaacag gaaaagatcg ccgtgttccg ggacgccagc  3600
cggttcatcc tgaacctgac cagcgtgaag cccgaggact ccggcatcta tttctgcatg  3660
atcgtgggct cccccgagct gaccttcggc aagggaacac agctgtccgt ggtggacttc  3720
ctgcctacca cagcccagcc caccaagaag tctaccctga agaaaagagt gtgccggctg  3780
cccagacccg agacacagaa aggccctctg tgcagcccta tcaccctggg actgctggtg  3840
gctggcgtgc tggtgctgct ggtgtctctg ggagtggcca tccacctgtg ctgcagaaga  3900
aggcgggcca gactgcggtt catgaagcag ttctacaagg gctccggcgc caccaacttt  3960
tcactgctga aacaggctgg ggatgtggaa gaaaatcccg gcccaatggc cctgcctgtg  4020
accgctctgc tgctgcctct ggcactgctg ctgcatgccg ccagacccag ccagttcaga  4080
gtgtcccccc tggacagaac ctggaacctg ggcgagacag tggaactgaa gtgccaggtg  4140
ctgctgagca accccaccag cggctgcagc tggctgttcc agcctagagg cgctgccgcc  4200
agccctacct ttctgctgta cctgagccag aacaagccca aggccgccga gggcctggac  4260
acccagagat tcagcggcaa gagactgggc gacaccttcg tgctgaccct gtccgacttc  4320
agaagagaga acgagggcta ctacttctgc tccgccctga gcaatagcat catgtacttc  4380
agccacttcg tgcccgtgtt tctgcccgcc aagcctacaa ccacccctgc cccaagacct  4440
cccacacccg cccctacaat tgccagccag cctctgtctc tgaggcccga ggcttgtaga  4500
ccagctgctg gcggagccgt gcacaccaga ggactggact ttgcctgcga catctacatc  4560
tgggcccctc tggccggcac ttgcggagtg ctgctgctga gtctcgtgat caccctgtac  4620
tgcaaccacc ggaaccggcg gagagtgtgc aagtgcccta ggcccgtcgt gaagtccggc  4680
gacaagcctt ctctgagcgc cagatatgtc tga                                4713

SEQ ID NO: 86          moltype = AA  length = 13
FEATURE                Location/Qualifiers
REGION                 1..13
                       note = Synthetic sequence TCR1 alpha chain CDR3
source                 1..13
                       mol_type = protein
                       organism = synthetic construct
SEQUENCE: 86
CASSLVSGNT IYF                                                      13

SEQ ID NO: 87          moltype = AA  length = 15
FEATURE                Location/Qualifiers
REGION                 1..15
                       note = Synthetic sequence TCR1 alpha chain CDR3
source                 1..15
                       mol_type = protein
                       organism = synthetic construct
SEQUENCE: 87
CATKRDSGAG SYQLT                                                    15

SEQ ID NO: 88          moltype = AA  length = 14
FEATURE                Location/Qualifiers
REGION                 1..14
                       note = Synthetic sequence TCR2 alpha chain CDR3
source                 1..14
                       mol_type = protein
                       organism = synthetic construct
SEQUENCE: 88
CAVIGLGGTY KYIF                                                     14

SEQ ID NO: 89          moltype = AA  length = 12
FEATURE                Location/Qualifiers
REGION                 1..12
                       note = Synthetic sequence TCR5 alpha chain CDR3
source                 1..12
                       mol_type = protein
                       organism = synthetic construct
SEQUENCE: 89
CATNSGNTPL VF                                                       12

SEQ ID NO: 90          moltype = AA  length = 14
FEATURE                Location/Qualifiers
REGION                 1..14
                       note = Synthetic sequence TCR10 alpha chain CDR3
source                 1..14
                       mol_type = protein
                       organism = synthetic construct
SEQUENCE: 90
CVVDSGGGAD GLTF                                                     14

SEQ ID NO: 91          moltype = AA  length = 13
FEATURE                Location/Qualifiers
REGION                 1..13
                       note = Synthetic sequence TCR16 alpha chain CDR3
source                 1..13
                       mol_type = protein
                       organism = synthetic construct
SEQUENCE: 91
```

```
CAVHLLNDYK LSF                                              13

SEQ ID NO: 92          moltype = AA  length = 16
FEATURE                Location/Qualifiers
REGION                 1..16
                       note = Synthetic sequence TCR29 alpha chain CDR3
source                 1..16
                       mol_type = protein
                       organism = synthetic construct
SEQUENCE: 92
CAVRGGTTSG TYKYIF                                           16

SEQ ID NO: 93          moltype = DNA  length = 21
FEATURE                Location/Qualifiers
misc_feature           1..21
                       note = TCR alpha-chain primer
source                 1..21
                       mol_type = other DNA
                       organism = synthetic construct
SEQUENCE: 93
ggtgaatagg cagacagact t                                     21

SEQ ID NO: 94          moltype = DNA  length = 20
FEATURE                Location/Qualifiers
misc_feature           1..20
                       note = TCR beta-chain primer
source                 1..20
                       mol_type = other DNA
                       organism = synthetic construct
SEQUENCE: 94
gtggccaggc acaccagtgt                                       20

SEQ ID NO: 95          moltype = AA  length = 402
FEATURE                Location/Qualifiers
REGION                 1..402
                       note = Synthetic sequence inducible caspase-9
source                 1..402
                       mol_type = protein
                       organism = synthetic construct
SEQUENCE: 95
MLEGVQVETI SPGDGRTFPK RGQTCVVHYT GMLEDGKKVD SSRDRNKPFK FMLGKQEVIR  60
GWEEGVAQMS VGQRAKLTIS PDYAYGATGH PGIIPPHATL VFDVELLKLE SGGGSGVDGF  120
GDVGALESLR GNADLAYILS MEPCGHCLII NNVNFCRESG LRTRTGSNID CEKLRRRFSS  180
LHFMVEVKGD LTAKKMVLAL LELAQQDHGA LDCCVVVILS HGCQASHLQF PGAVYGTDGC  240
PVSVEKIVNI FNGTSCPSLG GKPKLFFIQA CGGEQKDHGF EVASTSPEDE SPGSNPEPDA  300
TPFQEGLRTF DQLDAISSLP TPSDIFVSYS TFPGFVSWRD PKSGSWYVET LDDIFEQWAH  360
SEDLQSLLLR VANAVSVKGI YKQMPGCFNF LRKKLFFKTS AS                    402

SEQ ID NO: 96          moltype = AA  length = 112
FEATURE                Location/Qualifiers
REGION                 1..112
                       note = Synthetic sequence TCR1,13 beta chain variable
                        region (mature)
source                 1..112
                       mol_type = protein
                       organism = synthetic construct
SEQUENCE: 96
GVSQDPRHKI TKRGQNVTFR CDPISEHNRL YWYRQTLGQG PEFLTYFQNE AQLEKSRLLS  60
DRFSAERPKG SFSTLEIQRT EQGDSAMYLC ASSSTGGHNE QFFGPGTRLT VL          112

SEQ ID NO: 97          moltype = AA  length = 113
FEATURE                Location/Qualifiers
REGION                 1..113
                       note = Synthetic sequence TCR1,13 alpha chain variable
                        region (mature)
source                 1..113
                       mol_type = protein
                       organism = synthetic construct
SEQUENCE: 97
QQGEEDPQAL SIQEGENATM NCSYKTSINN LQWYRQNSGR GLVHLILIRS NEREKHSGRL  60
RVTLDTSKKS SSLLITASRA ADTASYFCAT KRDSGAGSYQ LTFGKGTKLS VIP         113

SEQ ID NO: 98          moltype = AA  length = 111
FEATURE                Location/Qualifiers
REGION                 1..111
                       note = Synthetic sequence TCR2,14 beta chain variable
                        region (mature)
source                 1..111
                       mol_type = protein
```

```
                        organism = synthetic construct
SEQUENCE: 98
GVSQDPRHKI TKRGQNVTFR CDPISEHNRL YWYRQTLGQG PEFLTYFQNE AQLEKSRLLS  60
DRFSAERPKG SFSTLEIQRT EQGDSAMYLC ASSLVKGEKL FFGSGTQLSV L           111

SEQ ID NO: 99           moltype = AA  length = 113
FEATURE                 Location/Qualifiers
REGION                  1..113
                        note = Synthetic sequence TCR2,14 alpha chain variable
                         region (mature)
source                  1..113
                        mol_type = protein
                        organism = synthetic construct
SEQUENCE: 99
KQEVTQIPAA LSVPEGENLV LNCSFTDSAI YNLQWFRQDP GKGLTSLLLI QSSQREQTSG  60
RLNASLDKSS GRSTLYIAAS QPGDSATYLC AVIGLGGTYK YIFGTGTRLK VLA         113

SEQ ID NO: 100          moltype = AA  length = 111
FEATURE                 Location/Qualifiers
REGION                  1..111
                        note = Synthetic sequence TCR5 beta chain variable region
                         (mature)
source                  1..111
                        mol_type = protein
                        organism = synthetic construct
SEQUENCE: 100
GVSQDPRHKI TKRGQNVTFR CDPISEHNRL YWYRQTLGQG PEFLTYFQNE AQLEKSRLLS  60
DRFSAERPKG SFSTLEIQRT EQGDSAMYLC ASSLTTLDEQ YVGPGTRLTV T           111

SEQ ID NO: 101          moltype = AA  length = 109
FEATURE                 Location/Qualifiers
REGION                  1..109
                        note = Synthetic sequence TCR5 alpha chain variable region
                         (mature)
source                  1..109
                        mol_type = protein
                        organism = synthetic construct
SEQUENCE: 101
QQGEEDPQAL SIQEGENATM NCSYKTSINN LQWYRQNSGR GLVHLILIRS NEREKHSGRL  60
RVTLDTSKKS SSLLITASRA ADTASYFCAT NSGNTPLVFG KGTRLSVIA              109

SEQ ID NO: 102          moltype = AA  length = 111
FEATURE                 Location/Qualifiers
REGION                  1..111
                        note = Synthetic sequence TCR10 beta chain variable region
                         (mature)
source                  1..111
                        mol_type = protein
                        organism = synthetic construct
SEQUENCE: 102
GVSQDPRHKI TKRGQNVTFR CDPISEHNRL YWYRQTLGQG PEFLTYFQNE AQLEKSRLLS  60
DRFSAERPKG SFSTLEIQRT EQGDSAMYLC ASSMLTNYEQ YFGPGTRLTV T           111

SEQ ID NO: 103          moltype = AA  length = 113
FEATURE                 Location/Qualifiers
REGION                  1..113
                        note = Synthetic sequence TCR10 alpha chain variable region
                         (mature)
source                  1..113
                        mol_type = protein
                        organism = synthetic construct
SEQUENCE: 103
KNQVEQSPQS LIILEGKNCT LQCNYTVSPF SNLRWYKQDT GRGPVSLTIM TFSENTKSNG  60
RYTATLDADT KQSSLHITAS QLSDSASYIC VVDSGGGADG LTFGKGTHLI IQP         113

SEQ ID NO: 104          moltype = AA  length = 111
FEATURE                 Location/Qualifiers
REGION                  1..111
                        note = Synthetic sequence TCR16 beta chain variable region
                         (mature)
source                  1..111
                        mol_type = protein
                        organism = synthetic construct
SEQUENCE: 104
GVSQDPRHKI TKRGQNVTFR CDPISEHNRL YWYRQTLGQG PEFLTYFQNE AQLEKSRLLS  60
DRFSAERPKG SFSTLEIQRT EQGDSAMYLC ASSLVVGNEQ FFGPGTRLTV L           111

SEQ ID NO: 105          moltype = AA  length = 112
FEATURE                 Location/Qualifiers
```

```
REGION                 1..112
                       note = Synthetic sequence TCR16 alpha chain variable region
                        (mature)
source                 1..112
                       mol_type = protein
                       organism = synthetic construct
SEQUENCE: 105
KQEVTQIPAA LSVPEGENLV LNCSFTDSAI YNLQWFRQDP GKGLTSLLLI QSSQREQTSG  60
RLNASLDKSS GRSTLYIAAS QPGDSATYLC AVHLLNDYKL SFGAGTTVTV RA          112

SEQ ID NO: 106         moltype = AA  length = 111
FEATURE                Location/Qualifiers
REGION                 1..111
                       note = Synthetic sequence TCR29 beta chain variable region
                        (mature)
source                 1..111
                       mol_type = protein
                       organism = synthetic construct
SEQUENCE: 106
GVSQDPRHKI TKRGQNVTFR CDPISEHNRL YWYRQTLGQG PEFLTYFQNE AQLEKSRLLS  60
DRFSAERPKG SFSTLEIQRT EQGDSAMYLC ASSLVSGNTI YFGEGSWLTV V           111

SEQ ID NO: 107         moltype = AA  length = 115
FEATURE                Location/Qualifiers
REGION                 1..115
                       note = Synthetic sequence TCR29 alpha chain variable region
                        (mature)
source                 1..115
                       mol_type = protein
                       organism = synthetic construct
SEQUENCE: 107
KQEVTQIPAA LSVPEGENLV LNCSFTDSAI YNLQWFRQDP GKGLTSLLLI QSSQREQTSG  60
RLNASLDKSS GRSTLYIAAS QPGDSATYLC AVRGGTTSGT YKYIFGTGTR LKVLA       115

SEQ ID NO: 108         moltype = AA  length = 289
FEATURE                Location/Qualifiers
REGION                 1..289
                       note = Synthetic sequence TCR1,13 beta chain (full length)
                        (Cys modified) (mature)
source                 1..289
                       mol_type = protein
                       organism = synthetic construct
SEQUENCE: 108
GVSQDPRHKI TKRGQNVTFR CDPISEHNRL YWYRQTLGQG PEFLTYFQNE AQLEKSRLLS  60
DRFSAERPKG SFSTLEIQRT EQGDSAMYLC ASSSTGGHNE QFFGPGTRLT VLEDLKNVFP  120
PEVAVFEPSE AEISHTQKAT LVCLATGFYP DHVELSWWVN GKEVHSGVCT DPQPLKEQPA  180
LNDSRYCLSS RLRVSATFWQ NPRNHFRCQV QFYGLSENDE WTQDRAKPVT QIVSAEAWGR  240
ADCGFTSESY QQGVLSATIL YEILLGKATL YAVLVSALVL MAMVKRKDS              289

SEQ ID NO: 109         moltype = AA  length = 254
FEATURE                Location/Qualifiers
REGION                 1..254
                       note = Synthetic sequence TCR1,13 alpha chain (full
                       length)(Cys modified) (mature)
source                 1..254
                       mol_type = protein
                       organism = synthetic construct
SEQUENCE: 109
QQGEEDPQAL SIQEGENATM NCSYKTSINN LQWYRQNSGR GLVHLILIRS NEREKHSGRL  60
RVTLDTSKKS SSLLITASRA ADTASYFCAT KRDSGAGSYQ LTFGKGTKLS VIPNIQNPDP  120
AVYQLRDSKS SDKSVCLFTD FDSQTNVSQS KDSDVYITDK CVLDMRSMDF KSNSAVAWSN  180
KSDFACANAF NNSIIPEDTF FPSPESSCDV KLVEKSFETD TNLNFQNLSV IGFRILLLKV  240
AGFNLLMTLR LWSS                                                    254

SEQ ID NO: 110         moltype = AA  length = 287
FEATURE                Location/Qualifiers
REGION                 1..287
                       note = Synthetic sequence TCR2,14 beta chain (full length)
                        (Cys modified) (mature)
source                 1..287
                       mol_type = protein
                       organism = synthetic construct
SEQUENCE: 110
GVSQDPRHKI TKRGQNVTFR CDPISEHNRL YWYRQTLGQG PEFLTYFQNE AQLEKSRLLS  60
DRFSAERPKG SFSTLEIQRT EQGDSAMYLC ASSLVKGEKL FFGSGTQLSV LEDLNKVFPP  120
EVAVFEPSEA EISHTQKATL VCLATGFFPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSVSYQ QGVLSATILY EILLGKATLY AVLVSALVLM AMVKRKD                287
```

```
SEQ ID NO: 111          moltype = AA  length = 254
FEATURE                 Location/Qualifiers
REGION                  1..254
                        note = Synthetic sequence TCR2,14 alpha chain (full
                         length)(Cys modified) (mature)
source                  1..254
                        mol_type = protein
                        organism = synthetic construct
SEQUENCE: 111
KQEVTQIPAA LSVPEGENLV LNCSFTDSAI YNLQWFRQDP GKGLTSLLLI QSSQREQTSG  60
RLNASLDKSS GRSTLYIAAS QPGDSATYLC AVIGLGGTYK YIFGTGTRLK VLANIQNPDP  120
AVYQLRDSKS SDKSVCLFTD FDSQTNVSQS KDSDVYITDK CVLDMRSMDF KSNSAVAWSN  180
KSDFACANAF NNSIIPEDTF FPSPESSCDV KLVEKSFETD TNLNFQNLSV IGFRILLLKV  240
AGFNLLMTLR LWSS                                                    254

SEQ ID NO: 112          moltype = AA  length = 288
FEATURE                 Location/Qualifiers
REGION                  1..288
                        note = Synthetic sequence TCR5 beta chain (full length)
                         (Cys modified) (mature)
source                  1..288
                        mol_type = protein
                        organism = synthetic construct
SEQUENCE: 112
GVSQDPRHKI TKRGQNVTFR CDPISEHNRL YWYRQTLGQG PEFLTYFQNE AQLEKSRLLS  60
DRFSAERPKG SFSTLEIQRT EQGDSAMYLC ASSLTTLDEQ YVGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDS               288

SEQ ID NO: 113          moltype = AA  length = 250
FEATURE                 Location/Qualifiers
REGION                  1..250
                        note = Synthetic sequence TCR5 alpha chain (full
                         length)(Cys modified) (mature)
source                  1..250
                        mol_type = protein
                        organism = synthetic construct
SEQUENCE: 113
QQGEEDPQAL SIQEGENATM NCSYKTSINN LQWYRQNSGR GLVHLILIRS NEREKHSGRL  60
RVTLDTSKKS SSLLITASRA ADTASYFCAT NSGNTPLVFG KGTRLSVIAN IQNPDPAVYQ  120
LRDSKSSDKS VCLFTDFDSQ TNVSQSKDSD VYITDKCVLD MRSMDFKSNS AVAWSNKSDF  180
ACANAFNNSI IPEDTFFPSP ESSCDVKLVE KSFETDTNLN FQNLSVIGFR ILLLKVAGFN  240
LLMTLRLWSS                                                         250

SEQ ID NO: 114          moltype = AA  length = 288
FEATURE                 Location/Qualifiers
REGION                  1..288
                        note = Synthetic sequence TCR10 beta chain (full length)
                         (Cys modified) (mature)
source                  1..288
                        mol_type = protein
                        organism = synthetic construct
SEQUENCE: 114
GVSQDPRHKI TKRGQNVTFR CDPISEHNRL YWYRQTLGQG PEFLTYFQNE AQLEKSRLLS  60
DRFSAERPKG SFSTLEIQRT EQGDSAMYLC ASSMLTNYEQ YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDS               288

SEQ ID NO: 115          moltype = AA  length = 254
FEATURE                 Location/Qualifiers
REGION                  1..254
                        note = Synthetic sequence TCR10 alpha chain (full
                         length)(Cys modified) (mature)
source                  1..254
                        mol_type = protein
                        organism = synthetic construct
SEQUENCE: 115
KNQVEQSPQS LIILEGKNCT LQCNYTVSPF SNLRWYKQDT GRGPVSLTIM TFSENTKSNG  60
RYTATLDADT KQSSLHITAS QLSDSASYIC VVDSGGGADG LTFGKGTHLI IQPYIQNPDP  120
AVYQLRDSKS SDKSVCLFTD FDSQTNVSQS KDSDVYITDK CVLDMRSMDF KSNSAVAWSN  180
KSDFACANAF NNSIIPEDTF FPSPESSCDV KLVEKSFETD TNLNFQNLSV IGFRILLLKV  240
AGFNLLMTLR LWSS                                                    254

SEQ ID NO: 116          moltype = AA  length = 287
FEATURE                 Location/Qualifiers
REGION                  1..287
                        note = Synthetic sequence TCR16 beta chain (full length)
```

```
                         (Cys modified) (mature)
source                  1..287
                        mol_type = protein
                        organism = synthetic construct
SEQUENCE: 116
GVSQDPRHKI TKRGQNVTFR CDPISEHNRL YWYRQTLGQG PEFLTYFQNE AQLEKSRLLS  60
DRFSAERPKG SFSTLEIQRT EQGDSAMYLC ASSLVVGNEQ FFGPGTRLTV LEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKD               287

SEQ ID NO: 117          moltype = AA  length = 253
FEATURE                 Location/Qualifiers
REGION                  1..253
                        note = Synthetic sequence TCR16 alpha chain (full length)
                         (Cys modified) (mature)
source                  1..253
                        mol_type = protein
                        organism = synthetic construct
SEQUENCE: 117
KQEVTQIPAA LSVPEGENLV LNCSFTDSAI YNLQWFRQDP GKGLTSLLLI QSSQREQTSG  60
RLNASLDKSS GRSTLYIAAS QPGDSATYLC AVHLLNDYKL SFGAGTTVTV RANIQNPDPA  120
VYQLRDSKSS DKSVCLFTDF DSQTNVSQSK DSDVYITDKC VLDMRSMDFK SNSAVAWSNK  180
SDFACANAFN NSIIPEDTFF PSPESSCDVK LVEKSFETDT NLNFQNLSVI GFRILLLKVA  240
GFNLLMTLRL WSS                                                    253

SEQ ID NO: 118          moltype = AA  length = 288
FEATURE                 Location/Qualifiers
REGION                  1..288
                        note = Synthetic sequenceTCR29 beta chain (full length)
                         (mature)
source                  1..288
                        mol_type = protein
                        organism = synthetic construct
SEQUENCE: 118
GVSQDPRHKI TKRGQNVTFR CDPISEHNRL YWYRQTLGQG PEFLTYFQNE AQLEKSRLLS  60
DRFSAERPKG SFSTLEIQRT EQGDSAMYLC ASSLVSGNTI YFGEGSWLTV VEDLNKVFPP  120
EVAVFEPSEA EISHTQKATL VCLATGFFPD HVELSWWVNG KEVHSGVSTD PQPLKEQPAL  180
NDSRYCLSSR LRVSATFWQN PRNHFRCQVQ FYGLSENDEW TQDRAKPVTQ IVSAEAWGRA  240
DCGFTSVSYQ QGVLSATILY EILLGKATLY AVLVSALVLM AMVKRKDF              288

SEQ ID NO: 119          moltype = AA  length = 256
FEATURE                 Location/Qualifiers
REGION                  1..256
                        note = Synthetic sequence TCR29 alpha chain (full length)
                         (mature)
source                  1..256
                        mol_type = protein
                        organism = synthetic construct
SEQUENCE: 119
KQEVTQIPAA LSVPEGENLV LNCSFTDSAI YNLQWFRQDP GKGLTSLLLI QSSQREQTSG  60
RLNASLDKSS GRSTLYIAAS QPGDSATYLC AVRGGTTSGT YKYIFGTGTR LKVLANIQNP  120
DPAVYQLRDS KSSDKSVCLF TDFDSQTNVS QSKDSDVYIT DKTVLDMRSM DFKSNSAVAW  180
SNKSDFACAN AFNNSIIPED TFFPSPESSC DVKLVEKSFE TDTNLNFQNL SVIGFRILLL  240
KVAGFNLLMT LRLWSS                                                 256

SEQ ID NO: 120          moltype = AA  length = 214
FEATURE                 Location/Qualifiers
REGION                  1..214
                        note = Synthetic sequence CD8 co-receptor alpha chain
                         (mature)
source                  1..214
                        mol_type = protein
                        organism = synthetic construct
SEQUENCE: 120
SQFRVSPLDR TWNLGETVEL KCQVLLSNPT SGCSWLFQPR GAAASPTFLL YLSQNKPKAA  60
EGLDTQRFSG KRLGDTFVLT LSDFRRENEG YYFCSALSNS IMYFSHFVPV FLPAKPTTTP  120
APRPPTPAPT IASQPLSLRP EACRPAAGGA VHTRGLDFAC DIYIWAPLAG TCGVLLLSLV  180
ITLYCNHRNR RRVCKCPRPV VKSGDKPSLS ARYV                             214

SEQ ID NO: 121          moltype = AA  length = 189
FEATURE                 Location/Qualifiers
REGION                  1..189
                        note = Synthetic sequence CD8 co-receptor beta chain
                         isoform 1 (mature)
source                  1..189
                        mol_type = protein
                        organism = synthetic construct
SEQUENCE: 121
```

-continued

```
LQQTPAYIKV QTNKMVMLSC EAKISLSNMR IYWLRQRQAP SSDSHHEFLA LWDSAKGTIH  60
GEEVEQEKIA VFRDASRFIL NLTSVKPEDS GIYFCMIVGS PELTFGKGTQ LSVVDFLPTT  120
AQPTKKSTLK KRVCRLPRPE TQKGPLCSPI TLGLLVAGVL VLLVSLGVAI HLCCRRRRAR  180
LRFMKQFYK                                                          189

SEQ ID NO: 122         moltype = AA  length = 200
FEATURE                Location/Qualifiers
REGION                 1..200
                       note = Synthetic sequence CD8 co-receptor beta chain
                        isoform 2 (mature)
source                 1..200
                       mol_type = protein
                       organism = synthetic construct
SEQUENCE: 122
LQQTPAYIKV QTNKMVMLSC EAKISLSNMR IYWLRQRQAP SSDSHHEFLA LWDSAKGTIH  60
GEEVEQEKIA VFRDASRFIL NLTSVKPEDS GIYFCMIVGS PELTFGKGTQ LSVVDFLPTT  120
AQPTKKSTLK KRVCRLPRPE TQKGPLCSPI TLGLLVAGVL VLLVSLGVAI HLCCRRRRAR  180
LRFMKQLRLH PLEKCSRMDY                                              200

SEQ ID NO: 123         moltype = AA  length = 225
FEATURE                Location/Qualifiers
REGION                 1..225
                       note = Synthetic sequence CD8 co-receptor beta chain
                        isoform 3 (mature)
source                 1..225
                       mol_type = protein
                       organism = synthetic construct
SEQUENCE: 123
LQQTPAYIKV QTNKMVMLSC EAKISLSNMR IYWLRQRQAP SSDSHHEFLA LWDSAKGTIH  60
GEEVEQEKIA VFRDASRFIL NLTSVKPEDS GIYFCMIVGS PELTFGKGTQ LSVVDFLPTT  120
AQPTKKSTLK KRVCRLPRPE TQKGPLCSPI TLGLLVAGVL VLLVSLGVAI HLCCRRRRAR  180
LRFMKQKFNI VCLKISGFTT CCCFQILQIS REYGFGVLLQ KDIGQ                  225

SEQ ID NO: 124         moltype = AA  length = 225
FEATURE                Location/Qualifiers
REGION                 1..225
                       note = Synthetic sequence CD8 co-receptor beta chain
                        isoform 4 (mature)
source                 1..225
                       mol_type = protein
                       organism = synthetic construct
SEQUENCE: 124
LQQTPAYIKV QTNKMVMLSC EAKISLSNMR IYWLRQRQAP SSDSHHEFLA LWDSAKGTIH  60
GEEVEQEKIA VFRDASRFIL NLTSVKPEDS GIYFCMIVGS PELTFGKGTQ LSVVDFLPTT  120
AQPTKKSTLK KRVCRLPRPE TQKGPLCSPI TLGLLVAGVL VLLVSLGVAI HLCCRRRRAR  180
LRFMKQKFNI VCLKISGFTT CCCFQILQIS REYGFGVLLQ KDIGQ                  225

SEQ ID NO: 125         moltype = AA  length = 222
FEATURE                Location/Qualifiers
REGION                 1..222
                       note = Synthetic sequence CD8 co-receptor beta chain
                        isoform 5 (mature)
source                 1..222
                       mol_type = protein
                       organism = synthetic construct
SEQUENCE: 125
LQQTPAYIKV QTNKMVMLSC EAKISLSNMR IYWLRQRQAP SSDSHHEFLA LWDSAKGTIH  60
GEEVEQEKIA VFRDASRFIL NLTSVKPEDS GIYFCMIVGS PELTFGKGTQ LSVVDFLPTT  120
AQPTKKSTLK KRVCRLPRPE TQKGPLCSPI TLGLLVAGVL VLLVSLGVAI HLCCRRRRAR  180
LRFMKQPQGE GISGTFVPQC LHGYYSNTTT SQKLLNPWIL KT                     222

SEQ ID NO: 126         moltype = DNA  length = 930
FEATURE                Location/Qualifiers
misc_feature           1..930
                       note = Synthetic sequence TCR 29 beta chain (wild-type)
source                 1..930
                       mol_type = other DNA
                       organism = synthetic construct
SEQUENCE: 126
atgggcacca gcctcctctg ctggatggcc ctgtgtctcc tgggggcaga tcacgcagat  60
actggagtct cccaggaccc cagacacaag atcacaaaga ggggacagaa tgtaactttc  120
aggtgtgatc caatttctga acacaaccgc ctttattggt accgacagac cctggggcag  180
ggcccagagt ttctgactta cttccagaat gaagctcaac tagaaaaatc aaggctgctc  240
agtgatcggt tctctgcaga gaggcctaag ggatctttct ccaccttgga gatccagcgc  300
acagagcagg gggactcggc catgtatctc tgtgccagca gcttagtatc cggaaacacc  360
atatattttg gagagggaag ttggctcact gttgtagagg acctgaacaa ggtgttccca  420
cccgaggtcg ctgtgtttga gccatcagaa gcagagatct cccacaccca aaaggccaca  480
ctggtgtgcc tggccacagg cttcttcccc gaccacgtgg agctgagctg gtgggtgaat  540
gggaaggagg tgcacagtgg ggtcagcaca gacccgcagc cctcaagga gcagcccgcc  600
```

```
ctcaatgact ccagatactg cctgagcagc cgcctgaggg tctcggccac cttctggcag  660
aacccccgca accacttccg ctgtcaagtc cagttctacg ggctctcgga gaatgacgag  720
tggacccagg atagggccaa acccgtcacc cagatcgtca gcgccgaggc ctggggtaga  780
gcagactgtg gctttacctc ggtgtcctac cagcaagggg tcctgtctgc caccatcctc  840
tatgagatcc tgctagggaa ggccaccctg tatgctgtgc tggtcagcgc ccttgtgttg  900
atggccatgg tcaagagaaa ggatttctga                                   930

SEQ ID NO: 127         moltype = DNA  length = 828
FEATURE                Location/Qualifiers
misc_feature           1..828
                       note = Synthetic sequence TCR 29 alpha chain (wild-type)
source                 1..828
                       mol_type = other DNA
                       organism = synthetic construct
SEQUENCE: 127
atggagaccc tcttgggcct gcttatcctt tggctgcagc tgcaatgggt gagcagcaaa  60
caggaggtga cgcagattcc tgcagctctg agtgtcccag aaggagaaaa cttggttctc  120
aactgcagtt tcactgatag cgctatttac aacctccagt ggtttaggca ggaccctggg  180
aaaggtctca catctctgtt gcttattcag tcaagtcaga gagagcaaac aagtggaaga  240
cttaatgcct cgctggataa atcatcagga cgtagtactt tatacattgc agcttctcag  300
cctggtgact cagccaccta cctctgtgct gtgagagggg ggactacctc aggaacctac  360
aaatacatct ttggaacagg caccaggctg aaggttttag caaatatcca gaaccctgac  420
cctgccgtgt accagctgag agactctaaa tccagtgaca agtctgtctg cctattcacc  480
gattttgatt ctcaaacaaa tgtgtcacaa agtaaggatt ctgatgtgta tatcacagac  540
aaaactgtgc tagacatgag gtctatggac ttcaagagca acagtgctgt ggcctggagc  600
aacaaatctg actttgcatg tgcaaacgcc ttcaacaaca gcattattcc agaagacacc  660
ttcttcccca gcccagaaag ttcctgtgat gtcaagctgg tcgagaaaag ctttgaaaca  720
gatacgaacc taaactttca aaacctgtca gtgattgggt tccgaatcct cctcctgaaa  780
gtggccgggt ttaatctgct catgacgctg cggctgtggt ccagctga               828

SEQ ID NO: 128         moltype = AA  length = 9
FEATURE                Location/Qualifiers
REGION                 1..9
                       note = Control clone specific for a Y chromosome-associated
                        minor H antigen
source                 1..9
                       mol_type = protein
                       organism = synthetic construct
SEQUENCE: 128
FIDSYICQV                                                          9

SEQ ID NO: 129         moltype =   length =
SEQUENCE: 129
000

SEQ ID NO: 130         moltype = AA  length = 14
FEATURE                Location/Qualifiers
REGION                 1..14
                       note = Synthetic sequence TCR24 beta chain CDR3
source                 1..14
                       mol_type = protein
                       organism = synthetic construct
SEQUENCE: 130
ATSKTRIAQE TQYF                                                    14

SEQ ID NO: 131         moltype = AA  length = 9
FEATURE                Location/Qualifiers
REGION                 1..9
                       note = Synthetic Meganuclease sequence
source                 1..9
                       mol_type = protein
                       organism = synthetic construct
SEQUENCE: 131
LAGLIDADG                                                          9

SEQ ID NO: 132         moltype =   length =
SEQUENCE: 132
000

SEQ ID NO: 133         moltype = AA  length = 5
FEATURE                Location/Qualifiers
REGION                 1..5
                       note = Synthetic sequence - TCR2, 14 Vb CDR1
source                 1..5
                       mol_type = protein
                       organism = synthetic construct
SEQUENCE: 133
SEHNR                                                              5
```

-continued

```
SEQ ID NO: 134          moltype = AA  length = 6
FEATURE                 Location/Qualifiers
REGION                  1..6
                        note = Synthetic sequence - TCR2, 14 Vb CDR2
source                  1..6
                        mol_type = protein
                        organism = synthetic construct
SEQUENCE: 134
FQNEAQ                                                                6

SEQ ID NO: 135          moltype = AA  length = 6
FEATURE                 Location/Qualifiers
REGION                  1..6
                        note = Synthetic sequence - TCR2, 14 Va CDR1
source                  1..6
                        mol_type = protein
                        organism = synthetic construct
SEQUENCE: 135
DSAIYN                                                                6

SEQ ID NO: 136          moltype = AA  length = 7
FEATURE                 Location/Qualifiers
REGION                  1..7
                        note = Synthetic sequence - TCR2, 14 Va CDR2
source                  1..7
                        mol_type = protein
                        organism = synthetic construct
SEQUENCE: 136
IQSSQRE                                                               7
```

What is claimed is:

1. A method for treating or for preventing a relapse of a hyperproliferative disorder characterized by expression of an HA-1H antigen in a subject, the method comprising administering to the subject an effective amount of an engineered T cell comprising a heterologous polynucleotide encoding a binding protein that includes:

(a) a T cell receptor (TCR) α-chain variable (Va) domain comprising a CDR3 amino acid sequence of SEQ ID NO.: 88, a CDR2 amino acid sequence of SEQ ID NO.: 136, and a CDR1 amino acid sequence of SEQ ID NO.: 135, and;

(b) a TCR β-chain variable (VB) domain comprising a CDR3 amino acid sequence of SEQ ID NO.: 14, a CDR2 amino acid sequence of SEQ ID NO:134, and a CDR1 amino acid sequence of SEQ ID NO.: 133, wherein the encoded binding protein is capable of being expressed at a cell surface of the engineered T cell and specifically binding to a VLHDDLLEA (SEQ ID NO.: 66):HLA-A2 complex, and wherein the subject is positive for expression of the HLA-A2.

2. The method of claim 1, wherein the encoded binding protein is a TCR.

3. The method of claim 2, wherein the HLA comprises HLA-A*0201.

4. The method of claim 1, wherein the engineered T cell further comprises a heterologous polynucleotide encoding:

(a) a safety switch protein;

(b) a selection marker;

(c) a CD8 co-receptor β-chain; and/or (d) a CD8 co-receptor α-chain.

5. The method of claim 1, wherein the encoded VB domain has at least 90% identity to the amino acid sequence of SEQ ID NO.: 3 or 98, and the encoded Va domain has at least 90% identity to the amino acid sequence of SEQ ID NO.: 4 or 99.

6. The method of claim 5, wherein the encoded VB domain comprises the amino acid sequence of SEQ ID NO.: 3 or 98, and the encoded Va domain comprises the amino acid sequence of SEQ ID NO.: 4 or 99.

7. The method of claim 1, wherein the encoded binding protein comprises:

a TCR α-chain having at least 90% identity to the amino acid sequence of SEQ ID NO.: 30 or 111; and/or a TCR β-chain having at least 90% identity to the amino acid sequence of SEQ ID NO.: 29 or 110.

8. The method of claim 1, wherein the encoded binding protein comprises:

(i) a TCR β-chain comprising or consisting of the amino acid sequence of SEQ ID NO.: 29, and a TCR α-chain comprising or consisting of the amino acid sequence of SEQ ID NO.: 30; or (ii) a TCR β-chain comprising or consisting of the amino acid sequence of SEQ ID NO.: 110, and a TCR α-chain comprising or consisting of the amino acid sequence of SEQ ID NO.: 111.

9. The method of claim 1, wherein the heterologous polynucleotide encodes the amino acid sequence of SEQ ID NO.: 54.

10. A method for treating or for preventing a relapse of a hyperproliferative disorder characterized by expression of an HA-1H antigen in a subject, the method comprising administering to the subject an effective amount of a T cell expressing a T cell receptor (TCR) that comprises:

a β-chain comprising a variable (VB) domain comprising the amino acid sequence of SEQ ID NO.: 98; and an α-chain comprising a variable (Va) domain comprising the amino acid sequence of SEQ ID NO.: 99, wherein the TCR is capable of specifically binding to a VLHDDLLEA (SEQ ID NO.: 66):HLA-A2 complex, wherein the subject is positive for expression of the HLA-A2, and wherein the T cell comprises a CD8+ T cell, a CD4+ T cell, or both.

11. The method of claim 10, wherein the TCR comprises:

(i) a TCR β-chain comprising or consisting of the amino acid sequence of SEQ ID NO.: 29, and a TCR α-chain comprising or consisting of the amino acid sequence of SEQ ID NO.: 30; or (ii) a TCR β-chain comprising or consisting of the amino acid sequence of SEQ ID NO.: 110, and a TCR α-chain comprising or consisting of the amino acid sequence of SEQ ID NO.: 111.

12. The method of claim 1, wherein the engineered T cell is administered to the subject in a composition comprising the engineered T cell and a pharmaceutically acceptable carrier, diluent, or excipient.

13. A method for treating or for preventing a relapse of a hyperproliferative disorder characterized by expression of an HA-1" antigen in a subject, the method comprising administering to the subject an effective amount of an engineered T cell comprising a heterologous polynucleotide encoding a binding protein that includes:

(a) a TCR α-chain variable (Vα) domain, wherein the encoded Va domain
  (i) comprises a CDR3 amino acid sequence of SEQ ID NO.: 88, and
  (ii) has at least about 90% sequence identity to the Vα domain amino acid sequence of SEQ ID NO.: 4 or 99, provided that the encoded Vα domain comprises no change in amino acid sequence of CDR1 and CDR2, and;

(b) a TCR β-chain variable (Vβ) domain, wherein encoded the Vβ domain
  (i) comprises a CDR3 amino acid sequence of SEQ ID NO.: 14, and
  (ii) has at least about 90% sequence identity to the amino acid sequence of SEQ ID NOs.: 3 or 98, provided that the encoded Vβ domain comprises no change in amino acid sequence of CDR1 and CDR2, wherein the encoded binding protein is capable of being expressed at a cell surface of the engineered T cell and specifically binding to a VLHDDLLEA (SEQ ID NO.: 66):HLA-A2 complex, and wherein the subject is positive for expression of the HLA-A2.

14. The method of claim 1, wherein the hyperproliferative disorder comprises a hematological malignancy.

15. The method of claim 14, wherein the hematological malignancy comprises a leukemia, a lymphoma, a myelodysplastic disorder, or a myeloma.

16. The method of claim 14, wherein the hematological malignancy comprises (A) a leukemia selected from acute myeloid leukemia (AML), acute lymphocytic leukemia (ALL), mixed phenotype acute leukemia (MPAL), chronic myeloid leukemia (CML), B cell prolymphocytic leukemia, hairy cell leukemia, or chronic lymphocytic leukemia (CLL), (B) a lymphoma is selected from Hodgkin's lymphoma (HL), non-Hodgkin's lymphoma (NHL), a central nervous system lymphoma, small lymphocytic lymphoma (SLL), CD37+ dendritic cell lymphoma, lymphoplasmacytic lymphoma, splenic marginal zone lymphoma, extra-nodal marginal zone B-cell lymphoma of mucosa-associated (MALT) lymphoid tissue, nodal marginal zone B-cell lymphoma, follicular lymphoma, mantle cell lymphoma, diffuse large B-cell lymphoma, mediastinal (thymic) large B-cell lymphoma, precursor B-lymphoblastic lymphoma, immunoblastic large cell lymphoma, intravascular large B-cell lymphoma, primary effusion lymphoma, or Burkitt's lymphoma; or (C) a myelodysplastic disorder selected from refractory cytopenia with unilineage dysplasia (refractory anemia, refractory neutropenia, and refractory thrombocytopenia), refractory anemia with ring sideroblasts (RARS), refractory anemia with ring sideroblasts—thrombocytosis (RARS-t), refractory cytopenia with multinieage dysplasia (RCMD), refractory cytopenia with multinieage dysplasia and ring sideroblasts (RCMD-RS), refractory anemia with excess blasts (RAEB), myelodysplasia unclassifiable, or refractory cytopenia of childhood.

17. The method of claim 1, wherein the subject is receiving or previously received a hematopoietic cell transplant (HCT) a lymphodepleting chemotherapy, or both a hematopoietic cell transplant (HCT) and a lymphodepleting chemotherapy.

18. The method of claim 10, wherein the hyperproliferative disorder comprises a hematological malignancy.

19. The method of claim 18, wherein the hematological malignancy comprises a leukemia, a lymphoma, a myelodysplastic disorder, or a myeloma.

20. The method of claim 18, wherein the hematological malignancy comprises (A) a leukemia selected from acute myeloid leukemia (AML), acute lymphocytic leukemia (ALL), mixed phenotype acute leukemia (MPAL), chronic myeloid leukemia (CML), B cell prolymphocytic leukemia, hairy cell leukemia, or chronic lymphocytic leukemia (CLL), (B) a lymphoma is selected from Hodgkin's lymphoma (HL), non-Hodgkin's lymphoma (NHL), a central nervous system lymphoma, small lymphocytic lymphoma (SLL), CD37+ dendritic cell lymphoma, lymphoplasmacytic lymphoma, splenic marginal zone lymphoma, extra-nodal marginal zone B-cell lymphoma of mucosa-associated (MALT) lymphoid tissue, nodal marginal zone B-cell lymphoma, follicular lymphoma, mantle cell lymphoma, diffuse large B-cell lymphoma, mediastinal (thymic) large B-cell lymphoma, precursor B-lymphoblastic lymphoma, immunoblastic large cell lymphoma, intravascular large B-cell lymphoma, primary effusion lymphoma, or Burkitt's lymphoma; or (C) a myelodysplastic disorder selected from refractory cytopenia with unilineage dysplasia (refractory anemia, refractory neutropenia, and refractory thrombocytopenia), refractory anemia with ring sideroblasts (RARS), refractory anemia with ring sideroblasts—thrombocytosis (RARS-t), refractory cytopenia with multinieage dysplasia (RCMD), refractory cytopenia with multinieage dysplasia and ring sideroblasts (RCMD-RS), refractory anemia with excess blasts (RAEB), myelodysplasia unclassifiable, or refractory cytopenia of childhood.

21. The method of claim 10, wherein the subject is receiving or previously received a hematopoietic cell transplant (HCT) a lymphodepleting chemotherapy, or both a hematopoietic cell transplant (HCT) and a lymphodepleting chemotherapy.

22. The method of claim 10, wherein the method comprises administering to the subject a composition comprising a plurality of the T cell, wherein at least about 30% of the T cells in the composition are $CD4^+$ T cells and at least about 30% of the T cells in the composition are $CD8^+$ T cells, wherein the CD4+ T cells and the CD8+ T cells are present in about a 1:1 ratio in the composition, and wherein the composition contains substantially no naïve T cells.

* * * * *